US011338043B2

(12) United States Patent
Van Berkel et al.

(10) Patent No.: US 11,338,043 B2
(45) **Date of Patent: *May 24, 2022**

(54) ANTIBODY-CONJUGATES WITH IMPROVED THERAPEUTIC INDEX FOR TARGETING HER2 TUMOURS AND METHOD FOR IMPROVING THERAPEUTIC INDEX OF ANTIBODY-CONJUGATES

(71) Applicant: SYNAFFIX B.V., AB Oss (NL)

(72) Inventors: Sander Sebastiaan Van Berkel, HR Lent (NL); Jorge Merijn Mathieu Verkade, NC Eindhoven (NL); Maria Antonia Wijdeven, HR Lent (NL); Ryan Heesbeen, CM Nijmegen (NL); Petrus Josephus Jacobus Maria Van De Sande, BE Eindhoven (NL); Remon Van Geel, CM Lithoijen (NL); Brian Maria Gerardus Janssen, MJ Eindhoven (NL); Inge Catharina Josephina Hurkmans, DG Asten (NL); Floris Louis Van Delft, KZ Nijmegen (NL)

(73) Assignee: SYNAFFIX B.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/076,293

(22) PCT Filed: Feb. 8, 2017

(86) PCT No.: PCT/EP2017/052790

§ 371 (c)(1),
(2) Date: Aug. 7, 2018

(87) PCT Pub. No.: WO2017/137457

PCT Pub. Date: Aug. 17, 2017

(65) Prior Publication Data

US 2019/0262466 A1 Aug. 29, 2019

(30) Foreign Application Priority Data

Feb. 8, 2016 (EP) .................................... 16154712
Feb. 8, 2016 (EP) .................................... 16154739
(Continued)

(51) Int. Cl.
*A61K 47/68* (2017.01)
*A61K 38/07* (2006.01)
(Continued)

(52) U.S. Cl.
CPC .......... *A61K 47/6889* (2017.08); *A61K 38/07* (2013.01); *A61K 47/34* (2013.01);
(Continued)

(58) Field of Classification Search
None
See application file for complete search history.

(56) References Cited

U.S. PATENT DOCUMENTS 5,602,119 A 2/1997 Vazquez et al.
8,207,303 B2 6/2012 Cardarelli et al.
(Continued)

FOREIGN PATENT DOCUMENTS

CN 104623687 A 5/2015
EP 2 481 725 A1 8/2012
(Continued)

OTHER PUBLICATIONS

Lu et al. ("Lu", J. Am. Chem. Soc., 2010, 132, 1747-1749) (Year: 2020).*

(Continued)

*Primary Examiner* — Karl J Puttlitz
(74) *Attorney, Agent, or Firm* — Foley & Lardner LLP

(57) ABSTRACT

The present invention concerns novel and improved antibody-conjugates for targeting HER2. The inventors found N
(Continued)

that when antibody-conjugates were prepared using a specific mode of conjugation, they exhibit an improved therapeutic index. The mode of conjugation comprises a first step (i) of contacting a glycoprotein comprising 1-4 core N-acetylglucosamine moieties with a compound of the formula $S(F^1)_x$-P in the presence of a catalyst, wherein $S(F^1)_x$ is a sugar derivative comprising x functional groups F1 capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety, to obtain a modified antibody; and a second step (ii) of reacting the modified antibody with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$. The invention also relates to a use for improving the therapeutic index of an antibody-conjugate and to a method for targeting HER2-expressing cells.

10 Claims, 9 Drawing Sheets

Specification includes a Sequence Listing.

(30) Foreign Application Priority Data

Jun. 8, 2016 (EP) .................................... 16173595
Aug. 8, 2016 (JP) ............................ JP2016-155929

(51) Int. Cl.

| | |
|---|---|
| ***C07K 16/30*** | (2006.01) |
| ***A61K 47/65*** | (2017.01) |
| ***A61K 47/54*** | (2017.01) |
| ***A61K 47/59*** | (2017.01) |
| ***A61P 35/02*** | (2006.01) |
| ***A61K 47/34*** | (2017.01) |
| ***A61K 47/42*** | (2017.01) |
| ***C07K 16/32*** | (2006.01) |
| ***C07K 16/28*** | (2006.01) |
| *A61K 45/06* | (2006.01) |
| *A61K 39/00* | (2006.01) |

(52) U.S. Cl.

CPC ............ *A61K 47/42* (2013.01); *A61K 47/549* (2017.08); *A61K 47/59* (2017.08); *A61K 47/65* (2017.08); *A61K 47/6803* (2017.08); *A61K 47/6811* (2017.08); *A61K 47/6817* (2017.08); *A61K 47/6849* (2017.08); *A61K 47/6851* (2017.08); *A61K 47/6869* (2017.08); *A61P 35/02* (2018.01); *C07K 16/2878* (2013.01); *C07K 16/30* (2013.01); *C07K 16/32* (2013.01); *A61K 45/06* (2013.01); *A61K 2039/505* (2013.01); *C07K 2317/24* (2013.01)

(56) References Cited

U.S. PATENT DOCUMENTS

| | | | | |
|---|---|---|---|---|
| 2005/0256030 | A1 * | 11/2005 | Feng .................... | C07D 277/46 530/329 |
| 2005/0276812 | A1 | 12/2005 | Ebens et al. | |
| 2007/0190597 | A1 * | 8/2007 | Agnew ................ | A61K 47/549 435/68.1 |
| 2009/0047248 | A1 | 2/2009 | Sun et al. | |
| 2010/0260709 | A1 | 10/2010 | Brandl et al. | |
| 2017/0029490 | A1 | 2/2017 | Winters et al. | |

FOREIGN PATENT DOCUMENTS

| | | | | | |
|---|---|---|---|---|---|
| WO | WO-01/88535 | A1 | | 11/2001 | |
| WO | WO-03/082842 | A1 | | 10/2003 | |
| WO | WO-2006/000085 | A1 | | 1/2006 | |
| WO | WO-2008/060927 | A2 | | 5/2008 | |
| WO | WO-2008/070291 | A2 | | 6/2008 | |
| WO | WO-2009/067108 | A1 | | 5/2009 | |
| WO | WO-2011/136645 | A1 | | 11/2011 | |
| WO | WO-2014/065661 | A1 | | 5/2014 | |
| WO | WO-2014/100762 | A1 | | 6/2014 | |
| WO | WO-2014/177771 | A1 | | 11/2014 | |
| WO | WO-2015/057063 | A1 | | 4/2015 | |
| WO | WO-2015/057064 | A1 | | 4/2015 | |
| WO | WO-2015/057065 | A1 | | 4/2015 | |
| WO | WO-2015/057066 | A1 | | 4/2015 | |
| WO | WO-2015/095952 | A1 | | 7/2015 | |
| WO | WO-2015095953 | A1 | * | 7/2015 | ............. A61P 35/02 |
| WO | WO-2016/022027 | A1 | | 4/2016 | |
| WO | WO-2016/053107 | A1 | | 4/2016 | |
| WO | WO-2016/170186 | A1 | | 10/2016 | |

OTHER PUBLICATIONS

U.S. Appl. No. 16/076,281, filed Aug. 7, 2018.
U.S. Appl. No. 16/076,279, filed Aug. 7, 2018.
U.S. Appl. No. 16/076,310, filed Aug. 7, 2018.
Babic, et al., “Synthesis of 1-C-linked diphosphate analogues of UDP-N-Ac-glucosamine and UDP-N-Ac-muramic acid”, Tetrahedron 64(38): 9093-9100 (2008).
Beeril, et al, “Sortase Enzyme-Mediated Generation of Site-Specifically Conjugated Antibody Drug Conjugates with High In Vitro and In Vivo Potency”, Public Library of Science 10(7): e013117-1 (2015).
Erickson, et al., “The Effect of Different Linkers on Target Cell Catabolism and Pharmacokinetics/Pharmacodynamics of Trastuzumab Maytansinoid Conjugages”, Molecular Cancer Therapeutics 11(5): 1133-1142 (2012).
International Search Report and Written Opinion, dated May 29, 2017, issued in International Application No. PCT/EP2017/052791.
International Search Report and Written Opinion, dated Jun. 27, 2017, issued in corresponding International Application No. PCT/EP2017/052790.
International Search Report and Written Opinion, dated May 12, 2017, issued in International Application No. PCT/EP2017/052788.
International Search Report and Written Opinion, dated Jun. 7, 2017, issued in International Application No. PCT/EP2017/052719.
Krueger, et al., “Inhibitors of HCV NS5B polymerase: Synthesis and structure-activity relationships of N-alkyl-4-hydroxyquinolon-3-yl-benzothiadi azine sulfamides”, Bioorganic & Medicinal Chemistry Letters 16(13): 3367-3370 (2006).
Lhospice, et al., “Site-Specific Conjugation of Monmethyl Auristatin E to Anti-CD30 Antibodies Improves Their Pharmacokinetics and Therapeutic Index in Roden Models”, Molecular Pharmaceutics 12(6): 1863-1871 (2015).
Li, et al., “An Anti-HER2 Antibody Conjugated with Monomethyl Auristatin E is Highly Effective in HER2-Positive Human Gastric Cancer”, Cancer Biology & Therapy 17(4): 346-354 (2016).
Melagraki, et al., “Identification of a series of novel derivatives as potent HCV inhibitors by a ligand-based virtual screening optimized procedure”, Bioorganic & Medicinal Chemistry 15(23): 7237-7247 (2007).
Murphy-Benenato, et al., “Discovery of Efficacious Pseudomonas aeruginosa-Targeted Siderophore-Conjugated Monocarbams by Application of a Semi-Mechanistic Pharmacokinetic/Pharmacodynamic Model”, Journal of Medicinal Chemistry 58(5): 2195-2205 (2015).
Phillips, et al., “Targeting HER2-Positive Breast Cancer with Trastuzumab-DM1, an Antibody-Cytotoxic Drug Conjugate”, Cancer Research 68(22): 9280-9290 (2008).
Pillow, et al., “Site-Specific Trastuzumab Maytansinoid Antibody—Drug Conjugates with Improved Therapeutic Activity through Linker and Antibody Engineering”, Journal of Medicinal Chemistry 57(19): 7890-7899 (2014).

(56) References Cited

OTHER PUBLICATIONS

Scott, et al., "Development and Properties of ß-Glucuronide Linkers for Monoclonal Antibody—Drug Conjugates", Bioconjugate Chemistry 17(3): 831-840 (2006).
Senter, et al., "Self-Hydrolyzing Maleimides Improve the Stability and Pharmacological Properties of Antibody-Drug Conjugates", Nature Biotechnology 32(10): 1059-1062 (2014).
Somu, et al., "Antitubercular Nucleosides that Inhibit Siderophore Biosynthesis: SAR of the Glycosyl Domain", Journal of Medicinal Chemistry 49(26): 7623-7635 (2006).
Van Geel, et al., "Chemoenzymatic Conjugation of Toxic Payloads to the Globally Conserved N-Glycan of Native mAbs Provides Homogeneous and Highly Efficacious Antibody—Drug Conjugates", Bioconjugate Chemistry 26(11): 2233-2242 (2015).
Yao, et al., "A Novel Humanized Anti-HER2 Antibody Conjugated with MMAE Exerts Potent Anti-Tumor Activity", Breast Cancer Research and Treatment 153(1): 123-133 (2015).
"Seattle Genetics' Antibody-Drug Conjugate Receives FDA Okay to Treat Lymphomas", Genetic Engineering & Biotechnology News, 2011 (3 pages).
Horwitz et al., "MDX-060 Monoclonal Antibody in Treating Patients With Refractory or Relapsed Lymphoma", US National Library of Medicine, 2003 (9 pages).

* cited by examiner

BOI = biomolecule of interest

D = MOI = molecule of interest (or target molecule)

$F_1$ = native or engineered functional group $Q_1$ = reactive group specific for $F_1$ n = 1,2,3...

11a $R^1$ = OH; $R^2$ = $(CH_2)_2SH$

11b $R^1$ = OH; $R^2$ = $CH_2N_3$

11c $R^1$ = OH; $R^2$ = $CF_2N_3$

11d $R^1$ = $N_3$; $R^2$ = $CH_3$

13a $a = 0,1$ 14

13b, c or d $a = 0,1$

15a K = $CH_2$ (2-GalNAc)
15b K = $CF_2$ (2-GalNAc)
16 K = absent (6-GalNAc)

17

| | $F^1$ | $Q^1$ | $Z^3$ | |
|---|---|---|---|---|
| natural |  |  |  | 10a |
| | |  |  | 10b |
| |  |  X = leaving group |  | 10c |
| engineered |  |  |  | 10a |
| |  |  Y = O or NH |  | 10d |
| |  |  |  | 10e |
| |  |  |  | 10f |
| | |  |  | 10g |
| |  |  Z = H, Me, pyridyl |  | 10h* |

*will eliminate $N_2$

81 R =

82 R =

83 R =

84 R =

85 R =

SEQUENCE LISTING

```
<160> NUMBER OF SEQ ID NOS: 2

<210> SEQ ID NO 1
<211> LENGTH: 1258
<212> TYPE: PRT
<213> ORGANISM: Artificial sequence
<220> FEATURE:
<223> OTHER INFORMATION: fusion protein EndoSH

<400> SEQUENCE: 1

Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
            20                  25                  30
```

-continued

```
Lys Glu Ile Leu Ala Lys Ala Gln Gln Ala Asp Lys Gln Ala Gln Glu
        35                  40                  45

Leu Ala Lys Met Lys Ile Pro Glu Lys Ile Pro Met Lys Pro Leu His
    50                  55                  60

Gly Pro Leu Tyr Gly Gly Tyr Phe Arg Thr Trp His Asp Lys Thr Ser
65                  70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
            100                 105                 110

Leu Phe Trp Lys Glu Leu Ala Thr Lys His Val Pro Lys Leu Asn Lys
        115                 120                 125

Gln Gly Thr Arg Val Ile Arg Thr Ile Pro Trp Arg Phe Leu Ala Gly
    130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
            180                 185                 190

Ile Pro Lys Val Asp Lys Lys Glu Asp Thr Ala Gly Val Glu Arg Ser
        195                 200                 205

Ile Gln Val Phe Glu Glu Ile Gly Lys Leu Ile Gly Pro Lys Gly Val
    210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255

Gln Val Tyr Gly Ser Gln Gly Glu Lys Gly Gly Trp Glu Pro Val Ser
            260                 265                 270

Asn Arg Pro Glu Lys Thr Met Glu Glu Arg Trp Gln Gly Tyr Ser Lys
        275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
        355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
        435                 440                 445

Leu Glu Gly Leu Asn Lys Phe Lys Lys Leu Ala Gln Leu Asp Leu Ile
```

```
    450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
        515                 520                 525

Arg Glu Thr Leu Ala Gly Leu Asp Ala Ala Thr Leu Thr Ser Leu Glu
    530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590

His Tyr Pro Asp Thr Tyr Gly Lys Thr Ser Leu Arg Leu Pro Val Ala
        595                 600                 605

Asn Glu Lys Val Asp Leu Gln Ser Gln Leu Leu Phe Gly Thr Val Thr
    610                 615                 620

Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
                645                 650                 655

Asn Asn Phe Lys Val Ser Tyr Glu Asn Tyr Thr Val Lys Val Thr Asp
            660                 665                 670

Ser Thr Leu Gly Thr Thr Thr Asp Lys Thr Leu Ala Thr Asp Lys Glu
        675                 680                 685

Glu Thr Tyr Lys Val Asp Phe Phe Ser Pro Ala Asp Lys Thr Lys Ala
    690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
            740                 745                 750

Ile Ser Leu Gly Trp Asp Ser Lys Gln Ser Ile Ile Phe Lys Leu Lys
        755                 760                 765

Glu Asp Gly Leu Ile Lys His Trp Arg Phe Phe Asn Asp Ser Ala Arg
    770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
            820                 825                 830

Gln Gly Glu Arg Ala Thr Ala Phe Ser Asn Thr Leu Asn Asn Ile Thr
        835                 840                 845

Ser Lys Tyr Trp Arg Val Val Phe Asp Thr Lys Gly Asp Arg Tyr Ser
    850                 855                 860

Ser Pro Val Val Pro Glu Leu Gln Ile Leu Gly Tyr Pro Leu Pro Asn
865                 870                 875                 880
```

```
Ala Asp Thr Ile Met Lys Thr Val Thr Thr Ala Lys Glu Leu Ser Gln
                885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
        915                 920                 925

Ala Ile Asn Ala Asn Ala Gly Val Leu Lys Asp Cys Ile Glu Lys Arg
    930                 935                 940

Gln Leu Leu Lys Lys Gly Gly Gly Gly Ser Gly Gly Gly Gly Ser Gly
945                 950                 955                 960

Gly Gly Gly Ser His His His His His His Glu Phe Gly Gly Gly Gly
                965                 970                 975

Ser Gly Gly Gly Gly Ser Gly Gly Gly Gly Ser Ala Pro Ala Pro Val
            980                 985                 990

Lys Gln Gly Pro Thr Ser Val Ala  Tyr Val Glu Val Asn  Asn Asn Ser
        995                 1000                1005

Met Leu  Asn Val Gly Lys Tyr  Thr Leu Ala Asp Gly  Gly Gly Asn
    1010                1015                1020

Ala Phe  Asp Val Ala Val Ile  Phe Ala Ala Asn Ile  Asn Tyr Asp
    1025                1030                1035

Thr Gly  Thr Lys Thr Ala Tyr  Leu His Phe Asn Glu  Asn Val Gln
    1040                1045                1050

Arg Val  Leu Asp Asn Ala Val  Thr Gln Ile Arg Pro  Leu Gln Gln
    1055                1060                1065

Gln Gly  Ile Lys Val Leu Leu  Ser Val Leu Gly Asn  His Gln Gly
    1070                1075                1080

Ala Gly  Phe Ala Asn Phe Pro  Ser Gln Gln Ala Ala  Ser Ala Phe
    1085                1090                1095

Ala Lys  Gln Leu Ser Asp Ala  Val Ala Lys Tyr Gly  Leu Asp Gly
    1100                1105                1110

Val Asp  Phe Asp Asp Glu Tyr  Ala Glu Tyr Gly Asn  Asn Gly Thr
    1115                1120                1125

Ala Gln  Pro Asn Asp Ser Ser  Phe Val His Leu Val  Thr Ala Leu
    1130                1135                1140

Arg Ala  Asn Met Pro Asp Lys  Ile Ile Ser Leu Tyr  Asn Ile Gly
    1145                1150                1155

Pro Ala  Ala Ser Arg Leu Ser  Tyr Gly Gly Val Asp  Val Ser Asp
    1160                1165                1170

Lys Phe  Asp Tyr Ala Trp Asn  Pro Tyr Tyr Gly Thr  Trp Gln Val
    1175                1180                1185

Pro Gly  Ile Ala Leu Pro Lys  Ala Gln Leu Ser Pro  Ala Ala Val
    1190                1195                1200

Glu Ile  Gly Arg Thr Ser Arg  Ser Thr Val Ala Asp  Leu Ala Arg
    1205                1210                1215

Arg Thr  Val Asp Glu Gly Tyr  Gly Val Tyr Leu Thr  Tyr Asn Leu
    1220                1225                1230

Asp Gly  Gly Asp Arg Thr Ala  Asp Val Ser Ala Phe  Thr Arg Glu
    1235                1240                1245

Leu Tyr  Gly Ser Glu Ala Val  Arg Thr Pro
    1250                1255
```

<210> SEQ ID NO 2
<211> LENGTH: 410

-continued

<212> TYPE: PRT
<213> ORGANISM: Artificial sequence
<220> FEATURE:
<223> OTHER INFORMATION: His-TnGalNAcT(33-421)

<400> SEQUENCE: 2

```
Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Ile Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly Trp Gly Gly Glu Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380
```

-continued

```
Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410
```

ANTIBODY-CONJUGATES WITH IMPROVED THERAPEUTIC INDEX FOR TARGETING HER2 TUMOURS AND METHOD FOR IMPROVING THERAPEUTIC INDEX OF ANTIBODY-CONJUGATES

CROSS-REFERENCE TO RELATED APPLICATIONS

This application is the National Phase of International Patent Application No. PCT/EP2017/052790, filed Feb. 8, 2017, published on Aug. 17, 2017 as WO 2017/137457 A1, which claims priority to European Patent Application No. 16154712.0, filed Feb. 8, 2016, European Patent Application No. 16154739.3, filed Feb. 8, 2016, European Patent Application No. 16173595.6, filed Jun. 8, 2016, and Japanese Patent Application No. 2016-155929, filed Aug. 8, 2016. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Aug. 7, 2018, is named 069818-4020_2018-08-07_Sequence_Listing.txt and is 16 KB.

FIELD OF THE INVENTION

The present invention is in the field of bioconjugation. More specifically, the invention relates to a specific mode of conjugation to prepare bioconjugates that have a beneficial effect on the therapeutic index of the bioconjugate, in particular in the targeting of HER2-expressing tumours.

BACKGROUND OF THE INVENTION

Bioconjugation is the process of linking two or more molecules, of which at least one is a biomolecule. The biomolecule(s) may also be referred to as "biomolecule(s) of interest", the other molecule(s) may also be referred to as "target molecule" or "molecule of interest". Typically the biomolecule of interest (BOI) will consist of a protein (or peptide), a glycan, a nucleic acid (or oligonucleotide), a lipid, a hormone or a natural drug (or fragments or combinations thereof). The other molecule of interest (MOI) may also be a biomolecule, hence leading to the formation of homo- or heterodimers (or higher oligomers), or the other molecule may possess specific features that are imparted onto the biomolecule of interest by the conjugation process. For example, the modulation of protein structure and function by covalent modification with a chemical probe for detection and/or isolation has evolved as a powerful tool in proteome-based research and biomedical applications. Fluorescent or affinity tagging of proteins is key to studying the trafficking of proteins in their native habitat. Vaccines based on protein-carbohydrate conjugates have gained prominence in the fight against HIV, cancer, malaria and pathogenic bacteria, whereas carbohydrates immobilized on microarrays are instrumental in elucidation of the glycome. Synthetic DNA and RNA oligonucleotides (ONs) require the introduction of a suitable functionality for diagnostic and therapeutic applications, such as microarray technology, antisense and gene-silencing therapies, nanotechnology and various materials sciences applications. For example, attachment of a cell-penetrating ligand is the most commonly applied strategy to tackle the low internalization rate of ONs encountered during oligonucleotide-based therapeutics (antisense, siRNA). Similarly, the preparation of oligonucleotide-based microarrays requires the selective immobilization of ONs on a suitable solid surface, e.g. glass.

There are numerous examples of chemical reactions suitable to covalently link two (or more) molecular structures. However, labelling of biomolecules poses high restrictions on the reaction conditions that can be applied (solvent, concentration, temperature), while the desire of chemoselective labelling limits the choice of reactive groups. For obvious reasons, biological systems generally flourish best in an aqueous environment meaning that reagents for bioconjugation should be suitable for application in aqueous systems. In general, two strategic concepts can be recognized in the field of bioconjugation technology: (a) conjugation based on a functional group already present in the biomolecule of interest, such as for example a thiol, an amine, an alcohol or a hydroxyphenol unit or (b) a two-stage process involving engineering of one (or more) unique reactive groups into a BOI prior to the actual conjugation process.

The first approach typically involves a reactive amino acid side-chain in a protein (e.g. cysteine, lysine, serine and tyrosine), or a functional group in a glycan (e.g. amine, aldehyde) or nucleic acid (e.g. purine or pyrimidine functionality or alcohol). As summarized inter alia in G. T. Hermanson, "*Bioconjugate Techniques*", Elsevier, 3$^{rd}$ Ed. 2013, incorporated by reference, a large number of reactive functional groups have become available over the years for chemoselective targeting of one of these functional groups, such as maleimide, haloacetamide, activated ester, activated carbonate, sulfonyl halide, activated thiol derivative, alkene, alkyne, allenamide and more, each of which requiring its own specific conditions for conjugation (pH, concentration, stoichiometry, light, etc.). Most prominently, cysteine-maleimide conjugation stands out for protein conjugation by virtue of its high reaction rate and chemoselectivity. However, when no cysteine is available for conjugation, as in many proteins and certainly in other biomolecules, other methods are often required, each suffering from its own shortcomings.

An elegant and broadly applicable solution for bioconjugation involves the two-stage approach. Although more laborious, two-stage conjugation via engineered functionality typically leads to higher selectivity (site-specificity) than conjugation on a natural functionality. Besides that, full stability can be achieved by proper choice of construct, which can be an important shortcoming of one stage conjugation on native functionality, in particular for cysteine-maleimide conjugation. Typical examples of a functional group that may be imparted onto the BOI include (strained) alkyne, (strained) alkene, norbornene, tetrazine, azide, phosphine, nitrile oxide, nitrone, nitrile imine, diazo compound, carbonyl compound, (O-alkyl)hydroxylamine and hydrazine, which may be achieved by either chemical or molecular biology approach. Each of the above functional groups is known to have at least one reaction partner, in many cases involving complete mutual reactivity. For example, cyclooctynes react selectively and exclusively with 1,3-dipoles, strained alkenes with tetrazines and phosphines with azides, leading to fully stable covalent bonds. However, some of the above functional groups have the disadvantage of being highly lipophilic, which may compromise conjugation efficiency, in particular in combination with a lipophilic molecule of interest (see below).

The final linking unit between the biomolecule and the other molecule of interest should preferentially also be fully compatible with an aqueous environment in terms of solubility, stability and biocompatibility. For example, a highly lipophilic linker may lead to aggregation (during and/or after conjugation), which may significantly increase reaction times and/or reduce conjugation yields, in particular when the MOI is also of hydrophobic nature. Similarly, highly lipophilic linker-MOI combination may lead to unspecific binding to surfaces or specific hydrophobic patches on the same or other biomolecules. If the linker is susceptible to aqueous hydrolysis or other water-induced cleavage reactions, the components comprising the original bioconjugate separate by diffusion. For example, certain ester moieties are not suitable due to saponification while 3-hydroxycarbonyl or γ-dicarbonyl compounds could lead to retro-aldol or retro-Michael reaction, respectively. Finally, the linker should be inert to functionalities present in the bioconjugate or any other functionality that may be encountered during application of the bioconjugate, which excludes, amongst others, the use of linkers featuring for example a ketone or aldehyde moiety (may lead to imine formation), an α,β-unsaturated carbonyl compound (Michael addition), thioesters or other activated esters (amide bond formation).

Compounds made of linear oligomers of ethylene glycol, so-called polyethylene glycol (PEG) linkers, enjoy particular popularity nowadays in biomolecular conjugation processes. PEG linkers are highly water soluble, non-toxic, non-antigenic, and lead to negligible or no aggregation. For this reason, a large variety of linear, bifunctional PEG linkers are commercially available from various sources, which can be selectively modified at either end with a (bio)molecule of interest. PEG linkers are the product of a polymerization process of ethylene oxide and are therefore typically obtained as stochastic mixtures of chain length, which can be partly resolved into PEG constructs with an average weight distribution centred around 1, 2, 4 kDa or more (up to 60 kDa). Homogeneous, discrete PEGs (dPEGs) are also known with molecular weights up to 4 kDa and branched versions thereof go up to 15 kDa. Interestingly, the PEG unit itself imparts particular characteristics onto a biomolecule. In particular, protein PEGylation may lead to prolonged residence in vivo, decreased degradation by metabolic enzymes and a reduction or elimination of protein immunogenicity. Several PEGylated proteins have been FDA-approved and are currently on the market.

By virtue of its high polarity, PEG linkers are perfectly suitable for bioconjugation of small and/or water-soluble moieties under aqueous conditions. However, in case of conjugation of hydrophobic, non-water-soluble molecules of interest, the polarity of a PEG unit may be insufficient to offset hydrophobicity, leading to significantly reduced reaction rates, lower yields and induced aggregation issues. In such case, lengthy PEG linkers and/or significant amounts of organic co-solvents may be required to solubilize the reagents. For example, in the field of antibody-drug conjugates, the controlled attachment of a distinct number of toxic payloads to a monoclonal antibody is key, with a payload typically selected from the group of auristatins E or F, maytansinoids, duocarmycins, calicheamicins or pyrrolobenzodiazepines (PBDs), with many others are underway. With the exception of auristatin F, all toxic payloads are poorly to non-water-soluble, which necessitates organic co-solvents to achieve successful conjugation, such as 25% dimethylacetamide (DMA) or 50% propylene glycol (PG). In case of hydrophobic payloads, despite the use of aforementioned co-solvents, large stoichiometries of reagents may be required during conjugation while efficiency and yield may be significantly compromised due to aggregation (in process or after product isolation), as for example described by Senter et al. in *Nat. Biotechn.* 2014, 24, 1256-1263, incorporated by reference. The use of long PEG spacers (12 units or more) may partially enhance solubility and/or conjugation efficiency, but it has been shown that long PEG spacers may lead to more rapid in vivo clearance, and hence negatively influence the pharmacokinetic profile of the ADC.

Using conventional linkers (e.g. PEG), effective conjugation is often hampered by the relatively low solubility of the linker-conjugate in aqueous media, especially when a relative water-insoluble or hydrophobic target molecule is used. In their quest for a short, polar spacer that enables fast and efficient conjugation of hydrophobic moieties, the inventors have developed the sulfamide linker, which was found to improve the solubility of the linker-conjugate, which in turn significantly improves the efficiency of the conjugation and reduces both in process and product aggregation. This is disclosed in patent application PCT/NL2015/050697 (WO 2016/053107), which is incorporated herein in its entirety.

Linkers are known in the art, and disclosed in e.g. WO 2008/070291, incorporated by reference. WO 2008/070291 discloses a linker for the coupling of targeting agents to anchoring components. The linker contains hydrophilic regions represented by polyethylene glycol (PEG) and an extension lacking chiral centers that is coupled to a targeting agent.

WO 01/88535, incorporated by reference, discloses a linker system for surfaces for bioconjugation, in particular a linker system having a novel hydrophilic spacer group. The hydrophilic atoms or groups for use in the linker system are selected from the group consisting of O, NH, C=O (keto group), O—C=O (ester group) and $CR^3R^4$, wherein $R^3$ and $R^4$ are independently selected from the group consisting of H, OH, $C_1$-$C_4$ alkoxy and $C_1$-$C_4$ acyloxy.

WO 2014/100762, incorporated by reference, describes compounds with a hydrophilic self-immolative linker, which is cleavable under appropriate conditions and incorporates a hydrophilic group to provide better solubility of the compound. The compounds comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker. The hydrophilic self-immolative linker is e.g. a benzyloxycarbonyl group.

SUMMARY OF THE INVENTION

The invention relates to a method or use for increasing the therapeutic index of a bioconjugate, i.e. the conjugate of a biomolecule and a target molecule. The inventors surprisingly found that a bioconjugate prepared via a specific mode of conjugation exhibits a greater therapeutic index compared to the same bioconjugate, i.e. the same biomolecule, the same target molecule (e.g. active substance) and the same biomolecule drug ratio, obtained via a different mode of conjugation. The mode of conjugating a biomolecule to a target molecule is exposed in the linker itself and/or in the attachment point of the linker to the biomolecule. That the linker and/or attachment point could have an effect on the therapeutic index of a bioconjugate, such as an antibody-drug-conjugate, could not be envisioned based on the current knowledge. In the field, linkers are considered inert when it comes to treatment and are solely present as a consequence of the preparation of the bioconjugate. That the selection of a specific mode of conjugation has an effect on the therapeutic index is unprecedented and a breakthrough discovery in the field of bioconjugates, in particular antibody-drug-conjugates.

The bioconjugates according to the invention are on one hand more efficacious (therapeutically effective) as the same bioconjugates, i.e. the same biomolecule, the same target molecule (e.g. active substance) and the same biomolecule/target molecule ratio, obtained via a different mode of conjugation, and/or on the other hand exhibit a greater tolerability. This finding has dramatic implications on the treatment of subjects with the bioconjugate according to the invention, as the therapeutic window widens. As a result of the expansion of the therapeutic window, the treatment dosages may be lowered and as a consequence potential, unwanted, side-effects are reduced.

In one embodiment, the mode of conjugation according to the invention comprises:

(i) contacting a glycoprotein comprising 1-4 core N-acetylglucosamine substituents with a compound of the formula $S(F^1)_x$-P in the presence of a catalyst, wherein $S(F^1)_x$ is a sugar derivative comprising x functional groups $F^1$ capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety, to obtain a modified antibody according to Formula (24):

(24)

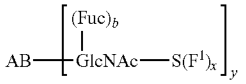

wherein $S(F^1)_x$ and x are as defined above; AB represents an antibody; GlcNAc is N-acetylglucosamine; Fuc is fucose; b is 0 or 1; and y is 1, 2, 3 or 4; and (ii) reacting the modified antibody with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$.

In one embodiment, the mode of conjugation according to the invention ensure that the bioconjugate contains a linker L comprising a group according to formula (1) or a salt thereof:

1

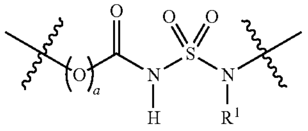

The inventors surprisingly found that a bioconjugate prepared such that it contains a linker L comprising a group according to formula (1) or a salt thereof exhibits a greater therapeutic index compared to the same bioconjugate, i.e. the same biomolecule, the same target molecule (e.g. active substance) and the same biomolecule drug ratio, containing a linker without the group according to formula (1) present.

In group according to formula (1), a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein D is optionally connected to N via a spacer moiety.

In the context of the present invention, the mode of conjugation is being used to connect an biomolecule B with a target molecule D via a linker L. Conjugation refers to the specific mode of connecting the biomolecule to the target molecule. The bioconjugate according to the invention is represented by formula (A):

B-L-D (A), wherein:

B is a biomolecule;

L is a linker linking B and D;

D is a target molecule; and each occurrence of "-" is independently a bond or a spacer moiety.

For the embodiment wherein the mode of conjugation is referred to as "sulfamide linkage", the following embodiments are preferred:

1. Method for increasing the therapeutic index of a bioconjugate, comprising the step of preparing the bioconjugate of formula (A):

B-L-D (A), wherein:

B is a biomolecule;

L is a linker linking B and D;

D is a target molecule; and each occurrence of "-" is independently a bond or a spacer moiety, by reacting a reactive group $Q^1$ on a target molecule (D) with a functional group $F^1$ on a biomolecule (B), such that L comprises a group according to formula (1) or a salt thereof:

1

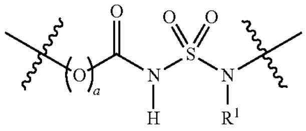

wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S or $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety.

2. The method according to embodiment 1, further comprising a step of administering the bioconjugate to a subject in need thereof.
3. The method according to embodiment 2, wherein the subject is a cancer patient.
4. The method according to any of the preceding embodiments, wherein the biomolecule is an antibody and the bioconjugate is an antibody-drug-conjugate.
5. The method according to any of the preceding embodiments, wherein target molecule D is an active substance, preferably a cytotoxin.
6. The method according to any of the preceding embodiments, wherein the bioconjugate has the formula B-$Z^3$-L-D, wherein $Z^3$ is obtained by the reacting reactive group $Q^1$ with the functional group F.
7. The method according to embodiment 6, wherein $Z^3$ is obtained by the reacting a linker-conjugate having formula $Q^1$-L-D, wherein L comprises a group according to formula (1) or a salt thereof:

1

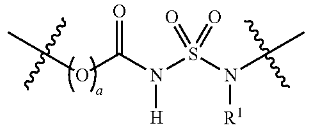

with a biomolecule having formula B-$F^1$, wherein B, D, a and $R^1$ are as defined in embodiment 1.

8. The process according to embodiment 7, wherein the linker-conjugate is according to formula (4a) or (4b), or a salt thereof:

4a

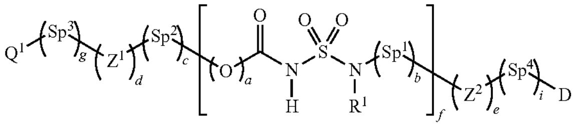

4b

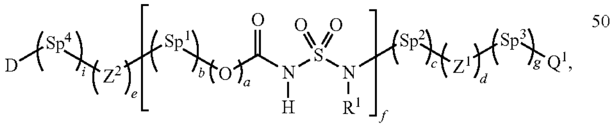

wherein:

a is independently 0 or 1;
b is independently 0 or 1;
c is 0 or 1;
d is 0 r 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or N(R');
$Z^2$ is a connecting group that connects D or $Sp^4$ to $Sp^1$, $N(R^1)$, O or C(O); and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, $-[(Sp^1)_b(Z^2)_e(Sp^4)_iD]$ or $-[(Sp^2)_c(Z^1)_d(Sp^3)_g Q^1]$, wherein D is a target molecule and $Sp^1$, $Sp^2$, $Sp^3$, $Sp^4$, $Z^1$, $Z^2$, D, $Q^1$, b, c, d, e, g and i are as defined above.

9. Process according to embodiment 8, wherein $Sp^1$, $Sp^2$, $Sp^3$ and $Sp^4$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.
10. Process according to embodiment 8 or 9, wherein $Z^1$ and $Z^2$ are independently selected from the group consisting —O—, —S—, —$NR^2$—, —N═N—, —C(O)—, —C(O)$NR^2$—, —OC(O)—, —OC(O)O—, —OC(O)$NR^2$, —$NR_2$C(O)—, —$NR^2$C(O)O—, —$NR^2$C(O)$NR^2$—, —SC(O)—, —SC(O)O—, —SC(O)$NR^2$—, —S(O), —$S(O)_2$—, —$OS(O)_2$—, —$OS(O)_2$O—, —$OS(O)_2$$NR^2$—, —OS(O)—, —OS(O)O—, —OS(O)$NR^2$—, —$ONR^2$C(O)—, —$ONR^2$C(O)O—, —$ONR^2$C(O)$NR^2$—, —$NR^2$OC(O)—, —$NR^2$OC(O)O—, —$NR^2$OC(O)$NR^2$—, —$ONR^2$C(S)—, —$ONR^2$C(S)O—, —$ONR^2$C(S)$NR^2$—, —$NR^2$OC(S)—, —$NR^2$OC(S)O—, —$NR^2$OC(S)$NR^2$—, —OC(S)—, —OC(S)O—, —OC(S)$NR^2$—, —$NR^2$C(S)—, —$NR^2$C(S)O—, —$NR^2$C(S)$NR^2$—, —$SS(O)_2$—, —$SS(O)_2$O—, —$SS(O)_2$$NR^2$—, —$NR_2$OS(O)—, —$NR_2$OS(O)O—, —$NR_2$OS(O)$NR^2$—, —$NR_2$$OS(O)_2$—, —$NR_2$$OS(O)_2$O—, —$NR_2$$OS(O)_2$$NR^2$—, —$ONR^2$S(O)—, —$ONR^2$S(O)O—, —$ONR^2$S(O)$NR^2$—, —$ONR^2$$S(O)_2$O—, —$ONR^2$$S(O)_2$$NR^2$—, —$ONR^2$$S(O)_2$—, —OP(O)$(R^2)_2$—, —SP(O)$(R^2)_2$—, —$NR^2$P(O)$(R^2)_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

11. Process according to any one of embodiments 8-10, wherein $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S or $NR^3$, wherein $R^3$ is independently selected from the group consisting of hydrogen and $C_1$-$C_4$ alkyl groups, and wherein $Q^1$ is according to formula (9a), (9q), (9n), (9o) or (9p), (9t) or (9zh):

9a

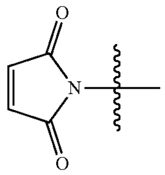

9q

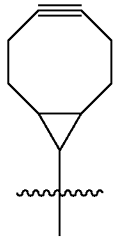

9n

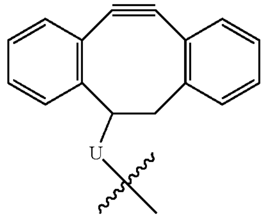

9o

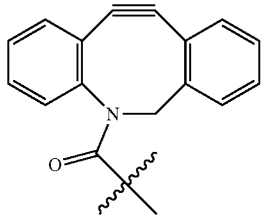

9p

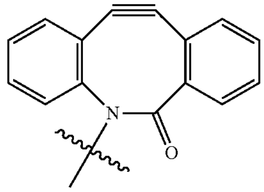

-continued

9t

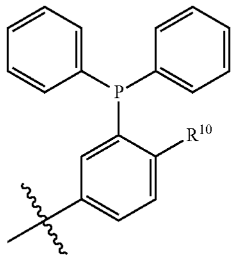

9zh

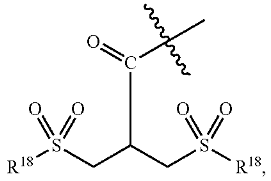

wherein:

U is O or $NR^9$, and $R^9$ is hydrogen, a linear or branched $C_1$-$C_{12}$ alkyl group or a $C_4$-$C_{12}$ (hetero)aryl group.

$R^{10}$ is a (thio)ester group; and $R^{18}$ is selected from the group consisting of, optionally substituted, $C_1$-$C_{12}$ alkyl groups and $C_4$-$C_{12}$ (hetero) aryl groups.

12. The method according to any of the preceding embodiments, wherein the reaction between reactive group $Q^1$ and functional group $F^1$ is a conjugation reaction selected from thiol-alkene conjugation to from a connecting moiety $Z^3$ that may be represented as (10a) or (10b), amino-(activated) carboxylic acid conjugation to from a connecting moiety $Z^3$ that may be represented as (10c), ketone-hydrazino conjugation to from a connecting moiety $Z^3$ that may be represented as (10d) wherein Y=NH, ketone-oxyamino conjugation to from a connecting moiety $Z^3$ that may be represented as (10d) wherein Y=O, alkyne-azide conjugation to from a connecting moiety $Z^3$ that may be represented as (10e) or (10g) and alkene-1,2,4,5-tetrazine conjugation or alkyne-1,2,4,5-tetrazine conjugation to from a connecting moiety $Z^3$ that may be represented as (10h) from which $N_2$ eliminates, wherein moieties (10a), (10b), (10c), (10d), (10e), (10g) and (10h) are represented by:

10a

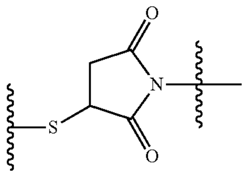

10b

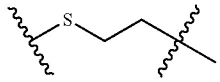

10c

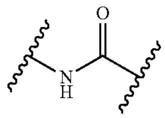

-continued

10d

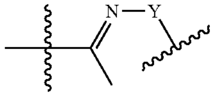

10e

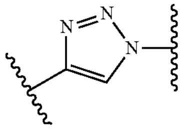

10g

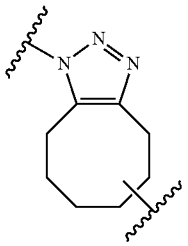

10h

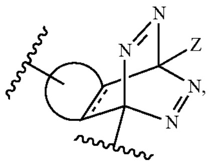

wherein Z is selected from hydrogen, methyl and pyridyl.

13. The method according to any of the preceding embodiments, wherein a=0.

14. Bioconjugate for use in the treatment of a subject in need thereof, wherein the bioconjugate is represented by formula (A):

B-L-D (A), wherein:

B is a biomolecule;

L is a linker linking B and D;

D is a target molecule; and each occurrence of "-" is independently a bond or a spacer moiety, wherein L comprises a group according to formula (1) or a salt thereof:

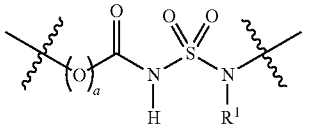

1 wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety.

15. Bioconjugate for use according to embodiment 14, for use in the treatment of cancer.

The present invention thus concerns in a first aspect a method or use for increasing the therapeutic index of a bioconjugate, wherein the mode of conjugation according to the invention is comprised in or used to prepare the bioconjugate. In one embodiment, the mode of conjugation comprises steps (i) and (ii) as defined herein. In an alternative embodiment, the mode of conjugation comprises the step of preparing the bioconjugate of formula (A) such that linker L as defined above is comprised in the bioconjugate. In one embodiment, the method or use according to the invention further comprises administering the bioconjugate to a subject in need thereof. The invention according to the first aspect can also be worded as the use of the mode of conjugation as defined above in a bioconjugate for increasing the therapeutic index of the bioconjugate, or to the use of linker L as defined above in a bioconjugate for increasing the therapeutic index of the bioconjugate.

In a further aspect, the present invention concerns the treatment of a subject in need thereof, comprising the administration of the bioconjugate according to the invention. Typically, the bioconjugate is administered in a therapeutically effective dose. In view of the increased therapeutic efficacy, administration may occur less frequent as in treatment with conventional bioconjugates and/or in a lower dose. Alternatively, in view of the increased tolerability, administration may occur more frequent as in treatment with conventional bioconjugates and/or in a higher dose. Administration may be in a single dose or may e.g. occur 1-4 times a month, preferably 1-2 times a month, more preferable administration occurs once every 3 or 4 weeks, most preferably every 4 weeks. As will be appreciated by the person skilled in the art, the dose of the bioconjugate according to the invention may depend on many factors and optimal doses can be determined by the skilled person via routine experimentation. The bioconjugate is typically administered in a dose of 0.01-50 mg/kg body weight of the subject, more accurately 0.03-25 mg/kg or most accurately 0.05-10 mg/kg, or alternatively 0.1-25 mg/kg or 0.5-10 mg/kg.

In one embodiment, the administration of the bioconjugate according to the invention is at a dose that is lower than the $TD_{50}$ of the same bioconjugate but not comprising the mode of conjugation according to the invention, preferably the dose is at most 99-90%, more preferably at most 89-60%, even more preferable 59-30%, most preferably at most 29-10% of the $TD_{50}$ of the same bioconjugate but not comprising the mode of conjugation according to the invention. Alternatively, the administration of the bioconjugate according to the invention is at a dose that is higher than the $TD_{50}$ of the same bioconjugate but not comprising the mode of conjugation according to the invention, preferably the dose is at most 10-29%, more preferably at most 30-59%, even more preferable 60-89%, most preferably at most 90-99% of the $TD_{50}$ of the same bioconjugate but not comprising the mode of conjugation according to the invention.

In one embodiment, the administration of the bioconjugate according to the invention is at a dose that is lower than the $ED_{50}$ of the same bioconjugate but not comprising the mode of conjugation according to the invention, preferably the dose is at most 99-90%, more preferably at most 89-60%, even more preferable 59-30%, most preferably at most 29-10% of the $ED_{50}$ of the same bioconjugate but not comprising the mode of conjugation according to the invention. Alternatively, the administration of the bioconjugate according to the invention is at a dose that is higher than the $TD_{50}$ of the same bioconjugate but not comprising the mode of conjugation according to the invention, preferably the dose is at most a factor 1.1-1.49 higher, more preferably at most a factor 1.5-1.99 higher, even more preferable a factor 2-4.99 higher, most preferably at most a factor 5-10 higher of the $TD_{50}$ of the same bioconjugate but not comprising the mode of conjugation according to the invention.

The preparation of the bioconjugate typically comprises the step of reacting linker-conjugate having the formula $Q^1$-L-D, wherein L and D are as defined above and $Q^1$ is a reactive group capable of reacting with a functional group F, with a biomolecule having the formula B-$F^1$, wherein B is as defined above and $F^1$ is a functional group capable of reacting with $Q^1$. Herein, $Q^1$ and $F^1$ react to form a connecting group $Z^3$, which is located in the bioconjugate according to formula (A) in the spacer moiety between B and L.

DESCRIPTION OF EMBODIMENTS

Figure 1:
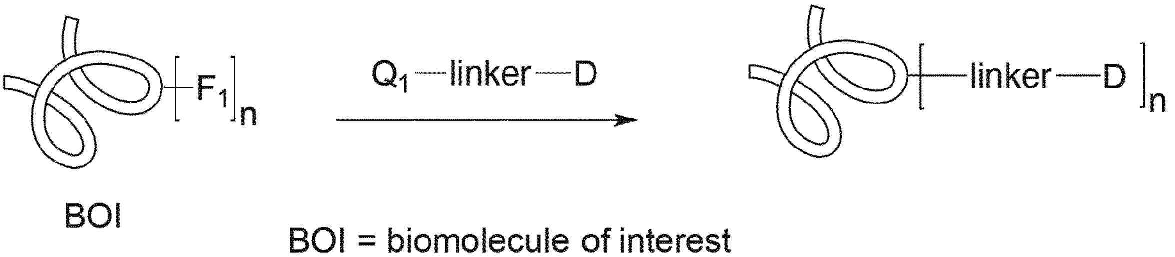
FIG. 1 describes the general concept of conjugation of biomolecules: a biomolecule of interest (BOI) containing one or more functional groups $F^1$ is incubated with (excess of) a target molecule D (also referred to as molecule of interest or MOI) covalently attached to a reactive group $Q^1$ via a specific linker. In the process of bioconjugation, a chemical reaction between $F^1$ and $Q^1$ takes place, thereby forming a bioconjugate comprising a covalent connection between the BOI and the MOI. The BOI may e.g. be a peptide/protein, a glycan or a nucleic acid.
Figure 1:
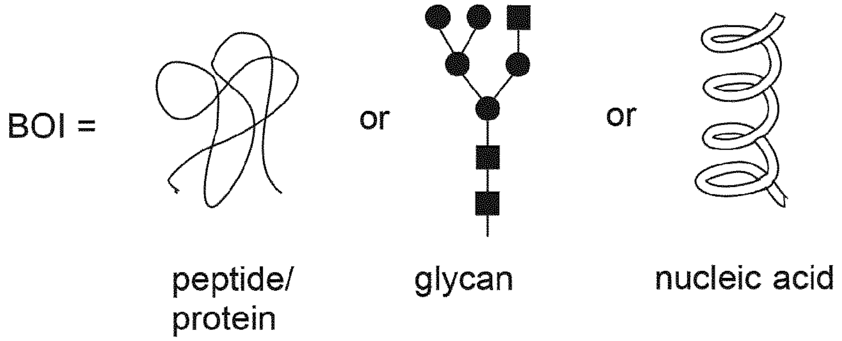

In the context of the present invention, the conjugation reaction involves on the one hand the biomolecule (BOI) containing a functional group $F^1$, and on the other hand the target molecule (MOI) containing a reactive group $Q^1$, or a "linker-conjugate" as defined herein, wherein $Q^1$ reacts with $F^1$ to form a connecting group that joins the BOI and the MOI in a bioconjugate. Herein, reactive group $Q^1$ is joined via a linker to the MOI, said linker comprising the sulfamide moiety according to formula (1):

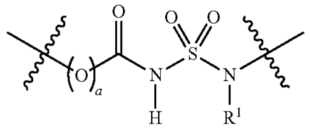

1

Reactive group $Q^1$ may be attached to either ends of the moiety of formula (1), in which case the MOI is attached to the opposite end of the moiety of formula (1). In one embodiment, reactive group $Q^1$ is attached to the moiety of formula (1) via the carbonyl end and the MOI is attached via the sulfamide end of the moiety of formula (1). In one embodiment, reactive group $Q^1$ is attached to the moiety of formula (1) via the sulfamide end and the MOI is attached via the carbonyl end of the moiety of formula (1).

Definitions

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the elements is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

Unsubstituted alkyl groups have the general formula $C_nH_{2n+1}$ and may be linear or branched.

Optionally, the alkyl groups are substituted by one or more substituents further specified in this document. Examples of alkyl groups include methyl, ethyl, propyl, 2-propyl, t-butyl, 1-hexyl, 1-dodecyl, etc.

A cycloalkyl group is a cyclic alkyl group. Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl and cyclohexyl.

An alkenyl group comprises one or more carbon-carbon double bonds, and may be linear or branched. Unsubstituted alkenyl groups comprising one C—C double bond have the general formula $C_nH_{2n-1}$. Unsubstituted alkenyl groups comprising two C—C double bonds have the general formula $C_nH_{2n-3}$. An alkenyl group may comprise a terminal carbon-carbon double bond and/or an internal carbon-carbon double bond. A terminal alkenyl group is an alkenyl group wherein a carbon-carbon double bond is located at a terminal position of a carbon chain. An alkenyl group may also comprise two or more carbon-carbon double bonds. Examples of an alkenyl group include ethenyl, propenyl, isopropenyl, t-butenyl, 1,3-butadienyl, 1,3-pentadienyl, etc. Unless stated otherwise, an alkenyl group may optionally be substituted with one or more, independently selected, substituents as defined below. Unless stated otherwise, an alkenyl group may optionally be interrupted by one or more heteroatoms independently selected from the group consisting of O, N and S.

An alkynyl group comprises one or more carbon-carbon triple bonds, and may be linear or branched. Unsubstituted alkynyl groups comprising one C—C triple bond have the general formula $C_nH_{2n-3}$. An alkynyl group may comprise a terminal carbon-carbon triple bond and/or an internal carbon-carbon triple bond. A terminal alkynyl group is an alkynyl group wherein a carbon-carbon triple bond is located at a terminal position of a carbon chain. An alkynyl group may also comprise two or more carbon-carbon triple bonds. Unless stated otherwise, an alkynyl group may optionally be substituted with one or more, independently selected, substituents as defined below. Examples of an alkynyl group include ethynyl, propynyl, isopropynyl, t-butynyl, etc. Unless stated otherwise, an alkynyl group may optionally be interrupted by one or more heteroatoms independently selected from the group consisting of O, N and S.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero) arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero) cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) or an arene (e.g. benzene) may be annulated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

Unless stated otherwise, alkyl groups, cycloalkyl groups, alkenyl groups, alkynyl groups, (hetero)aryl groups, (hetero) arylalkyl groups, alkyl(hetero)aryl groups, alkylene groups, alkenylene groups, alkynylene groups, cycloalkylene groups, cycloalkenylene groups, cycloalkynylene groups, (hetero)arylene groups, alkyl(hetero)arylene groups, (hetero)arylalkylene groups, (hetero)arylalkenylene groups, (hetero)arylalkynylene groups, alkenyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^{20})_3Si$—, wherein $R^{20}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA). Examples of a sugar derivative also include compounds herein denoted as $S(F^1)_x$, wherein S is a sugar or a sugar derivative, and wherein S comprises x functional groups $F^1$.

A core N-acetylglucosamine substituent (core-GlcNAc substituent) or core N-acetylglucosamine moiety is herein defined as a GlcNAc that is bonded via $C_1$ to an antibody, preferably via an N-glycosidic bond to the amide nitrogen atom in the side chain of an asparagine amino acid of the antibody. The core-GlcNAc substituent may be present at a native glycosylation site of an antibody, but it may also be introduced on a different site on the antibody. Herein, a core-N-acetylglucosamine substituent is a monosaccharide substituent, or if said core-GlcNAc substituent is fucosylated, a disaccharide core-GlcNAc-(α1-6-Fuc) substituent, further referred to as GlcNAc(Fuc). Herein, a "core-GlcNAc substituent" is not to be confused with a "core-GlcNAc". A core-GlcNAc is herein defined as the inner GlcNAc that is part of a poly- or an oligosaccharide comprising more than two saccharides, i.e. the GlcNAc via which the poly- or oligosaccharide is bonded to an antibody.

An antibody comprising a core-N-acetylglucosamine substituent as defined herein is thus an antibody, comprising a monosaccharide core-GlcNAc substituent as defined above, or if said core-GlcNAc substituent is fucosylated, a disaccharide core-GlcNAc(Fuc) substituent. If a core-GlcNAc substituent or the GlcNAc in a GlcNAc-$S(F^1)_x$ substituent is fucosylated, fucose is most commonly linked α-1,6 to O6 of the core-GlcNAc substituent. A fucosylated core-GlcNAc substituent is denoted core-GlcNAc(Fuc), a fucosylated GlcNAc-$S(F^1)_x$ substituent is denoted GlcNAc(Fuc)-$S(F^1)_x$.

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein.

Examples of glycoproteins include PSMA (prostate-specific membrane antigen), CAL (candida antartica lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also antigen-binding fragments of an antibody, for example an antibody Fab fragment, $F(ab')_2$, Fv fragment or Fc fragment from a cleaved antibody, a scFv-Fc fragment, a minibody, a diabody, a bispecific antibody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab. In a preferred embodiment, the glycoprotein comprising a core-N-acetylglucosamine substituent (core-GlcNAc substituent) is an antibody comprising a core-N-acetylglucosamine substituent (core-GlcNAc substituent), preferably a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody. When said antibody is a whole antibody, the antibody preferably comprises one or more, more preferably one, core-GlcNAc substituent on each heavy chain, said core-GlcNAc substituent being optionally fucosylated. Said whole antibody thus preferably comprises two or more, preferably two, optionally fucosylated, core-GlcNAc substituents. When said antibody is a single chain antibody or an antibody fragment, e.g. a Fab fragment, the antibody preferably comprises one or more core-GlcNAc substituents, which are optionally fucosylated. In the antibody comprising a core-GlcNAc substituent, said core-GlcNAc substituent may be situated anywhere on the antibody, provided that said substituent does not hinder the antigen-binding site of the antibody. In a preferred embodiment, said core N-acetylglucosamine substituent is present at a native N-glycosylation site of the antibody.

A linker is herein defined as a moiety that connects two or more elements of a compound. For example in a bioconjugate, a biomolecule and a target molecule are covalently connected to each other via a linker; in the linker-conjugate a reactive group $Q^1$ is covalently connected to a target molecule via a linker; in a linker-construct a reactive group $Q^1$ is covalently connected to a reactive group $Q^2$ via a linker. A linker may comprise one or more spacer-moieties.

A spacer-moiety is herein defined as a moiety that spaces (i.e. provides distance between) and covalently links together two (or more) parts of a linker. The linker may be part of e.g. a linker-construct, the linker-conjugate or a bioconjugate, as defined below.

A bioconjugate is herein defined as a compound wherein a biomolecule is covalently connected to a target molecule via a linker. A bioconjugate comprises one or more biomolecules and/or one or more target molecules. The linker may comprise one or more spacer moieties. An antibody-conjugate refers to a bioconjugate wherein the biomolecule is an antibody.

A biomolecule is herein defined as any molecule that can be isolated from nature or any molecule composed of smaller molecular building blocks that are the constituents of macromolecular structures derived from nature, in particular nucleic acids, proteins, glycans and lipids. Herein, the biomolecule may also be referred to as biomolecule of interest (BOI). Examples of a biomolecule include an enzyme, a (non-catalytic) protein, a polypeptide, a peptide, an amino acid, an oligonucleotide, a monosaccharide, an oligosaccharide, a polysaccharide, a glycan, a lipid and a hormone.

A target molecule, also referred to as a molecule of interest (MOI), is herein defined as molecular structure possessing a desired property that is imparted onto the biomolecule upon conjugation.

The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt.

The term "pharmaceutically accepted" salt means a salt that is acceptable for administration to a patient, such as a mammal (salts with counterions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

Herein, a sulfamide linker and conjugates of said sulfamide linker are disclosed. The term "sulfamide linker" refers to a linker comprising a sulfamide group, more particularly an acylsulfamide group [—C(O)—N(H)—$S(O)_2$—$N(R^1)$—] and/or a carbamoyl sulfamide group [—O—C(O)—N(H)—$S(O)_2$—$N(R^1)$—].

Herein, the term "therapeutic index" (TI) has the conventional meaning well known to a person skilled in the art, and refers to the ratio of the dose of drug that is toxic (i.e. causes adverse effects at an incidence or severity not compatible with the targeted indication) for 50% of the population ($TD_{50}$) divided by the dose that leads to the desired pharmacological effect in 50% of the population (effective dose or $ED_{50}$). Hence, $TI=TD_{50}/ED_{50}$. The therapeutic index may be determined by clinical trials or for example by plasma exposure tests. See also Muller, et al. *Nature Reviews Drug Discovery* 2012, 11, 751-761. At an early development stage, the clinical TI of a drug candidate is often not yet known. However, understanding the preliminary TI of a drug candidate is of utmost importance as early as possible, since TI is an important indicator of the probability of the successful development of a drug. Recognizing drug candidates with potentially suboptimal TI at earliest possible stage helps to initiate mitigation or potentially re-deploy resources. At this early stage, TI is typically defined as the quantitative ratio between efficacy (minimal effective dose in a mouse xenograft) and safety (maximum tolerated dose in mouse or rat).

Herein, the term "therapeutic efficacy" denotes the capacity of a substance to achieve a certain therapeutic effect, e.g. reduction in tumour volume. Therapeutic effects can be measured determining the extent in which a substance can achieve the desired effect, typically in comparison with another substance under the same circumstances. A suitable measure for the therapeutic efficacy is the $ED_{50}$ value, which may for example be determined during clinical trials or by plasma exposure tests. In case of preclinical therapeutic efficacy determination, the therapeutic effect of a bioconjugate (e.g. an ADC), can be validated by patient-derived tumour xenografts in mice in which case the efficacy refers to the ability of the ADC to provide a beneficial effect. Alternatively the tolerability of said ADC in a rodent safety study can also be a measure of the therapeutic effect.

Herein, the term "tolerability" refers to the maximum dose of a specific substance that does not cause adverse effects at an incidence or severity not compatible with the targeted indication. A suitable measure for the tolerability for a specific substance is the $TD_{50}$ value, which may for example be determined during clinical trials or by plasma exposure tests.

Mode of Conjugation

In the context of the present invention, the "mode of conjugation" refers to the process that is used to conjugate a target molecule D to a biomolecule B, in particular an antibody AB, as well as to the structural features of the resulting bioconjugate, in particular of the linker that connects the target molecule to the biomolecule, that are a direct consequence of the process of conjugation. Thus, in one embodiment, the mode of conjugation refers to a process for conjugation a target molecule to a biomolecule, in particular an antibody. In an alternative embodiment, the mode of conjugation refers to structural features of the linker and/or to the attachment point of the linker to the biomolecule that are a direct consequence of the process for conjugation a target molecule to a biomolecule, in particular an antibody.

In the context of the present invention, the mode of conjugation comprises at least one of "core-GlcNAc functionalization" and "sulfamide linkage" as defined further below. Preferably, the mode of conjugation comprises both the "core-GlcNAc functionalization" and "sulfamide linkage" as defined further below.

Core-GlcNAc Functionalization

In one embodiment, the mode of conjugation according to the invention is referred to as "core-GlcNAc functionalization", which refers to a process comprising:

(i) contacting a glycoprotein comprising 1-4 core N-acetylglucosamine moieties with a compound of the formula $S(F^1)_x$-P in the presence of a catalyst, wherein $S(F^1)_x$ is a sugar derivative comprising x functional groups $F^1$ capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety, to obtain a modified antibody according to Formula (24):

(24)

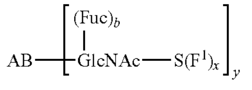

wherein $S(F^1)_x$ and x are as defined above; AB represents an antibody; GlcNAc is N-acetylglucosamine; Fuc is fucose; b is 0 or 1; and y is 1, 2, 3 or 4; and (ii) reacting the modified antibody with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$.

In the present embodiment, the antibody is conjugated via a glycan that is trimmed to a core-GlcNAc residue (optionally substituted with a fucose). This residue is functionalized with a sugar derivative $S(F^1)_x$, comprising 1 or 2 functional groups $F^1$, which are subsequently reacted with a functional group $Q^1$ present on a linker-conjugate comprising target molecule D. The structural feature of the resulting linker L that links the antibody with the target molecule, that are a direct consequence of the conjugation process include:

(a) The point of attachment of the linker L to the antibody AB is at a specific amino acid residue which is glycosylated in the naturally occurring antibody or is an artificially introduced glycosylation site, by mutation of specific amino acid residues in the antibody. As such, the point of attachment of the linker to the antibody can be specifically selected, which affords a highly predictable target molecule to antibody ratio (or DAR: "drug antibody ratio").

(b) The linker L is conjugated to a core-GlcNAc moiety of the antibody, and has the general structure $-S-(M)_{pp}-Z^3-L^2(D)_r$. Herein, S is the sugar derivative which is typically connected via O4 to the core-GlcNAc moiety and via any one of C2, C3, C4 and C6, preferably via C6, to $Z^3$, optionally via spacer M (i.e. pp=0 or 1). $Z^3$ is a connecting group that is obtained by the reaction between $Q^1$ and $F^1$. Options for $Q^1$, $F^1$ and $Z^3$ are known to the skilled person and discussed in further detail below. $Z^3$ is connected via linker $L^2$ to at least one target molecule D (i.e. r≥1).

(c) In a preferred embodiment, linker L, in particular linker $L^2$, comprises the group according to formula (1) or a salt thereof as defined for mode of conjugation referred to "sulfamide linkage". It has been found that when the mode of conjugation according to the present embodiment is combined with the "sulfamide linkage" mode of conjugation, the best results were obtained in terms of improving the therapeutic index of the resulting bioconjugates.

The inventors surprisingly found that using the above process for conjugating the target molecule to the antibody has a beneficial effect on the therapeutic index of the antibody-conjugate. In other words, the therapeutic index of antibody-conjugates having the mode of conjugation according to the present embodiment have an improved therapeutic index over antibody-conjugates not having the mode of conjugation according to the present embodiment.

The use of the mode of conjugation according to the present invention is distinct from a process of preparing an antibody-conjugate, wherein the mode of conjugation is used to prepare the antibody-conjugate. Although many modes of conjugation to prepare antibody-conjugates exists, the inventors have found that selecting a specific mode of conjugation, while keeping the antibody and the target molecule(s) constant, beneficially affects the therapeutic index of the conjugates.

Within the context of the present mode of conjugation referred to as "core-GlcNAc functionalization", in one embodiment the mode of conjugation comprises the step of preparing the bioconjugate of formula (A):

B-L-D (A), wherein:

B is a biomolecule;

L is a linker linking B and D;

D is a target molecule; and each occurrence of "-" is independently a bond or a spacer moiety, by reacting a reactive group $Q^1$ on a target molecule (D) with a functional group $F^1$ on a biomolecule (B), such that L comprises a group according to formula (1) or a salt thereof:

1

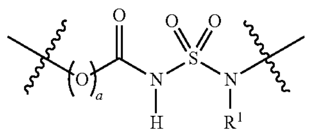

wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S or $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety.

Step (i)

In step (i), a glycoprotein comprising 1-4 core N-acetylglucosamine moieties is contacted with a compound of the formula $S(F^1)_x$-P in the presence of a catalyst, wherein $S(F^1)_x$ is a sugar derivative comprising x functional groups $F^1$ capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety. Herein, the glycoprotein is typically an antibody, such as an antibody that has been trimmed to a core-GlcNAc residue as described further below.

Step (i) affords a modified antibody according to Formula (24):

(24)

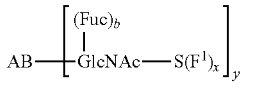

wherein $S(F^1)_x$ and x are as defined above; AB represents an antibody; GlcNAc is N-acetylglucosamine; Fuc is fucose; b is 0 or 1; and y is 1, 2, 3 or 4.

In a preferred embodiment, y=1, 2 or 4, more preferably y=1 or 2 (e.g. when AB is a single chain antibody), or alternatively y=2 or 4 (e.g. when AB is a double chain antibody). Most preferably y=2.

In one embodiment, the antibody comprising a core-GlcNAc substituent, wherein said core-GlcNAc substituent is optionally fucosylated, is of the Formula (21), wherein AB represents an antibody, GlcNAc is N-acetylglucosamine, Fuc is fucose, b is 0 or 1 and y is 1 to 4, preferably y is 1 or 2.

(21)

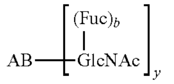

Such antibody comprising a core-GlcNAc substituent are known in the art and can be prepared by methods known by the skilled person. In one embodiment, the process according to the invention further comprises the deglycosylation of an antibody glycan having a core N-acetylglucosamine, in the presence of an endoglycosidase, in order to obtain an antibody comprising a core N-acetylglucosamine substituent, wherein said core N-acetylglucosamine and said core N-acetylglucosamine substituent are optionally fucosylated. Depending on the nature of the glycan, a suitable endoglycosidase may be selected. The endoglycosidase is preferably selected from the group consisting of EndoS, EndoA, EndoE, EfEndo18A, EndoF, EndoM, EndoD, EndoH, EndoT and EndoSH and/or a combination thereof, preferably of EndoS, EndoA, EndoF, EndoM, EndoD, EndoH and EndoSH enzymes and/or a combination thereof, the selection of which depends on the nature of the glycan. EndoSH is further defined below in the fourth aspect of the present invention. In a further preferred embodiment, the endoglycosidase is EndoS, EndoS49, EndoF, EndoH, EndoSH or a combination thereof, more preferably EndoS, EndoS49, EndoF, EndoSH or a combination thereof. In a further preferred embodiment, the endoglycosidase is EndoS, EndoF or a combination thereof. In a further preferred embodiment, the endoglycosidase is EndoS. In another preferred embodiment the endoglycosidase is EndoS49. In another preferred embodiment the endoglycosidase is EndoSH. Herien, EndoF typically refers to one of EndoF1, EndoF2 and EndoF3.

In step (i), modification of antibody (21a), wherein y=1, leads to a modified antibody comprising one GlcNAc-$S(F^1)_x$ substituent (22) and modification of antibody (21b), wherein y=2, leads to a modified antibody comprising two GlcNAc-$S(F^1)_x$ substituents (23). In one embodiment, preferably when AB is a double chain antibody, y=2 or 4. In one embodiment, preferably when AB is a single chain antibody, y=1 or 2.

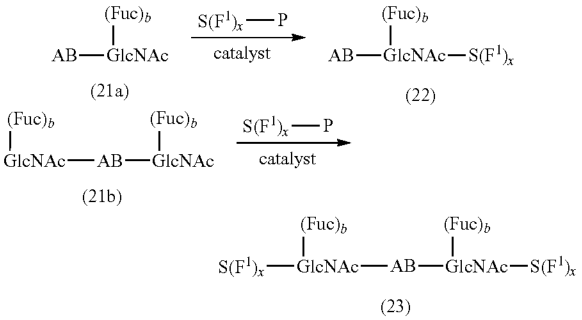

(21a) (22) (21b) (23)

In a preferred embodiment, the antibody AB is capable of targeting tumours that express an antigen selected from 5T4 (TPBG), åv-integrin/ITGAV, BCMA, C4.4a, CA-IX, CD19, CD19b, CD22, CD25, CD30, CD33, CD37, CD40, CD56, CD70, CD74, CD79b, c-KIT (CD119), CD138/SDC1, CEACAM5 (CD66e), Cripto, CS1, DLL3, EFNA4, EGFR, EGFRvIII, Endothelin B Receptor (ETBR), ENPP3 (AGS-16), EpCAM, EphA2, FGFR2, FGFR3, FOLR1 (folate receptor a), gpNMB, guanyl cyclase C (GCC), HER2, Erb-B2, Lamp-1, Lewis Y antigen, LIV-1 (SLC39A6, ZIP6), Mesothelin (MSLN), MUC1 (CA6, huDS6), MUC16/EA-125, NaPi2b, Nectin-4, Notch3, P-cadherin, PSMA/FOLH1, PTK7, SLITRK6 (SLC44A4), STEAP1, TF (CD142), Trop-1, Trop-2/EGP-1, Trop-3, Trop-4, preferably HER2-expressing tumours.

In a preferred embodiment, the antibody AB is capable of targeting HER2-expressing tumours, including but not limited to low HER2-expressing tumours, more preferably the antibody AB is selected from the group consisting of from trastuzumab, margetuximab, pertuzumab, HuMax-Her2, ertumaxomab, HB-008, ABP-980, BCD-022, CanMab, Herzuma, HD201, CT-P6, PF-05280014, COVA-208, FS-102, MCLA-128, CKD-10101, HT-19 and functional analogues thereof, most preferably trastuzumab.

$S(F^1)_x$ is defined as a sugar derivative comprising x functional groups $F^1$, wherein x is 1 or 2 and $F^1$ is a functional group capable of reacting with $Q^1$ present on the linker-conjugate to form a connecting moiety $Z^3$. The sugar derivative $S(F^1)_x$ may comprise 1 or 2 functional groups $F^1$. When $S(F^1)_x$ comprises 2 functional groups $F^1$, each functional group $F^1$ is independently selected, i.e. one $S(F^1)_x$ may comprise different functional groups F. In one embodiment, x=1. In one embodiment, x=2. Sugar derivative $S(F^1)_x$ is derived from a sugar or a sugar derivative S, e.g. an amino sugar or an otherwise derivatized sugar. Examples of sugars and sugar derivatives include galactose (Gal), mannose (Man), glucose (Glc), glucuronic acid (GlucA) and fucose (Fuc). An amino sugar is a sugar wherein a hydroxyl (OH) group is replaced by an amino group and examples include N-acetylglucosamine (GlcNAc) and N-acetylgalactosamine (GalNAc). Examples of an otherwise derivatized sugar include glucuronic acid (GlucA) and N-acetylneuraminic acid (sialic acid). Sugar derivative $S(F^1)_x$ is preferably derived from galactose (Gal), mannose (Man), N-acetylglucosamine (GlcNAc), glucose (Glc), N-acetylgalactosamine (GalNAc), glucuronic acid (GlucA), fucose (Fuc) and N-acetylneuraminic acid (sialic acid), preferably from the group consisting of GlcNAc, Glc, Gal and GalNAc. More preferably $S(F^1)_x$ is derived from Gal or GalNAc, and most preferably $S(F^1)_x$ is derived from GalNAc.

Compounds of the formula $S(F^1)_x$-P, wherein a nucleoside monophosphate or a nucleoside diphosphate P is linked to a sugar derivative $S(F^1)_x$, are known in the art. For example Wang et al., *Chem. Eur. J.* 2010, 16, 13343-13345, Piller et al., *ACS Chem. Biol.* 2012, 7, 753, Piller et al., *Bioorg. Med. Chem. Lett.* 2005, 15, 5459-5462 and WO 2009/102820, all incorporated by reference herein, disclose a number of compounds $S(F^1)_x$-P and their syntheses. In a preferred embodiment nucleoside mono- or diphosphate P in $S(F^1)_x$-P is selected from the group consisting of uridine diphosphate (UDP), guanosine diphosphate (GDP), thymidine diphosphate (TDP), cytidine diphosphate (CDP) and cytidine monophosphate (CMP), more preferably P is selected from the group consisting of uridine diphosphate (UDP), guanosine diphosphate (GDP) and cytidine diphosphate (CDP), most preferably P=UDP.

The 1 or 2 functional groups $F^1$ in $S(F^1)_x$ may be linked to the sugar or sugar derivative S in several ways. The 1 or 2 functional groups $F^1$ may be bonded to $C_2$, $C_3$, $C_4$ and/or $C_6$ of the sugar or sugar derivative, instead of a hydroxyl (OH) group. It should be noted that, since fucose lacks an OH-group on $C_6$, if $F^1$ is bonded to $C_6$ of Fuc, then $F^1$ takes the place of an H-atom. When $F^1$ is an azido group, it is preferred that $F^1$ is bonded to $C_2$, $C_4$ or $C_6$. As was described above, the one or more azide substituent in $S(F^1)_x$ may be bonded to $C_2$, $C_3$, $C_4$ or $C_6$ of the sugar or sugar derivative S, instead of a hydroxyl (OH) group or, in case of 6-azido-fucose (6-AzFuc), instead of a hydrogen atom. Alternatively or additionally, the N-acetyl substituent of an amino sugar derivative may be substituted by an azidoacetyl substituent. In a preferred embodiment $S(F^1)_x$ is selected from the group consisting of 2-azidoacetamido-2-deoxy-galactose (GalNAz), 2-azidodifluoroacetamido-2-deoxy-galactose ($F_2$-GalNAz), 6-azido-6-deoxygalactose (6-AzGal), 6-azido-6-deoxy-2-acetamidogalactose (6-AzGalNAc or 6-$N_3$-GalNAc), 4-azido-4-deoxy-2-acetamidogalactose (4-AzGalNAc), 6-azido-6-deoxy-2-azidoacetamido-2-deoxygalactose (6-AzGalNAz), 2-azidoacetamido-2-deoxyglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamido-2-deoxyglucose (6-AzGlcNAz), more preferably from the group consisting of GalNAz, 4-AzGalNAc and 6-AzGalNAc. Examples of $S(F^1)_x$-P wherein $F^1$ is an azido group are shown below. When $F^1$ is a keto group, it is preferred that $F^1$ is bonded to $C_2$ instead of the OH-group of S. Alternatively $F^1$ may be bonded to the N-atom of an amino sugar derivative, preferably a 2-amino sugar derivative. The sugar derivative then comprises an —NC(O)$R^{36}$ substituent. $R^{36}$ is preferably a $C_2$-$C_{24}$ alkyl group, optionally substituted. More preferably, $R^{36}$ is an ethyl group. In a preferred embodiment $S(F^1)_x$ is selected from the group consisting of 2-deoxy-(2-oxopropyl)galactose (2-ketoGal), 2-N-propionylgalactosamine (2-N-propionylGalNAc), 2-N-(4-oxopentanoyl)galactosamine (2-N-LevGal) and 2-N-butyrylgalactosamine (2-N-butyrylGalNAc), more preferably 2-ketoGalNAc and 2-N-propionylGalNAc. Examples of $S(F^1)_x$-P wherein $F^1$ is a keto group are shown below. When $F^1$ is an alkynyl group, preferably a terminal alkynyl group or a (hetero)cycloalkynyl group, it is preferred that said alkynyl group is present on a 2-amino sugar derivative. An example of $S(F^1)_x$ wherein $F^1$ is an alkynyl group is 2-(but-3-yonic acid amido)-2-deoxy-galactose. An example of $S(F^1)_x$-P wherein $F^1$ is an alkynyl group is shown below.

In one embodiment, $F^1$ is selected from the group consisting of an azido group, a keto group and an alkynyl group. An azido group is an azide functional group —$N_3$. A keto group is a —$[C(R^{37})_2]_oC(O)R^{36}$ group, wherein $R^{36}$ is a methyl group or an optionally substituted $C_2$-$C_{24}$ alkyl group, $R^{37}$ is independently selected from the group consisting of hydrogen, halogen and $R^{36}$, and o is 0-24, preferably 0-10, and more preferably 0, 1, 2, 3, 4, 5 or 6. Preferably, $R^{37}$ is hydrogen. An alkynyl group is preferably a terminal alkynyl group or a (hetero)cycloalkynyl group as defined above. In one embodiment the alkynyl group is a —$[C(R^{37})_2]_oC{\equiv}C$—$R^{37}$ group, wherein $R^{37}$ and o are as defined above; $R^{37}$ is preferably hydrogen.

In one embodiment, $F^1$ is an azide or an alkyne moiety. Most preferably, $F^1$ is an azido group (—$N_3$). In one embodiment, $F^1$ is an azide moiety, $Q^1$ is an (cyclo)alkyne moiety, and $Z^3$ is a triazole moiety.

Several examples (25-28) of uridine diphosphates linked to azido- or alkynyl-substituted sugars and sugar derivatives, $S(F^1)_x$-UDP, are shown below.

(25)

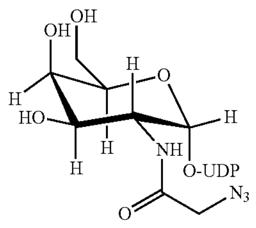

(26)

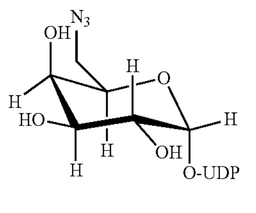

-continued (27)

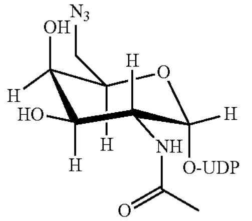

(28)

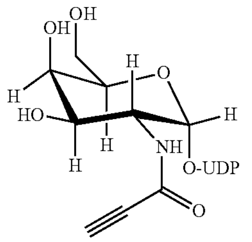

Preferably, $S(F^1)_x$-P is selected from the group consisting of GalNAz-UDP (25), 6-AzGal-UDP (26), 6-AzGalNAc-UDP (6-azido-6-deoxy-N-acetylgalactosamine-UDP) (27), 4-AzGalNAz-UDP, 6-AzGalNAz-UDP, 6-AzGlc-UDP, 6-AzGlcNAz-UDP and 2-(but-3-yonic acid amido)-2-deoxy-galactose-UDP (28). Most preferably, $S(F^1)_x$-P is GalNAz-UDP (25) or 6-AzGalNAc-UDP (27).

Suitable catalyst that are capable of transferring the $S(F^1)_x$ moiety to the core-GlcNAc moiety are known in the art. A suitable catalyst is a catalyst wherefore the specific sugar derivative nucleotide $S(F^1)_x$-P in that specific process is a substrate. More specifically, the catalyst catalyzes the formation of a β(1,4)-glycosidic bond. Preferably, the catalyst is selected from the group of galactosyltransferases and N-acetylgalactosaminyltransferases, more preferably from the group of β(1,4)-N-acetylgalactosaminyltransferases (GalNAcT) and P/(1,4)-galactosyltransferases (GalT), most preferably from the group of β(1,4)-N-acetylgalactosaminyltransferases having a mutant catalytic domain. Suitable catalysts and mutants thereof are disclosed in WO 2014/065661, WO 2016/022027 and PCT/EP2016/059194 (WO 2016/170186), all incorporated herein by reference. In one embodiment, the catalyst is a wild-type galactosyltransferase or N-acetylgalactosaminyl-transferase, preferably a N-acetylgalactosaminyltransferase. In an alternative embodiment, the catalyst is a mutant galactosyltransferase or N-acetylgalactosaminyltransferases, preferably a mutant N-acetylgalactosaminyltransferase. Mutant enzymes described in WO 2016/022027 and PCT/EP2016/059194 (WO 2016/170186) are especially preferred.

These galactosyltransferase (mutant) enzyme catalysts are able to recognize internal sugars and sugar derivatives as an acceptor. Thus, sugar derivative $S(F^1)_x$ is linked to the core-GlcNAc substituent in step (i), irrespective of whether said GlcNAc is fucosylated or not.

Step (i) is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer. Step (i) is preferably performed at a temperature in the range of about 4 to about 50° C., more preferably in the range of about 10 to about 45° C., even more preferably in the range of about 20 to about 40° C., and most preferably in the range of about 30 to about 37° C. Step (i) is preferably performed a pH in the range of about 5 to about 9, preferably in the range of about 5.5 to about 8.5, more preferably in the range of about 6 to about 8. Most preferably, step (i) is performed at a pH in the range of about 7 to about 8.

Step (ii)

In step (ii), the modified antibody is reacted with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$. Such reaction occurs under condition such that reactive group $Q^1$ is reacted with the functional group $F^1$ of the biomolecule to covalently link the biomolecule to the linker-conjugate. Linker-conjugates and preferred embodiments thereof are defined further below. The linker $L^2$ preferably comprises the group according to formula (1) or a salt thereof, and said linker is further defined below.

Complementary functional groups $Q^1$ for the functional group $F^1$ on the modified antibody are known in the art. Preferably, reactive group $Q^1$ and functional group $F^1$ are capable of reacting in a bioorthogonal reaction, as those reactions do not interfere with the biomolecules present during this reaction. Bioorthogonal reactions and functional groups suitable therein are known to the skilled person, for example from Gong and Pan, *Tetrahedron Lett.* 2015, 56, 2123-2132, and include Staudinger ligations and copper-free Click chemistry. It is thus preferred that $Q^1$ is selected from the group consisting of 1,3-dipoles, alkynes, (hetero)cyclooctynes, cyclooctenes, tetrazines, ketones, aldehydes, alkoxyamines, hydrazines and triphenylphosphine. For example, when $F^1$ is an azido group, linking of the azide-modified antibody and the linker-conjugate preferably takes place via a cycloaddition reaction. Functional group $Q^1$ is then preferably selected from the group consisting of alkynyl groups, preferably terminal alkynyl groups, and (hetero) cycloalkynyl groups. For example, when $F^1$ is a keto group, linking of the keto-modified antibody with the linker-conjugate preferably takes place via selective conjugation with hydroxylamine derivatives or hydrazines, resulting in respectively oximes or hydrazones. Functional group $Q^1$ is then preferably a primary amino group, e.g. an —$NH_2$ group, an aminooxy group, e.g. —O—$NH_2$, or a hydrazinyl group, e.g. —N(H)$NH_2$. The linker-conjugate is then preferably $H_2N$-$L^2(D)_r$, $H_2N$—O-$L^2(D)_r$ or $H_2N$—N(H)-$L^2(D)_r$ respectively. For example, when $F^1$ is an alkynyl group, linking of the alkyne-modified antibody with the linker-conjugate preferably takes place via a cycloaddition reaction, preferably a 1,3-dipolar cycloaddition. Functional group $Q^1$ is then preferably a 1,3-dipole, such as an azide, a nitrone or a nitrile oxide. The linker-conjugate is then preferably $N_3$-$L^2(D)_r$.

In a preferred embodiment, in step (ii) an azide on the azide-modified antibody according to the invention reacts with an alkynyl group, preferably a terminal alkynyl group, or a (heter)cycloalkynyl group of the linker-conjugate via a cycloaddition reaction. This cycloaddition reaction of a molecule comprising an azide with a molecule comprising a terminal alkynyl group or a (hetero)cycloalkynyl group is one of the reactions that is known in the art as "click chemistry". In the case of a linker-conjugate comprising a terminal alkynyl group, said cycloaddition reaction needs to be performed in the presence of a suitable catalyst, preferably a Cu(I) catalyst. However, in a preferred embodiment, the linker-conjugate comprises a (hetero)cycloalkynyl group, more preferably a strained (hetero)cycloalkynyl group. When the (hetero)cycloalkynyl is a strained (hetero) cycloalkynyl group, the presence of a catalyst is not required, and said reaction may even occur spontaneously by a reaction called strain-promoted azide-alkyne cycloaddition (SPAAC). This is one of the reactions known in the art as "metal-free click chemistry". Strained (hetero)cycloalkynyl groups are known in the art and are described in more detail below.

Therefore, in a preferred embodiment, step (ii) comprises reacting a modified antibody with a linker-conjugate, wherein said linker-conjugate comprises a (hetero)cycloalkynyl group and one or more molecules of interest, wherein said modified antibody is an antibody comprising a GlcNAc-$S(F^1)_x$ substituent, wherein GlcNAc is an N-acetylglucosamine, wherein $S(F^1)_x$ is a sugar derivative comprising x functional groups $F^1$ wherein $F^1$ is an azido group and x is 1 or 2, wherein said GlcNAc-$S(F^1)_x$ substituent is bonded to the antibody via $C_1$ of the N-acetylglucosamine of said GlcNAc-$S(F^1)_x$ substituent, and wherein said GlcNAc is optionally fucosylated. In a further preferred embodiment, said (hetero)cycloalkynyl group is a strained (hetero)cycloalkynyl group.

Target molecule D may be selected from the group consisting of an active substance, a reporter molecule, a polymer, a solid surface, a hydrogel, a nanoparticle, a microparticle and a biomolecule.

In the context of D, the term "active substance" relates to a pharmacological and/or biological substance, i.e. a substance that is biologically and/or pharmaceutically active, for example a drug, a prodrug, a diagnostic agent, a protein, a peptide, a polypeptide, a peptide tag, an amino acid, a glycan, a lipid, a vitamin, a steroid, a nucleotide, a nucleoside, a polynucleotide, RNA or DNA. Examples of peptide tags include cell-penetrating peptides like human lactoferrin or polyarginine. An example of a glycan is oligomannose. An example of an amino acid is lysine.

When the target molecule is an active substance, the active substance is preferably selected from the group consisting of drugs and prodrugs. More preferably, the active substance is selected from the group consisting of pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, enediynes, an inhibitory peptide, amanitin, deBouganin, duocarmycins, maytansines, auristatins, indolinobenzodiazepines or pyrrolobenzodiazepines (PBDs). In view of their poor water solubility, preferred active substances include vinca alkaloids, anthracyclines, camptothecins, taxanes, tubulysins, amanitin, duocarmycins, maytansines, auristatins, indolinobenzodiazepines and pyrrolobenzodiazepines, in particular vinca alkaloids, anthracyclines, camptothecins, taxanes, tubulysins, amanitin, maytansines and auristatins.

The term "reporter molecule" herein refers to a molecule whose presence is readily detected, for example a diagnostic agent, a dye, a fluorophore, a radioactive isotope label, a contrast agent, a magnetic resonance imaging agent or a mass label.

A wide variety of fluorophores, also referred to as fluorescent probes, is known to a person skilled in the art. Several fluorophores are described in more detail in e.g. G. T. Hermanson, "*Bioconjugate Techniques*", Elsevier, 3rd Ed.

2013, Chapter 10: *"Fluorescent probes"*, p. 395-463, incorporated by reference. Examples of a fluorophore include all kinds of Alexa Fluor (e.g. Alexa Fluor 555), cyanine dyes (e.g. Cy3 or Cy5) and cyanine dye derivatives, coumarin derivatives, fluorescein and fluorescein derivatives, rhodamine and rhodamine derivatives, boron dipyrromethene derivatives, pyrene derivatives, naphthalimide derivatives, phycobiliprotein derivatives (e.g. allophycocyanin), chromomycin, lanthanide chelates and quantum dot nanocrystals. In view of their poor water solubility, preferred fluorophores include cyanine dyes, coumarin derivatives, fluorescein and derivatives thereof, pyrene derivatives, naphthalimide derivatives, chromomycin, lanthanide chelates and quantum dot nanocrystals, in particular coumarin derivatives, fluorescein, pyrene derivatives and chromomycin.

Examples of a radioactive isotope label include $^{99m}Tc$, $^{111}In$, $^{114m}In$, $^{115}In$, $^{18}F$, $^{14}C$, $^{64}Cu$, $^{131}I$, $^{125}I$, $^{123}I$, $^{212}Bi$, $^{88}Y$, $^{90}Y$, $^{67}Cu$, $^{186}Rh$, $^{188}Rh$, $^{66}Ga$, $^{67}Ga$ and $^{10}B$, which is optionally connected via a chelating moiety such as e.g. DTPA (diethylenetriaminepentaacetic anhydride), DOTA (1,4,7,10-tetraazacyclododecane-N,N'N",N'"tetraacetic acid), NOTA (1,4,7-triazacyclononane N,N',N"-triacetic acid), TETA (1,4,8,11-tetraazacyclotetradecane-N,N',N", N'"-tetraacetic acid), DTTA ($N^1$-(p-isothiocyanatobenzyl)-diethylenetriamine-$N^1$,$N^2$,$N^3$,$N^3$-tetraacetic acid), deferoxamine or DFA (N'-[5-[[4-[[5-(acetylhydroxyamino)pentyl] amino]-1,4-dioxobutyl]hydroxyamino]pentyl]-N-(5-aminopentyl)-N-hydroxybutanediamide) or HYNIC (hydrazinonicotinamide). Isotopic labelling techniques are known to a person skilled in the art, and are described in more detail in e.g. G. T. Hermanson, "*Bioconjugate Techniques*", Elsevier, $3^{rd}$ Ed. 2013, Chapter 12: *"Isotopic labelling techniques"*, p. 507-534, incorporated by reference.

Polymers suitable for use as a target molecule D in the compound according to the invention are known to a person skilled in the art, and several examples are described in more detail in e.g. G. T. Hermanson, "*Bioconjugate Techniques*", Elsevier, $3^{rd}$ Ed. 2013, Chapter 18: *"PEGylation and synthetic polymer modification"*, p. 787-838, incorporated by reference. When target molecule D is a polymer, target molecule D is preferably independently selected from the group consisting of a polyethylene glycol (PEG), a polyethylene oxide (PEO), a polypropylene glycol (PPG), a polypropylene oxide (PPO), a 1,xx-diaminoalkane polymer (wherein xx is the number of carbon atoms in the alkane, and preferably xx is an integer in the range of 2 to 200, preferably 2 to 10), a (poly)ethylene glycol diamine (e.g. 1,8-diamino-3,6-dioxaoctane and equivalents comprising longer ethylene glycol chains), a polysaccharide (e.g. dextran), a poly(amino acid) (e.g. a poly(L-lysine)) and a poly(vinyl alcohol). In view of their poor water solubility, preferred polymers include a 1,xx-diaminoalkane polymer and poly(vinyl alcohol).

Solid surfaces suitable for use as a target molecule D are known to a person skilled in the art. A solid surface is for example a functional surface (e.g. a surface of a nanomaterial, a carbon nanotube, a fullerene or a virus capsid), a metal surface (e.g. a titanium, gold, silver, copper, nickel, tin, rhodium or zinc surface), a metal alloy surface (wherein the alloy is from e.g. aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc and/or zirconium), a polymer surface (wherein the polymer is e.g. polystyrene, polyvinylchloride, polyethylene, polypropylene, poly(dimethylsiloxane) or polymethylmethacrylate, polyacrylamide), a glass surface, a silicone surface, a chromatography support surface (wherein the chromatography support is e.g. a silica support, an agarose support, a cellulose support or an alumina support), etc. When target molecule D is a solid surface, it is preferred that D is independently selected from the group consisting of a functional surface or a polymer surface. Hydrogels are known to the person skilled in the art. Hydrogels are water-swollen networks, formed by cross-links between the polymeric constituents. See for example A. S. Hoffman, *Adv. Drug Delivery Rev.* 2012, 64, 18, incorporated by reference. When the target molecule is a hydrogel, it is preferred that the hydrogel is composed of poly(ethylene)glycol (PEG) as the polymeric basis.

Micro- and nanoparticles suitable for use as a target molecule D are known to a person skilled in the art. A variety of suitable micro- and nanoparticles is described in e.g. G. T. Hermanson, "*Bioconjugate Techniques*", Elsevier, $3^{rd}$ Ed. 2013, Chapter 14: *"Microparticles and nanoparticles"*, p. 549-587, incorporated by reference. The micro- or nanoparticles may be of any shape, e.g. spheres, rods, tubes, cubes, triangles and cones. Preferably, the micro- or nanoparticles are of a spherical shape. The chemical composition of the micro- and nanoparticles may vary. When target molecule D is a micro- or a nanoparticle, the micro- or nanoparticle is for example a polymeric micro- or nanoparticle, a silica micro- or nanoparticle or a gold micro- or nanoparticle. When the particle is a polymeric micro- or nanoparticle, the polymer is preferably polystyrene or a copolymer of styrene (e.g. a copolymer of styrene and divinylbenzene, butadiene, acrylate and/or vinyltoluene), polymethylmethacrylate (PMMA), polyvinyltoluene, poly(hydroxyethyl methacrylate (pHEMA) or polyethylene glycol dimethacrylate/2-hydroxyethyl methacrylate) [poly(EDGMA/HEMA)]. Optionally, the surface of the micro- or nanoparticles is modified, e.g. with detergents, by graft polymerization of secondary polymers or by covalent attachment of another polymer or of spacer moieties, etc.

Target molecule D may also be a biomolecule. Biomolecules, and preferred embodiments thereof, are described in more detail below. When target molecule D is a biomolecule, it is preferred that the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides.

Preferred options for D are described further below for the antibody-conjugate according to the third aspect. The bioconjugates in the context of the present invention may contain more than one target molecule D, which may be the same or different. In one embodiment, the bioconjugate of the present invention may contain more than one, preferably two, target molecules connected to the same S (i.e. one of x, r and q>1, preferably one of x, r and q=2), preferably to the same $Z^3$ (i.e. one of r and q>1, preferably one of r and q=2). Most preferably in the context of the present embodiment, r=2. Preferably, those target molecules are different, more preferably they both are active substances, more preferably anti-cancer agents, most preferably cytotoxins. In one embodiment, the bioconjugate of the present invention comprises two distinct target molecules, preferably two distinct active substances, more preferably two distinct anti-cancer agents, most preferably two distinct cytotoxins.

Preferably, the linker-conjugate comprises a (hetero)cycloalkynyl group. In a preferred embodiment said linker-conjugate has the Formula (31):

(31)

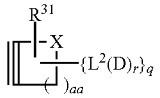

wherein:

$L^2$ is a linker as defined herein;

D is a target molecule;

r is 1-20;

$R^{31}$ is independently selected from the group consisting of hydrogen, halogen, —$OR^{35}$, —$NO_2$, —CN, —$S(O)_2R^{35}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{31}$ may be linked together to form an annelated cycloalkyl or an annelated (hetero)arene substituent, and wherein $R^{35}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

X is $C(R^{31})_2$, O, S or $NR^{32}$, wherein $R^{32}$ is $R^{31}$ or $L^2(D)_r$, and wherein $L^2$, D and r are as defined above;

q is 0 or 1, with the proviso that if q is 0 then X is $NL^2(D)_r$; and aa is 0, 1, 2, 3, 4, 5, 6, 7 or 8.

In another preferred embodiment said linker-conjugate has the Formula (31b):

(31b)

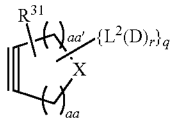

wherein:

$L^2$ is a linker as defined herein;

D is a target molecule;

r is 1-20;

$R^{31}$ is independently selected from the group consisting of hydrogen, halogen, —$OR^{35}$, —$NO_2$, —CN, —$S(O)_2R^{35}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{31}$ may be linked together to form an annelated cycloalkyl or an annelated (hetero)arene substituent, and wherein $R^{35}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

X is $C(R^{31})_2$, O, S or $NR^{32}$, wherein $R^{32}$ is $R^{31}$ or $L^2(D)_r$, and wherein $L^2$, D and r are as defined above;

q is 0 or 1, with the proviso that if q is 0 then X is $NL^2(D)_r$;

aa is 0, 1, 2, 3, 4, 5, 6, 7 or 8;

aa' is 0, 1, 2, 3, 4, 5, 6, 7 or 8; and aa+aa'<10.

In a further preferred embodiment, aa+aa' is 4, 5, 6 or 7, more preferably aa+aa' is 4, 5 or 6 and most preferably aa+aa' is 5.

In another preferred embodiment said linker-conjugate has the Formula (31c):

(31c)

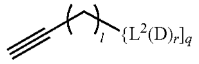

wherein:

$L^2$ is a linker as defined herein;

D is a target molecule;

r is 1-20;

q is 0 or 1, with the proviso that if q is 0 then X is $NL^2(D)_r$; and l is 0-10.

In a preferred embodiment, if q is 1 then X is $C(R^{31})_2$, O, S or $NR^{31}$.

In another preferred embodiment, a is 5, i.e. said (hetero)cycloalkynyl group is preferably a (hetero)cyclooctyne group. In another preferred embodiment, X is $C(R^{32})_2$ or $NR^{32}$. When X is $C(R^{32})_2$ it is preferred that $R^{32}$ is hydrogen. When X is $NR^{32}$, it is preferred that $R^{32}$ is $L^2(D)_r$. In yet another preferred embodiment, r is 1 to 10, more preferably, r is 1, 2, 3, 4, 5, 6 7 or 8, more preferably r is 1, 2, 3, 4, 5 or 6, most preferably r is 1, 2, 3 or 4.

The $L^2(D)_r$ substituent may be present on a C-atom in said (hetero)cycloalkynyl group, or, in case of a heterocycloalkynyl group, on the heteroatom of said heterocycloalkynyl group. When the (hetero)cycloalkynyl group comprises substituents, e.g. an annelated cycloalkyl, the $L^2(D)_r$ substituent may also be present on said substituents.

The methods to connect a linker $L^2$ to a (hetero)cycloalkynyl group on the one end and to a target molecule on the other end, in order to obtain a linker-conjugate, depend on the exact the nature of the linker, the (hetero)cycloalkynyl group and the target molecule. Suitable methods are known in the art.

Preferably, the linker-conjugate comprises a (hetero)cyclooctyne group, more preferably a strained (hetero)cyclooctyne group. Suitable (hetero)cycloalkynyl moieties are known in the art. For example DIFO, DIFO2 and DIFO3 are disclosed in US 2009/0068738, incorporated by reference. DIBO is disclosed in WO 2009/067663, incorporated by reference. DIBO may optionally be sulphated (S-DIBO) as disclosed in *J. Am. Chem. Soc.* 2012, 134, 5381. BARAC is disclosed in *J. Am. Chem. Soc.* 2010, 132, 3688-3690 and US 2011/0207147, all incorporated by reference.

Preferred examples of linker-conjugates comprising a (hetero)cyclooctyne group are shown below.

(32)

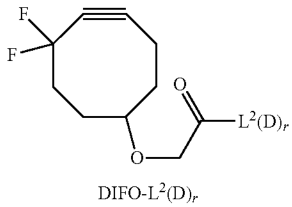

DIFO-$L^2(D)_r$

-continued (33)

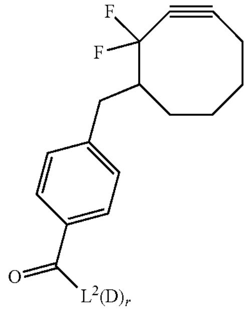

DIFO2-$L^2(D)_r$ (34)

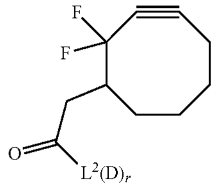

DIFO3-$L^2(D)_r$ (35)

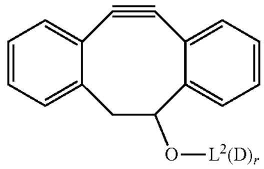

DIBO-$L^2(D)_r$ (36)

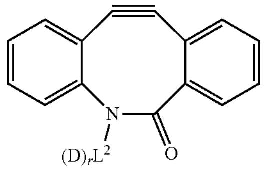

BARAC-$L^2(D)_r$ (36a)

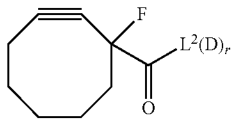

MFCO-$L^2(D)_r$

Other cyclooctyne moieties that are known in the art are DIBAC (also known as ADIBO or DBCO) and BCN. DIBAC is disclosed in *Chem. Commun.* 2010, 46, 97-99, incorporated by reference. BCN is disclosed in WO 2011/136645, incorporated by reference.

In a preferred embodiment, said linker-conjugate has the Formula (32), (33), (34), (35) or (36).

In another preferred embodiment, said linker-conjugate has the Formula (37):

(37)

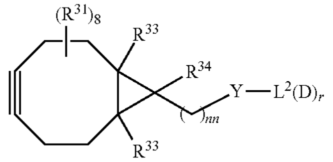

wherein:

$R^1$, $L^2$, D and r are as defined above;

Y is O, S or $NR^{32}$, wherein $R^{32}$ is as defined above;

$R^{33}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

$R^{34}$ is selected from the group consisting of hydrogen, Y-$L^2(D)_r$, —$(CH_2)_{nn}$—Y-$L^2(D)_r$, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted; and nn is 1, 2, 3, 4, 5, 6, 7, 8, 9 or 10.

In a further preferred embodiment, $R^{31}$ is hydrogen. In another preferred embodiment, $R^{33}$ is hydrogen. In another preferred embodiment, n is 1 or 2. In another preferred embodiment, $R^{34}$ is hydrogen, Y-$L^2(D)_r$ or —$(CH_2)_{nn}$—Y-$L^2(D)_r$. In another preferred embodiment, $R^{32}$ is hydrogen or $L^2(D)_r$. In a further preferred embodiment, the linker-conjugate has the Formula 38:

(38)

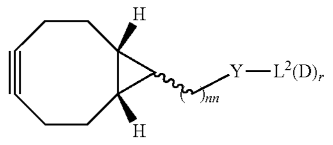

BCN-$L^2D_r$ wherein Y, $L^2$, D, nn and r are as defined above.

In another preferred embodiment, said linker-conjugate has the Formula (39):

(39)

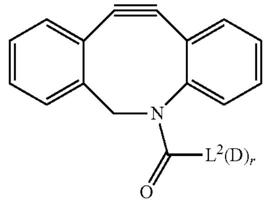

wherein $L^2$, D and r are as defined above.

In another preferred embodiment, said linker-conjugate has the Formula (35):

(35)

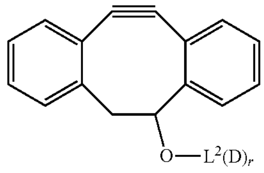

wherein $L^2$, D and r are as defined above.

The value of pp and the nature of M depend on the azide-substituted sugar or sugar derivative $S(F^1)_x$ that is present in the azide-modified antibody according to the invention that is linked to a linker-conjugate. If an azide in $S(F^1)_x$ is present on the C2, C3, or C4 position of the sugar or the sugar derivative (instead of a sugar OH-group), then pp is 0. If the $S(F^1)_x$ is an azidoacetamido-2-deoxy-sugar derivative, $S(F^1)_x$ is e.g. GalNAz or GlcNAz, then pp is 1 and M is —N(H)C(O)$CH_2$—. If the azide in $S(F^1)_x$ is present on the $C_6$ position of the sugar or the sugar derivative, then pp is 0 and M is absent.

Linkers ($L^2$), also referred to as linking units, are well known in the art. In a linker-conjugate as described herein, L is linked to a target molecule as well as to a functional group $Q^1$. $L^2$ may for example be selected from the group consisting of linear or branched $C_1$-$C_{200}$ alkylene groups, $C_2$-$C_{200}$ alkenylene groups, $C_2$-$C_{200}$ alkynylene groups, $C_3$-0200 cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, S and $NR^{35}$, wherein $R^{35}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups. Most preferably, the heteroatom is O. Examples of suitable linking units include (poly)ethylene glycol diamines (e.g. 1,8-diamino-3,6-dioxaoctane or equivalents comprising longer ethylene glycol chains), polyethylene glycol or polyethylene oxide chains, polypropylene glycol or polypropylene oxide chains and 1,xx-diaminoalkanes wherein xx is the number of carbon atoms in the alkane.

Another class of suitable linkers comprises cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas.

Preferred linkers $L^2$ are defined further below for the embodiment on "sulfamide linkage" as well as for the antibody-conjugate according to the third aspect. Preferred linker-conjugates are also defined further below.

Step (ii) is preferably performed at a temperature in the range of about 20 to about 50° C., more preferably in the range of about 25 to about 45° C., even more preferably in the range of about 30 to about 40° C., and most preferably in the range of about 32 to about 37° C. Step (ii) is preferably performed a pH in the range of about 5 to about 9, preferably in the range of about 5.5 to about 8.5, more preferably in the range of about 6 to about 8. Most preferably, step (ii) is performed at a pH in the range of about 7 to about 8. Step (ii) is preferably performed in water. More preferably, said water is purified water, even more preferably ultrapure water or Type I water as defined according to ISO 3696. Suitable water is for example milliQ® water. Said water is preferably buffered, for example with phosphate-buffered saline or tris. Suitable buffers are known to a person skilled in the art. In a preferred embodiment, step (ii) is performed in milliQ water which is buffered with phosphate-buffered saline or tris.

In one embodiment, the reaction of step (ii) is a(n) (cyclo)alkyne-azide conjugation to from a connecting moiety $Z^3$ that is represented by (10e), (10i), (10g), (10j) or (10k), preferably by (10e), (10i), (10g), most preferably by (10g), as represented by:

10e

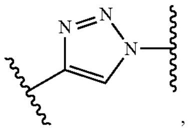

,

10i

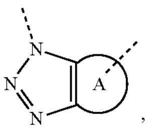

,

10g

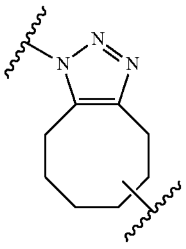

,

10j

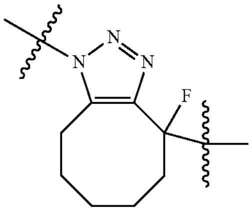

-continued

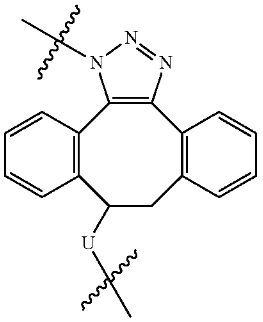

10k wherein cycle A is a 7-10-membered (hetero)cyclic moiety. Connecting moieties (10e), (10j) and (10k) may exist in either one of the possible two regioisomers.

The bioconjugate that comprises or that is obtained by the present mode of conjugation is preferably represented by Formula (40) or (40b):

(40)

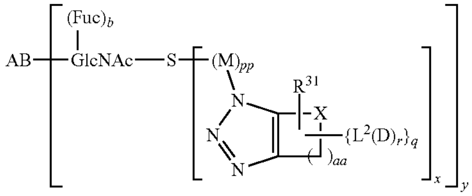

(40b)

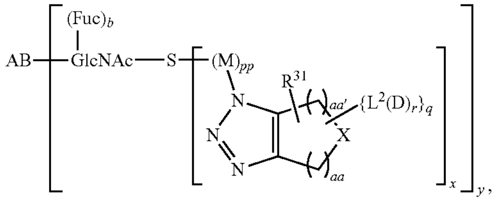

wherein:

AB is an antibody, S is a sugar or a sugar derivative, GlcNAc is N-acetylglucosamine;

$R^{31}$ is independently selected from the group consisting of hydrogen, halogen, —$OR^{35}$, —$NO_2$, —CN, —$S(O)_2R^{35}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{31}$ may be linked together to form an annelated cycloalkyl or an annelated (hetero)arene substituent, and wherein $R^{35}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

X is $C(R^{31})_2$, O, S or $NR^{32}$, wherein $R^{32}$ is $R^{31}$ or $L^2(D)_r$, wherein $L^2$ is a linker, and D is as defined in claim 1;

r is 1-20;

q is 0 or 1, with the proviso that if q is 0 then X is $NL^2(D)_r$;

aa is 0, 1, 2, 3, 4, 5, 6, 7 or 8;

aa' is 0, 1, 2, 3, 4, 5, 6, 7 or 8; and aa+aa'<10.

b is 0 or 1;

pp is 0 or 1;

M is —$N(H)C(O)CH_2$—, —$N(H)C(O)CF_2$—, —$CH_2$—, —$CF_2$— or a 1,4-phenylene containing 0-4 fluorine substituents, preferably 2 fluorine substituents which are preferably positioned on C2 and C6 or on C3 and C5 of the phenylene;

x is 1 or 2;

y is 1-4;

Fuc is fucose.

In a preferred embodiment, the antibody-conjugate according to the invention is of the Formula (41):

(41)

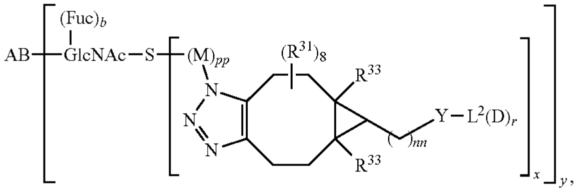

wherein AB, $L^2$, D, Y, S, M, x, y, b, pp, $R^{32}$, GlcNAc, $R^{31}$, $R^{33}$, $R^{34}$, nn and r are as defined above and wherein said N-acetylglucosamine is optionally fucosylated (b is 0 or 1).

In a further preferred embodiment, $R^{31}$, $R^{33}$ and $R^{34}$ are hydrogen and nn is 1 or 2, and in an even more preferred embodiment x is 1.

In another preferred embodiment, the antibody-conjugate is of the Formula (42):

(42)

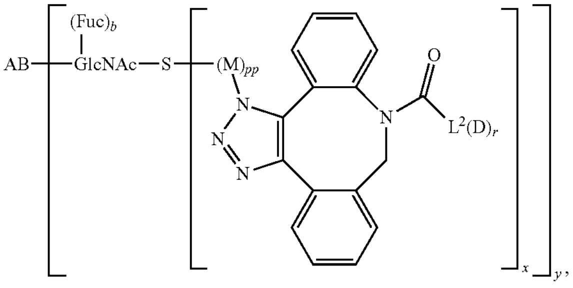

wherein AB, $L^2$, D, S, b, pp, x, y, M and GlcNAc are as defined above, and wherein said N-acetylglucosamine is optionally fucosylated (b is 0 or 1); or according to regioisomer (42b):

(42b)

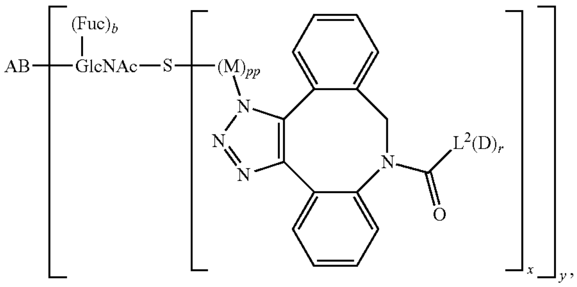

wherein AB, $L^2$, D, S, b, pp, x, y, M and GlcNAc are as defined above, and wherein said N-acetylglucosamine is optionally fucosylated.

In another preferred embodiment, the antibody-conjugate is of the Formula (35b):

(35b)

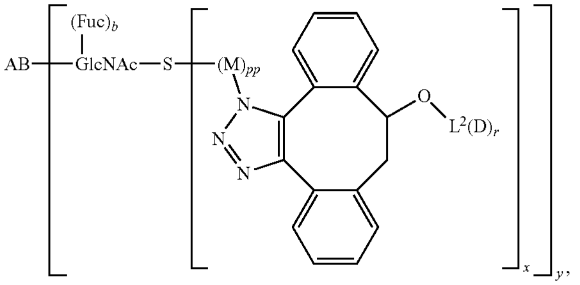

wherein AB, $L^2$, D, S, b, pp, x, y, M and GlcNAc are as defined above, and wherein said N-acetylglucosamine is optionally fucosylated.

In another preferred embodiment, the antibody-conjugate is of the Formula (40c):

(40c)

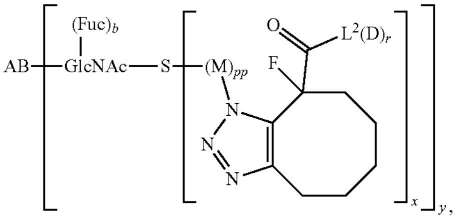

wherein AB, $L^2$, D, S, b, pp, x, y, M and GlcNAc are as defined above, and wherein said N-acetylglucosamine is optionally fucosylated.

In another preferred embodiment, the antibody-conjugate is of the Formula (40d):

(40d)

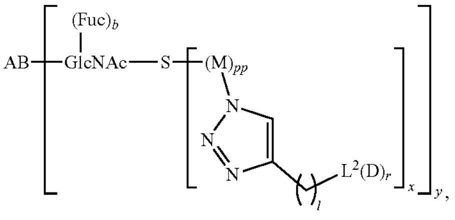

wherein AB, $L^2$, D, S, b, pp, x, y, M and GlcNAc are as defined above, wherein l is 0-10 and wherein said N-acetylglucosamine is optionally fucosylated.

Sulfamide Linkage

In one embodiment, the mode of conjugation according to the invention is referred to as "sulfamide linkage", which refers to the presence of a specific linker L which links the biomolecule B and the target molecule D. All said about the linker L in the context of the present embodiment preferably also applies to the linker, in particular linker $L^2$, according to the embodiment on core-GlcNAc functionalization as mode of conjugation. The linker L comprises a group according to formula (1) or a salt thereof:

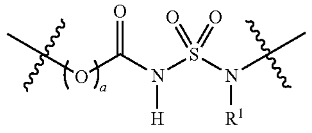

1 wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein D is optionally connected to N via a spacer moiety.

When the group of formula (1) comprises a salt, the salt is preferably a pharmaceutically acceptable salt.

In a preferred embodiment, linker L according to the invention comprises a group according to formula (1) wherein a is 0, or a salt thereof. In this embodiment, linker L thus comprises a group according to formula (2) or a salt thereof:

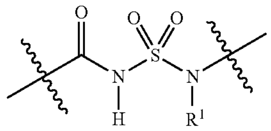

2 wherein $R^1$ is as defined above.

In another preferred embodiment, linker L according to the invention comprises a group according to formula (1) wherein a is 1, or a salt thereof. In this embodiment, linker L thus comprises a group according to formula (3) or a salt thereof:

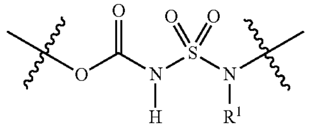

3 wherein $R^1$ is as defined above.

In the groups according to formula (1), (2) and (3), $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero) arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein D is optionally connected to N via a spacer moiety;

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_{10}$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a preferred embodiment, $R^1$ is hydrogen. In another preferred embodiment, $R^1$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^1$ is a (poly)ethyleneglycol chain comprising a terminal —OH group. In another preferred embodiment, $R^1$ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably $R^1$ is hydrogen or methyl, and most preferably $R^1$ is hydrogen.

In another preferred embodiment, $R^1$ is a further target molecule D. Optionally, D is connected to N via one or more spacer-moieties. The spacer-moiety, if present, is defined as a moiety that spaces, i.e. provides a certain distance between, and covalently links D and N.

Target molecule D and preferred embodiments thereof are defined in more detail above.

To obtain the bioconjugate of formula (A), the group of formula (1) can be introduced in one of three options. First of all, the linker L comprising the group according to formula (1) or a salt thereof may be present in the linker-conjugate represented by $Q^1$-D, wherein L is the spacer between $Q^1$ and D. Secondly, the linker L comprising the group according to formula (1) or a salt thereof may be present in the biomolecule represented by B-$F^1$, wherein L is the spacer between B and $F^1$. Thirdly, the group according to formula (1) or a salt thereof may be formed during the conjugation reaction itself. In the latter option, $Q^1$ and $F^1$ are selected as such that their reaction product, i.e. connecting group $Z^3$, contains or is the group according to formula (1) or a salt thereof. Preferably, the group according to formula (1) or a salt thereof is introduced according to the first or second of the above mentioned options, most preferably according to the first option. In case the group according to formula (1) or a salt thereof is already present as such during the conjugation reaction, the positive effect on solubility and absence of in-process aggregation, as recited above, improve the efficiency of the conjugation reaction. In case the group according to formula (1) or a salt thereof is present in the linker-conjugate, even hydrophobic drugs can readily be subjected to the conjugation reaction.

Linker-Conjugate

The linker-conjugate is represented by $Q^1$-D, preferably by $Q^1$-L-D, wherein D is a target molecule, L is a linker linking $Q^1$ and D as further defined above, $Q^1$ is a reactive group capable of reacting with functional group $F^1$ on the biomolecule and each occurrence of "-" is independently a bond or a spacer moiety. In one embodiment, "-" is a spacer moiety as defined herein. In one embodiment, "-" is a bond, typically a covalent bond. The linker-conjugate is a compound wherein a target molecule is covalently connected to a reactive group $Q^1$, preferably via a linker or spacer, most preferably via linker L as defined above. The linker-conjugate may be obtained via reaction of a reactive group $Q^2$ present on a linker-construct with a reactive group present on a target molecule.

Preferably, the group according to formula (1), or the salt thereof, is situated in between $Q^1$ and D. In other words, reactive group $Q^1$ is covalently bonded to a first end of the group according to formula (1), and target molecule D is covalently bonded to a second end of the group according to formula (1). Herein, "first end" and "second end" both refer to either the carbonyl or carboxy end of the group according to formula (1) or to the sulfamide end of the group according to formula (1), but logically not to the same end.

As will be appreciated by the person skilled in the art, the linker-conjugate according to the invention may comprise more than one target molecule D, e.g. two, three, four, five, etc. Consequently, the linker-conjugate may thus comprise more than one "second end". Similarly, the linker-conjugate may comprise more than one reactive group $Q^1$, i.e. the linker-conjugate may comprise more than one first end. When more than one reactive group $Q^1$ is present the groups $Q^1$ may be the same or different, and when more than one target molecule D is present the target molecule D may be the same or different.

The linker-conjugate according to the invention may therefore also be denoted as $(Q^1)_{y'}Sp(D)_z$, wherein y' is an integer in the range of 1 to 10 and z is an integer in the range of 1 to 10. Herein:

y' is an integer in the range of 1 to 10;

z is an integer in the range of 1 to 10;

$Q^1$ is a reactive group capable of reacting with a functional group $F^1$ present on a biomolecule;

D is an target molecule;

Sp is a spacer moiety, wherein a spacer moiety is defined as a moiety that spaces (i.e. provides a certain distance between) and covalently links reactive group $Q^1$ and target molecule D, preferably wherein said spacer moiety is linker L as defined above, and thus comprises a group according to formula (1) or a salt thereof.

Preferably, y' is 1, 2, 3 or 4, more preferably y' is 1 or 2 and most preferably, y' is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y' is 1 or 2, preferably 1, and z is 1, 2, 3 or 4, yet even more preferably y' is 1 or 2, preferably 1, and z is 1, 2 or 3, yet even more preferably y' is 1 or 2, preferably 1, and z is 1 or 2, and most preferably y' is 1 and z is 1. In a preferred embodiment, the linker-conjugate is according to the formula $Q^1Sp(D)_4$, $Q^1Sp(D)_3$, $Q^1Sp(D)_2$ or $Q^1SpD$.

D is preferably an "active substance" or "pharmaceutically active substance", and refers to a pharmacological and/or biological substance, i.e. a substance that is biologically and/or pharmaceutically active, for example a drug, a prodrug, a diagnostic agent. Preferably, the active substance is selected from the group consisting of drugs and prodrugs. More preferably, the active substance is a pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, enediynes, an inhibitory peptide, amanitin, deBouganin, duocarmycins, maytansines, auristatins, pyrrolobenzodiazepines (PBDs) or indolinobenzodiazepines (IBDs). Preferred active substances include enediynes, anthracyclines, camptothecins, taxanes, tubulysins, amanitin, duocarmycins, maytansines, auristatins, pyrrolobenzodiazepines or indolinobenzodiazepines, in particular enediynes, anthracyclines, pyrrolobenzodiazepines (PBDs), maytansines and auristatins.

The linker-conjugate comprises a reactive group $Q^1$ that is capable of reacting with a functional group $F^1$ present on a biomolecule. Functional groups are known to a person skilled in the art and may be defined as any molecular entity that imparts a specific property onto the molecule harbouring it. For example, a functional group in a biomolecule may constitute an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne or a phosphine moiety. Herein, the term "reactive group" may refer to a certain group that comprises a functional group, but also to a functional group itself. For example, a cyclooctynyl group is a reactive group comprising a functional group, namely a C—C triple bond. Similarly, an N-maleimidyl group is a reactive group, comprising a C—C double bond as a functional group. However, a functional group, for example an azido functional group, a thiol functional group or an amino functional group, may herein also be referred to as a reactive group. The linker-conjugate may comprise more than one reactive group $Q^1$. When the linker-conjugate comprises two or more reactive groups $Q^1$, the reactive groups $Q^1$ may differ from each other. Preferably, the linker-conjugate comprises one reactive group $Q^1$.

Reactive group $Q^1$ that is present in the linker-conjugate, is able to react with a functional group $F^1$ that is present in a biomolecule to form connecting group $Z^3$. In other words, reactive group $Q^1$ needs to be complementary to a functional group $F^1$ present in a biomolecule. Herein, a reactive group is denoted as "complementary" to a functional group when said reactive group reacts with said functional group selectively to form connecting group $Z^3$, optionally in the presence of other functional groups. Complementary reactive and functional groups are known to a person skilled in the art, and are described in more detail below.

In a preferred embodiment, reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups, allenamide groups, 1,2-quinone groups or triazine groups.

In a preferred embodiment, $Q^1$ is an N-maleimidyl group. When $Q^1$ is an N-maleimidyl group, $Q^1$ is preferably unsubstituted. $Q^1$ is thus preferably according to formula (9a), as shown below. A preferred example of such a maleimidyl group is 2,3-diaminopropionic acid (DPR) maleimidyl, which may be connected to the remainder of the linker-conjugate through the carboxylic acid moiety.

In another preferred embodiment, $Q^1$ is a halogenated N-alkylamido group. When $Q^1$ is a halogenated N-alkylamido group, it is preferred that $Q^1$ is according to formula (9b), as shown below, wherein k is an integer in the range of 1 to 10 and $R^4$ is selected from the group consisting of —Cl, —Br and —I. Preferably k is 1, 2, 3 or 4, more preferably k is 1 or 2 and most preferably k is 1. Preferably, $R^4$ is —I or —Br. More preferably, k is 1 or 2 and $R^4$ is —I or —Br, and most preferably k is 1 and $R^4$ is —I or Br.

In another preferred embodiment, $Q^1$ is a sulfonyloxy N-alkylamido group. When $Q^1$ is a sulfonyloxy N-alkylamido group, it is preferred that $Q^1$ is according to formula (9b), as shown below, wherein k is an integer in the range of 1 to 10 and $R^4$ is selected from the group consisting of —O-mesyl, —O-phenylsulfonyl and —O-tosyl. Preferably k is 1, 2, 3 or 4, more preferably k is 1 or 2, even more preferably k is 1. Most preferably k is 1 and $R^4$ is selected from the group consisting of —O-mesyl, —O-phenylsulfonyl and —O-tosyl.

In another preferred embodiment, $Q^1$ is an ester group. When $Q^1$ is an ester group, it is preferred that the ester group is an activated ester group. Activated ester groups are known to the person skilled in the art. An activated ester group is herein defined as an ester group comprising a good leaving group, wherein the ester carbonyl group is bonded to said good leaving group. Good leaving groups are known to the person skilled in the art. It is further preferred that the activated ester is according to formula (9c), as shown below, wherein $R^5$ is selected from the group consisting of —N-succinimidyl (NHS), —N-sulfo-succinimidyl (sulfo-NHS), -(4-nitrophenyl), -pentafluorophenyl or -tetrafluorophenyl (TFP).

In another preferred embodiment, $Q^1$ is a carbonate group. When $Q^1$ is a carbonate group, it is preferred that the carbonate group is an activated carbonate group. Activated carbonate groups are known to a person skilled in the art. An activated carbonate group is herein defined as a carbonate group comprising a good leaving group, wherein the carbonate carbonyl group is bonded to said good leaving group. It is further preferred that the carbonate group is according to formula (9d), as shown below, wherein $R^7$ is selected from the group consisting of —N— succinimidyl, —N-sulfo-succinimidyl, -(4-nitrophenyl), -pentafluorophenyl or -tetrafluorophenyl.

In another preferred embodiment, $Q^1$ is a sulfonyl halide group according to formula (9e) as shown below, wherein X is selected from the group consisting of F, Cl, Br and I. Preferably X is Cl or Br, more preferably Cl.

In another preferred embodiment, $Q^1$ is a thiol group (9f), or a derivative or a precursor of a thiol group. A thiol group may also be referred to as a mercapto group. When $Q^1$ is a derivative or a precursor of a thiol group, the thiol derivative is preferably according to formula (9g), (9h) or (9zb) as shown below, wherein $R^8$ is an, optionally substituted, $C_1$-$C_{12}$ alkyl group or a $C_2$-$C_{12}$ (hetero)aryl group, V is O or S and $R^{16}$ is an, optionally substituted, $C_1$-$C_{12}$ alkyl group. More preferably $R^8$ is an, optionally substituted, $C_1$-$C_6$ alkyl group or a $C_2$-$C_6$ (hetero)aryl group, and even more preferably $R^8$ is methyl, ethyl, n-propyl, i-propyl, n-butyl, s-butyl, t-butyl or phenyl. Even more preferably, $R^8$ is methyl or phenyl, most preferably methyl. More preferably $R^{16}$ is an optionally substituted $C_1$-$C_6$ alkyl group, and even more preferably $R^{16}$ is methyl, ethyl, n-propyl, i-propyl, n-butyl, s-butyl or t-butyl, most preferably methyl. When $Q^1$ is a thiol-derivative according to formula (9g) or (9zb), and $Q^1$ is reacted with a reactive group $F^1$ on a biomolecule, said thiol-derivative is converted to a thiol group during the process. When $Q^1$ is according to formula (9h), $Q^1$ is —SC(O)OR$^8$ or —SC(S)OR$^8$, preferably SC(O)OR$^8$, wherein $R^8$, and preferred embodiments thereof, are as defined above.

In another preferred embodiment, $Q^1$ is an alkenyl group, wherein the alkenyl group is linear or branched, and wherein the alkenyl group is optionally substituted. The alkenyl group may be a terminal or an internal alkenyl group. The alkenyl group may comprise more than one C—C double bond, and if so, preferably comprises two C—C double bonds. When the alkenyl group is a dienyl group, it is further preferred that the two C—C double bonds are separated by one C—C single bond (i.e. it is preferred that the dienyl group is a conjugated dienyl group). Preferably said alkenyl group is a $C_2$-$C_{24}$ alkenyl group, more preferably a $C_2$-$C_{12}$ alkenyl group, and even more preferably a $C_2$-$C_6$ alkenyl group. It is further preferred that the alkenyl group is a terminal alkenyl group. More preferably, the alkenyl group is according to formula (9i) as shown below, wherein l is an integer in the range of 0 to 10, preferably in the range of 0 to 6, and p is an integer in the range of 0 to 10, preferably 0 to 6. More preferably, l is 0, 1, 2, 3 or 4, more preferably l is 0, 1 or 2 and most preferably l is 0 or 1. More preferably, p is 0, 1, 2, 3 or 4, more preferably p is 0, 1 or 2 and most preferably p is 0 or 1. It is particularly preferred that p is 0 and l is 0 or 1, or that p is 1 and l is 0 or 1.

In another preferred embodiment, $Q^1$ is an alkynyl group, wherein the alkynyl group is linear or branched, and wherein the alkynyl group is optionally substituted. The alkynyl group may be a terminal or an internal alkynyl group. Preferably said alkynyl group is a $C_2$-$C_{24}$ alkynyl group, more preferably a $C_2$-$C_{12}$ alkynyl group, and even more preferably a $C_2$-$C_6$ alkynyl group. It is further preferred that the alkynyl group is a terminal alkynyl group. More preferably, the alkynyl group is according to formula (9j) as shown below, wherein l is an integer in the range of 0 to 10, preferably in the range of 0 to 6. More preferably, l is 0, 1, 2, 3 or 4, more preferably l is 0, 1 or 2 and most preferably l is 0 or 1. In a further preferred embodiment, the alkynyl group is according to formula (9j) wherein l is 3.

In another preferred embodiment, $Q^1$ is a cycloalkenyl group. The cycloalkenyl group is optionally substituted. Preferably said cycloalkenyl group is a $C_3$-$C_{24}$ cycloalkenyl group, more preferably a $C_3$-$C_{12}$ cycloalkenyl group, and even more preferably a $C_3$-$C_8$ cycloalkenyl group. In a preferred embodiment, the cycloalkenyl group is a trans-cycloalkenyl group, more preferably a trans-cyclooctenyl group (also referred to as a TCO group) and most preferably a trans-cyclooctenyl group according to formula (9zi) or (9zj) as shown below. In another preferred embodiment, the cycloalkenyl group is a cyclopropenyl group, wherein the cyclopropenyl group is optionally substituted. In another preferred embodiment, the cycloalkenyl group is a norbornenyl group, an oxanorbornenyl group, a norbornadienyl group or an oxanorbornadienyl group, wherein the norbornenyl group, oxanorbornenyl group, norbornadienyl group or an oxanorbornadienyl group is optionally substituted. In a further preferred embodiment, the cycloalkenyl group is according to formula (9k), (9l), (9m) or (9zc) as shown below, wherein T is $CH_2$ or O, $R^9$ is independently selected from the group consisting of hydrogen, a linear or branched $C_1$-$C_{12}$ alkyl group or a $C_4$-$C_{12}$ (hetero)aryl group, and $R^{19}$ is selected from the group consisting of hydrogen and fluorinated hydrocarbons. Preferably, $R^9$ is independently hydrogen or a $C_1$-$C_6$ alkyl group, more preferably $R^9$ is independently hydrogen or a $C_1$-$C_4$ alkyl group. Even more preferably $R^9$ is independently hydrogen or methyl, ethyl, n-propyl, i-propyl, n-butyl, s-butyl or t-butyl. Yet even more preferably $R^9$ is independently hydrogen or methyl. In a further preferred embodiment, $R^{19}$ is selected from the group of hydrogen and —$CF_3$, —$C_2F_5$, —$C_3F_7$ and —$C_4F_9$, more preferably hydrogen and —$CF_3$. In a further preferred embodiment, the cycloalkenyl group is according to formula (9k), wherein one $R^9$ is hydrogen and the other $R_9$ is a methyl group. In another further preferred embodiment, the cycloalkenyl group is according to formula (9l), wherein both $R^9$ are hydrogen. In these embodiments it is further preferred that l is 0 or 1. In another further preferred embodiment, the cycloalkenyl group is a norbornenyl (T is $CH_2$) or an oxanorbornenyl (T is O) group according to formula (9m), or a norbornadienyl (T is $CH_2$) or an oxanorbornadienyl (T is O) group according to formula (9zc), wherein $R^9$ is hydrogen and $R^{19}$ is hydrogen or —$CF_3$, preferably —$CF_3$.

In another preferred embodiment, $Q^1$ is a (hetero)cycloalkynyl group. The (hetero)cycloalkynyl group is optionally substituted. Preferably, the (hetero)cycloalkynyl group is a (hetero)cyclooctynyl group, i.e. a heterocyclooctynyl group or a cyclooctynyl group, wherein the (hetero)cyclooctynyl group is optionally substituted. In a further preferred embodiment, the (hetero)cyclooctynyl group is substituted with one or more halogen atoms, preferably fluorine atoms, more preferably the (hetero)cyclooctynyl group is substituted with one fluorine atom, as in mono-fluoro-cyclooctcyne (MFCO). Preferably, the mono-fluoro-cyclooctcyne group is according to formula (9zo). In a further preferred embodiment, the (hetero)cyclooctynyl group is according to formula (9n), also referred to as a DIBO group, (9o), also referred to as a DIBAC group or (9p), also referred to as a BARAC group, or (9zk), also referred to as a COMBO group, all as shown below, wherein U is O or NR$^9$, and preferred embodiments of $R^9$ are as defined above. The aromatic rings in (9n) are optionally O-sulfonylated at one or more positions, whereas the rings of (9o) and (9p) may be halogenated at one or more positions. For (9n), U is preferably O.

In an especially preferred embodiment, the nitrogen atom attached to $R^1$ in compound (4b) is the nitrogen atom in the ring of the heterocycloalkyne group such as the nitrogen atom in (9o). In other words, c, d and g are 0 in compound (4b) and $R^1$ and $Q^1$, together with the nitrogen atom they are attached to, form a heterocycloalkyne group, preferably a heterocyclooctyne group, most preferably the heterocyclooctyne group according to formula (9o) or (9p). Herein, the carbonyl moiety of (9o) is replaced by the sulfonyl group of the group according to formula (1). Alternatively, the nitrogen atom to which $R^1$ is attached is the same atom as the atom designated as U in formula (9n). In other words, when $Q^1$ is according to formula (9n), U may be the right nitrogen atom of the group according to formula (1), or U=NR$^9$ and $R^9$ is the remainder of the group according to formula (1) and $R^1$ is the cyclooctyne moiety.

In another preferred embodiment, $Q^1$ is an, optionally substituted, bicyclo[6.1.0]non-4-yn-9-yl]group, also referred to as a BCN group. Preferably, the bicyclo[6.1.0]non-4-yn-9-yl] group is according to formula (9q) as shown below.

In another preferred embodiment, $Q^1$ is a conjugated (hetero)diene group capable of reacting in a Diels-Alder reaction. Preferred (hetero)diene groups include optionally substituted tetrazinyl groups, optionally substituted 1,2-quinone groups and optionally substituted triazine groups. More preferably, said tetrazinyl group is according to formula (9r), as shown below, wherein $R^9$ is selected from the group consisting of hydrogen, a linear or branched $C_1$-$C_{12}$ alkyl group or a $C_4$-$C_{12}$ (hetero)aryl group. Preferably, $R^9$ is hydrogen, a $C_1$-$C_6$ alkyl group or a $C_4$-$C_{10}$ (hetero)aryl group, more preferably $R^9$ is hydrogen, a $C_1$-$C_4$ alkyl group or a $C_4$-$C_6$ (hetero)aryl group. Even more preferably $R^9$ is hydrogen, methyl, ethyl, n-propyl, i-propyl, n-butyl, s-butyl, t-butyl or pyridyl. Yet even more preferably $R^9$ is hydrogen, methyl or pyridyl. More preferably, said 1,2-quinone group is according to formula (9zl) or (9zm). Said triazine group may be any regioisomer. More preferably, said triazine group is a 1,2,3-triazine group or a 1,2,4-triazine group, which may be attached via any possible location, such as indicated in formula (9zn). The 1,2,3-triazine is most preferred as triazine group.

In another preferred embodiment, $Q^1$ is an azido group according to formula (9s) as shown below. In another preferred embodiment, $Q^1$ is an, optionally substituted, triarylphosphine group that is suitable to undergo a Staudinger ligation reaction. Preferably, the phosphine group is according to formula (9t) as shown below, wherein $R^{10}$ is a (thio)ester group. When $R^{10}$ is a (thio)ester group, it is preferred that $R^{10}$ is —C(O)—V-$R^{11}$, wherein V is O or S and $R^{11}$ is a $C_1$-$C_{12}$ alkyl group. Preferably, $R^{11}$ is a $C_1$-$C_6$ alkyl group, more preferably a $C_1$-$C_4$ alkyl group. Most preferably, $R^{11}$ is a methyl group.

In another preferred embodiment, $Q^1$ is a nitrile oxide group according to formula (9u) as shown below.

In another preferred embodiment, $Q^1$ is a nitrone group. Preferably, the nitrone group is according to formula (9v) as shown below, wherein $R^{12}$ is selected from the group consisting of linear or branched $C_1$-$C_{12}$ alkyl groups and $C_6$-$C_{12}$ aryl groups. Preferably, $R^{12}$ is a $C_1$-$C_6$ alkyl group, more preferably $R^{12}$ is a $C_1$-$C_4$ alkyl group. Even more preferably $R^{12}$ is methyl, ethyl, n-propyl, i-propyl, n-butyl, s-butyl or t-butyl. Yet even more preferably $R^{12}$ is methyl.

In another preferred embodiment, $Q^1$ is a nitrile imine group. Preferably, the nitrile imine group is according to formula (9w) or (9zd) as shown below, wherein $R^{13}$ is selected from the group consisting of linear or branched $C_1$-$C_{12}$ alkyl groups and $C_6$-$C_{12}$ aryl groups. Preferably, $R^{13}$ is a $C_1$-$C_6$ alkyl group, more preferably $R^{13}$ is a $C_1$-$C_4$ alkyl group. Even more preferably $R^{13}$ is methyl, ethyl, n-propyl, i-propyl, n-butyl, s-butyl or t-butyl. Yet even more preferably $R^{13}$ is methyl.

In another preferred embodiment, $Q^1$ is a diazo group. Preferably, the diazo group is according to formula (9x) as shown below, wherein $R^{14}$ is selected from the group consisting of hydrogen or a carbonyl derivative. More preferably, $R^{14}$ is hydrogen.

In another preferred embodiment, $Q^1$ is a ketone group. More preferably, the ketone group is according to formula (9y) as shown below, wherein $R^{15}$ is selected from the group consisting of linear or branched $C_1$-$C_{12}$ alkyl groups and $C_6$-$C_{12}$ aryl groups. Preferably, $R^{15}$ is a $C_1$-$C_6$ alkyl group, more preferably $R^{15}$ is a $C_1$-$C_4$ alkyl group. Even more preferably $R^{15}$ is methyl, ethyl, n-propyl, i-propyl, n-butyl, s-butyl or t-butyl. Yet even more preferably $R^{15}$ is methyl.

In another preferred embodiment, $Q^1$ is an (O-alkyl) hydroxylamino group. More preferably, the (O-alkyl)hydroxylamino group is according to formula (9z) as shown below.

In another preferred embodiment, $Q^1$ is a hydrazine group. Preferably, the hydrazine group is according to formula (9za) as shown below.

In another preferred embodiment, $Q^1$ is a halogenated N-maleimidyl group or a sulfonylated N-maleimidyl group. When $Q^1$ is a halogenated or sulfonylated N-maleimidyl group, $Q^1$ is preferably according to formula (9ze) as shown below, wherein $R^6$ is independently selected from the group consisting of hydrogen F, Cl, Br, I —$SR^{18a}$ and —$OS(O)_2R^{18b}$, wherein $R^{18a}$ is an optionally substituted $C_4$-$C_{12}$ (hetero)aryl groups, preferably phenyl or pyrydyl, and $R^{18b}$ is selected from the group consisting of, optionally substituted, $C_1$-$C_{12}$ alkyl groups and $C_4$-$C_{12}$ (hetero)aryl groups, preferably tolyl or methyl, and with the proviso that at least one $R^6$ is not hydrogen. When $R^6$ is halogen (i.e. when $R^6$ is F, Cl, Br or I), it is preferred that $R^6$ is Br. In one embodiment, the halogenated N-maleimidyl group is halogenated 2,3-diaminopropionic acid (DPR) maleimidyl, which may be connected to the remainder of the linker-conjugate through the carboxylic acid moiety.

In another preferred embodiment, $Q^1$ is a carbonyl halide group according to formula (9zf) as shown below, wherein X is selected from the group consisting of F, Cl, Br and I. Preferably, X is Cl or Br, and most preferably, X is Cl.

In another preferred embodiment, $Q^1$ is an allenamide group according to formula (9zg).

In another preferred embodiment, $Q^1$ is a 1,1-bis(sulfonylmethyl)methylcarbonyl group according to formula (9zh), or an elimination derivative thereof, wherein $R^{18}$ is selected from the group consisting of, optionally substituted, $C_1$-$C_{12}$ alkyl groups and $C_4$-$C_{12}$ (hetero)aryl groups. More preferably, $R^{18}$ is an, optionally substituted, $C_1$-$C_6$ alkyl group or a $C_4$-$C_6$ (hetero)aryl group, and most preferably a phenyl group.

9a

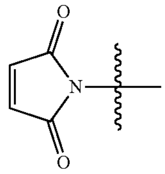

9b

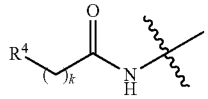

9c

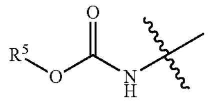

9d

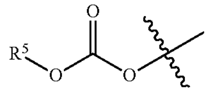

9e

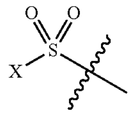

9f

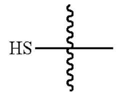

-continued
9g
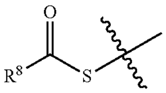
9h
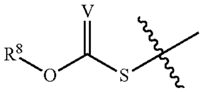
9i
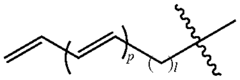
9j
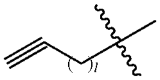
9k
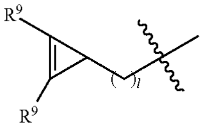
9l
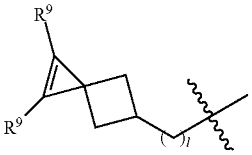
9m
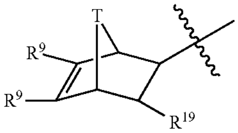
9n
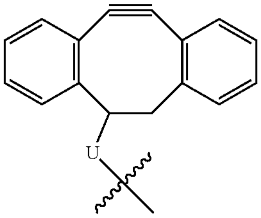
9o
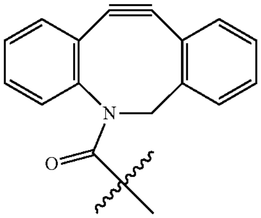
9p
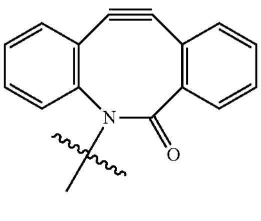
-continued
9q
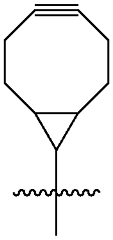
9r
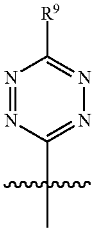
9s
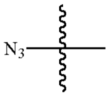
9t
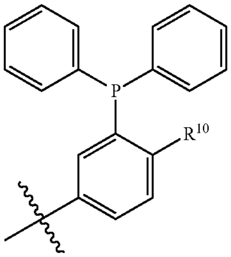
9u
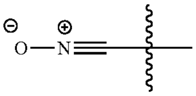
9v
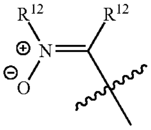
9w
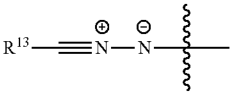
9x
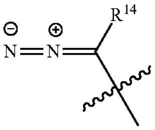
9y
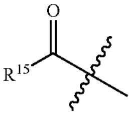
9z
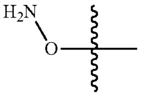

-continued

9za

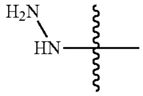

9zb

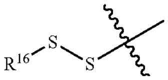

9zc

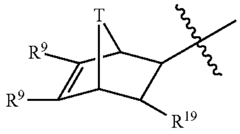

9zd

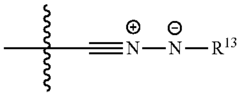

9ze

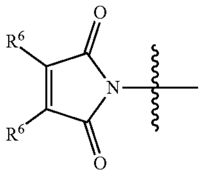

9zf

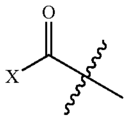

9zg

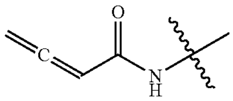

9zh

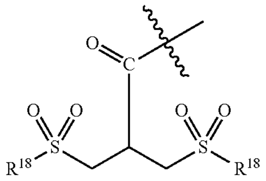

9zi

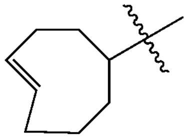

9zj

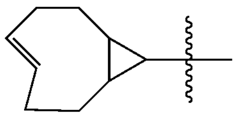

9zo

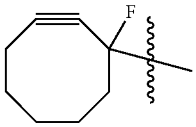

-continued

9zk

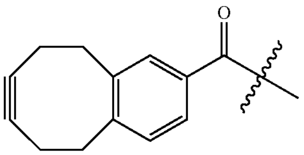

9zl

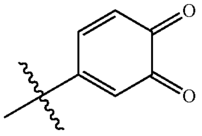

9zm

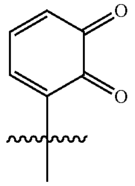

9zn

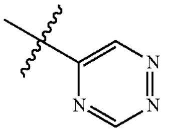

wherein k, l, X, T, U, V, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$ and $R^{19}$ are as defined above.

In a preferred embodiment of the conjugation process according to the invention as described herein below, conjugation is accomplished via a cycloaddition, such as a Diels-Alder reaction or a 1,3-dipolar cycloaddition, preferably the 1,3-dipolar cycloaddition. According to this embodiment, the reactive group $Q^1$ (as well as $F^1$ on the biomolecule) is selected from groups reactive in a cycloaddition reaction. Herein, reactive groups $Q^1$ and $F^1$ are complementary, i.e. they are capable of reacting with each other in a cycloaddition reaction, the obtained cyclic moiety being connecting group $Z^3$.

For a Diels-Alder reaction, one of $F^1$ and $Q^1$ is a diene and the other of $F^1$ and $Q^1$ is a dienophile. As appreciated by the skilled person, the term "diene" in the context of the Diels-Alder reaction refers to 1,3-(hetero)dienes, and includes conjugated dienes ($R_2C{\equiv}CR{-}CR{=}CR_2$), imines (e.g. $R^2C{=}CR{-}N{=}CR_2$ or $R^2C{\equiv}CR{-}CR{=}NR$, $R^2C{=}N{-}N{=}CR_2$) and carbonyls (e.g. $R^2C{\equiv}CR{-}CR{=}O$ or $O{=}CR{-}CR{=}O$). Hetero-Diels-Alder reactions with N- and O-containing dienes are known to a person skilled in the art. Any diene known in the art to be suitable for Diels-Alder reactions may be used as reactive group $Q^1$ or $F^1$. Preferred dienes include tetrazines as described above, 1,2-quinones as described above and triazines as described above. Although any dienophile known in the art to be suitable for Diels-Alder reactions may be used as reactive groups $Q^1$ or F, the dienophile is preferably an alkene or alkyne group as described above, most preferably an alkyne group. For conjugation via a Diels-Alder reaction, it is preferred that $F^1$ is the diene and $Q^1$ is the dienophile. Herein, when $Q^1$ is a diene, $F^1$ is a dienophile and when $Q^1$ is a dienophile, $F^1$ is a diene. Most preferably, $Q^1$ is a dienophile, preferably $Q^1$ is or comprises an alkynyl group, and $F^1$ is a diene, preferably a tetrazine, 1,2-quinone or triazine group.

For a 1,3-dipolar cycloaddition, one of $F^1$ and $Q^1$ is a 1,3-dipole and the other of $F^1$ and $Q^1$ is a dipolarophile. Any 1,3-dipole known in the art to be suitable for 1,3-dipolar cycloadditions may be used as reactive group $Q^1$ or F. Preferred 1,3-dipoles include azido groups, nitrone groups, nitrile oxide groups, nitrile imine groups and diazo groups. Although any dipolarophile known in the art to be suitable for 1,3-dipolar cycloadditions may be used as reactive groups $Q^1$ or $F^1$, the dipolarophile is preferably an alkene or alkyne group, most preferably an alkyne group. For conjugation via a 1,3-dipolar cycloaddition, it is preferred that $F^1$ is the 1,3-dipole and $Q^1$ is the dipolarophile. Herein, when $Q^1$ is a 1,3-dipole, $F^1$ is a dipolarophile and when $Q^1$ is a dipolarophile, $F^1$ is a 1,3-dipole. Most preferably, $Q^1$ is a dipolarophile, preferably $Q^1$ is or comprises an alkynyl group, and $F^1$ is a 1,3-dipole, preferably an azido group.

Thus, in a preferred embodiment, $Q^1$ is selected from dipolarophiles and dienophiles. Preferably, $Q^1$ is an alkene or an alkyne group. In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q), (9zk) and (9zo) as defined above and depicted below, such as selected from the formulae (9j), (9n), (9o), (9p), (9q) and (9zk), more preferably selected from the formulae (9n), (9o), (9p), (9q) and (9zk) or from the formulae (9j), (9n), (9q) and (9zo). Most preferably, $Q^1$ is a bicyclo[6.1.0]non-4-yn-9-yl] group, preferably of formula (9q). These groups are known to be highly effective in the conjugation with azido-functionalized biomolecules as described herein, and when the sulfamide linker according to the invention is employed in such linker-conjugates, any aggregation is beneficially reduced to a minimum.

Figure 5:
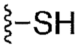
FIG. 5 shows a representative set of functional groups ($F^1$) in a biomolecule, either naturally present or introduced by engineering, which upon reaction with reactive group $Q^1$ lead to connecting group $Z^3$. Functional group $F^1$ may also be artificially introduced (engineered) into a biomolecule at any position of choice.
Figure 5:
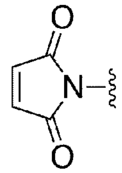
Figure 5:
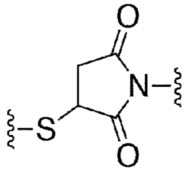
Figure 5:
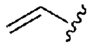
Figure 5:
Figure 5:
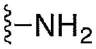
Figure 5:
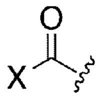
Figure 5:
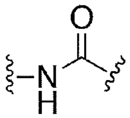
Figure 5:
Figure 5:
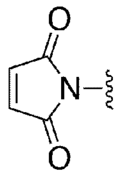
Figure 5:
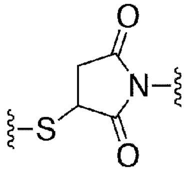
Figure 5:
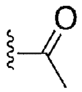
Figure 5:
Figure 5:
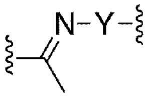
Figure 5:
Figure 5:
Figure 5:
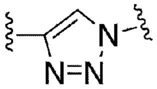
Figure 5:
Figure 5:
Figure 5:
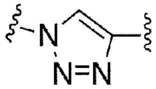
Figure 5:
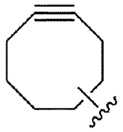
Figure 5:
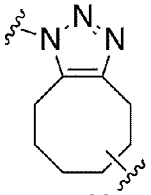
Figure 5:
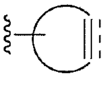
Figure 5:
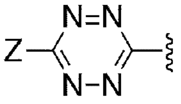
Figure 5:
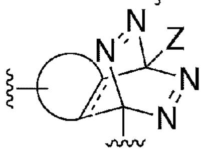
Figure 6:
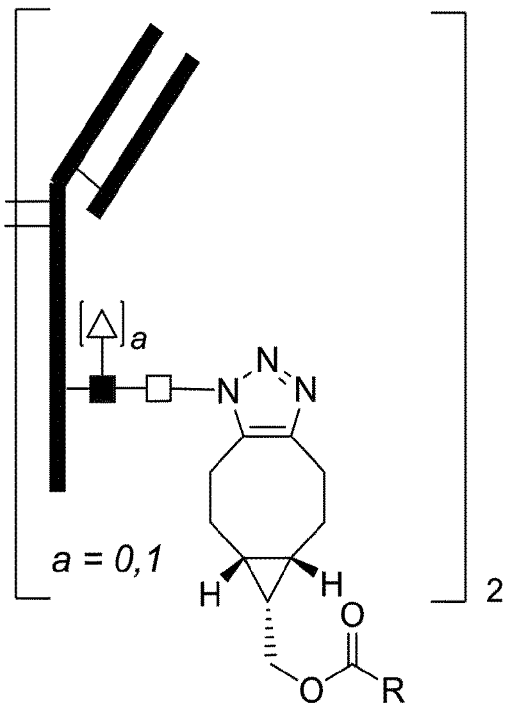
FIG. 6 shows preferred bioconjugates according to the invention. Conjugates 81-85 are prepared and the therapeutic index thereof investigated in the examples. Conjugates 81-85 are conjugated to trastuzumab as antibody.
Figure 6:
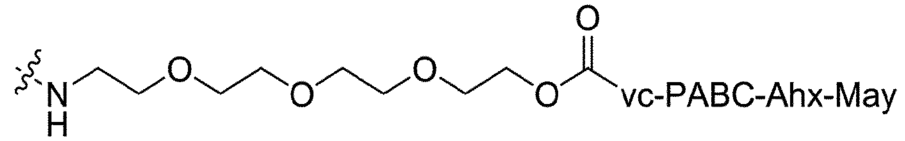
Figure 6:
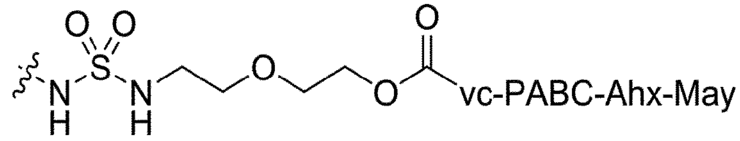
Figure 6:
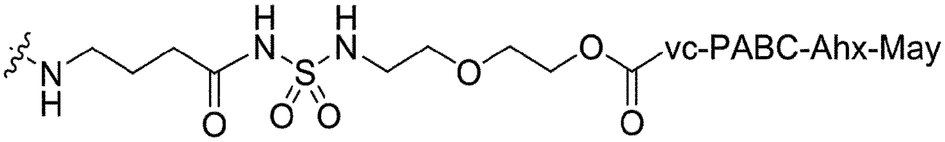
Figure 6:
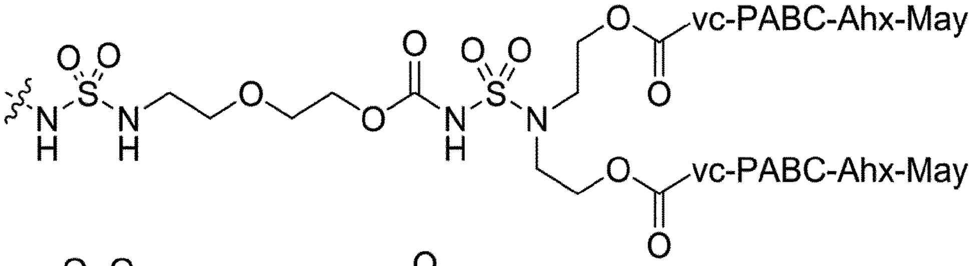
Figure 6:
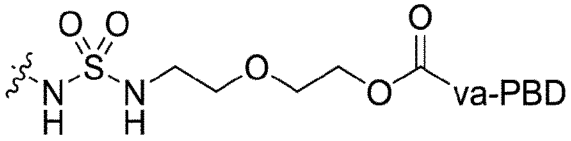
Figure 7A:
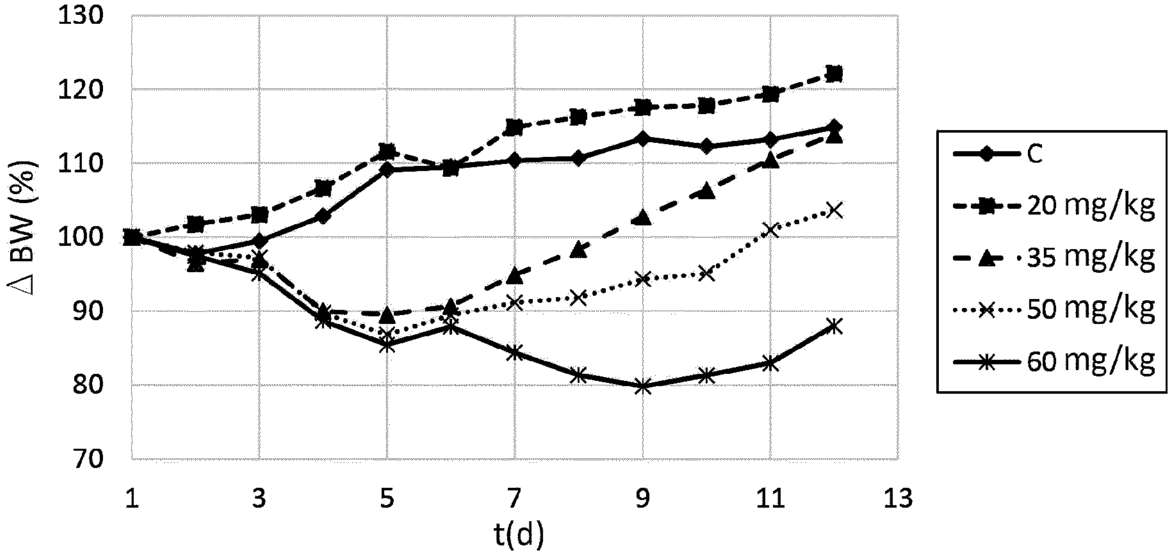
FIGS. 7A-E depict the results of the tolerability studies of Example 34 for control antibody-conjugate Kadcyla (FIG. 7A) and antibody-conjugates according to the invention 84 (FIG. 7B), 81 (FIG. 7C), 82 (FIG. 7D), 83 (FIG. 7E). Percentage body weight change (ΔBW), based on 100% on the start of treatment (day 1), over time is depicted. C=vehicle treated.
Figure 7B:
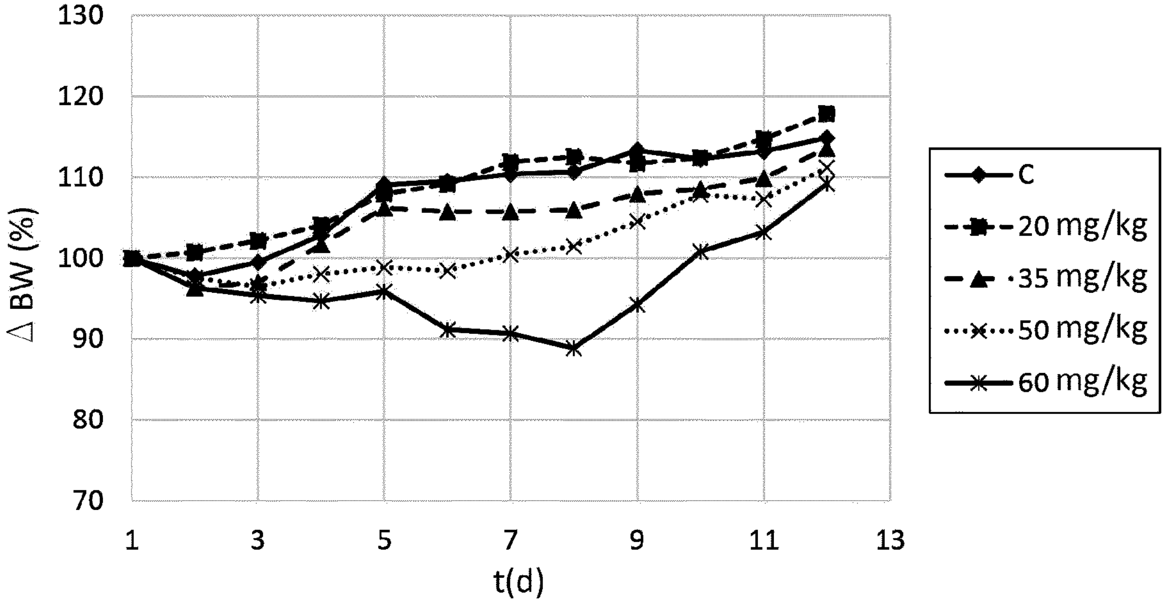
Figure 7C:
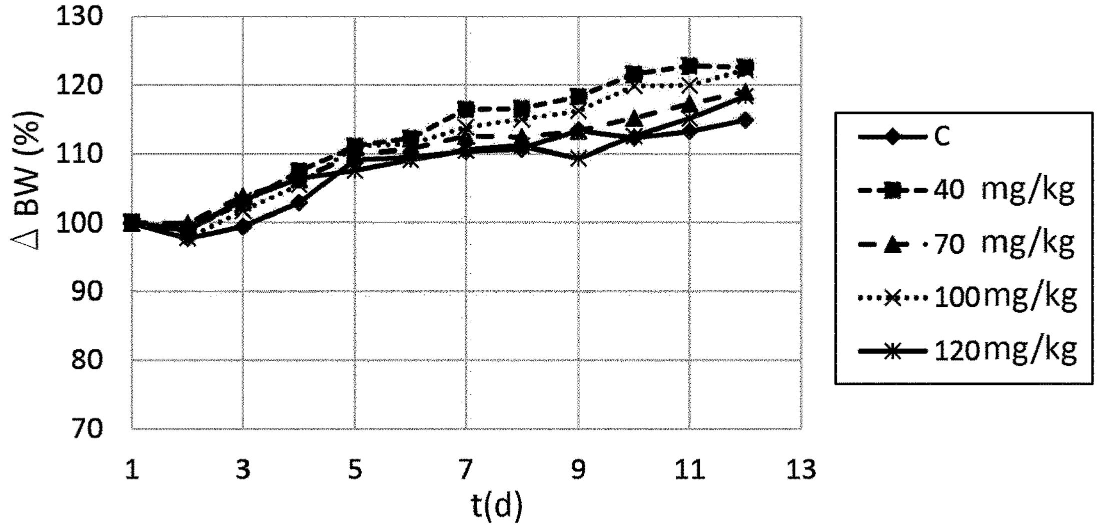
Figure 7D:
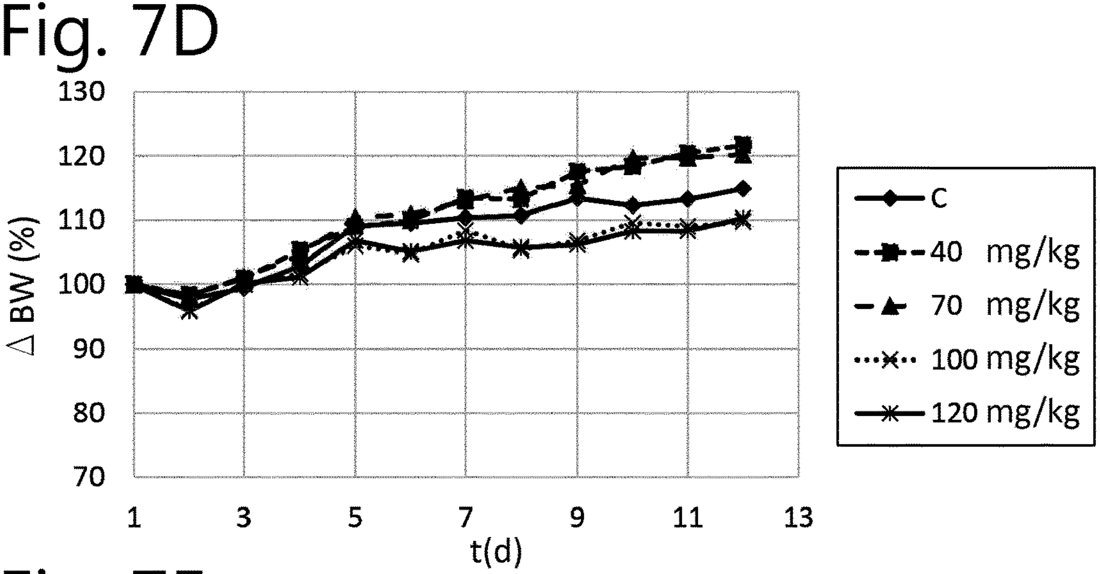
Figure 7E:
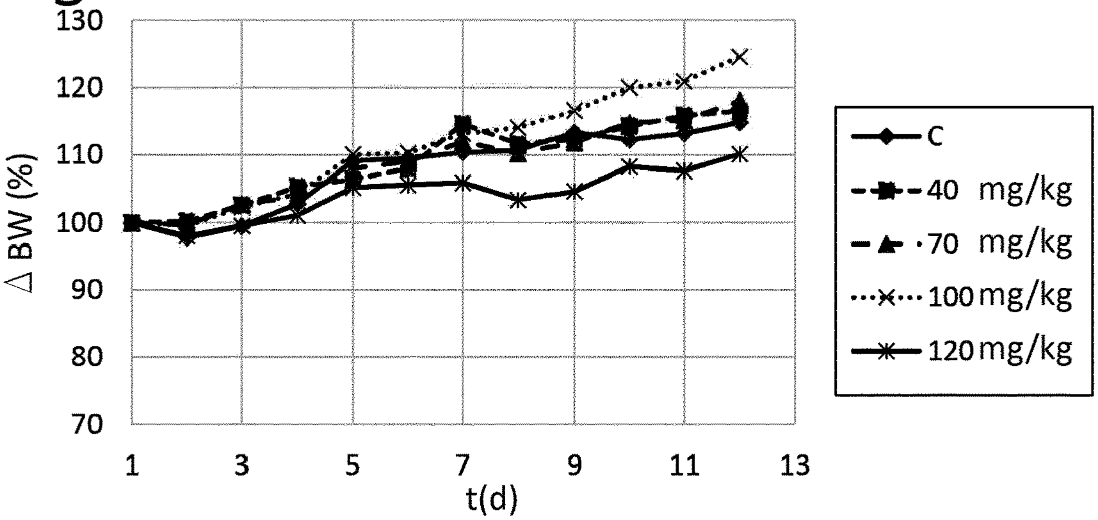

As was described above, in the linker-conjugate, $Q^1$ is capable of reacting with a reactive group $F^1$ that is present on a biomolecule. Complementary reactive groups $F^1$ for reactive group $Q^1$ are known to a person skilled in the art, and are described in more detail below. Some representative examples of reaction between $F^1$ and $Q^1$ and their corresponding products comprising connecting group $Z^3$ are depicted in FIG. 5.

As described above, D and $Q^1$ are covalently attached in the linker-conjugate according to the invention, preferably via linker L as defined above. Covalent attachment of D to the linker may occur for example via reaction of a functional group $F^2$ present on D with a reactive group $Q^2$ present on the linker. Suitable organic reactions for the attachment of D to a linker are known to a person skilled in the art, as are functional groups $F^2$ that are complementary to a reactive group $Q^2$. Consequently, D may be attached to the linker via a connecting group Z.

The term "connecting group" herein refers to the structural element connecting one part of a compound and another part of the same compound. As will be understood by the person skilled in the art, the nature of a connecting group depends on the type of organic reaction with which the connection between the parts of said compound was obtained. As an example, when the carboxyl group of R—C(O)—OH is reacted with the amino group of $H_2N$—R' to form R—C(O)—N(H)—R', R is connected to R' via connecting group Z, and Z may be represented by the group —C(O)—N(H)—.

Reactive group $Q^1$ may be attached to the linker in a similar manner. Consequently, $Q^1$ may be attached to the spacer-moiety via a connecting group Z.

Numerous reactions are known in the art for the attachment of a target molecule to a linker, and for the attachment of a reactive group $Q^1$ to a linker. Consequently, a wide variety of connecting groups Z may be present in the linker-conjugate.

In one embodiment, the linker-conjugate is a compound according to the formula:

$$(Q^1)_{y'}(Z^w)Sp(Z^x)(D)_z,$$

wherein:

y' is an integer in the range of 1 to 10;

z is an integer in the range of 1 to 10;

$Q^1$ is a reactive group capable of reacting with a functional group $F^1$ present on a biomolecule;

D is a target molecule;

Sp is a spacer moiety, wherein a spacer moiety is defined as a moiety that spaces (i.e. provides a certain distance between) and covalently links $Q^1$ and D;

$Z^2$ is a connecting group connecting $Q^1$ to said spacer moiety;

$Z^x$ is a connecting group connecting D to said spacer moiety; and wherein said spacer moiety is linker L, and thus comprises a group according to formula (1) or a salt thereof, wherein the group according to formula (1) is as defined above.

In a preferred embodiment, a in the group according to formula (1) is 0. In another preferred embodiment, a in the group according to formula (1) is 1.

Preferred embodiments for y' and z are as defined above for $(Q^1)_y Sp(D)_z$. It is further preferred that the compound is according to the formula $Q^1(Z^w)Sp(Z^x)(D)_4$, $Q^1(Z^w)Sp(Z^x)(D)_3$, $Q^1(Z^w)Sp(Z^x)(D)_2$ or $Q^1(Z^w)Sp(Z^x)D$, more preferably $Q^1(Z^w)Sp(Z^x)(D)_2$ or $Q^1(Z^w)Sp(Z^x)D$ and most preferably $Q^1(Z^w)Sp(Z^x)D$, wherein $Z^w$ and $Z^x$ are as defined above.

Preferably, $Z^w$ and $Z^x$ are independently selected from the group consisting of —O—, —S—, —$NR^2$—, —N═N—, —C(O)—, —C(O)$NR^2$—, —OC(O)—, —OC(O)O—, —OC(O)$NR^2$, —$NR_2$C(O)—, —$NR^2$C(O)O—, —$NR^2$C(O)$NR^2$—, —SC(O)—, —SC(O)O—, —SC(O)$NR^2$—, —S(O)—, —$S(O)_2$—, —$OS(O)_2$—, —$OS(O)_2$O—, —$OS(O)_2NR^2$—, —OS(O)—, —OS(O)O—, —OS(O)$NR^2$—, —O$NR^2$C(O)—, —O$NR^2$C(O)O—, —O$NR^2$C(O)$NR^2$—, —$NR^2$OC(O)—, —$NR^2$OC(O)O—, —$NR^2$OC(O)$NR^2$—, —O$NR^2$C(S)—, —O$NR^2$C(S)O—, —O$NR^2$C(S)$NR^2$—, —$NR^2$OC(S)—, —$NR^2$OC(S)O—, —$NR^2$OC(S)$NR^2$—, —OC(S)—, —OC(S)O—, —OC(S)$NR^2$—, —$NR^2$C(S)—, —$NR^2$C(S)O—, —$NR^2$C(S)$NR^2$—, —$SS(O)_2$—, —$SS(O)_2$O—, —$SS(O)_2NR^2$—, —$NR_2$OS(O)—, —$NR_2$OS(O)O—, —$NR^2$OS(O)$NR^2$—, —$NR^2OS(O)_2$—, —$NR^2OS(O)_2$O—, —$NR^2OS(O)_2NR^2$—, —O$NR^2$S(O)—, —O$NR^2$S(O)O—, —O$NR^2$S(O)$NR^2$—, —$ONR^2S(O)_2$O—, —$ONR^2S(O)_2NR^2$—, —$ONR^2S(O)_2$—, —OP(O)$(R^2)_2$—, —SP(O)$(R^2)_2$—, —$NR^2$P(O)$(R^2)_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Preferred embodiments for D and $Q^1$ are as defined above.

In one embodiment, the linker-conjugate is compound according to formula (4a) or (4b), or a salt thereof:

4a

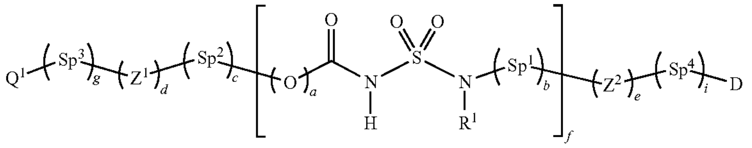

4b

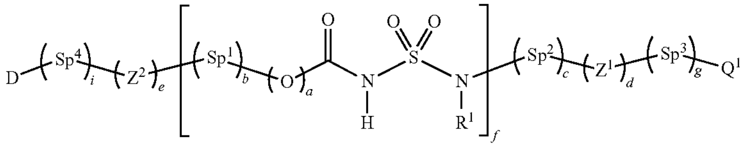

wherein:

a is independently 0 or 1;

b is independently 0 or 1;

c is 0 or 1;

d is 0 or 1;

e is 0 or 1;

f is an integer in the range of 1 to 150;

g is 0 or 1;

i is 0 or 1;

D is a target molecule;

$Q^1$ is a reactive group capable of reacting with a functional group $F^1$ present on a biomolecule;

$Sp^1$ is a spacer moiety;

$Sp^2$ is a spacer moiety;

$Sp^3$ is a spacer moiety;

$Sp^4$ is a spacer moiety;

$Z^1$ is a connecting group that connects $Q^1$ or $Sp^3$ to $Sp^2$, O or C(O) or $N(R^1)$;

$Z^2$ is a connecting group that connects D or $Sp^4$ to $Sp^1$, $N(R^1)$, O or C(O); and $R^1$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, $-[(Sp^1)_b(Z^2)_e(Sp^4)_iD]$ or $-[(Sp^2)_c(Z^1)_d(Sp^3)_gQ^1]$, wherein D is a further target molecule and $Sp^1$, $Sp^2$, $Sp^3$, $Sp^4$, $Z^1$, $Z^2$, $Q^1$, b, c, d, e, g and i are as defined above.

In a preferred embodiment, a is 1 in the compound according to formula (4a) or (4b). In another preferred embodiment, a is 0 in the compound according to formula (4a) or (4b).

As defined above, $Z^1$ is a connecting group that connects $Q^1$ or $Sp^3$ to $Sp^2$, O or C(O) or $N(R^1)$, and $Z^2$ is a connecting group that connects D or $Sp^4$ to $Sp^1$, $N(R^1)$, O or C(O). As described in more detail above, the term “connecting group” refers to a structural element connecting one part of a compound and another part of the same compound.

In a compound according to formula (4a), connecting group $Z^1$, when present (i.e. when d is 1), connects $Q^1$ (optionally via a spacer moiety $Sp^3$) to the O-atom or the C(O) group of the compound according to formula (4a), optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ to the O-atom (a is 1) or to the C(O) group (a is 0) of the linker-conjugate according to formula (4a). When $Z^1$ is present (i.e. when d is 1), $Sp^3$ is present (i.e. g is 1) and $Sp^2$ is absent (i.e. c is 0), $Z^1$ connects spacer moiety $Sp^3$ to the O-atom (a is 1) or to the C(O) group (a is 0) of the linker-conjugate according to formula (4a). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker-conjugate according to formula (4a). When $Z^1$ is present (i.e. when d is 1), $Sp^3$ is absent (i.e. g is 0) and $Sp^2$ is present (i.e. c is 1), $Z^1$ connects $Q^1$ to spacer moiety $Sp^2$ of the linker-conjugate according to formula (4a).

In a compound according to formula (4b), connecting group $Z^1$, when present (i.e. when d is 1), connects $Q^1$ (optionally via a spacer moiety $Sp^3$) to the N-atom of the $N(R^1)$ group in the linker-conjugate according to formula (4b), optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ to the N-atom of the $N(R^1)$ group of the linker-conjugate according to formula (4b). When $Z^1$ is present (i.e. when d is 1), $Sp^3$ is present (i.e. g is 1) and $Sp^2$ is absent (i.e. c is 0), $Z^1$ connects spacer moiety $Sp^3$ to the N-atom of the $N(R^1)$ group of the linker-conjugate according to formula (4b). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker-conjugate according to formula (4b). When $Z^1$ is present (i.e. when d is 1), $Sp^3$ is absent (i.e. g is 0) and $Sp^2$ is present (i.e. c is 1), $Z^1$ connects $Q^1$ to spacer moiety $Sp^2$ of the linker-conjugate according to formula (4b).

In the compound according to formula (4a), when c, d and g are all 0, then $Q^1$ is attached directly to the O-atom (when a is 1) or to the C(O) group (when a is 0) of the linker-conjugate according to formula (4a).

In the compound according to formula (4b), when c, d and g are all 0, then $Q^1$ is attached directly to the N-atom of the $N(R^1)$ group of the linker-conjugate according to formula (4b).

In a compound according to formula (4a), connecting group $Z^2$, when present (i.e. when e is 1), connects D (optionally via a spacer moiety $Sp^4$) to the N-atom of the $N(R^1)$ group in the linker-conjugate according to formula (4a), optionally via a spacer moiety $Sp^1$. More particularly, when $Z^2$ is present (i.e. e is 1), and when $Sp^1$ and $Sp^4$ are absent (i.e. b is 0 and i is 0), $Z^2$ connects D to the N-atom of the $N(R^1)$ group of the linker-conjugate according to formula (4a). When $Z^2$ is present (i.e. when e is 1), $Sp^4$ is present (i.e. i is 1) and $Sp^1$ is absent (i.e. b is 0), $Z^2$ connects spacer moiety $Sp^4$ to the N-atom of the $N(R^1)$ group of the linker-conjugate according to formula (4a). When $Z^2$ is present (i.e. e is 1), and when $Sp^1$ and $Sp^4$ are present (i.e. b is 1 and i is 1), $Z^2$ connects spacer moiety $Sp^1$ to spacer moiety $Sp^4$ of the linker-conjugate according to formula (4a). When $Z^2$ is present (i.e. when e is 1), $Sp^4$ is absent (i.e. i is 0) and $Sp^1$ is present (i.e. b is 1), $Z^2$ connects D to spacer moiety $Sp^1$ of the linker-conjugate according to formula (4a).

In the compound according to formula (4a), when b, e and i are all 0, then D is attached directly to N-atom of the $N(R^1)$ group of the linker-conjugate according to formula (4a).

In the compound according to formula (4b), when b, e and i are all 0, then D is attached directly to the O-atom (when a is 1) or to the C(O) group (when a is 0) of the linker-conjugate according to formula (4b).

As will be understood by the person skilled in the art, the nature of a connecting group depends on the type of organic reaction with which the connection between the specific parts of said compound was obtained. A large number of organic reactions are available for connecting a reactive group $Q^1$ to a spacer moiety, and for connecting a target molecule to a spacer-moiety. Consequently, there is a large variety of connecting groups $Z^1$ and $Z^2$.

In a preferred embodiment of the linker-conjugate according to formula (4a) and (4b), $Z^1$ and $Z^2$ are independently selected from the group consisting of —O—, —S—, —SS—, $—NR^2—$, —N═N—, —C(O)—, $—C(O)NR^{2}-$, —OC(O)—, —OC(O)O—, $—OC(O)NR^2$, $—NR_2C(O)—$, $—NR^2C(O)O—$, $—NR^2C(O)NR^2—$, —SC(O)—, —SC(O)O—, $—S—C(O)NR^2—$, —S(O)—, $—S(O)_2—$, $—OS(O)_2—$, $—OS(O)_2O—$, $—OS(O)_2NR^2—$, —OS(O)—, —OS(O)O—, $—OS(O)NR^2—$, $—ONR^2C(O)—$, $—ONR^2C(O)O—$, $—ONR^2C(O)NR^2—$, $—NR^2OC(O)—$, $—NR^2OC(O)O—$, $—NR^2OC(O)NR^2—$, $—ONR^2C(S)—$, $—ONR^2C(S)O—$, $—ONR^2C(S)NR^2—$, $—NR^2OC(S)—$, $—NR^2OC(S)O—$, $—NR^2OC(S)NR^2—$, —OC(S)—, —OC(S)O—, $—OC(S)NR^2—$, $—NR^2C(S)—$, $—NR^2C(S)O—$, $—NR^2C(S)NR^2—$, $—SS(O)_2—$, $—SS(O)_2O—$, $—SS(O)_2NR^2—$, $—NR^2OS(O)—$, $—NR^2OS(O)O—$, $—NR^2OS(O)NR^2—$, $—NR^2OS(O)_2—$, $—NR^2OS(O)_2O—$, $—NR^2OS(O)_2NR^2—$, $—ONR^2S(O)—$, $—ONR^2S(O)O—$, $—ONR^2S(O)NR^2—$, $—ONR^2S(O)_2O—$, $—ONR^2S(O)_2NR^2—$, $—ONR^2S(O)_2—$, $—OP(O)(R^2)_2—$, $—SP(O)(R^2)_2—$, $—NR^2P(O)(R^2)_2—$ and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

As described above, in the compound according to formula (4a) or (4b), $Sp^1$, $Sp^2$, $Sp^3$ and $Sp^4$ are spacer-moieties. $Sp^1$, $Sp^2$, $Sp^3$ and $Sp^4$ may be, independently, absent or present (b, c, g and i are, independently, 0 or 1). $Sp^1$, if present, may be different from $Sp^2$, if present, from $Sp^3$ and/or from $Sp^4$, if present.

Spacer-moieties are known to a person skilled in the art. Examples of suitable spacer-moieties include (poly)ethylene glycol diamines (e.g. 1,8-diamino-3,6-dioxaoctane or equivalents comprising longer ethylene glycol chains), polyethylene glycol chains or polyethylene oxide chains, polypropylene glycol chains or polypropylene oxide chains and 1,xx-diaminoalkanes wherein xx is the number of carbon atoms in the alkane.

Another class of suitable spacer-moieties comprises cleavable spacer-moieties, or cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are disulphide-linkers that are cleaved upon reduction, peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas. Herein, suitable cleavable spacer-moieties also include spacer moieties comprising a specific, cleavable, sequence of amino acids. Examples include e.g. spacer-moieties comprising a Val-Ala (valine-alanine) or Val-Cit (valine-citrulline) moiety.

In a preferred embodiment of the linker-conjugate according to formula (4a) and (4b), spacer moieties $Sp^1$, $Sp^2$, $Sp^3$ and/or $Sp^4$, if present, comprise a sequence of amino acids. Spacer-moieties comprising a sequence of amino acids are known in the art, and may also be referred to as peptide linkers. Examples include spacer-moieties comprising a Val-Cit moiety, e.g. Val-Cit-PABC, Val-Cit-PAB, Fmoc-Val-Cit-PAB, etc. Preferably, a Val-Cit-PABC moiety is employed in the linker-conjugate.

In a preferred embodiment of the linker-conjugate according to formula (4a) and (4b), spacer moieties $Sp^1$, $Sp^2$, $Sp^3$ and $Sp^4$, if present, are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$ and $Sp^4$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_5$-$C_{100}$ cycloalkynylene groups, $C_7$-$C_{100}$ alkylarylene groups, $C_7$-$C_{100}$ arylalkylene groups, $C_5$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$, $Sp^2$, $Sp^3$ and $Sp^4$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_5$-$C_{50}$ cycloalkynylene groups, $C_7$-$C_{50}$ alkylarylene groups, $C_7$-$C_{50}$ arylalkylene groups, $C_5$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$, $Sp^2$, $Sp^3$ and $Sp^4$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably O, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or S, wherein $R^3$ is independently selected from the group consisting of hydrogen and $C_1$-$C_4$ alkyl groups, preferably hydrogen or methyl.

Preferred spacer moieties $Sp^1$, $Sp^2$, $Sp^3$ and $Sp^4$ thus include $-(CH_2)_n-$, $-(CH_2CH_2)_n-$, $-(CH_2CH_2O)_n-$, $-(OCH_2CH_2)_n-$, $-(CH_2CH_2O)_nCH_2CH_2-$, $-CH_2CH_2(OCH_2CH_2)_n-$, $-(CH_2CH_2CH_2O)_n-$, $-(OCH_2CH_2CH_2)_n-$, $-(CH_2CH_2CH_2O)_nCH_2CH_2CH_2-$ and $-CH_2CH_2CH_2(OCH_2CH_2CH_2)_n-$, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Since $Sp^1$, $Sp^2$, $Sp^3$ and $Sp^4$ are independently selected, $Sp^1$, if present, may be different from $Sp^2$, if present, from $Sp^3$ and/or from $Sp^4$, if present.

Reactive groups $Q^1$ are described in more detail above. In the linker-conjugate according to formula (4a) and (4b), it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, carbonyl halide groups, allenamide groups and 1,1-bis(sulfonylmethyl)methylcarbonyl groups or elimination derivatives thereof. In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj) or (9zk), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zo) and preferred embodiments thereof, are as defined above. In a preferred embodiment, $Q^1$ is according to formula (9a), (9b), (9c), (9f), (9j), (9n), (9o), (9p), (9q), (9s), (9t), (9zh), (9zo) or (9r). In an even further preferred embodiment, $Q^1$ is according to formula (9a), (9j), (9n), (9o), (9q), (9p), (9t), (9zh), (9zo) or (9s), and in a particularly preferred embodiment, $Q^1$ is according to formula (9a), (9q), (9n), (9o), (9p), (9t), (9zo) or (9zh), and preferred embodiments thereof, as defined above.

Target molecule D and preferred embodiments for target molecule D in the linker-conjugate according to formula (4a) and (4b) are as defined above.

As described above, $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is D, $-[(Sp^1)_b(Z^2)_e(Sp^4)_iD]$ or $-[(Sp^2)_c(Z^1)_d(Sp^3)_gQ^1]$, wherein D is a further target molecule and $Sp^1$, $Sp^2$, $Sp^3$, $Sp^4$, $Z^1$, $Z^2$, $Q^1$, b, c, d, e, g and i are as defined above.

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_1$ alkyl group, wherein the alkyl group is optionally substituted and optionally interrupted by one or more heteroatoms selected from O, S and $NR^3$, preferably 0, wherein $R^3$ is independently selected from the group consisting of hydrogen and $C_1$-$C_4$ alkyl groups. In a further preferred embodiment, $R^1$ is hydrogen. In another further preferred embodiment, $R^1$ is a $C_1$-$C_{20}$ alkyl group, more preferably a $C_1$-$C_{16}$ alkyl group, even more preferably a $C_1$-$C_1$ alkyl group, wherein the alkyl group is optionally interrupted by one or more O-atoms, and wherein the alkyl group is optionally substituted with an —OH group, preferably a terminal —OH group. In this embodiment it is further preferred that $R^1$ is a polyethyleneglycol chain comprising a terminal —OH group. In another further preferred embodiment, $R^1$ is a $C_1$-$C_{12}$ alkyl group, more preferably a $C_1$-$C_6$ alkyl group, even more preferably a $C_1$-$C_4$ alkyl group, and yet even more preferably $R^1$ is selected from the group consisting of methyl, ethyl, n-propyl, i-propyl, n-butyl, s-butyl and t-butyl.

In another preferred embodiment, $R^1$ is a further target molecule D, $-[(Sp^1)_b(Z^2)_e(Sp^4)_iD]$ or $-[(Sp^2)_c(Z^1)_d(Sp^3)_g Q^1]$, wherein D is a target molecule and $Sp^1$, $Sp^2$, $Sp^3$, $Sp^4$, $Z^1$, $Z^2$, $Q^1$, b, c, d, e, g and i are as defined above. When $R^1$ is D or $-[(Sp^1)_b(Z^2)_e(Sp^4)_iD]$, it is further preferred that the linker-conjugate is according to formula (4a). In this embodiment, linker-conjugate (4a) comprises two target molecules D, which may be the same or different. When $R^1$ is $-[(Sp^1)_b(Z^2)_e(Sp^4)_iD]$, $Sp^1$, b, $Z^2$, e, $Sp^4$, i and D in $-[(Sp)_b(Z^2)_e(Sp^4)_iD]$ may be the same or different from $Sp^1$, b, $Z^2$, e, $Sp^4$, i and D in $-[(Sp)_b(Z^2)_e(Sp^4)_iD]$ that is attached to the N-atom of $N(R^1)$. In a preferred embodiment, both $-[(Sp^1)_b(Z^2)_e(Sp^4)_iD]$ and $-[(Sp^1)_b(Z^2)_e(Sp^4)_iD]$ on the N-atom of $N(R^1)$ are the same.

When $R^1$ is $-[(Sp^2)_c(Z^1)_d(Sp^3)_gQ^1]$, it is further preferred that the linker-conjugate is according to formula (4b). In this embodiment, linker-conjugate (4b) comprises two target molecules $Q^1$, which may be the same or different. When $R^1$ is $-[(Sp^2)_c(Z^1)_d(Sp^3)_gQ^1]$, $Sp^2$, c, $Z^1$, d, $Sp^3$, g and D in $-[(Sp^1)_b(Z^2)_e(Sp^4)_iD]$ may be the same or different from $Sp^1$, b, $Z^2$, e, $Sp^4$, i and $Q^1$ in the other $-[(Sp^2)_c(Z^1)_d(Sp^3)_gQ^1]$ that is attached to the N-atom of $N(R^1)$. In a preferred embodiment, $-[(Sp^2)_c(Z^1)_d(Sp^3)_gQ^1]$ groups on the N-atom of $N(R^1)$ are the same.

In the linker-conjugate according to formula (4a) and (4b), f is an integer in the range of 1 to 150. The linker-conjugate may thus comprise more than one group according to formula (1), the group according to formula (1) being as defined above. When more than one group according to formula (1) is present, i.e. when f is 2 or more, then a, b, $Sp^1$ and $R^1$ are independently selected. In other words, when f is 2 or more, each a is independently 0 or 1, each b is independently 0 or 1, each $Sp^1$ may be the same or different and each $R^1$ may be the same or different. In a preferred embodiment, f is an integer in the range of 1 to 100, preferably in the range of 1 to 50, more preferably in the range of 1 to 25, and even more preferably in the range of 1 to 15. More preferably, f is 1, 2, 3, 4, 5, 6, 7, 8, 9 or 10, even more preferably f is 1, 2, 3, 4, 5, 6, 7 or 8, yet even more preferably f is 1, 2, 3, 4, 5 or 6, yet even more preferably f is 1, 2, 3 or 4, and most preferably f is 1 in this embodiment. In another preferred embodiment, f is an integer in the range of 2 to 150, preferably in the range of 2 to 100, more preferably in the range of 2 to 50, more preferably in the range of 2 to 25, and even more preferably in the range of 2 to 15. More preferably, f is 2, 3, 4, 5, 6, 7, 8, 9 or 10, even more preferably f is 2, 3, 4, 5, 6, 7 or 8, yet even more preferably f is 2, 3, 4, 5 or 6, yet even more preferably f is 2, 3 or 4, and most preferably f is 2 in this embodiment.

As described above, in a preferred embodiment, a is 0 in the compound according to formula (4a) or (4b). The linker-conjugate may therefore also be a compound according to formula (6a) or (6b), or a salt thereof:

6a

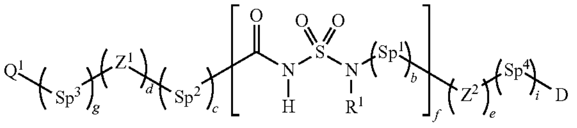

6b

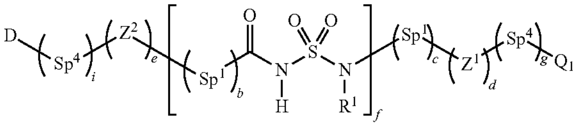

wherein a, b, c, d, e, f, g, i, D, $Q^1$, $Sp^1$, $Sp^2$, $Sp^3$, $Sp^4$, $Z^1$, $Z^2$ and $R^1$, and their preferred embodiments, are as defined above for (4a) and (4b).

As described above, in another preferred embodiment, a is 1 in the compound according to formula (4a) or (4b). The linker-conjugate may therefore also be a compound according to formula (7a) or (7b), or a salt thereof:

7a

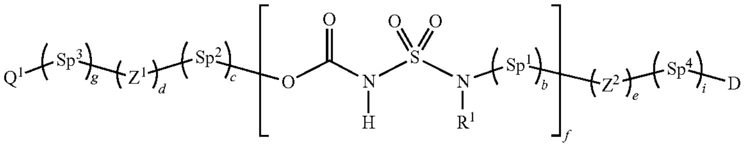

7b

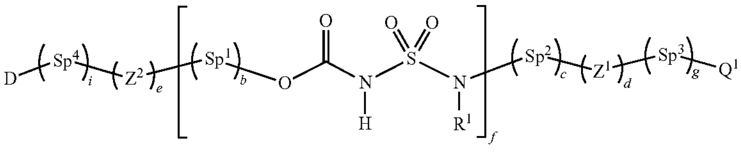

wherein a, b, c, d, e, f, g, i, D, $Q^1$, $Sp^1$, $Sp^2$, $Sp^3$, $Sp^4$, $Z^1$, $Z^2$ and $R^1$, and their preferred embodiments, are as defined above for (4a) and (4b).

When $Sp^4$ is absent in the linker-conjugate according to formula (4a), i.e. when i is 0, D is linked to $Z^2$ (when e is 1), to $Sp^1$ (when e is 0 and b is 1) or to $N(R^1)$ (when e is 0 and b is 0). When $Sp^4$ is absent in the linker-conjugate according to formula (4b), i.e. when i is 0, D is linked to $Z^2$ (when e is 1), to $Sp^1$ (when e is 0 and b is 1), to the O-atom (when a is 1 and b and e are 0) or to the C(O) group (when a is 0 and b and e are 0). The linker-conjugate therefore also may be a compound according to formula (4c) or (4d), or a salt thereof:

4c

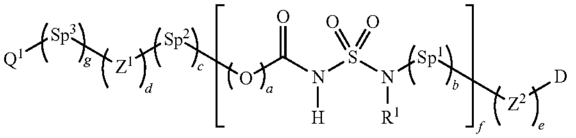

4d

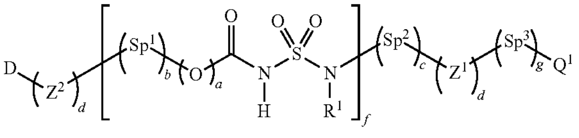

wherein a, b, c, d, e, f, g, D, $Q^1$, $Sp^1$, $Sp^2$, $Sp^3$, $Z^1$, $Z^2$ and $R^1$, and their preferred embodiments, are as defined above for (4a) and (4b).

In a preferred embodiment, in the linker-conjugate according to formula (4c) or (4d), a is 0. In another preferred embodiment, in the linker-conjugate according to formula (4c) or (4d), a is 1.

In a specific embodiment of the linker-conjugate, particularly a linker-conjugate according to formula (4a), (4b), (4c), (4d), (6a), (6b), (7a) or (7b), $Sp^1$, $Sp^2$ $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, wherein $R^3$ is independently selected from the group consisting of hydrogen and $C_1$-$C_4$ alkyl groups, and $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg) (9zh), (9zi), (9zj) or (9zk), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zo) and preferred embodiments thereof, are as defined above. In a preferred embodiment, $Q^1$ is according to formula (9a), (9b), (9c), (9f), (9j), (9n), (9o), (9p), (9q), (9s) (9t), (9zh), (9zo) or (9r). In an even further preferred embodiment, $Q^1$ is according to formula (9a), (9j), (9n), (9o), (9p), (9q), (9t), (9zh), (9zo) or (9s), and in a particularly preferred embodiment, $Q^1$ is according to formula (9a), (9q), (9n), (9p), (9t), (9zh), (9zo) or (9o), and preferred embodiments thereof, as defined above.

Linker L, as preferably comprised in the linker-conjugate according to formula (4a), (4b), (4c), (4d), (6a), (6b), (7a) or (7b) as defined above, linker as defined above may be represented by formula (8a) and (8b), respectively:

8a

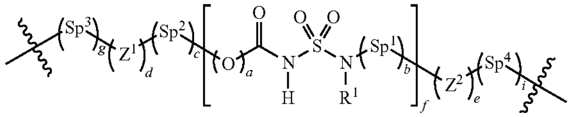

8b

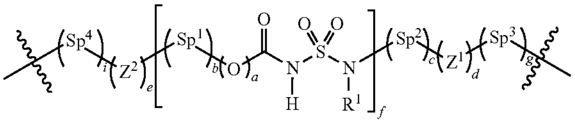

As will be understood by the person skilled in the art, preferred embodiments of spacer-moieties (8a) and (8b) may depend on e.g. the nature of reactive groups $Q^1$ and D in the linker-conjugate, the synthetic method to prepare the linker-conjugate (e.g. the nature of complementary functional group $F^2$ on a target molecule), the nature of a bioconjugate that is prepared using the linker-conjugate (e.g. the nature of complementary functional group $F^1$ on the biomolecule).

When $Q^1$ is for example a cyclooctynyl group according to formula (9n), (9o), (9p), (9q) or (9zk) as defined above, then preferably $Sp^3$ is present (g is 1).

When for example the linker-conjugate was prepared via reaction of a reactive group $Q^2$ that is a cyclooctynyl group according to formula (9n), (9o), (9p), (9q) or (9zk) with an azido functional group $F^2$, then preferably $Sp^4$ is present (i is 1).

Furthermore, it is preferred that at least one of $Sp^1$, $Sp^2$, $Sp^3$ and $Sp^4$ is present, i.e. at least one of b, c, g, and i is not 0. In another preferred embodiment, at least one of $Sp^1$ and $Sp^4$ and at least one of $Sp^2$ and $Sp^3$ are present.

When f is 2 or more, it is preferred that $Sp^1$ is present (b is 1).

These preferred embodiments of the linker-moiety (8a) and (8b) also hold for the linker-conjugate when comprised in the bioconjugates according to the invention as described in more detail below.

Preferred embodiments of $Sp^1$, $Sp^2$, $Sp^3$ and $Sp^4$ are as defined above.

Biomolecule

The biomolecule is represented by B-$F^1$, wherein B is a biomolecule and $F^1$ is a functional group capable of reacting with reactive group $Q^1$ on the linker-conjugate and "-" is a bond or a spacer moiety. Alternatively, the biomolecule is a modified antibody represented by formula (24), wherein $F^1$ is a functional group capable of reacting with reactive group $Q^1$ on the linker-conjugate. The modified antibody represented by formula (24) and preferred embodiments thereof are defined in detail above.

In one embodiment, "-" is a spacer moiety as defined herein. In one embodiment, "-" is a bond, typically a covalent bond. The biomolecule may also be referred to as "biomolecule of interest" (BOI). The biomolecule may be a biomolecule as naturally occurring, wherein functional group $F^1$ is a already present in the biomolecule of interest, such as for example a thiol, an amine, an alcohol or a hydroxyphenol unit. Conjugation with the linker-conjugate then occurs via the first approach as defined above. Alternatively, the biomolecule may be a modified biomolecule, wherein functional group $F^1$ is specifically incorporated into the biomolecule of interest and conjugation with the linker-conjugate occurs via this engineered functionality, i.e. the two-stage approach of bioconjugation as defined above.

Such modification of biomolecules to incorporate a specific functionality is known, e.g. from WO 2014/065661, incorporated herein by reference in its entirety.

In the bioconjugate according to the invention, biomolecule B is preferably selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. More preferably, biomolecule B is selected from the group consisting of proteins, including glycoproteins and antibodies, polypeptides, peptides and glycans. Most preferably, biomolecule B is an antibody or an antigen-binding fragment thereof.

Functional group $F^1$ is capable of reacting with reactive group $Q^1$ on the linker-conjugate to form a connecting group $Z^3$. To a skilled person, it is clear which functional group $F^1$ is capable of reacting with a complementary reactive group $Q^1$. Functional groups $F^1$ that are complementary to reactive groups $Q^1$, as defined above, and known to a person skilled in the art, are described in more detail below. Some representative examples of reaction between $F^1$ and $Q^1$ and their corresponding products comprising connecting group $Z^3$ are depicted in FIG. 5.

In the process for the preparation of a bioconjugate according to the invention, a reactive group $Q^1$ that is present in the linker-conjugate is typically reacted with functional group $F^1$. More than one functional group $F^1$ may be present in the biomolecule. When two or more functional groups are present, said groups may be the same or different. In another preferred embodiment, the biomolecule comprises two or more functional groups F, which may be the same or different, and two or more functional groups react with a complementary reactive group Q of a linker-conjugate. For example a biomolecule comprising two functional groups F, i.e. $F^1$ and $F^2$, may react with two linker-conjugates comprising a functional group $Q^1$, which may be the same or different, to form a bioconjugate.

Examples of a functional group $F^1$ in a biomolecule comprise an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne, a cyclopropene moiety or a phosphine moiety. In view of the preferred mode of conjugation by cycloaddition, it is preferred that $F^1$ is group capable of reacting in a cycloaddition, such as a diene, a dienophile, a 1,3-dipole or a dipolarophile, preferably $F^1$ is selected from a 1,3-dipole (typically an azido group, nitrone group, nitrile oxide group, nitrile imine group or diazo group) or a dipolarophile (typically an alkenyl or alkynyl group). Herein, $F^1$ is a 1,3-dipole when $Q^1$ is a dipolarophile and $F^1$ is a dipolarophile when $Q^1$ is a 1,3-dipole, or $F^1$ is a diene when $Q^1$ is a dienophile and $F^1$ is a dienophile when $Q^1$ is a diene. Most preferably, $F^1$ is a 1,3-dipole, preferably $F^1$ is or comprises an azido group.

Figure 2:
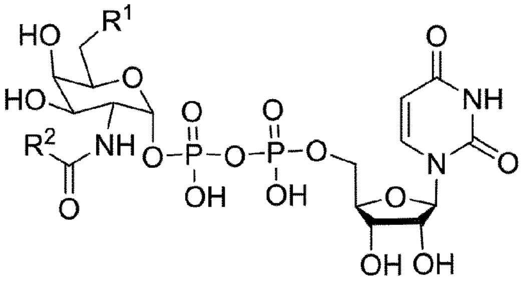
FIG. 2 shows several structures of derivatives of UDP sugars of galactosamine, which may be modified with e.g. a 3-mercaptopropionyl group (11a), an azidoacetyl group (11b), or an azidodifluoroacetyl group (11c) at the 2-position, or with an azido azidoacetyl group at the 6-position of N-acetyl galactosamine (11d).

Several examples of a functional group that is placed into a biomolecule are shown in FIG. 2. FIG. 2 shows several structures of derivatives of UDP sugars of galactosamine, which may be modified with e.g. a thiopropionyl group (11a), an azidoacetyl group (11b), or an azidodifluoroacetyl group (11c) at the 2-position, or with an azido group at the 6-position of N-acetyl galactosamine (11d). In one embodiment, functional group $F^1$ is a thiopropionyl group, an azidoacetyl group, or an azidodifluoroacetyl group.

Figure 3:
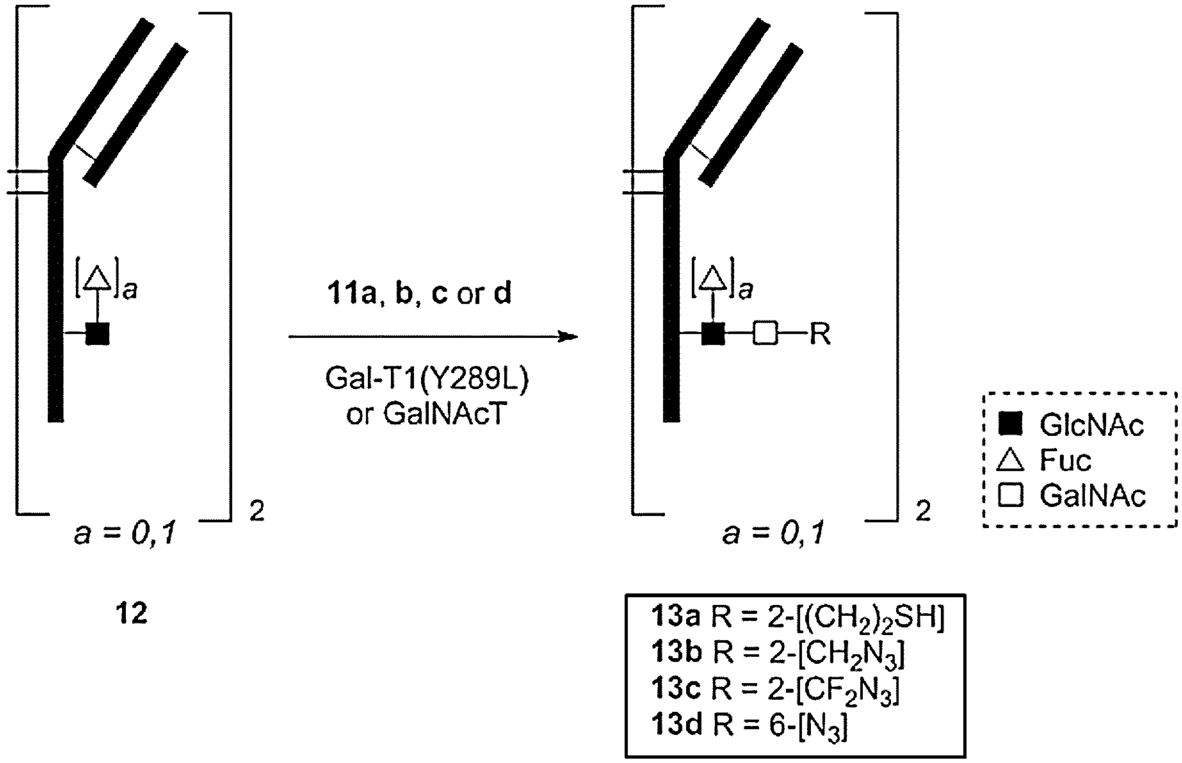
FIG. 3 schematically displays how any of the UDP-sugars 11a-d may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a β-glycosidic 1-4 linkage between a GalNAc derivative and GlcNAc (compounds 13a-d, respectively).

FIG. 3 schematically displays how any of the UDP-sugars 11a-d may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a 3-glycosidic 1-4 linkage between a GalNAc derivative and GlcNAc (compounds 13a-d, respectively).

Preferred examples of naturally present functional groups $F^1$ include a thiol group and an amino group. Preferred examples of a functional group that is prepared by chemical synthesis for incorporation into the biomolecule include a ketone group, a terminal alkyne group, an azide group, a cyclo(hetero)alkyne group, a cyclopropene group, or a tetrazine group.

As was described above, complementary reactive groups $Q^1$ and functional groups $F^1$ are known to a person skilled in the art, and several suitable combinations of $Q^1$ and $F^1$ are described above, and shown in FIG. 5. A list of complementary groups $Q^1$ and $F^1$ is disclosed in in Table 3.1, pages 230-232 of Chapter 3 of G. T. Hermanson, "*Bioconjugate Techniques*", Elsevier, $3^{rd}$ Ed. 2013 (ISBN:978-0-12-382239-0), and the content of this Table is expressly incorporated by reference herein.

Bioconjugate

A bioconjugate is herein defined as a compound wherein a biomolecule is covalently connected to a target molecule D via a linker. A bioconjugate comprises one or more biomolecules and/or one or more target molecules. The linker may comprise one or more spacer moieties. The bioconjugate according to the invention is conveniently prepared by the process for preparation of a bioconjugate according to the invention, wherein the linker-conjugate comprising reactive group $Q^1$ is conjugated to a biomolecule comprising functional group F. In this conjugation reaction, groups $Q^1$ and $F^1$ react with each other to form a connecting group $Z^3$ which connects the target molecule D with the biomolecule B. All preferred embodiments described herein for the linker-conjugate and the biomolecule thus equally apply to the bioconjugate according to the invention, except for all said for $Q^1$ and F, wherein the bioconjugate according to the invention contains the reaction product of $Q^1$ and $F^1$, i.e. connecting group $Z^3$. In one aspect, the invention also concerns the bioconjugates, preferably the antibody-conjugates, described herein.

The bioconjugate according to the invention has formula (A):

$$B\text{-}L\text{-}D \qquad (A),$$

wherein:

B is a biomolecule, preferably an antibody AB;

L is a linker linking B and D;

D is a target molecule; and each occurrence of "-" is independently a bond or a spacer moiety.

In a first preferred embodiment, the bioconjugate is obtainable by the mode of conjugation defined as "core-GlcNAc functionalization", i.e. by steps (i) and (ii) as defined above. In a second preferred embodiment, the bioconjugate according to formula (A) has a linker L comprising a group according to formula (1) or a salt thereof:

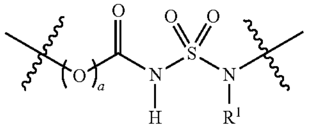

1 wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is a target molecule D, wherein D is optionally connected to N via a spacer moiety.

In one embodiment, "-" is a spacer moiety as defined herein. In one embodiment, "-" is a bond, typically a covalent bond.

In a preferred embodiment, the bioconjugate is presented by B-$Z^3$-L-D, wherein B, L, D and "-" are as defined above and $Z^3$ is a connecting group which is obtainable by reaction of $Q^1$ with $F^1$. Preferably, moiety $Z^3$ is obtainable by a cycloaddition, preferably a 1,3-dipolar cycloaddition reaction, most preferably $Z^3$ is a 1,2,3-triazole ring, which is located in a spacer moiety, preferably the spacer moiety between B and L, most preferably between B and the carbonyl or carboxyl end of the group according to formula (1).

When the bioconjugate according to the invention comprises a salt of the group according to formula (1), the salt is preferably a pharmaceutically acceptable salt.

The bioconjugate according to the invention may comprise more than one target molecule. Similarly, the bioconjugate may comprise more than one biomolecule. Biomolecule B and target molecule D, and preferred embodiments thereof, are described in more detail above. Preferred embodiments for D in the bioconjugate according to the invention correspond to preferred embodiments of D in the linker-conjugate according to the invention as were described in more detail above. Preferred embodiments for the linker (8a) or (8b) in the bioconjugate according to the invention correspond to preferred embodiments of the linker in the linker-conjugate, as were described in more detail above. Preferred embodiments for B in the bioconjugate according to the invention correspond to preferred embodiments of B in the biomolecule according to the invention as were described in more detail above.

The bioconjugate according to the invention may also be defined as a bioconjugate wherein a biomolecule is conjugated to a target molecule via a spacer-moiety, wherein the spacer-moiety comprises a group according to formula (1), or a salt thereof, wherein the group according to formula (1) is as defined above.

The bioconjugate according to the invention may also be denoted as $(B)_{y'}Sp(D)_z$, wherein y' is an integer in the range of 1 to 10 and z is an integer in the range of 1 to 10.

The invention thus also relates to a bioconjugate according to the formula:

$$(B)_{y'}Sp(D)_z,$$

wherein:

y' is an integer in the range of 1 to 10;

z is an integer in the range of 1 to 10;

B is a biomolecule;

D is a target molecule;

Sp is a spacer moiety, wherein a spacer moiety is defined as a moiety that spaces (i.e. provides a certain distance between) and covalently links biomolecule B and target molecule D; and wherein said spacer moiety comprises a group according to formula (1) or a salt thereof, wherein the group according to formula (1) is as defined above.

In a preferred embodiment, said spacer moiety further comprises a moiety that is obtainable by a cycloaddition, preferably a 1,3-dipolar cycloaddition reaction, most preferably a 1,2,3-triazole ring, which is located between B and said group according to formula (1).

Preferably, y' is 1, 2, 3 or 4, more preferably y' is 1 or 2 and most preferably, y' is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y' is 1 or 2, preferably 1, and z is 1, 2, 3 or 4, yet even more preferably y' is 1 or 2, preferably 1, and z is 1, 2 or 3, yet even more preferably y' is 1 or 2, preferably 1, and z is 1 or 2, and most preferably y' is 1 and z is 1. In a preferred embodiment, the bioconjugate is according to the formula $BSp(D)_4$, $BSp(D)_3$, $BSp(D)_2$ or BSpD. In another preferred embodiment, the bioconjugate is according to the formula $BSp(D)_8$, $BSp(D)_4$ or $BSp(D)_2$, more preferably $BSp(D)_4$ or $BSp(D)_2$.

As described above, the bioconjugate according to the invention comprises a group according to formula (1) as defined above, or a salt thereof. In a preferred embodiment, the bioconjugate comprises a group according to formula (1) wherein a is 0, or a salt thereof. In this embodiment, the bioconjugate thus comprises a group according to formula (2) or a salt thereof, wherein (2) is as defined above.

In another preferred embodiment, the bioconjugate comprises a group according to formula (1) wherein a is 1, or a salt thereof. In this embodiment, the bioconjugate thus comprises a group according to formula (3) or a salt thereof, wherein (3) is as defined above.

In the bioconjugate according to the invention, $R^1$, spacer moiety Sp, as well as preferred embodiments of $R^1$ and Sp, are as defined above for the linker-conjugate according to the invention.

In a preferred embodiment, the bioconjugate is according to formula (5a) or (5b), or a salt thereof:

5a

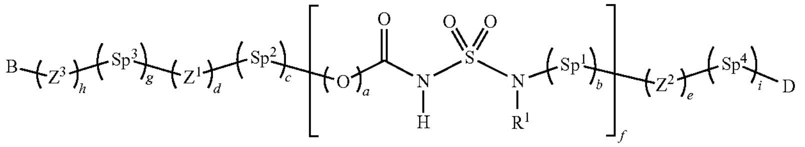

5b

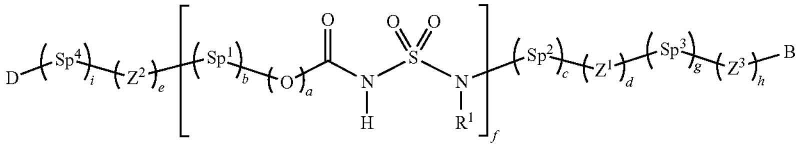

wherein a, b, c, d, e, f, g, h, i, D, $Sp^1$, $Sp^2$, $Sp^3$, $Sp^4$, $Z^1$, $Z^2$, $Z^3$ and $R^1$, and preferred embodiments thereof, are as defined above for linker-conjugate (4a) and (4b); and h is 0 or 1;

$Z^3$ is a connecting group that connects B to $Sp^3$, $Z^1$, $Sp^2$, O or C(O); and B is a biomolecule.

Preferably, h is 1.

Preferred embodiments of biomolecule B are as defined above.

When the bioconjugate according to the invention is a salt of (5a) or (5b), the salt is preferably a pharmaceutically acceptable salt.

$Z^3$ is a connecting group. As described above, the term "connecting group" herein refers to the structural element connecting one part of a compound and another part of the same compound. Typically, a bioconjugate is prepared via reaction of a reactive group $Q^1$ present in the linker-conjugate with a functional group $F^1$ present in a biomolecule. As will be understood by the person skilled in the art, the nature of connecting group $Z^3$ depends on the type of organic reaction that was used to establish the connection between the biomolecule and the linker-conjugate. In other words, the nature of $Z^3$ depends on the nature of reactive group $Q^1$ of the linker-conjugate and the nature of functional group $F^1$ in the biomolecule. Since there is a large number of different chemical reactions available for establishing the connection between a biomolecule and a linker-conjugate, consequently there is a large number of possibilities for $Z^3$.

Several examples of suitable combinations of $F^1$ and $Q^1$, and of connecting group $Z^3$ that will be present in a bioconjugate when a linker-conjugate comprising $Q^1$ is conjugated to a biomolecule comprising a complementary functional group F, are shown in FIG. 5.

When $F^1$ is for example a thiol group, complementary groups $Q^1$ include N-maleimidyl groups and alkenyl groups, and the corresponding connecting groups $Z^3$ are as shown in FIG. 5. When $F^1$ is a thiol group, complementary groups $Q^1$ also include allenamide groups.

When $F^1$ is for example an amino group, complementary groups $Q^1$ include ketone groups and activated ester groups, and the corresponding connecting groups $Z^3$ are as shown in FIG. 5.

When $F^1$ is for example a ketone group, complementary groups $Q^1$ include (O-alkyl)hydroxylamino groups and hydrazine groups, and the corresponding connecting groups $Z^3$ are as shown in FIG. 5.

When $F^1$ is for example an alkynyl group, complementary groups $Q^1$ include azido groups, and the corresponding connecting group $Z^3$ is as shown in FIG. 5.

When $F^1$ is for example an azido group, complementary groups $Q^1$ include alkynyl groups, and the corresponding connecting group $Z^3$ is as shown in FIG. 5.

When $F^1$ is for example a cyclopropenyl group, a trans-cyclooctene group or a cyclooctyne group, complementary groups $Q^1$ include tetrazinyl groups, and the corresponding connecting group $Z^3$ is as shown in FIG. 5. In these particular cases, $Z^3$ is only an intermediate structure and will expel $N_2$, thereby generating a dihydropyridazine (from the reaction with alkene) or pyridazine (from the reaction with alkyne).

Additional suitable combinations of $F^1$ and $Q^1$, and the nature of resulting connecting group $Z^3$ are known to a person skilled in the art, and are e.g. described in G. T. Hermanson, "*Bioconjugate Techniques*", Elsevier, 3rd Ed. 2013 (ISBN:978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, "*Bioconjugate Techniques*", Elsevier, 3rd Ed. 2013 (ISBN:978-0-12-382239-0), and the content of this Table is expressly incorporated by reference herein.

In the bioconjugate according to (5a) and (5b), it is preferred that at least one of $Z^3$, $Sp^3$, $Z^1$ and $Sp^2$ is present, i.e. at least one of h, g, d and c is not 0. It is also preferred that at least one of $Sp^1$, $Z^2$ and $Sp^4$ is present, i.e. that at least one of b, e and i is not 0. More preferably, at least one of $Z^3$, $Sp^3$, $Z^1$ and $Sp^2$ is present and at least one of Sp, $Z^2$ and $Sp^4$ is present, i.e. it is preferred that at least one of b, e and i is not 0 and at least one of h, g, d and c is not 0.

Process for the Preparation of a Bioconjugate

In the various aspects of the present invention, the bioconjugate according to the invention is typically obtained by a process for the preparation of a bioconjugate as defined herein. As the presence of the group according to formula (1) or a salt thereof in linker L of the bioconjugate is key in the present invention, any method of preparing the bioconjugate can be used as long as the obtained bioconjugate comprises linker L as defined herein. The group according to formula (1) may be present in linker L between B and $Z^3$, i.e. it originates form the biomolecule, or between $Z^3$ and D, i.e. it originates from the linker-conjugate, or $Z^3$ is or comprises the group according to formula (1), i.e. the group according to formula (1) is formed upon conjugation. Preferably, the group according to formula (1) is present in linker L between B and $Z^3$ or between $Z^3$ and D, most preferably, the group according to formula (1) is present in linker L between $Z^3$ and D. Likewise, the exact mode of conjugation, including the nature of $Q^1$ and $F^1$ have a great flexibility in the context of the present invention. Many techniques for conjugating BOIs to MOIs are known to a person skilled in the art and can be used in the context of the present invention. In one embodiment, the conjugation method comprises steps (i) and (ii) as defined above.

In one embodiment, the mode of conjugation is selected from any of the conjugation modes depicted in FIG. 5, i.e. from thiol-alkene conjugation (preferably cysteine-alkene conjugation, preferably wherein the alkene is a pendant alkene (—C═CH$_2$) or a maleimide moiety, most preferably a maleimide moiety) to from a connecting moiety $Z^3$ that may be represented as (10a) or (10b), amino-(activated) carboxylic acid conjugation (wherein the (activated) carboxylic acid is represented by —C(O)X, wherein X is a leaving group) to from a connecting moiety $Z^3$ that may be represented as (10c), ketone-hydrazino conjugation (preferably acetyl-hydrazino conjugation) to from a connecting moiety $Z^3$ that may be represented as (10d) wherein Y═NH, ketone-oxyamino conjugation (preferably acetyl-oxyamino conjugation) to from a connecting moiety $Z^3$ that may be represented as (10d) wherein Y═O, alkyne-azide conjugation (preferably wherein the alkyne is a pendant alkyne (—C≡CH) or a cyclooctyne moiety, most preferably a cyclooctyne moiety) to from a connecting moiety $Z^3$ that may be represented as (10e), (10f), (10i), (10g), (10j) or (10k), alkene-1,2,4,5-tetrazine conjugation or alkyne-1,2,4,5-tetrazine conjugation to from a connecting moiety $Z^3$ that may be represented as (10h) from which $N_2$ will eliminate, giving dihydropyridazine products. Especially preferred conjugation modes are cysteine-alkene conjugation and alkyne-azide conjugation, more preferably cysteine-maleimide conjugation and cyclooctyne-azide conjugation.

The bioconjugate according to the invention is typically prepared by a process comprising the step of reacting a reactive group $Q^1$ of the linker-conjugate as defined herein with a functional group $F^1$ of the biomolecule, also referred to as a biomolecule. The linker-conjugate and the biomolecule, and preferred embodiments thereof, are described in more detail above. Such a process is known to a person skilled in the art as conjugation or bioconjugation. FIG. 1 shows the general concept of conjugation of biomolecules: a biomolecule of interest (BOI) comprising one or more functional groups $F^1$ is incubated with (excess of) a target molecule D (also referred to as molecule of interest or MOI), covalently attached to a reactive group $Q^1$ via a specific linker. In the process of bioconjugation, a chemical reaction between $F^1$ and $Q^1$ takes place, thereby forming a bioconjugate comprising a covalent bond between the BOI and the MOI. The BOI may e.g. be a peptide/protein, a glycan or a nucleic acid.

The bioconjugation reaction typically comprises the step of reacting a reactive group $Q^1$ of the linker-conjugate with a functional group $F^1$ of a the biomolecule, wherein a bioconjugate of formula (A) is formed, wherein linker L comprises a group according to formula (1) or a salt thereof:

1

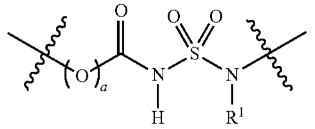

wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, which is optionally connected to N via a spacer moiety.

In a preferred embodiment, the bioconjugate is prepared via a cycloaddition, such as a (4+2)-cycloaddition (e.g. a Diels-Alder reaction) or a (3+2)-cycloaddition (e.g. a 1,3-dipolar cycloaddition). Preferably, the conjugation is a Diels-Alder reaction or a 1,3-dipolar cycloaddition. The preferred Diels-Alder reaction is the inverse-electron demand Diels-Alder cycloaddition. In another preferred embodiment, the 1,3-dipolar cycloaddition is used, more preferably the alkyne-azide cycloaddition, and most preferably wherein $Q^1$ is or comprises an alkyne group and $F^1$ is an azido group. Cycloadditions, such as Diels-Alder reactions and 1,3-dipolar cycloadditions are known in the art, and the skilled person knowns how to perform them.

When $Q^1$ reacts with $F^1$, a covalent connection between the biomolecule and the target molecule originating of the linker-conjugate is formed. Complementary reactive groups $Q^1$ and functional groups $F^1$ are described in more detail above and below.

In a preferred embodiment of the process for preparing the bioconjugate, a is 0 in the group according to formula (1). In this embodiment, the linker-conjugate thus comprises a group according to formula (2), as defined above. In another preferred embodiment of the process for preparing the bioconjugate, a is 1 in the group according to formula (1). In this embodiment, the linker-conjugate thus comprises a group according to formula (3), as defined above.

Biomolecules are described in more detail above. Preferably, in the process according to the invention the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. More preferably, biomolecule B is selected from the group consisting of proteins, including glycoproteins and antibodies, polypeptides, peptides and glycans. Most preferably, B is an antibody or an antigen-binding fragment thereof.

In the process for preparing the bioconjugate, it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups and allenamide groups.

In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj) or (9zk), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zo), and preferred embodiments thereof, are as defined above for the linker-conjugate according to the invention. More preferably, $Q^1$ is according to formula (9a), (9b), (9c), (9f), (9j), (9n), (9o), (9p), (9q), (9s), (9t), (9ze), (9zh), (9zo) or (9r). Even more preferably, $Q^1$ is according to formula (9a), (9j), (9n), (9o), (9p), (9q), (9t), (9ze), (9zh), (9zo) or (9s), and most preferably, $Q^1$ is according to formula (9a), (9p), (9q), (9n), (9t), (9ze), (9zh), (9zo) or (9o), and preferred embodiments thereof, as defined above.

In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q), (9zo) and (9zk), as defined above. Most preferably, $Q^1$ is a bicyclo[6.1.0]non-4-yn-9-yl] group, preferably of formula (9q).

In a further preferred embodiment of the process for preparing the bioconjugate, the linker-conjugate is according to formula (4a) or (4b), or a salt thereof:

4a

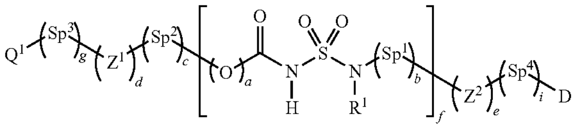

4b

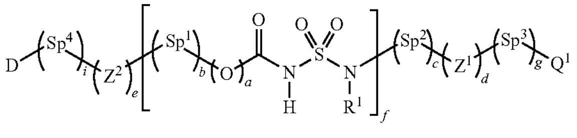

wherein:

a is independently 0 or 1;
b is independently 0 or 1;
c is 0 or 1;
d is 0 r 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or N(R');
$Z^2$ is a connecting group that connects D or $Sp^4$ to $Sp^1$, $N(R^1)$, O or C(O); and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, $-[(Sp^1)_b(Z^2)_e(Sp^4)_i D]$ or $-[(Sp^2)_c(Z^1)_d(Sp^3)_g Q^1]$, wherein D is a target molecule and $Sp^1$, $Sp^2$, $Sp^3$, $Sp^4$, $Z^1$, $Z^2$, $Q^1$, b, c, d, e, g and i are as defined above.

$Sp^1$, $Sp^2$, $Sp^3$ and $Sp^4$ are, independently, spacer moieties, in other words, $Sp^1$, $Sp^2$, $Sp^3$ and $Sp^4$ may differ from each other. $Sp^1$, $Sp^2$, $Sp^3$ and $Sp^4$ may be present or absent (b, c, g and i are, independently, 0 or 1). However, it is preferred that at least one of $Sp^1$, $Sp^2$, $Sp^3$ and $Sp^4$ is present, i.e. it is preferred that at least one of b, c, g and i is not 0.

If present, preferably $Sp^1$, $Sp^2$, $Sp^3$ and $Sp^4$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$ and $Sp^4$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_5$-$C_{100}$ cycloalkynylene groups, $C_7$-$C_{100}$ alkylarylene groups, $C_7$-$C_{100}$ arylalkylene groups, $C_5$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$, $Sp^2$, $Sp^3$ and $Sp^4$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_5$-$C_{50}$ cycloalkynylene groups, $C_7$-$C_{50}$ alkylarylene groups, $C_7$-$C_{50}$ arylalkylene groups, $C_5$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$, $Sp^2$, $Sp^3$ and $Sp^4$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably 0, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or S—S, wherein $R^3$ is independently selected from the group consisting of hydrogen and $C_1$-$C_4$ alkyl groups, preferably hydrogen or methyl.

Particularly preferred spacer moieties $Sp^1$, $Sp^2$, $Sp^3$ and $Sp^4$ include $—(CH_2)_n—$, $—(CH_2CH_2)_n—$, $—(CH_2CH_2O)_n—$, $—(OCH_2CH_2)_n—$, $—(CH_2CH_2O)_nCH_2CH_2—$, $—CH_2CH_2(OCH_2CH_2)_n—$, $—(CH_2CH_2CH_2O)_n—$, $—(OCH_2CH_2CH_2)_n—$, $—(CH_2CH_2CH_2O)_nCH_2CH_2CH_2—$ and $—CH_2CH_2CH_2(OCH_2CH_2CH_2)_n—$, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

In another preferred embodiment of the process according to the invention, in the linker-conjugates according to formula (4a) and (4b), spacer moieties $Sp^1$, $Sp^2$, $Sp^3$ and/or $Sp^4$, if present, comprise a sequence of amino acids. Spacer-moieties comprising a sequence of amino acids are known in the art, and may also be referred to as peptide linkers. Examples include spacer-moieties comprising a Val-Ala moiety or a Val-Cit moiety, e.g. Val-Cit-PABC, Val-Cit-PAB, Fmoc-Val-Cit-PAB, etc.

As described above, $Z^1$ and $Z^2$ are a connecting groups. In a preferred embodiment of the process according to the invention, $Z^1$ and $Z^2$ are independently selected from the group consisting of —O—, —S—, $—NR^2—$, —N=N—, —C(O)—, $—C(O)NR^2—$, —OC(O)—, —OC(O)O—, $—OC(O)NR^2$, $—NR_2C(O)—$, $—NR^2C(O)O—$, $—NR^2C(O)NR^2—$, —SC(O)—, —SC(O)O—, $—SC(O)NR^2—$, —S(O)—, $—S(O)_2—$, $—OS(O)_2—$, $—OS(O)_2O—$, $—OS(O)_2NR^2—$, —OS(O)—, —OS(O)O—, $—OS(O)NR^2—$, $—ONR^2C(O)—$, $—ONR^2C(O)O—$, $—ONR^2C(O)NR^2—$, $—NR^2OC(O)—$, $—NR^2OC(O)O—$, $—NR^2OC(O)NR^2—$, $—ONR^2C(S)—$, $—ONR^2C(S)O—$, $—ONR^2C(S)NR^2—$, $—NR^2OC(S)—$, $—NR^2OC(S)O—$, $—NR^2OC(S)NR^2—$, —OC(S)—, —OC(S)O—, $—OC(S)NR^2—$, $—NR^2C(S)—$, $—NR^2C(S)O—$, $—NR^2C(S)NR^2—$, $—SS(O)_2—$, $—SS(O)_2O—$, $—SS(O)_2NR^2—$, $—NR^2OS(O)—$, $—NR^2OS(O)O—$, $—NR^2OS(O)NR^2—$, $—NR^2OS(O)_2—$, $—NR^2OS(O)_2O—$, $—NR^2OS(O)_2NR^2—$, $—ONR^2S(O)—$, $—ONR^2S(O)O—$, $—ONR^2S(O)NR^2—$, $—ONR^2S(O)_2O—$, $—ONR^2S(O)_2NR^2—$, $—ONR^2S(O)_2—$, $—OP(O)(R^2)_2—$, $—SP(O)(R^2)_2—$, $—NR^2P(O)(R^2)_2—$ and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In a particularly preferred process according to the invention, $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, wherein $R^3$ is independently selected from the group consisting of hydrogen and $C_1$-$C_4$ alkyl groups, and wherein $Q^1$ is according to formula (9a), (9j), (9p), (9q), (9n), (9t), (9ze), (9zh), (9zo) or (9o):

9a

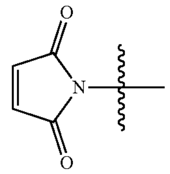

-continued

9q

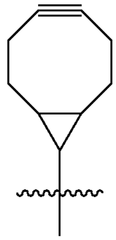

9n

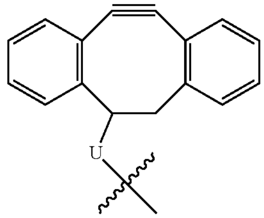

9j

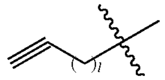

9o

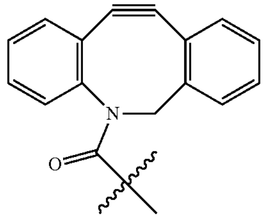

9p

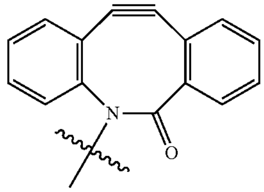

9ze

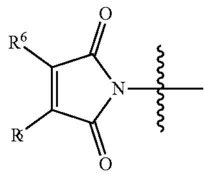

9t

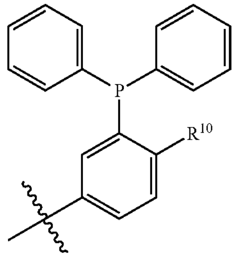

-continued

9zh

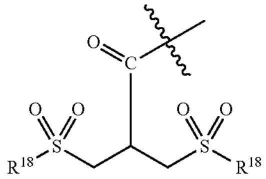

9zo

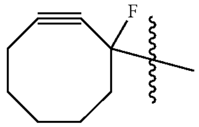

wherein:

l is an integer in the range 0-10;

$R^{10}$ is a (thio)ester group; and $R^{18}$ is selected from the group consisting of, optionally substituted, $C_1$-$C_{12}$ alkyl groups and $C_4$-$C_{12}$ (hetero) aryl groups.

Figure 4:
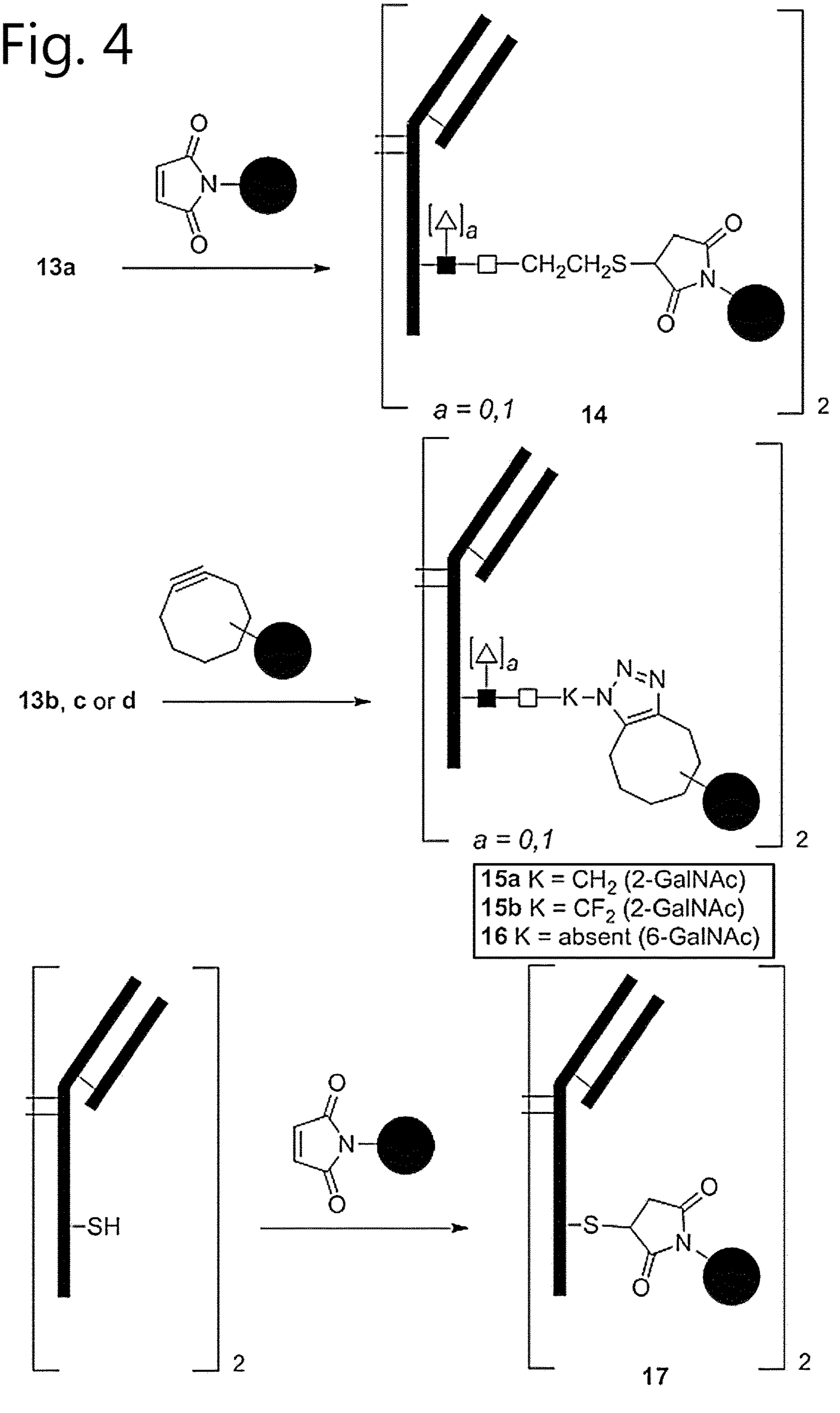
FIG. 4 shows how a modified antibody 13a-d may undergo a bioconjugation process by means of nucleophilic addition to maleimide (as for 3-mercaptopropionyl-galactosamine-modified 13a leading to thioether conjugate 14, or for conjugation to a engineered cysteine residue leading to thioether conjugate 17) or upon strain-promoted cycloaddition with a cyclooctyne reagent (as for 13b, 13c or 13d leading to triazoles 15a, 15b or 16, respectively).

An embodiment of the process for preparing the bioconjugate is depicted in FIG. 4. FIG. 4 shows how a modified antibody 13a-d may undergo a bioconjugation process by means of nucleophilic addition with maleimide (as for 3-mercaptopropionyl-galactosamine-modified 13a leading to thioether conjugate 14, or for conjugation to an engineered cysteine residue leading to thioether conjugate 17) or upon strain-promoted cycloaddition with a cyclooctyne reagent (as for 13b, 13c or 13d, leading to triazoles 15a, 15b or 16, respectively).

In addition to the increased therapeutic index of the bioconjugates according to the invention, a further advantages of the process for the preparation of a bioconjugate as described herein, and of the linker-conjugates and sulfamide linker according to the invention is that conjugation efficiency increases in case a sulfamide linker is used instead of a typical polyethylene glycol (PEG) spacer. An additional advantage of a sulfamide group, in particular of an acylsulfamide or a carbamoylsulfamide group, is its high polarity, which imparts a positive effect on the solubility of a linker comprising such group, and on the construct as a whole, before, during and after conjugation. In view of this increased polarity, conjugation with linker-conjugate containing the sulfamide linker according to the invention are particularly suited to conjugate hydrophobic target compounds to a biomolecule. The high polarity of the sulfamides also has a positive impact in case hydrophobic moieties are conjugated to a biomolecule of interest, which is known to require large amounts of organic co-solvent during conjugation and/or induce aggregation of the bioconjugate. High levels of co-solvent (up to 25% of DMF or even 50% of DMA, propylene glycol, or DMSO) may induce protein denaturation during the conjugation process and/or may require special equipment in the manufacturing process. Thus, the problem of aggregation associated with the hydrophobic linking moieties in bioconjugates is efficiently solved by using the sulfamide linker according to the invention in the spacer between the target molecule and the reactive group $Q^1$ in the linker-conjugate in the formation of the bioconjugate. An additional advantage of a sulfamide linker according the invention, and its use in bioconjugation processes, is its ease of synthesis and high yields.

For evidence of these beneficial effects of the use of the sulfamide linker according to the present invention, reference is made to PCT/NL2015/050697 (WO 2016/053107), in particular to Tables 1-3, FIGS. 11-14, 23 and 24, and Examples 57, 58, 60 and 61 therein. These Tables, Figures and Examples of PCT/NL2015/050697 (WO 2016/053107) are incorporated herein.

Application

The invention thus concerns in a first aspect the use of a mode of conjugation comprising at least one of "core-GlcNAc functionalization" and "sulfamide linkage", as defined above, for increasing the therapeutic index of a bioconjugate. The invention according to the present aspect can also be worded as a method for increasing the therapeutic index of a bioconjugate. In a preferred embodiment, the mode of conjugation is being used to connect a biomolecule B with a target molecule D via a linker L, wherein the mode of conjugation comprises:

(i) contacting a glycoprotein comprising 1-4 core N-acetylglucosamine moieties with a compound of the formula $S(F^1)_x$-P in the presence of a catalyst, wherein $S(F^1)_x$ is a sugar derivative comprising x functional groups $F^1$ capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety, to obtain a modified glycoprotein according to Formula (24):

(24)

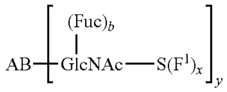

wherein $S(F^1)_x$ and x are as defined above; AB represents an antibody; GlcNAc is N-acetylglucosamine; Fuc is fucose; b is 0 or 1; and y is 1, 2, 3 or 4; and (ii) reacting the modified glycoprotein with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$.

Herein, the biomolecule is preferably an antibody, the bioconjugate is preferably an antibody-conjugate.

Herein, the therapeutic index is increased compared to a bioconjugate which does not comprise or is obtainable by the mode of conjugation according to the invention. Thus, in a first embodiment, the therapeutic index is increased compared to a bioconjugate not obtainable by steps (i) and (ii) as defined above, or—in other words—not containing the structural feature of the resulting linker L that links the antibody with the target molecule, that are a direct consequence of the conjugation process. Thus, in a second embodiment, the therapeutic index is increased compared to a bioconjugate of formula (A), wherein linker L does not comprise a group according to formula (1) or a salt thereof.

The inventors surprisingly found that the therapeutic index of the bioconjugates according to the invention was significantly increased when mode of conjugation according to the present invention was used, even if all other factors, in particular the type of biomolecule and the type of target molecule and biomolecule-target molecule-ratio, were kept constant. The increased therapeutic index could solely be attributed to the mode of conjugation according to the invention. The increased therapeutic index is preferably an increased therapeutic index in the treatment of cancer, in particular in targeting of HER2-expressing tumours.

The method according to the first aspect of the invention may also be worded as aspect a method for increasing the therapeutic index of a bioconjugate, comprising the step of providing a bioconjugate having the mode of conjugation according to the invention.

The inventors found that the mode of conjugation according to the invention, as comprised in the bioconjugates according to the invention, has an effect on both aspects of the therapeutic index: (a) on the therapeutic efficacy and (b) on the tolerability. Thus, the present use or method for increasing the therapeutic index is preferably for (a) increasing the therapeutic efficacy, and/or (b) increasing the tolerability of a bioconjugate of formula (A). Preferably the bioconjugate is an antibody-conjugate and the present use or method is for increasing the therapeutic index of an antibody-conjugate, preferably for (a) increasing the therapeutic efficacy of the antibody-conjugate, and/or (b) increasing the tolerability of the antibody-conjugate. In one embodiment, the present method or use is for increasing the therapeutic efficacy of the bioconjugate, preferably the antibody-conjugate. In one embodiment, the present method or use is for increasing the tolerability of the bioconjugate, preferably the antibody-conjugate.

Thus, in one embodiment, the use or method according to the first aspect is for increasing the therapeutic efficacy of a bioconjugate of formula (A). Herein, "increasing the therapeutic efficacy" can also be worded as "lowering the effective dose", "lowering the $ED_{50}$ value" or "increasing the protective index". Likewise, in one embodiment, the method according to the first aspect is for increasing the tolerability of a bioconjugate of formula (A). Herein, "increasing the tolerability" can also be worded as "increasing the maximum tolerated dose (MTD)", "increasing the $TD_{50}$ value", "increasing the safety" or "reducing the toxicity". In one especially preferred embodiment, the method according to the first aspect is for (a) increasing the therapeutic efficacy and (b) increasing the tolerability of a bioconjugate of formula (A).

The method according to the first aspect is largely non-medical. In one embodiment, the method is a non-medical or a non-therapeutic method for increasing the therapeutic index of a bioconjugate.

The first aspect of the invention can also be worded as a mode of conjugation for use in improving the therapeutic index (therapeutic efficacy and/or tolerability) of a bioconjugate, wherein the mode of conjugation is as defined above. In one embodiment, the present aspect is worded as a the mode of conjugation according to the "core-GlcNAc functionalization" as defined above for use in improving the therapeutic efficacy of a bioconjugate of formula (A), wherein L and (A) are as defined above. In one embodiment, the present aspect is worded as a mode of conjugation for use in improving the therapeutic index (therapeutic efficacy and/or tolerability) of a bioconjugate, preferably an antibody-conjugate. In other words, the first aspect concerns the use of a mode of conjugation for the preparation of a bioconjugate, preferably an antibody-conjugate, for improving the therapeutic index (therapeutic efficacy and/or tolerability) of the bioconjugate. The invention according to the first aspect can also be worded as the use of a mode of conjugation in a bioconjugate, preferably an antibody-conjugate, or in the preparation of a bioconjugate, preferably an antibody-conjugate, for increasing the therapeutic index (therapeutic efficacy and/or tolerability) of the bioconjugate. The use as defined herein may be referred to as non-medical or non-therapeutic use.

In one embodiment, the method, use or mode of conjugation for use according to the first aspect of the invention further comprises the administration of the bioconjugate according to the invention to a subject in need thereof, in particular a patient suffering from a disorder associated with HER2 expression, e.g. selected from breast cancer, pancreatic cancer, bladder cancer, or gastric cancer. In one embodiment, the subject is a cancer patient, more suitably a patient suffering from HER2-expressing tumours. The use of bioconjugates such as antibody-drug-conjugates, is well-known in the field of cancer treatment, and the bioconjugates according to the invention are especially suited in this respect.

Typically, the bioconjugate is administered in a therapeutically effective dose. Administration may be in a single dose or may e.g. occur 1-4 times a month, preferably 1-2 times a month. In a preferred embodiment, administration occurs once every 3 or 4 weeks, most preferably every 4 weeks. In view of the increased therapeutic efficacy, administration may occur less frequent as would be the case during treatment with conventional bioconjugates. As will be appreciated by the person skilled in the art, the dose of the bioconjugate according to the invention may depend on many factors and the optimal dosing regime can be determined by the skilled person via routine experimentation. The bioconjugate is typically administered in a dose of 0.01-50 mg/kg body weight of the subject, more accurately 0.03-25 mg/kg or most accurately 0.05-10 mg/kg, or alternatively 0.1-25 mg/kg or 0.5-10 mg/kg. In one embodiment, administration occurs via intravenous injection.

Method for Targeting HER2-Expressing Cells

The invention concerns in a second aspect a method for targeting HER2-expressing cells, including but not limited to low HER2-expressing cells, comprising the administration of the bioconjugate according to the invention. HER2-expressing cells may also be referred to as HER2-expressing tumour cells. The subject in need thereof is most preferably a cancer patient. The use of bioconjugates such as antibody-drug-conjugates, is well-known in the field of cancer treatment, and the bioconjugates according to the invention are especially suited in this respect. The method as described is typically suited for the treatment of cancer. The bioconjugate according to the invention is described a great detail above, which equally applies to the bioconjugate used in the second aspect of the invention. The second aspect of the invention can also be worded as a bioconjugate according to the invention for use in targeting HER2-expressing cells in a subject in need thereof. In other words, the second aspect concerns the use of a according to the invention for the preparation of a medicament for use in the targeting HER2-expressing cells in a subject in need thereof.

In the context of the present aspect, the targeting of HER2-expressing cells includes one or more of treating, imaging, diagnosing, preventing the proliferation of, containing and reducing HER2-expressing cells, in particular HER2-expressing tumours. Most preferably, the present aspect is for the treatment of HER2-expressing tumours.

In one embodiment, the present aspect concerns a method for the treatment of a subject in need thereof. The second aspect of the invention can also be worded as a bioconjugate according to the invention for use in the treatment of a subject in need thereof, preferably for the treatment of cancer. In other words, the second aspect concerns the use of a bioconjugate according to the invention for the preparation of a medicament for use in the treatment of a subject in need thereof, preferably for use in the treatment of cancer.

In the context of the present aspect, the subject suitably suffers from a disorder associated with HER2-expression, in particular a disorder selected form breast cancer, pancreatic cancer, bladder cancer, or gastric cancer In the context of the present aspect, it is preferred that target molecule D is an anti-cancer agent, preferably a cytotoxin.

In the method according to the second aspect, the bioconjugate is typically administered in a therapeutically effective dose. Administration may be in a single dose or may e.g. occur 1-4 times a month, preferably 1-2 times a month. In a preferred embodiment, administration occurs once every 3 or 4 weeks, most preferably every 4 weeks. As will be appreciated by the person skilled in the art, the dose of the bioconjugate according to the invention may depend on many factors and the optimal dosing regime can be determined by the skilled person via routine experimentation. The bioconjugate is typically administered in a dose of 0.01-50 mg/kg body weight of the subject, more accurately 0.03-25 mg/kg or most accurately 0.05-10 mg/kg, or alternatively 0.1-25 mg/kg or 0.5-10 mg/kg. In one embodiment, administration occurs via intravenous injection.

In view of the increased therapeutic efficacy, administration may occur less frequent as in treatment with conventional bioconjugates and/or at a lower dose. In one embodiment, the administration of the bioconjugate according to the invention is at a dose that is lower than the $TD_{50}$ of the same bioconjugate but not comprising the mode of conjugation according to the invention, preferably the dose is at most 99-90%, more preferably at most 89-60%, even more preferable at most 59-30%, most preferably at most 29-10% of the $TD_{50}$ of the same bioconjugate but not comprising the mode of conjugation according to the invention. In one embodiment, the administration of the bioconjugate according to the invention occurs less frequent as administration would occur for the same bioconjugate but not comprising the mode of conjugation according to the invention, preferably the number of administration events is at most 75%, more preferably at most 50% of the number of administration events of the same bioconjugate but not comprising the mode of conjugation according to the invention. Alternatively, in view of the increased tolerability, administration may occur in a higher dose as in treatment with conventional bioconjugates. In one embodiment, the administration of the bioconjugate according to the invention is at a dose that is higher than the $TD_{50}$ of the same bioconjugate but not comprising the mode of conjugation according to the invention, preferably the dose is at most 25-50%, more preferably at most 50-75%, most preferably at most 75-100% of the $TD_{50}$ of the same bioconjugate but not comprising the mode of conjugation according to the invention.

In view of the increased therapeutic efficacy, administration may occur less frequent as in treatment with conventional bioconjugates and/or at a lower dose. In one embodiment, the administration of the bioconjugate according to the invention is at a dose that is lower than the $ED_{50}$ of the same bioconjugate but not comprising the mode of conjugation according to the invention, preferably the dose is at most 99-90%, more preferably at most 89-60%, even more preferable at most 59-30%, most preferably at most 29-10% of the $ED_{50}$ of the same bioconjugate but not comprising the mode of conjugation according to the invention. In one embodiment, the administration of the bioconjugate according to the invention occurs less frequent as administration would occur for the same bioconjugate but not comprising the mode of conjugation according to the invention, preferably the number of administration events is at most 75%, more preferably at most 50% of the number of administration events of the same bioconjugate but not comprising the mode of conjugation according to the invention. Alternatively, in view of the increased tolerability, administration may occur in a higher dose as in treatment with conventional bioconjugates. In one embodiment, the administration of the bioconjugate according to the invention is at a dose that is higher than the $TD_{50}$ of the same bioconjugate but not comprising the mode of conjugation according to the invention, preferably the dose is at most a factor 1.1-1.49 higher, more preferably at most a factor 1.5-1.99 higher, even more preferable a factor 2-4.99 higher, most preferably at most a factor 5-10 higher of the $TD_{50}$ of the same bioconjugate but not comprising the mode of conjugation according to the invention.

In one embodiment, the use or method or conjugation mode for use according to the present aspect is a bioconjugate for use in the treatment of a subject in need thereof, wherein the bioconjugate is represented by formula (A):

$$B\text{-}L\text{-}D \quad \text{(A)},$$

wherein:

B is a biomolecule;

L is a linker linking B and D;

D is a target molecule; and each occurrence of "-" is independently a bond or a spacer moiety, wherein L comprises a group according to formula (1) or a salt thereof:

1

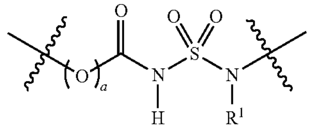

wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety.

Antibody-Conjugates According to the Invention

In a third aspect, the invention pertains to antibody-conjugates that are particularly suitable in targeting HER2-expressing tumours. The antibody-conjugates according to the invention comprise an antibody AB connected to a target molecule D via a linker L, wherein the antibody-conjugate comprises or is obtainable by the mode of conjugation according to the invention. In particular, the antibody-conjugates according to the invention are obtainable by:

(i) contacting a glycoprotein comprising 1-4 core N-acetylglucosamine moieties with a compound of the formula $S(F^1)_x$-P in the presence of a catalyst, wherein $S(F^1)_x$ is a sugar derivative comprising x functional groups $F^1$ capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety, to obtain a modified antibody according to Formula (24):

(24)

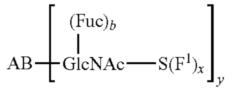

wherein $S(F^1)_x$ and x are as defined above; AB represents an antibody; GlcNAc is N-acetylglucosamine; Fuc is fucose; b is 0 or 1; and y is 1, 2, 3 or 4; and (ii) reacting the modified antibody with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$.

Herein, antibody AB is capable of targeting HER2-expressing tumours and target molecule D is selected from the group consisting of taxanes, anthracyclines, camptothecins, epothilones, mytomycins, combretastatins, vinca alkaloids, maytansinoids, calicheamycins and enediynes, duocarmycins, tubulysins, amatoxins, dolastatins and auristatins, pyrrolobenzodiazepine dimers, indolino-benzodiazepine dimers, radioisotopes, therapeutic proteins and peptides and toxins (or fragments thereof), kinase inhibitors, MEK inhibitors, KSP inhibitors, and analogs or prodrugs thereof. Alternatively, target molecule D is a cytotoxin. In one embodiment according to the present aspect, target molecule D is selected from the group consisting of maytansinoids, pyrrolobenzodiazepine dimers, indolino-benzodiazepine dimers, enediynes, auristatins and anthracyclines. In a preferred embodiment according to the present aspect, target molecule D is a maytansinoids or pyrrolobenzodiazepine dimer, more preferably an auristatine selected from the group consisting of MMAD, MMAE, MMAF and functional analogues thereof or maytansinoid selected from the group of DM1, DM3, DM4 and Ahx-May or any functional derivative thereof, most preferably D=Ahx-May or any functional derivative thereof. Alternatively, D is a pyrrolobenzodiazepine dimer.

The preferred embodiments for steps (i) and (ii), as defined above, equally apply to the antibody-conjugate according to the invention. The skilled person knowns how to translate these preferred features into structural features of the present antibody-conjugates. In a preferred embodiment, the antibody-conjugate according to the present aspect is according to formula (A) and preferably linker L contains the group according to formula (1) or a salt thereof, wherein (A) and (1) are as defined above.

Preferred options for $S(F^1)_x$ are described above. In one preferred embodiment, $S(F^1)_x$ is 6-azido-6-deoxy-N-acetylgalactosamine (6-AzGalNAc or 6-$N_3$-GalNAc).

In a preferred embodiment, the antibody AB capable of targeting HER2-expressing tumours is selected from the group consisting of from trastuzumab, margetuximab, pertuzumab, HuMax-Her2, ertumaxomab, HB-008, ABP-980, BCD-022, CanMab, Herzuma, HD201, CT-P6, PF-05280014, COVA-208, FS-102, MCLA-128, CKD-10101, HT-19 and functional analogues thereof. More preferably, the antibody AB capable of targeting HER2-expressing tumours is trastuzumab or a functional analogue thereof.

In an especially preferred embodiment, the antibody AB is trastuzumab, and target molecule D is selected from the group consisting of maytansinoids, auristatines and pyrrolobenzodiazepine dimer, preferably auristatines selected from the group consisting of MMAD, MMAE, MMAF and functional analogues thereof or maytansinoids selected form the group consisting of DM1, DM3, DM4, Ahx-May and functional analogues thereof. Most preferably, D=Ahx-May.

In a preferred embodiment, the antibody-conjugate according is represented by Formula (40) or (40b):

(40)

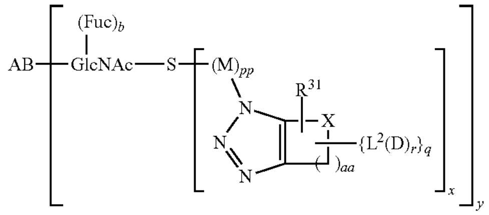

(40b)

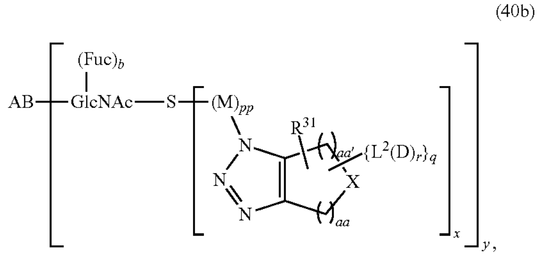

wherein:

$R^{31}$ is independently selected from the group consisting of hydrogen, halogen, —$OR^{35}$, —$NO_2$, —CN, —$S(O)_2R^{35}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{31}$ may be linked together to form an annelated cycloalkyl or an annelated (hetero)arene substituent, and wherein $R^{35}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

X is $C(R^{31})_2$, O, S or $NR^{32}$, wherein $R^{32}$ is $R^{31}$ or $L^3(D)_r$, wherein $L^3$ is a linker, and D is as defined in claim 1;

r is 1-20;

q is 0 or 1, with the proviso that if q is 0 then X is N-$L^2(D)_r$;

aa is 0, 1, 2, 3, 4, 5, 6, 7 or 8;

aa' is 0, 1, 2, 3, 4, 5, 6, 7 or 8; and aa+aa'<10.

b is 0 or 1;

pp is 0 or 1;

M is —$N(H)C(O)CH_2$—, —$N(H)C(O)CF_2$—, —$CH_2$—, —$CF_2$— or a 1,4-phenylene containing 0-4 fluorine substituents, preferably 2 fluorine substituents which are preferably positioned on $C_2$ and $C_6$ or on $C_3$ and $C_5$ of the phenylene;

y is 1-4;

Fuc is fucose.

Preferably, aa=2, aa'=3, X=$C(R^{31})_2$ (i.e. a fused cyclooctene ring is present), wherein one $R^{31}$=H and the other $R^{31}$ is linked together with the further $R^{31}$ substituent present in the structure according to formula (20b) to form an annelated cyclopropyl ring sharing carbon atoms 5 and 6 of the cyclooctene moiety (when the carbon atoms shared with the triazole ring are numbered 1 and 2). In a preferred embodiment, the antibody is according to any one of Formulae (41), (42), (42b), (35b), (40c) and (40d) as defined above.

Preferred features of the antibody-conjugate according to the invention are described above, in particular in the description of step (ii) of the "core-GlcNAc functionalization" as mode of conjugation, and the products thereof.

In one embodiment, the antibody-conjugate according to the present aspect is a bioconjugate represented by formula (A):

B-L-D (A), wherein:

B is a biomolecule;

L is a linker linking B and D;

D is a target molecule; and each occurrence of "-" is independently a bond or a spacer moiety, wherein L comprises a group according to formula (1) or a salt thereof:

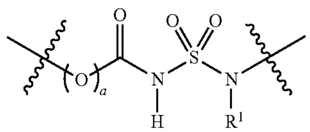

1 wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety.

Preferred antibody-conjugates according to the present aspect are listed here below as conjugates (I)-(XXIV). In one embodiment, the antibody-conjugate according to the present aspect is selected from the conjugates defined here below as (I)-(XXIV), preferably selected from the conjugates defined here below as (I)-(X), more preferably selected from the conjugates defined here below as (I)-(VI).

(I) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—$S(O)_2$—NH—$(CH_2$—$CH_2$—$O)_2$—C(O)-Val-Cit-PABC-, D=Ahx-May (conjugate 82);

(II) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—$(CH_2)_3$—C(O)—NH—$S(O)_2$—NH—$(CH_2$—$CH_2$—$O)_2$—C(O)-Val-Cit-PABC-, D=Ahx-May (conjugate 83);

(III) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—($CH_2$—$CH_2$—O)$_4$—C(O)-Val-Cit-PABC-, D=Ahx-May (conjugate 81);

(IV) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—($CH_2$—$CH_2$—O)$_4$—C(O)—N($CH_2$—$CH_2$—O—C(O)-Val-Cit-PABC-D)$_2$, each occurrence of D=Ahx-May;

(V) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—NH—S(O)$_2$—N($CH_2$—$CH_2$—O—C(O)-Val-Cit-PABC-D)$_2$, each occurrence of D=Ahx-May (conjugate 84);

(VI) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)-Val-Ala-, D=PBD (conjugate 85);

(VII) AB=trastuzumab, wherein $S(F^1)_x$ is connected to the core-GlcNAc linked to amino acid N300, $S(F^1)_x$=2-azidoacetamido-2-deoxy-galactose, $Q^1$ is according to formula (9q), $L^2$=—$CH_2$—O—C(O)—NH—($CH_2$—$CH_2$—O)$_4$—C(O)—, D=Ahx-May (conjugate 96);

(VIII) AB=trastuzumab, wherein $S(F^1)_x$ is connected to the core-GlcNAc linked to amino acid N300, $S(F^1)_x$=2-azidoacetamido-2-deoxy-galactose, $Q^1$ is according to formula (9q), $L^2$=—$CH_2$—O—C(O)—NH—S(O)$_2$—NH—($CH_2$—$CH_2$—O)$_4$—C(O)—, D=Ahx-May (conjugate 95);

(IX) AB=trastuzumab, wherein $S(F^1)_x$ is connected to the core-GlcNAc linked to amino acid N300, $S(F^1)_x$=2-azidodifluoroacetamido-2-deoxy-galactose, $Q^1$ is according to formula (9q), $L^2$=—$CH_2$—O—C(O)—NH—S(O)$_2$—NH—($CH_2$—$CH_2$—O)$_4$—C(O)—, D=Ahx-May (conjugate 97);

(X) AB=trastuzumab, wherein $S(F^1)_x$ is connected to the core-GlcNAc linked to amino acid N300, $S(F^1)_x$=2-azidodifluoroacetamido-2-deoxy-galactose, $Q^1$ is according to formula (9q), $L^2$=—$CH_2$—O—C(O)—NH—($CH_2$—$CH_2$—O)$_4$—C(O)—, D=Ahx-May (conjugate 98);

(XI) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9n), wherein U=O, $L^2$=—C(O)—NH—S(O)$_2$—NH—($CH_2$—$CH_2$—O)$_2$—C(O)—NH—S(O)$_2$—N($CH_2$—$CH_2$—O—C(O)-Val-Cit-PABC-D)$_2$, each occurrence of D=Ahx-May.

(XII) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9zo), $L^2$=—C(O)—NH—($CH_2$)$_4$—C(O)—NH—($CH_2$)$_5$—O—C(O)—NH—S(O)$_2$—N($CH_2$—$CH_2$—O—C(O)-Val-Cit-PABC-D)$_2$, each occurrence of D=Ahx-May;

(XIII) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9j), wherein l=3, $L^2$=—O—C(O)—NH—S(O)$_2$—NH—($CH_2$—$CH_2$—O)$_2$—C(O)—NH—S(O)$_2$—N($CH_2$—$CH_2$—O—C(O)-Val-Cit-PABC-D)$_2$, each occurrence of D=Ahx-May;

(XIV) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)—NH—S(O)$_2$—NH—($CH_2$—$CH_2$—O)$_2$—C(O)-Val-Cit-PABC-D)$_2$, each occurrence of D=Ahx-May;

(XV) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D)$_2$, each occurrence of D=Ahx-May;

(XVI) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D)$_2$, each occurrence of D=Dox;

(XVII) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D)$_2$, each occurrence of D=MMAF;

(XVIII) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D)$_2$, each occurrence of D=MMAE;

(XIX) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—NH—S(O)$_2$—N($CH_2$—$CH_2$—O—C(O)-Val-Cit-PABC-D)$_2$, each occurrence of D=MMAE;

(XX) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D1)($CH_2$—$CH_2$—O—C(O)-Val-Cit-PABC-D2), with D1=MMAE and D2=MMAF;

(XXI) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D1)($CH_2$—$CH_2$—O—C(O)-Val-Cit-PABC-D2), with D1=MMAE and D2=Dox;

(XXII) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)—N($CH_2$—$CH_2$—O—C(O)-Val-Cit-PABC-D1)($CH_2$—$CH_2$—O—C(O)-Val-Cit-PABC-D2), with D1=MMAE and D2=Ahx-May;

(XXIII) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—S(O)$_2$—NH—($CH_2$—$CH_2$—O)$_2$—C(O)-Val-Cit-PABC-D, each occurrence of D=MMAE; and (XXIV) AB=trastuzumab, wherein $S(F^1)_x$ is connected to the core-GlcNAc linked to amino acid N300, $S(F^1)_x$=6-azido-6-deoxy-N-acetylgalactosamine, $Q^1$ is according to formula (9q), $L^2$=—$CH_2$—O—C(O)—NH—$(CH_2$—$CH_2$—$O)_4$—C(O)-Val-Cit-PABC-D, each occurrence of D=MMAE.

The skilled person understands that the antibody-conjugates defined here as (I)-(XXIV) do not contain $F^1=N_3$ nor $Q^1$=(9j), (9n), (9q) or (9zo), but the connecting group $Z^3$ resulting from reaction between $F^1$ and $Q^1$. More specifically, the antibody-conjugates (I)-(VI) and (XIV) to (XXIV) as defined above are according to formula (40b), wherein S=GalNAc, y=2, x=1, b=0 or 1, pp=0 (i.e. M is absent), aa=2, aa'=3, X=$C(R^{31})_2$, wherein one $R^{31}$=H and the other $R^{31}$ is linked together with the further $R^{31}$ substituent present in the structure according to formula (40b) to form an annelated cyclopropyl ring sharing carbon atoms 5 and 6 of the cyclooctene moiety (when the carbon atoms shared with the triazole ring are numbered 1 and 2, cf. structure (9q) above), q=1, r=1 or 2 and D and $L^2$ are defined above. More specifically, the antibody-conjugates (VII) and (VIII) as defined above are according to formula (40b), wherein S=GalNAc, y=2, x=1, b=0 or 1, pp=1, M=—N(H)C(O)$CH_2$—, aa=2, aa'=3, X=$C(R^{31})_2$, wherein one $R^{31}$=H and the other $R^{31}$ is linked together with the further $R^{31}$ substituent present in the structure according to formula (40b) to form an annelated cyclopropyl ring sharing carbon atoms 5 and 6 of the cyclooctene moiety (when the carbon atoms shared with the triazole ring are numbered 1 and 2, cf. structure (9q) above), q=1, r=1 or 2 and D and $L^2$ are defined above. More specifically, the antibody-conjugates (IX) and (X) as defined above are according to formula (40b), wherein S=GalNAc, y=2, x=1, b=0 or 1, pp=1, M=—N(H)C(O)$CF_2$—, aa=2, aa'=3, X=$C(R^{31})_2$, wherein one $R^{31}$=H and the other $R^{31}$ is linked together with the further $R^{31}$ substituent present in the structure according to formula (40b) to form an annelated cyclopropyl ring sharing carbon atoms 5 and 6 of the cyclooctene moiety (when the carbon atoms shared with the triazole ring are numbered 1 and 2, cf. structure (9q) above), q=1, r=1 or 2 and D and $L^2$ are defined above. More specifically, the antibody-conjugate (XI) as defined above is according to formula (40b), wherein S=GalNAc, y=2, x=1, b=0 or 1, pp=0 (i.e. M is absent), aa=3, aa'=2, X=$C(R^{31})_2$, wherein $R^{31}$=H, wherein two fused phenyl rings are annelated to respectively carbon atoms 3+4 and 7+8 of the cyclooctene moiety and $\{L^2(D)_r\}_q$ is connected to carbon atom 5 or 6 (when the carbon atoms shared with the triazole ring are numbered 1 and 2, cf. structure (10k) above), q=1, r=1 and D and $L^2$ are defined above. More specifically, the antibody-conjugate (XII) as defined above is according to formula (40b), wherein S=GalNAc, y=2, x=1, b=0 or 1, pp=0 (i.e. M is absent), aa=0, aa'=5, X=$C(R^{31})_2$, wherein one $R^{31}$=F and the other $R^{31}$ provides the connection with $\{L^2(D)_r\}_q$, q=1, r=1 and D and $L^2$ are defined above. More specifically, the antibody-conjugate (XIII) as defined above is according to formula (40d), wherein S=GalNAc, y=2, x=1, b=0 or 1, pp=0 (i.e. M is absent), I=3, q=1, r=1 and D and $L^2$ are defined above.

The antibody-conjugates according to the present aspect have an improved therapeutic index compared to known antibody-conjugates, wherein the therapeutic index is preferably for the treatment of HER2-expressing tumours. The improved therapeutic index may take the form of an improved therapeutic efficacy and/or an improved tolerability. In one embodiment, the antibody-conjugates according to the present aspect have an improved therapeutic efficacy compared to known antibody-conjugates for the treatment of HER2-expressing tumours. In one embodiment, the antibody-conjugates according to the present aspect have an improved tolerability compared to known antibody-conjugates for the treatment of HER2-expressing tumours.

The antibody-conjugates according to the invention outperform the known antibody-conjugates also in other aspects. The inventors have found that the present antibody-conjugates exhibit an increased stability (i.e. they exhibit less degradation over time). The inventors have also found that the present antibody-conjugates exhibit decreased aggregation issues (i.e. they exhibit less aggregation over time). In view of their improved therapeutic index, increased stability and decreased aggregation, the present antibody-conjugates are a marked improvement over prior art antibody-conjugates. The invention thus also concerns the use of the mode of conjugation as defined herein for improving stability of an bioconjugate, typically an antibody-conjugate. The invention thus also concerns the use of the mode of conjugation as defined herein for decreasing aggregation of an bioconjugate, typically an antibody-conjugate.

Endoglycosidases Fusion Enzyme

In a fourth aspect, the invention concerns a fusion enzyme comprising two endoglycosidases. In a particular example the two endoglycosidases EndoS and EndoH are connected via a linker, preferably a -$(Gly_4Ser)_3$-$(His)_6$-$(Gly_4Ser)_3$- linker. The fusion enzyme according to the invention as also referred to as EndoSH. The enzyme according to the invention has at least 50% sequence identity with SEQ ID NO: 1, preferably at least 70%, more preferably at least 80% sequence identity with SEQ ID NO: 1, such as at least 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1. Identity can be readily calculated by known methods and/or computer program methods known in the art such as BLASTP publicly available from NCBI and other sources (BLAST Manual, Altschul, S., et al., NCBI NLM NIH Bethesda, Md. 20894; Altschul, S., et al., J. Mol. Biol. 215:403-410 (1990). Preferably, the enzyme of the invention, having the above indicated sequence identity to SEQ ID NO: 1, has EndoS and EndoH activity. Most preferably, the enzyme according to the invention has 100% sequence identity with SEQ ID NO: 1.

Also encompassed are fusion enzymes of EndoS and EndoH, wherein the linker is replaced by another suitable linker known in the art, wherein said linker may be a rigid, or flexible. Preferably, said linker is a flexible linker allowing the adjacent protein domains to move relative freely to one another. Preferably, said flexible linker is composed of amino residues like glycine, serine, histidine and/or alanine and has a length of 3 to 59 amino acid residues, preferably 10 to 45 or 15 to 40 amino acid residues, such as 15, 16, 17, 18, 19, 20, 21, 22, 23, 24, 25, 26, 27, 28, 29, 30, 31, 32, 33, 34, 35, 36, 37, 38, 39 or 40 amino acid residues, or 20 to 38, 25 to 37 or 30 to 36 amino acid residues. Optionally, the fusion enzyme is covalently linked to, or comprises, a tag for ease of purification and or detection as known in the art, such as an Fc-tag, FLAG-tag, poly(His)-tag, HA-tag and Myc-tag.

Trimming of glycoproteins is known in the art, from e.g. WO 2007/133855 or WO 2014/065661. The enzyme according to the invention exhibits both EndoS and EndoH activity, and is capable of trimming glycans on glycoproteins (such as antibodies) at the core-GlcNAc unit, leaving only the core-GlcNAc residue on the glycoprotein (EndoS activity) as well as well as splitting off high-manose glycans (EndoH activity). Surprisingly, both activities of the fusion enzyme function smoothly at a pH around 7-8, while monomeric EndoH requires a pH of 6 to operate optimally. The fusion enzyme according to the invention can be prepared by routine techniques in the art, such as introducing an expression vector (e.g. plasmid) comprising the enzyme coding sequence into a host cell (e.g. *E. coli*) for expression, from which the enzyme can be isolated. A possible approach for the preparation and purification of the fusion enzyme according to the invention is given in examples 3-5, and its functioning is demonstrated in example 6, wherein trastuzumab is efficiently trimmed in a single step.

Sequence Identification of Fusion Protein EndoSH (SEQ. ID NO: 1):

1 MPSIDSLHYL SENSKKEFKE ELSKAGQESQ KVKEILAKAQ QADKQAQELA

51 KMKIPEKIPM KPLHGPLYGG YFRTWHDKTS DPTEKDKVNS MGELPKEVDL

101 AFIFHDWTKD YSLFWKELAT KHVPKLNKQG TRVIRTIPWR FLAGGDNSGI

151 AEDTSKYPNT PEGNKALAKA IVDEYVYKYN LDGLDVDVEH DSIPKVDKKE

201 DTAGVERSIQ VFEEIGKLIG PKGVDKSRLF IMDSTYMADK NPLIERGAPY

251 INLLLVQVYG SQGEKGGWEP VSNRPEKTME ERWQGYSKYI RPEQYMIGFS

301 FYEENAQEGN LWYDINSRKD EDKANGINTD ITGTRAERYA RWQPKTGGVK

351 GGIFSYAIDR DGVAHQPKKY AKQKEFKDAT DNIFHSDYSV SKALKTVMLK

401 DKSYDLIDEK DFPDKALREA VMAQVGTRKG DLERFNGTLR LDNPAIQSLE

451 GLNKFKKLAQ LDLIGLSRIT KLDRSVLPAN MKPGKDTLET VLETYKKDNK

501 EEPATIPPVS LKVSGLTGLK ELDLSGFDRE TLAGLDAATL TSLEKVDISG

551 NKLDLAPGTE NRQIFDTMLS TISNHVGSNE QTVKFDKQKP TGHYPDTYGK

601 TSLRLPVANE KVDLQSQLLF GTVTNQGTLI NSEADYKAYQ NHKIAGRSFV

651 DSNYHYNNFK VSYENYTVKV TDSTLGTTTD KTLATDKEET YKVDFFSPAD

701 KTKAVHTAKV IVGDEKTMMV NLAEGATVIG GSADPVNARK VFDGQLGSET

751 DNISLGWDSK QSIIFKLKED GLIKHWRFFN DSARNPETTN KPIQEASLQI

801 FNIKDYNLDN LLENPNKFDD EKYWITVDTY SAQGERATAF SNTLNNITSK

851 YWRVVFDTKG DRYSSPVVPE LQILGYPLPN ADTIMKTVTT AKELSQQKDK

901 FSQKMLDELK IKEMALETSL NSKIFDVTAI NANAGVLKDC IEKRQLLKKG

951 GGGSGGGGSG GGGSHHHHHH EFGGGGSGGG GSGGGGS*APA PVKQGPTSVA*

1001 *YVEVNNNSML NVGKYTLADG GGNAFDVAVI FAANINYDTG TKTAYLHFNE*

1051 *NVQRVLDNAV TQIRPLQQQG IKVLLSVLGN HQGAGFANFP SQQAASAFAK*

1101 *QLSDAVAKYG LDGVDFDDEY AEYGNNGTAQ PNDSSFVHLV TALRANMPDK*

1151 *IISLYNIGPA ASRLSYGGVD VSDKFDYAWN PYYGTWQVPG IALPKAQLSP*

1201 *AAVEIGRTSR STVADLARRT VDEGYGVYLT YNLDGGDRTA DVSAFTRELY*

1251 *GSEAVRTP*

(linker is underlined, EndoH sequence is denoted in italics)

EXAMPLES
Tables 1 and 2 below provides an overview of the bioconjugates prepared.
TABLE 1
| General structure of the bioconjugates |
|---|
| (a) 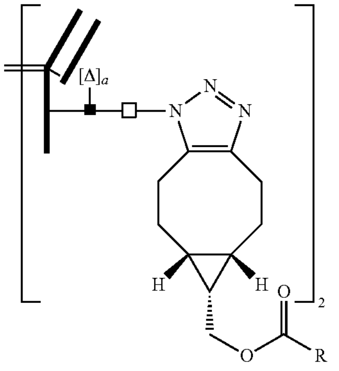 a = 0,1 |
| (b) 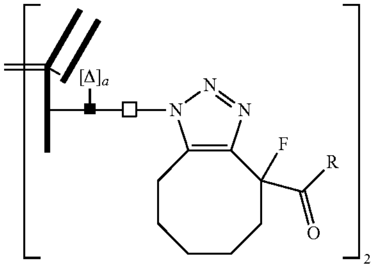 a = 0,1 |
TABLE 1-continued
| General structure of the bioconjugates |
|---|
| (c) 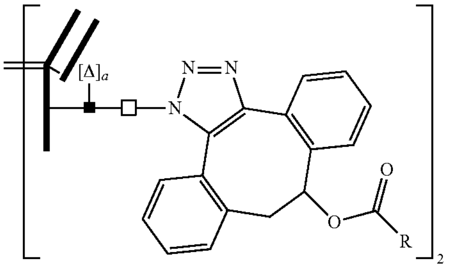 a = 0,1 |
| (d) 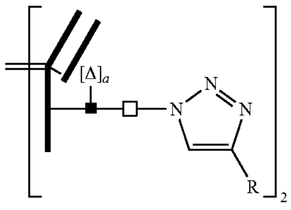 a = 0,1 |
TABLE 2
| List of exemplary bioconjugates | | | |
|---|---|---|---|
| | Reaction partners * | Structure $S(F^1)_x$ ** | R |
| I (82) | 13d + 78 | (a) 6-$N_3$-GalNAc | 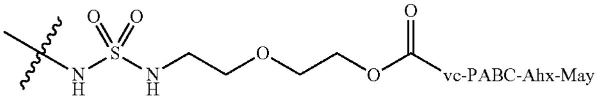 |
| II (83) | 13d + 80 | (a) 6-$N_3$-GalNAc | 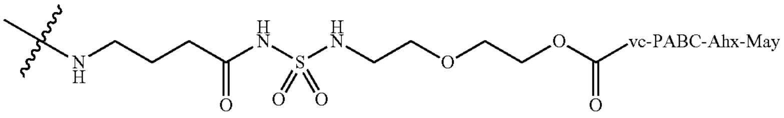 |
| III (81) | 13d + 77 | (a) 6-$N_3$-GalNAc | 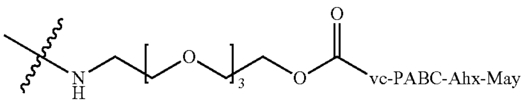 |

TABLE 2-continued
List of exemplary bioconjugates
| | Reaction partners * | Structure $S(F^1)_x$ ** | R |
|---|---|---|---|
| IV | 13d + 54 | (a) 6-$N_3$-GalNAc | 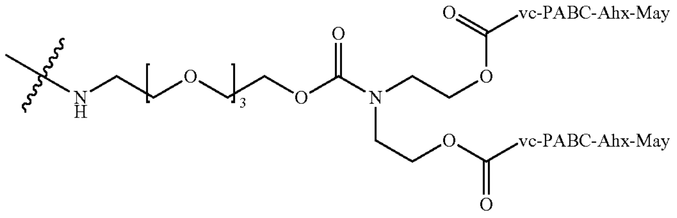 |
| V (84) | 13d + 73 | (a) 6-$N_3$-GalNAc | 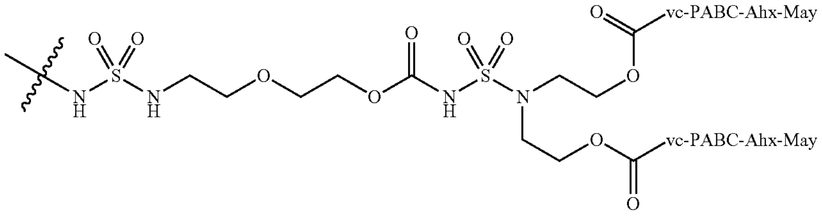 |
| VI (85) | 13d + 76 | (a) 6-$N_3$-GalNAc | 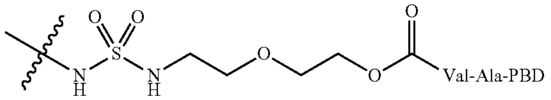 |
| VII (96) | 13b + 30 | (a) GalNAz | 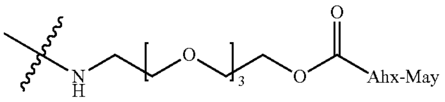 |
| VIII (95) | 13b + 33 | (a) GalNAz | 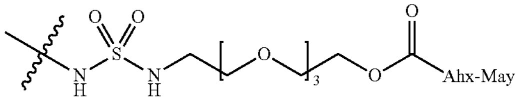 |
| IX (97) | 13c + 33 | (a) $F_2$-GalNAz | 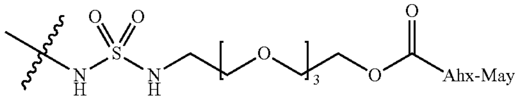 |
| X (98) | 13c + 30 | (a) $F_2$-GalNAz | 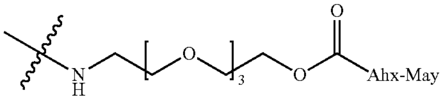 |
| XI | 13d + 44 | (c) 6-$N_3$-GalNAc | 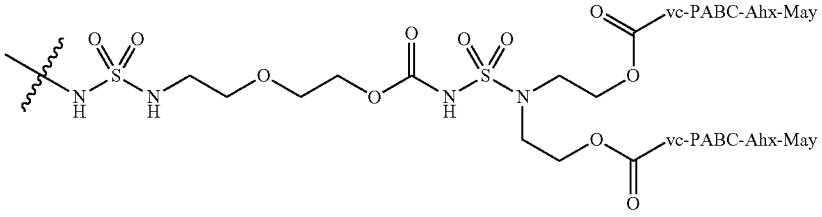 |
| XII | 13d + 48 | (b) 6-$N_3$-GalNAc | 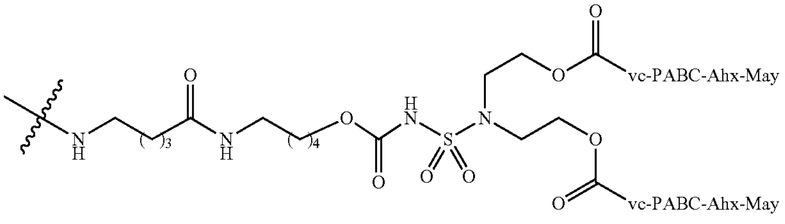 |

TABLE 2-continued
List of exemplary bioconjugates
| | Reaction partners * | Structure $S(F^1)_x$ ** | R |
|---|---|---|---|
| XIII | 13d + 51 | (d) 6-$N_3$-GalNAc | 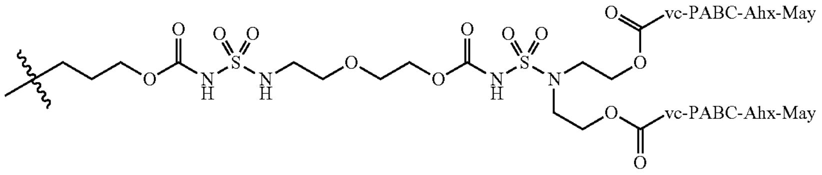 |
| XIV | 13d + 59 | (a) 6-$N_3$-GalNAc | 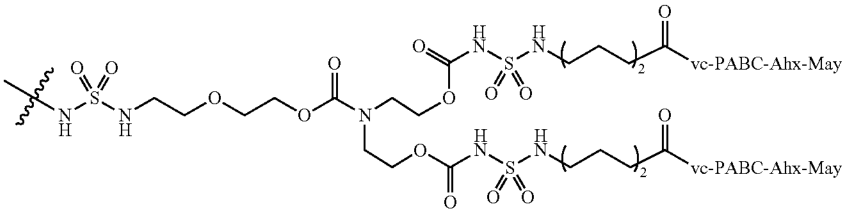 |
| XV | 13d + 60 | (a) 6-$N_3$-GalNAc | 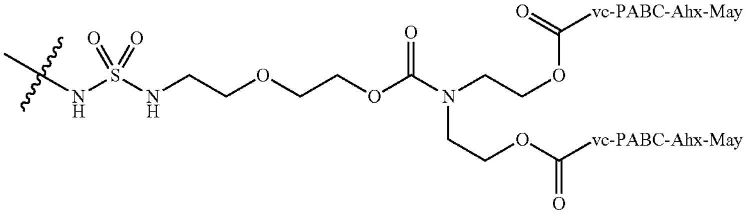 |
| XVI | 13d + 62 | (a) 6-$N_3$-GalNAc | 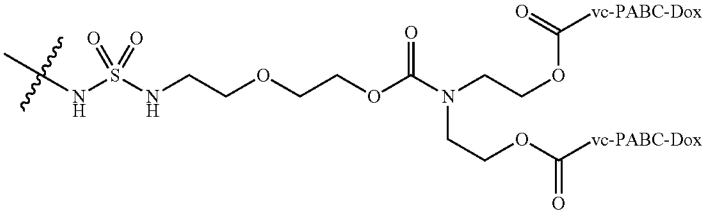 |
| XVII | 13d + 63 | (a) 6-$N_3$-GalNAc | 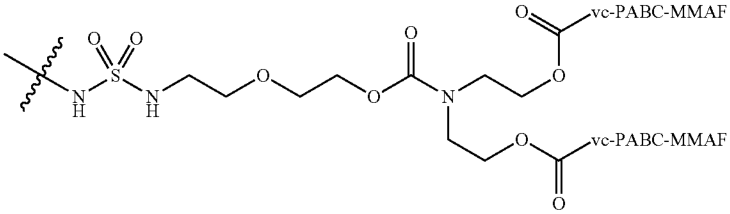 |
| XVIII | 13d + 64 | (a) 6-$N_3$-GalNAc | 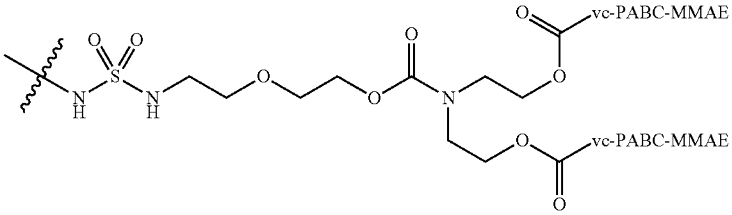 |
| XIX | 13d + 65 | (a) 6-$N_3$-GalNAc | 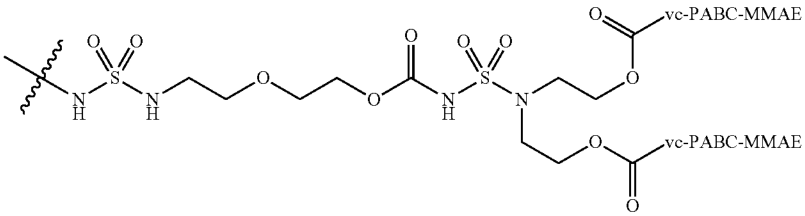 |

TABLE 2-continued

List of exemplary bioconjugates

| | Reaction partners * | Structure $S(F^1)_x$ ** | R |
|---|---|---|---|
| XX | 13d + 66 | (a) 6-$N_3$-GalNAc | 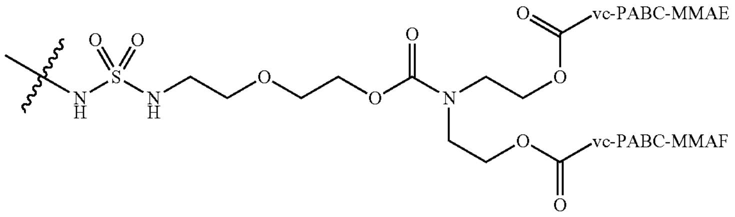 |
| XXI | 13d + 68 | (a) 6-$N_3$-GalNAc | 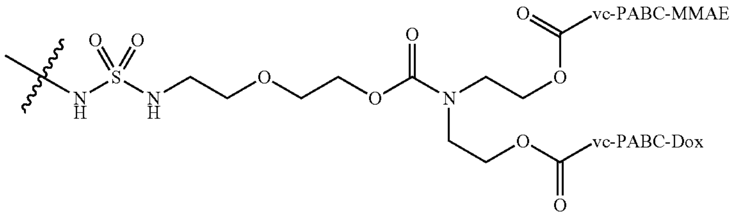 |
| XXII | 13d + 69 | (a) 6-$N_3$-GalNAc | 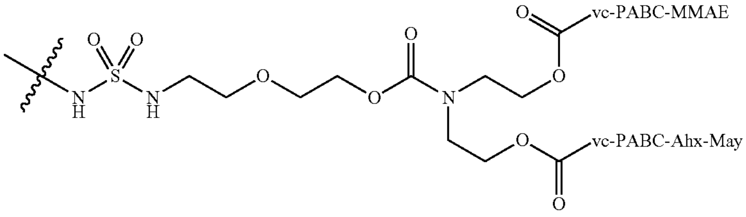 |
| XXIII | 13d + 111 | (a) 6-$N_3$-GalNAc | 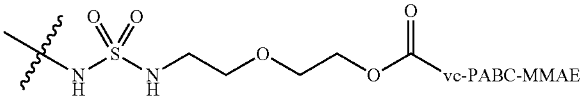 |
| XXIV | 13d + 112 | (a) 6-$N_3$-GalNAc | 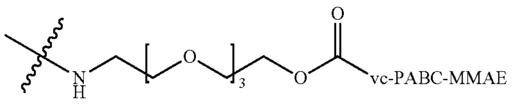 |

Notes:

* Reaction partners used to prepare the bioconjugate (see Examples below).

** General structure as defined in Table 1 and structure of $S(F^1)_x$. 6-$N_3$-GalNAc = 6-azido-6-deoxy-N-acetylgalactosamine; GalNAz = 2-azidoacetamido-2-deoxy-galactose; $F_2$-GalNAz = 2-azidodifluoroacetamido-2-deoxy-galactose.

RP-HPLC Analysis of Reduced Monoclonal Antibodies:

Prior to RP-HPLC analysis samples were reduced by incubating a solution of 10 μg (modified) IgG for 15 minutes at 37° C. with 10 mM DTT and 100 mM Tris pH 8.0 in a total volume of 50 μL. A solution of 49% ACN, 49% MQ and 2% formic acid (50 μL) was added to the reduced sample. Reverse phase HPLC was performed on a Agilent 1100 HPLC using a ZORBAX Phoroshell 300SB-C8 1×75 5 μm (Agilent Technologies) column run at 1 ml/min at 70° C. using a 16.9 minute linear gradient from 25 to 50% buffer B (with buffer A=90% MQ, 10% ACN, 0.1% TFA and buffer B=90% ACN, 10% MQ, 0.1% TFA).

Mass Spectral Analysis of Monoclonal Antibodies:

Prior to mass spectral analysis, IgGs were either treated with DTT, which allows analysis of both light and heavy chain, or treated with Fabricator™ (commercially available from Genovis, Lund, Sweden), which allows analysis of the Fc/2 fragment. For analysis of both light and heavy chain, a solution of 20 μg (modified) IgG was incubated for 5 minutes at 37° C. with 100 mM DTT in a total volume of 4 μL. If present, azide-functionalities are reduced to amines under these conditions. For analysis of the Fc/2 fragment, a solution of 20 μg (modified) IgG was incubated for 1 hour at 37° C. with Fabricator™ (1.25 U/μL) in phosphate-buffered saline (PBS) pH 6.6 in a total volume of 10 μL. After reduction or Fabricator-digestion the samples were washed trice with milliQ using an Amicon Ultra-0.5, Ultracel-10 Membrane (Millipore) resulting in a final sample volume of approximately 40 μL. Next, the samples were analysed by electrospray ionization time-of-flight (ESI-TOF) on a JEOL AccuTOF. Deconvoluted spectra were obtained using Magtran software.

Preparation of Protein Components: Examples 1-2

Example 1: Transient Expression and Purification of Trastuzumab

Trastuzumab was expressed from a stable CHO cell line by Bioceros (Utrecht, Netherlands). The supernatant (2.5 L) was purified using a XK 26/20 column packed with 50 mL protein A sepharose. In a single run 0.5 L supernatant was loaded onto the column followed by washing with at least 10 column volumes of 25 mM Tris pH 7.5, 150 mM NaCl. Retained protein was eluted with 0.1 M Glycine pH 2.7. The eluted product was immediately neutralized with 1.5 M Tris-HCl pH 8.8 and dialyzed against 25 mM Tris pH 8.0. Next the product was concentrated to approximately 20 mg/mL using a Vivaspin Turbo 15 ultrafiltration unit (Sartorius) and stored at −80° C. prior to further use.

Example 2: Transient Expression and Purification of his-TnGalNAcT(33-421)

His-TnGalNAcT(33-421) (identified by SEQ ID NO: 3) was transiently expressed in CHO K1 cells by Evitria (Zurich, Switzerland) at 5 L scale. The supernatant was purified using a XK 16/20 column packed with 25 mL Ni sepharose excel (GE Healthcare). Each run approximately 1.5 L supernatant was loaded onto the column followed by washing with at least 10 column volumes of buffer A (20 mM Tris buffer, 5 mM imidazole, 500 mM NaCl, pH 7.5). Retained protein was eluted with buffer B (20 mM Tris, 500 mM NaCl, 500 mM imidazole, pH 7.5). The buffer of the eluted fractions was exchanged to 25 mM Tris pH 8.0 using a HiPrep H26/10 desalting column (GE Healthcare). The purified protein was concentrated to at least 3 mg/mL using a Vivaspin Turbo 4 ultrafiltration unit (Sartorius) and stored at −80° C. prior to further use.

Sequence of his-TnGalNAcT(33-421) (SEQ. ID NO: 3):

```
  1  HHHHHHSPLR TYLYTPLYNA TQPTLRNVER LAANWPKKIP SNYIEDSEEY
 51  SIKNISLSNH TTRASVVHPP SSITETASKL DKNMTIQDGA FAMISPTPLL
101  ITKLMDSIKS YVTTEDGVKK AEAVVTLPLC DSMPPDLGPI TLNKTELELE
151  WVEKKFPEVE WGGRYSPPNC TARHRVAIIV PYRDRQQHLA IFLNHMHPFL
201  MKQQIEYGIF IVEQEGNKDF NRAKLMNVGF VESQKLVAEG WQCFVFHDID
251  LLPLDTRNLY SCPRQPRHMS ASIDKLHFKL PYEDIFGGVS AMTLEQFTRV
301  NGFSNKYWGW GGEDDDMSYR LKKINYHIAR YKMSIARYAM LDHKKSTPNP
351  KRYQLLSQTS KTFQKDGLST LEYELVQVVQ YHLYTHILVN IDERS
```

Examples 3-5: Production of Endoglycosidase EndoSH

Example 3: Cloning of Fusion Protein EndoSH into pET22B Expression Vector

A pET22B-vector containing an EndoS-$(G_4S)_3$-$(His)_6$-$(G_4S)_3$-EndoH (EndoSH) coding sequence (EndoSH being identified by SEQ ID NO: 1) between NdeI-HindIII sites was obtained from Genscript. The DNA sequence for the EndoSH fusion protein consists of the encoding residues 48-995 of EndoS fused via an N-terminal linked glycine-serine (GS) linker to the coding residues 41-313 of EndoH. The glycine-serine (GS) linker comprises a -$(G_4S)_3$-$(His)_6$-EF-$(G_4S)_3$- format, allowing spacing of the two enzymes and at the same time introducing a IMAC-purification tag.

Example 4: *E. coli* Expression of Fusion Protein EndoSH

Expression of the EndoSH fusion protein (identified by SEQ ID NO: 1) starts with the transformation of the plasmid (pET22b-EndoSH) into BL21 cells. Next step is the inoculation of 500 mL culture (LB medium+ Ampilicin) with BL21 cells. When the OD600 reached 0.7 the cultures were induced with 1 mM IPTG (500 μL of 1M stock solution).

Example 5: Purification of Fusion Protein EndoSH from *E. coli*

After overnight induction at 16° C. the cultures were pelleted by centrifugation. The pellets were resuspended in 40 mL PBS and incubated on ice with 5 ml lysozyme (10 mg/mL) for 30 minutes. After half an hour 5 ml 10% Triton-X-100 was added and sonicated (10 minutes) on ice. After the sonification the cell debris was removed by centrifugation (10 minutes 8000×g) followed by filtration through a 0.22 μM-pore diameter filter. The soluble extract was loaded onto a HisTrap HP 5 mL column (GE Healthcare). The column was first washed with buffer A (20 mM Tris buffer, 20 mM imidazole, 500 mM NaCl, pH 7.5). Retained protein was eluted with buffer B (20 mM Tris, 500 mM NaCl, 250 mM imidazole, pH 7.5, 10 mL). Fractions were analysed by SDS-PAGE on polyacrylamide gels (12%). The fractions that contained purified target protein were combined and the buffer was exchanged against 20 mM Tris pH 7.5 and 150 mM NaCl by dialysis performed overnight at 4° C. The purified protein was concentrated to at least 2 mg/mL using an Amicon Ultra-0.5, Ultracel-10 Membrane (Millipore). The product is stored at −80° C. prior to further use.

Remodelling of Trastuzumab: Examples 6-7

The preparation of the following modified biomolecules, suitable as biomolecule to be used in the method according to the invention, is described in PCT/NL2015/050697 (WO 2016/053107):

trastuzumab$(GalNAz)_2$ 13b (Examples 12, 13, 15, 16-1);

trastuzumab$(F_2$-$GalNAz)_2$ 13c (Examples 1, 7-13, 16-2)

Example 6: Preparation of Trimmed Trastuzumab by Means of Fusion Protein EndoSH

Glycan trimming of trastuzumab (obtained via stable expression in CHO cells performed by Bioceros (Utrecht, Netherlands)) was performed with fusion protein EndoSH. Thus, trastuzumab (100.8 mL, 2 g, 19.85 mg/ml in 25 mM Tris pH 8.0) was incubated with EndoSH (5.26 mL, 20 mg, 3.8 mg/mL in 25 mM Tris pH 7.5) for approximately 16 hours at 37° C. Mass spectral analysis of a fabricator-digested sample showed one major peak of the Fc/2-fragment (observed mass 24135 Da, approximately 90% of total Fc/2 fragment), corresponding to core-GlcNAc(Fuc)-substituted trastuzumab.

Example 7: Preparation of Trastuzumab(6-$N_3$-GalNAc)$_2$ 13d

Trimmed trastuzumab (11.8 mg/mL), obtained by EndoSH treatment of trastuzumab as described above in example 6, was incubated with the substrate 6-$N_3$-GalNAc-UDP (3.3 mM, commercially available from GlycoHub) and His-TnGalNAcT(33-421) (0.75 mg/mL) in 10 mM $MnCl_2$ and 25 mM Tris-HCl pH 8.0 at 30° C. The reaction was incubated overnight at 30° C. Biomolecule 13d was purified from the reaction mixture using a XK 26/20 column packed with 50 mL protein A sepharose using an AKTA purifier-10 (GE Healthcare). The eluted IgG was immediately neutralized with 1.5 M Tris-HCl pH 8.8 and dialyzed against PBS pH 7.4. Next the IgG was concentrated using an Amicon Ultra-0.5, Ultracel-10 Membrane (Millipore) to a concentration of 28.5 mg/mL. Mass spectral analysis of a fabricator-digested sample showed one major peak of the Fc/2-fragment (observed mass 24363 Da, approximately 90% of total Fc/2 fragment), corresponding to core 6-$N_3$-GalNAc-GlcNAc(Fuc)-substituted trastuzumab.

Linker-Conjugate Syntheses: Examples 8-23

Reference to PCT/NL2015/050697 (WO 2016/053107) is made for the synthesis of the following compounds that are suitable as linker-conjugates to be used in the method according to the invention, or a model thereof:

Compound 18 (Example 20);
Compound 20 (Examples 21, 23-25);
Compound 21 (Examples 26-27);
Compound 23 (Examples 29-31);
Compound 26 (Examples 36-38);
Compound 30 (Examples 43-1, 32);
Compound 33 (Examples 36-37, 47);
Compound 34 (Examples 36, 37, 48);
Compound 35 (Examples 36-37, 49);
Compound 36 (Examples 29, 50);
Compound 37 (Examples 51-53);
Compound 38 (Examples 29, 54-55);
Compound 39 (Examples 29, 54, 56).

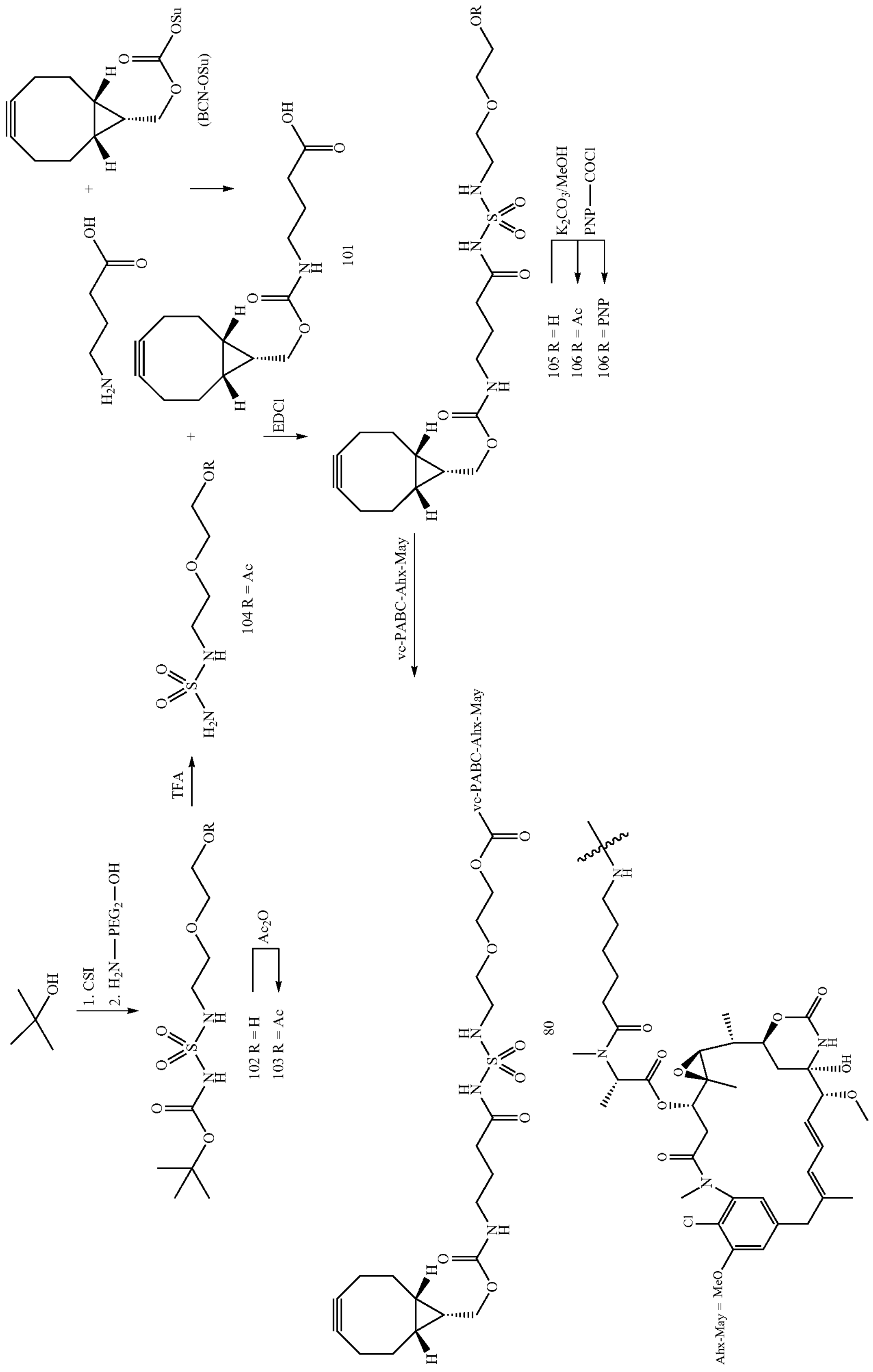
(BCN-OSu)
101
102 R = H
103 R = Ac
104 R = Ac
105 R = H
106 R = Ac
106 R = PNP
80
Ahx-May =

Example 8: Preparation of Compound 101

To a solution of BCN-OSu (1.00 g, 3.43 mmol) in a mixture of THF and water (80 mL/80 mL) were added γ-aminobutyric acid (0.60 g, 5.12 mmol) and $Et_3N$ (1.43 mL, 1.04 g, 10.2 mmol). The mixture was stirred for 4 h followed by addition of DCM (200 mL) and a saturated aqueous solution of $NH_4Cl$ (80 mL). After separation, the aqueous layer was extracted with DCM (2×200 mL). The combined organic layers were dried ($Na_2SO_4$) and concentrated. The residue was purified with column chromatography (MeOH in DCM 0→10%). The product was obtained as a colourless thick oil (730 mg, 2.61 mmol, 76%). $^1H$ NMR (400 MHz, $CDCl_3$) δ (ppm) 4.81 (bs, 1H), 4.15 (d, J=8.4 Hz, 2H), 3.30-3.21 (m, 2H), 2.42 (t, J=7.2 Hz, 2H), 2.35-2.16 (m, 6H), 1.85 (quintet, J=6.9 Hz, 2H), 1.64-1.51 (m, 2H), 1.35 (quintet, J=8.4 Hz, 1H), 1.00-0.90 (m, 2H)

Example 9: Preparation of Compound 102

Chlorosulfonyl isocyanate (CSI; 0.91 mL, 1.48 g, 10 mmol) was added to a cooled (−78° C.) solution of tert-butanol (5.0 mL, 3.88 g, 52 mmol) in $Et_2O$ (50 mL). The reaction mixture was allowed to warm to rt and was concentrated. The residue was suspended in DCM (200 mL) and subsequently $Et_3N$ (4.2 mL, 3.0 g, 30 mmol) and 2-(2-aminoethoxy)ethanol (1.0 mL, 1.05 g; 10 mmol) were added. The resulting mixture was stirred for 10 min and concentrated. The residue was purified twice with column chromatography (MeOH in DCM 0→10%). The product was obtained as a colourless thick oil (2.9 g, 10 mmol, 100%)$^1H$ NMR (400 MHz, $CDCl_3$) δ (ppm) 5.75 (bs, 1H), 3.79-3.74 (m, 2H), 3.67-3.62 (m, 2H), 3.61-3.57 (m, 2H), 3.35-3.28 (m, 2H), 1.50 (s, 9H).

Example 10: Preparation of Compound 103

To a solution of 102 (2.9 g, 10 mmol) in DCM (40 mL) were added $Ac_2O$ (2.9 mL, 3.11 g, 30.5 mmol) and $Et_3N$ (12.8 mL, 9.29 g, 91.8 mmol). The reaction mixture was stirred for 2 h, washed with a saturated aqueous solution of $NaHCO_3$ (50 mL) and dried ($Na_2SO_4$). The residue was purified twice with column chromatography (20%-100% EtOAc in heptane). The product was obtained as a colourless oil (2.5 g, 7.7 mmol, 77%)$^1H$ NMR (400 MHz, $CDCl_3$) δ (ppm) 5.48 (bs, 1H), 4.25-4.20 (m, 2H), 3.70-3.60 (m, 4H), 3.33-3.23 (m, 2H), 2.10 (s, 3H), 1.50 (s, 9H)

Example 11: Preparation of Compound 104

To a solution of 103 (80 mg, 0.25 mmol) in DCM (8 mL) was added TFA (2 mL). After 40 min, the reaction mixture was concentrated. The residue was taken up in toluene (30 mL) and the mixture was concentrated. The product was obtained as colourless oil (54 mg, 0.24 mmol, 95%). $^1H$ NMR (400 MHz, $CDCl_3$) δ (ppm) 5.15 (bs, 2H), 4.26-4.18 (m, 2H), 3.71-3.60 (m, 4H), 3.35-3.27 (m, 2H), 2.08 (s, 3H).

Example 12: Preparation of Compound 105

To a mixture of BCN-GABA (101) (67 mg, 0.24 mmol) and 104 (54 mg, 0.24 mmol) in DCM (20 mL) were added N-(3-dimethylaminopropyl)-N'-ethylcarbodiimide hydrochloride (EDCI.HCl; 55 mg, 0.29 mmol) and DMAP (2.8 mg, 23 μmol). The mixture was stirred for 16 and washed with a saturated aqueous solution of $NH_4Cl$ (20 mL). After separation, the aqueous layer was extracted with DCM (20 mL). The combined organic layers were dried ($Na_2SO_4$) and concentrated. The residue was purified with column chromatography (MeOH in DCM 0→10%). The product was obtained as a colourless thick oil (50 mg, 0.10 mmol, 42%). $^1H$ NMR (400 MHz, $CDCl_3$) δ (ppm) 5.83-5.72 (m, 1H), 5.14-5.04 (m, 1H), 4.23-4.19 (m, 2H), 4.15 (d, J=8.1 Hz, 2H), 3.67-3.57 (m, 4H), 3.29-3.18 (m, 4H), 2.41-2.32 (m, 2H), 2.31-2.15 (m, 6H), 2.10 (s, 3H), 1.85 (quintet, J=6.6 Hz, 2H), 1.65-1.49 (m, 2H), 1.38-1.28 (m, 1H), 1.00-0.89 (m, 2H)

Example 13: Preparation of Compound 106

To a solution of 105 (50 mg, 0.10 mmol) in MeOH (10 mL) was added $K_2CO_3$ (43 mg, 0.31 mmol). The mixture was stirred for 3h and diluted with a saturated aqueous solution of $NH_4Cl$ (20 mL). The mixture was extracted with DCM (3×20 mL). The combined organic layers were dried ($Na_2SO_4$) and concentrated. The product was obtained as a colourless film (39 mg, 0.09 mmol, 88%). $^1H$ NMR (400 MHz, $CDCl_3$) δ (ppm) 6.25 (bs, 1H), 5.26-5.18 (m, 1H), 4.15 (d, J=8.0 Hz, 2H), 3.77-3.71 (m, 2H), 3.63-3.53 (m, 4H), 3.33-3.27 (m, 2H), 3.27-3.17 (m, 2H), 2.45-2.34 (m, 2H), 2.34-2.14 (m, 6H), 1.85 (quintet, J=6.7 hz, 2H), 1.65-1.48 (m, 2H), 1.41-1.28 (m, 1H), 1.01-0.88 (m, 2H).

Example 14: Preparation of Compound 107

To a solution of 106 (152 mg, 0.34 mmol) in DCM (20 mL) were added p-nitrophenyl chloroformate (PNP-COCl; 69 mg, 0.34 mmol) and pyridine (28 μL, 27 mg, 0.34 mmol). The mixture was stirred for 1.5 h and concentrated. The residue was purified with column chromatography (50%→100% EtOAc in heptane). The product was obtained as a colourless thick oil (98 mg, 0.16 mmol, 47%). $^1H$ NMR (400 MHz, $CDCl_3$) δ (ppm) 8.31-8.26 (m, 2H), 7.46-7.40 (m, 2H), 5.69-5.59 (m, 1H), 4.98-4.91 (m, 1H), 4.46-4.42 (m, 2H), 4.18 (d, J=8.1 Hz, 2H), 3.79-3.75 (m, 2H), 3.69-3.64 (m, 2H), 3.33-3.24 (m, 4H), 2.39-2.31 (m, 2H), 2.32-2.18 (m, 6H), 1.84 (quintet, J=6.3 Hz 2H), 1.65-1.50 (m, 2H), 1.35 (quintet, J=8.5 Hz, 1H), 1.01-0.91 (m, 2H).

Example 15: Preparation of Linker-Conjugate 80

To a solution of Val-Cit-PABC-Ahx-May.TFA (20 mg; 15.6 μmol) in DMF (0.50 mL) were added triethylamine (6.5 μl; 4.7 mg; 47 μmol) and a solution of 107 (19 mg, 31 μmol) in DMF (311 μL). The mixture was left standing for 20 h and 2,2'-(ethylenedioxy)bis(ethylamine) (13.7 μL, 14 mg, 94 μmol) was added. After 2 h, extra 2,2'-(ethylenedioxy)bis (ethylamine) (13.7 μL, 14 mg, 94 μmol) was added. After 1.5 h, the reaction mixture was purified by RP HPLC (C18, 30%→90% MeCN (1% AcOH) in water (1% AcOH). The obtained product was additionally purified by silica column chromatography (DCM→MeOH/DCM 1/4). The desired product was obtained as a white film (16 mg, 9.9 μmol, 63%). LCMS ($ESI^+$) calculated for $C_{77}H_{110}ClN_{12}O_{22}S^+$ ($M-H_2O+H^+$) 1621.73 found 1621.74.

Example 16: Preparation of Compound 109

To a solution of 2-(2-(2-(2-aminoethoxy)ethoxy)ethoxy) ethanol (539 mg, 2.79 mmol) in DCM (100 mL) were added BCN-OSu (0.74 g, 2.54 mmol) and $Et_3N$ (1.06 mL, 771 mg, 7.62 mmol). The resulting solution was stirred for 2.5 h and washed with a saturated aqueous solution of $NH_4Cl$ (100 mL). After separation, the aqueous phase was extracted with DCM (100 mL). The combined organic phases were dried ($Na_2SO_4$) and concentrated. The residue was purified with column chromatography (MeOH in DCM 0→10%). The product was obtained as a colourless oil (965 mg, 2.61 mmol, quant). $^1H$ NMR (400 MHz, $CDCl_3$) δ (ppm) 5.93 (bs, 1H), 4.14 (d, J=8.0 Hz, 2H), 3.77-3.69 (m, 4H), 3.68-3.59 (m, 8H), 3.58-3.52 (m, 2H), 3.42-3.32 (m, 2H), 2.35-2.16 (m, 6H), 1.66-1.51 (m, 2H), 1.36 (quintet, J=8.7 Hz, 1H), 0.99-0.87 (m, 2H).

Example 17: Preparation of Compound 110

To a solution of 109 (0.96 g, 2.59 mmol) in DCM (50 mL) was added p-nitrophenyl chloroformate (680 mg, 3.37 mmol) and $Et_3N$ (1.08 mL, 784 mg, 7.75 mmol). The mixture was stirred for 16 h and concentrated. The residue was purified twice with column chromatography (20%-70% EtOAc in heptane (column 1) and 20%-100% EtOAc in heptane (column 2)). The product was obtained as a slightly yellow thick oil (0.91 g, 1.70 mmol, 66%). $^1H$ NMR (400 MHz, $CDCl_3$) δ (ppm) 8.31-8.26 (m, 2H), 7.42-7.37 (m, 2H), 5.19 (bs, 1H), 4.47-4.43 (m, 2H), 4.15 (d, J=8.0 Hz, 2H), 3.84-3.80 (m, 2H), 3.74-3.61 (m, 8H), 3.59-3.53 (m, 2H), 3.42-3.32 (m, 2H), 2.35-2.16 (m, 6H), 1.66-1.50 (m, 2H), 1.40-1.30 (m, 1H), 1.00-0.85 (m, 2H).

Example 18: Preparation of Linker-Conjugate 77

To a solution of Val-Cit-PABC-Ahx-May.TFA (23.4 mg; 18.2 μmol) in DMF (0.50 mL) were added triethylamine (6.5 μl; 4.7 mg; 47 μmol) and a solution of 110 (12.5 mg, 23.4 μmol) in DMF (373 μL). The mixture was left standing for 42 h and 2,2'-(ethylenedioxy)bis(ethylamine) (13.7 μL, 14 mg, 94 μmol) was added. After 4 h, the reaction mixture was purified by RP HPLC (C18, 30%→90% MeCN (1% AcOH) in water (1% AcOH). The obtained product was additionally purified by silica column chromatography (DCM→MeOH/DCM 1/4). The desired product was obtained as a colourless film (19.5 mg, 12.5 μmol, 68%). LCMS ($ESI^+$) calculated for $C_{77}H_{110}ClN_{10}O_{21}S^+$ ($M-H_2O+H^+$) 1545.75 found 1546.82.

Example 19: Preparation of Linker-Conjugate 78

A solution of Val-Cit-PABC-Ahx-May.TFA (20 mg; 15.6 μmol) in DMF (0.50 mL) were added triethylamine (6.5 μl; 4.7 mg; 47 μmol) and a solution of compound 99 (prepared via activation of compound 58 as disclosed in and prepared according to Example 50 of PCT/NL2015/050697 (WO 2016/053107); 24 mg, 46 μmol) in DMF (293 μL). The mixture was left standing for 21 h and 2,2'-(ethylenedioxy) bis(ethylamine) (14 μL, 14 mg, 96 μmol) was added. After 2 h, extra 2,2'-(ethylenedioxy)bis(ethylamine) (7 μL, 7.1 mg, 48 μmol) was added. After 1 h, the reaction mixture was purified by RP HPLC (C18, 30%-90% MeCN (1% AcOH) in water (1% AcOH). The obtained product was additionally purified by silica column chromatography (DCM→MeOH/DCM 1/4). The desired product was obtained as a colourless film (16 mg, 10 μmol, 64%). LCMS (ESI+) calculated for $C_{73}H_{103}ClN_{11}O_{21}S+$ (M−H2O+H+) 1536.67 found 1536.75.

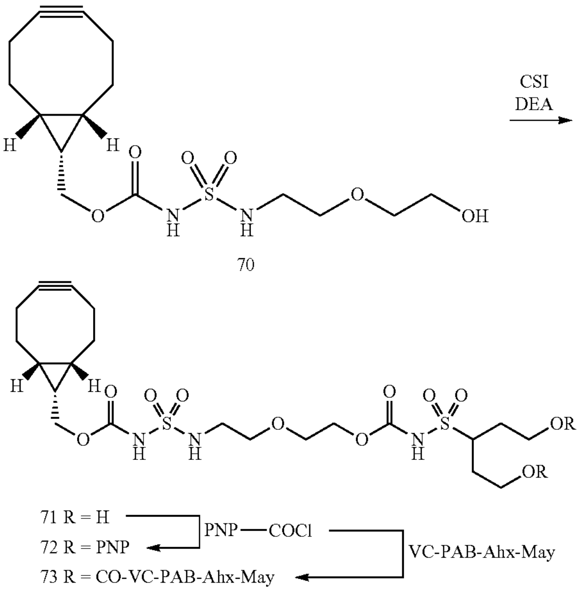

Example 20-1: Preparation of 70

To a solution of BCN-OH (2.0 g, 13.31 mmol) in DCM (200 mL) under a nitrogen atmosphere was added chlorosulfonyl isocyanate (1.16 mL, 13.31 mmol) and the resulting solution was stirred at rt for 30 min. Then, $Et_3N$ (3.7 mL, 26.62 mmol) was added dropwise followed by the dropwise addition of 2-(2-aminoethoxy)ethanol (1.47 mL, 14.64 mmol). After 15 min, sat. aqueous $NH_4Cl$ solution (200 mL) was added and the layers were separated. The water phase was extracted with DCM (2×150 mL), the combined organic layers were dried over sodium sulphate, filtered and concentrated in vacuo. Flash chromatography (0-10% MeOH in DCM) afforded the product (2.87 g, 7.96 mmol, 60%). $^1H$-NMR (400 MHz, CD3OD): δ 4.30 (d, J=8.4 Hz, 2H), 3.72-3.67 (m, 2H), 3.61 (t, J=5.2 Hz, 2H), 3.59-3.55 (m, 2H), 3.25 (t J=5.2 Hz, 2H), 2.38-2.20 (m, 6H), 1.74-1.58 (m, 2H), 1.45 (quint, J=8.8 Hz, 1H), 1.07-0.95 (m, 2H).

Example 20-2: Preparation of 72

To a stirring solution of 70 (47 mg, 0.13 mmol) in DCM (10 mL) was added CSI (11 μL, 18 mg, 0.13 mmol). After 30 min, $Et_3N$ (91 μL, 66 mg, 0.65 mmol) and a solution of diethanolamine (16 mg, 0.16 mmol) in DMF (0.5 mL) were added (provides intermediate 71). After 30 minutes p-nitrophenyl chloroformate (52 mg, 0.26 mmol) and $Et_3N$ (54 μL, 39 mg, 0.39 mmol) were added. After an additional 4.5 h, the reaction mixture was concentrated and the residue was purified by gradient column chromatography (33→66% EtOAc/heptane (1% AcOH)) to afford 72 as colourless oil (88 mg, 0.098 mmol, 75%). $^1H$ NMR (400 MHz, $CDCl_3$) δ (ppm) 8.28-8.23 (m, 4H), 7.42-7.35 (m, 4H), 4.52 (t, J=5.4 Hz, 4H), 4.30 (d, J=8.3 Hz, 2H), 4.27-4.22 (m, 2H), 3.86 (t, J=5.3 Hz, 4H), 3.69-3.65 (m, 2H), 3.64-3.59 (m, 2H), 3.30-3.22 (m, 2H), 2.34-2.14 (m, 6H), 1.62-1.46 (m, 2H), 1.38 (quintet, J=8.7 Hz, 1H), 1.04-0.92 (m, 2H).

Example 21: Preparation of Linker-Conjugate 73

A solution of 72 (3.9 mg, 4.3 μmol) and $Et_3N$ (3.0 μL, 2.2 mg, 21.5 μmol) in DMF (1 mL) was added to a solution of Val-Cit-PABC-Ahx-May.TFA (10 mg, 8.6 μmol) in DMF (100 μL). The mixture was allowed to react o.n. and was subsequently concentrated. The residue was purified via reversed phase (C18) HPLC chromatography (30-90% MeCN (1% AcOH) in $H_2O$ (1% AcOH) to give product 73 (3.9 mg, 1.32 μmol, 31%). LRMS ($ESI^+$) m/z calcd for $C_{136}H_{196}Cl_2N_{22}O_{43}S_2(M+2H^+)/2$=1480.13; found 1480.35. LRMS ($ESI^+$) m/z calcd for $C_{85}H_{119}ClN_{14}O_{31}S_2(M+2H^+)/2$=965.36; found 965.54. As a side-product, the mono-Ahx-May substituted derivative of 73 was isolated (not depicted). LRMS (ESI+) calculated for $C_{85}H_{119}ClN_{14}O_{31}S_2^{2+}$ m/z 965.36 found 965.54.

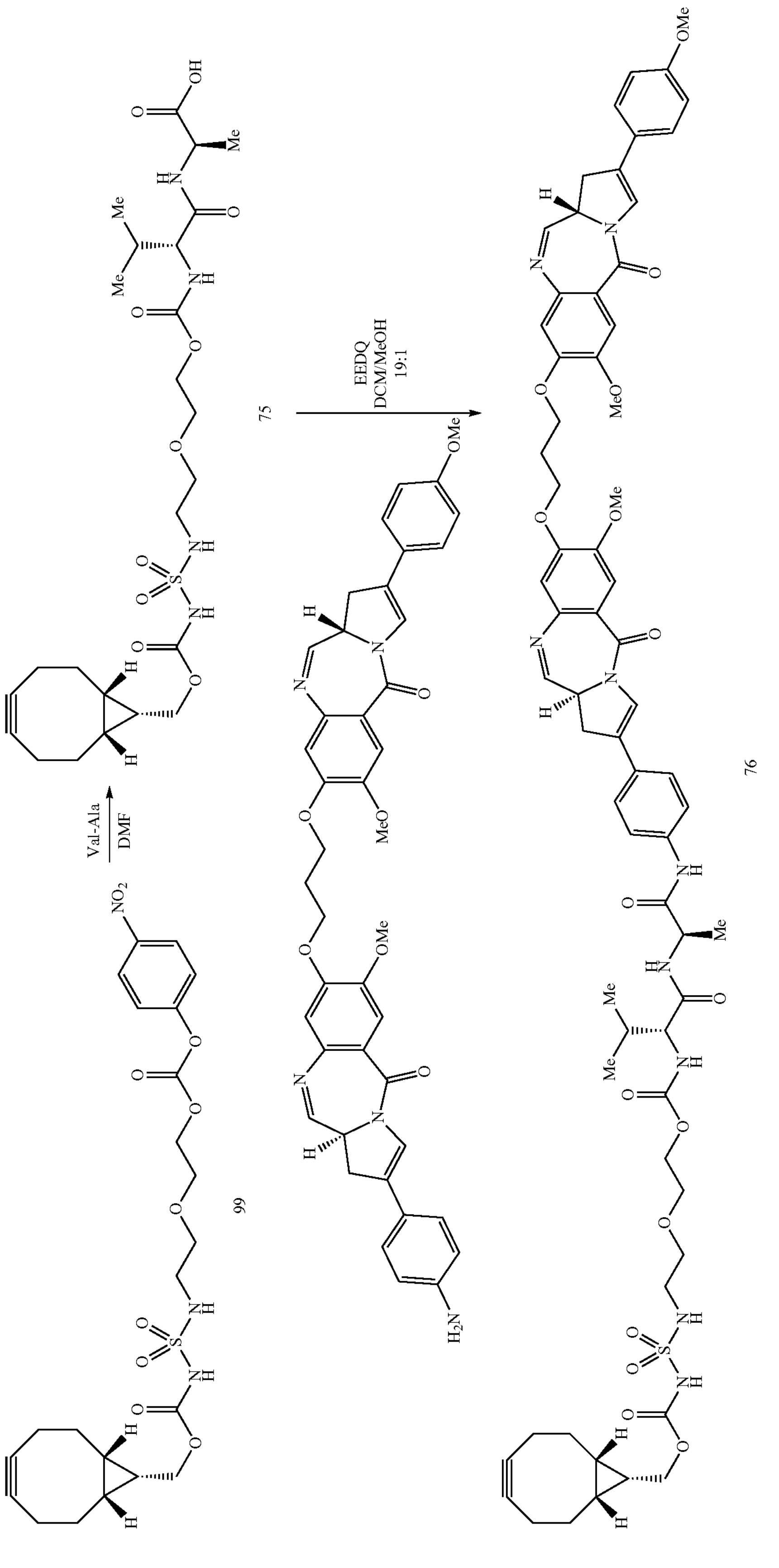
99
75
76

Example 22: Preparation of 75

To a suspension of $NH_2$-Val-Ala-OH (16 mg, 0.085 mmol) in DMF (0.5 mL) were added a solution of 99 (22 mg, 0.042 mmol) in DMF (0.5 mL) and $Et_3N$ (21 mg, 29 μL, 0.21 mmol). The resulting reaction mixture was rolled for 26 h and poured out in a mixture of DCM (10 mL) and potassium phosphate buffer (pH 3.0, 10 mL). After separation, the aqueous phase was extracted with DCM (20 mL). The combined organic layers were dried ($Na_2SO_4$) and concentrated. The residue was purified by column chromatography (50% EtOAc in heptane→EtOAc (1% AcOH in eluens). The product was obtained as a colourless film (18 mg, 31 μmol, 75%). $^1H$ NMR (400 MHz, $CDCl_3$) δ (ppm) 7.02 (d, J=7.1 Hz, 1H), 6.29 (bs, 1H), 5.92 (d, J=9.0 Hz, 1H), 4.56 (quintet, J=7.1 Hz, 1H), 4.42-4.35 (m, 1H), 4.28 (d, J=8.2 Hz, 2H), 4.10-4.01 (m, 2H), 3.72-3.55 (m, 4H), 3.35-3.25 (m, 2H), 2.35-2.10 (m, 6H), 1.63-1.48 (m, 2H), 1.45 (d, J=7.2 Hz, 3H), 1.39 (quintet, J=8.9 Hz, 1H), 1.02-0.94 (m, 2H), 0.97 (d, J=6.8 Hz, 3H), 0.92 (d, J=6.8 Hz, 3H).

Example 23: Preparation of Linker-Conjugate 76

To a vial containing 2-ethoxy-1-ethoxycarbonyl-1,2-dihydroquinoline (2.6 mg, 11 μmol) was added a solution of 75 (6.1 mg, 11 μmol) in a mixture of MeOH and DCM (5/95, 1.0 mL). The resulting mixture was left for 30 min. To the reaction mixture was added $NH_2$—PBD (5.0 mg, 6.9 μmol) in a mixture of MeOH and DCM (5/95, 0.5 mL). The resulting mixture was left standing for 74 h and concentrated. The residue was purified by silica gel chromatography (DCM→MeOH/DCM 1/9). The product was obtained as a colourless film (2.6 mg, 2.03 μmol). LCMS ($ESI^+$) calculated for $C_{66}H_{76}N_9O_{16}S$ ($M+^+$) 1282.51 found 1282.70.

Antibody-Drug-Conjugates Production: Example 24-32

Example 24: Conjugation of 13b with 30 to Obtain Conjugate 96 (VII)

The bioconjugate according to the invention was prepared by conjugation of compound 30 as linker-conjugate to modified biomolecule 13b as biomolecule. To a solution of trastuzumab(azide)$_2$ (13b) (15.5 mL, 255 mg, 16.47 mg/ml in PBS pH 7.4) was added DMA (1.45 mL) and compound 30 (255 μL, 40 mM solution DMA). The reaction was incubated overnight at rt followed by purification on a HiLoad 26/600 Superdex200 PG column (GE Healthcare) on an AKTA Purifier-10 (GE Healthcare). Mass spectral analysis of the reduced sample showed one major heavy chain product (observed mass 50938 Da, approximately 80% of total heavy chain fragment), corresponding to the conjugated heavy chain.

Example 25: Conjugation of 13b with 33 to Obtain Conjugate 95 (VIII)

The bioconjugate according to the invention was prepared by conjugation of compound 33 as linker-conjugate to modified biomolecule 13b as biomolecule. To a solution of trastuzumab(azide)$_2$ (13b) (607 μL, 10 mg, 16.47 mg/ml in PBS pH 7.4) was added MilliQ (50 μL) and compound 33 (10 μL, 40 mM solution in DMA). The reaction was incubated overnight at rt followed by purification on a Superdex200 10/300 GL (GE Healthcare) on an AKTA Purifier-10 (GE Healthcare). Mass spectral analysis of the reduced sample showed one major heavy chain product (observed mass 50982 Da, approximately 80% of total heavy chain fragment), corresponding to the conjugated heavy chain.

Example 26: Conjugation of 13c with 30 to Obtain Conjugate 98 (X)

The bioconjugate according to the invention was prepared by conjugation of compound 30 as linker-conjugate to modified biomolecule 13c as biomolecule. To a solution of trastuzumab(azide)$_2$ (13c) (14.25 mL, 250 mg, 17.55 mg/ml in PBS pH 7.4) was added DMA (1.4 mL) and compound 30 (250 μL, 40 mM solution DMA). The reaction was incubated overnight at rt followed by purification on a HiLoad 26/600 Superdex200 PG column (GE Healthcare) on an AKTA Purifier-10 (GE Healthcare). Mass spectral analysis of the reduced sample showed one major heavy chain product (observed mass 50969 Da, approximately 70% of total heavy chain fragment), corresponding to the conjugated heavy chain.

Example 27: Conjugation of 13c with 33 to Obtain Conjugate 97 (IX)

The bioconjugate according to the invention was prepared by conjugation of compound 33 as linker-conjugate to modified biomolecule 13c as biomolecule. To a solution of trastuzumab(azide)$_2$ (13c) (14.25 mL, 250 mg, 17.55 mg/ml in PBS pH 7.4) was added compound 33 (188 μL, 40 mM solution DMA). The reaction was incubated overnight at rt followed by purification on a HiLoad 26/600 Superdex200 PG column (GE Healthcare) on an AKTA Purifier-10 (GE Healthcare). Mass spectral analysis of the reduced sample showed one major heavy chain product (observed mass 51020 Da, approximately 90% of total heavy chain fragment), corresponding to the conjugated heavy chain.

Example 28: Conjugation of 13d with 78 to Obtain Conjugate 82 (1)

A bioconjugate according to the invention was prepared by conjugation of compound 78 as linker-conjugate to azide-modified trastuzumab as biomolecule. To a solution of trastuzumab-(6-$N_3$-GalNAc)$_2$ (13d) (8.18 mL, 270 mg, 33.0 mg/ml in PBS pH 7.4) was added PBS pH 7.4 (7.12 mL), DMF (2.48 mL) and compound 78 (225 μL, 40 mM solution in DMF). The reaction was incubated at rt overnight followed by purification on a HiLoad 26/600 Superdex200 PG (GE Healthcare) on an AKTA Purifier-10 (GE Healthcare). Mass spectral analysis of the fabricator-digested sample showed one major product (observed mass 25921 Da, approximately 90% of total Fc/2 fragment), corresponding to the conjugated Fc/2 fragment. RP-HPLC analysis of the reduced sample indicated an average DAR of 1.90.

Example 29: Conjugation of 13d with 80 to Obtain Conjugate 83 (11)

A bioconjugate according to the invention was prepared by conjugation of compound 80 as linker-conjugate to azide-modified trastuzumab as biomolecule. To a solution of trastuzumab-(6-$N_3$-GalNAc)$_2$ (13d) (8.18 mL, 270 mg, 33.0 mg/ml in PBS pH 7.4) was added PBS pH 7.4 (7.12 mL), DMF (2.49 mL) and compound 80 (210 μL, 40 mM solution in DMF). The reaction was incubated at rt for approximately 40 hrs followed by purification on a HiLoad 26/600 Superdex200 PG (GE Healthcare) on an AKTA Purifier-10 (GE Healthcare). Mass spectral analysis of the fabricator-digested sample showed one major product (observed mass 26010 Da, approximately 90% of total Fc/2 fragment), corresponding to the conjugated Fc/2 fragment. RP-HPLC analysis of the reduced sample indicated an average DAR of 1.93.

Example 30: Conjugation of 13d with 77 to Obtain Conjugate 81 (III)

A bioconjugate according to the invention was prepared by conjugation of compound 77 as linker-conjugate to azide-modified trastuzumab as biomolecule. To a solution of trastuzumab-(6-$N_3$-GalNAc)$_2$ (13d) (8.18 mL, 270 mg, 33.0 mg/ml in PBS pH 7.4) was added PBS pH 7.4 (5.328 mL), DMF (4.28 mL) and compound 77 (225 μL, 40 mM solution in DMF). After overnight incubation at rt RP-HPLC analysis indicated an incomplete reaction. Additional compound 77 (45 μL, 40 mM solution in DMF) was added to the reaction mixture and followed by overnight incubation at rt. The reaction was dialyzed against PBS pH 7.4 (0.5 L) and purified on a HiLoad 26/600 Superdex200 PG (GE Healthcare) on an AKTA Purifier-10 (GE Healthcare). Mass spectral analysis of the fabricator-digested sample showed one major product (observed mass 25931 Da, approximately 90% of total Fc/2 fragment), corresponding to the conjugated Fc/2 fragment. RP-HPLC analysis of the reduced sample indicated an average DAR of 1.91.

Example 31: Conjugation of 13d with 73 to Obtain Conjugate 84 (V)

A bioconjugate according to the invention was prepared by conjugation of compound 73 as linker-conjugate to azide-modified trastuzumab as biomolecule. To a solution of trastuzumab-(6-$N_3$-GalNAc)$_2$ (13d) (4.09 mL, 135 mg, 33.0 mg/ml in PBS pH 7.4) was added PBS pH 7.4 (2.66 mL), DMF (2.14 mL) and compound 73 (113 μL, 40 mM solution in DMF). The reaction was incubated at rt overnight followed by dialysis against PBS pH 7.4 (0.5 L) and purification on a HiLoad 26/600 Superdex200 PG (GE Healthcare) on an AKTA Purifier-10 (GE Healthcare). Mass spectral analysis of the fabricator-digested sample showed one major product (observed mass 227331 Da, approximately 90% of total Fc/2 fragment), corresponding to the conjugated Fc/2 fragment. RP-HPLC analysis of the reduced sample indicated an average DAR of 3.78.

Example 32: Conjugation of 13d with 76 to Obtain Conjugate 85 (VI)

The bioconjugate according to the invention was prepared by conjugation of 76 as linker-conjugate to modified biomolecule 13d as biomolecule. To a solution of trastuzumab (6-$N_3$-GalNAc)$_2$ (13d) (320 μL, 7.2 mg, 22.5 mg/ml in PBS pH 7.4) was added 76 (44.5 μL, 10 mM solution DMF) and DMF (66 μL). The reaction was incubated two times overnight at rt followed by dilution with PBS (1 mL) and concentration using an Amicon Ultra-0.5, Ultracel-10 Membrane spinfilters (Millipore). Next the conjugate was purified on a HiLoad 26/600 Superdex200 PG column (GE Healthcare) on an AKTA Purifier-10 (GE Healthcare). Mass spectral analysis of the sample after Fabricator™ treatment showed one major Fc/2 product (observed mass 25649 Da, approximately 90% of total Fc/2), corresponding to the conjugate 85.

Examples 33-39: Efficacy, Tolerability and Stability Studies

Example 33a: HER2 Efficacy Studies [T226 PDX-Model]

Figure 8A:
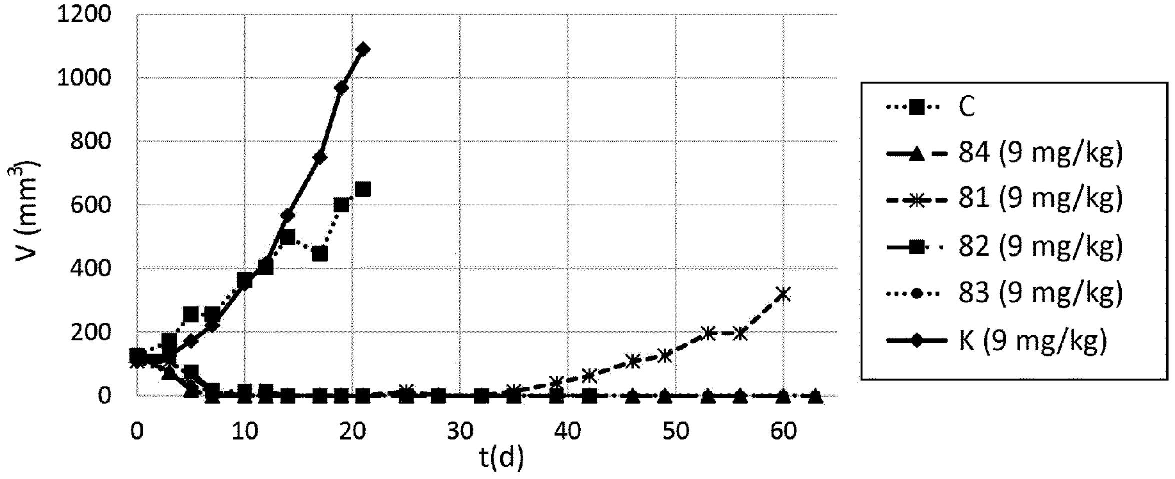
FIG. 8A depicts the results of the efficacy studies of Example 33 for control antibody-conjugate Kadcyla (K) and antibody-conjugates according to the invention 81-84. Similar results are depicted in FIG. 8B, wherein the efficacy of antibody-conjugates according to the invention 85 and control antibody-conjugate Kadcyla (K) are presented, and in FIG. 8C, wherein efficacies of antibody-conjugates according to the invention 95-98 are depicted. Efficacies are represented as the change in tumour volume over time, where a greater efficacy leads to a greater reduction or a lesser increase in tumour volume. C=vehicle treated.

Female SHO mice (Crl:SHO-Prkdcscid Hrhr), 6- to 9-week-old at the beginning of the experimental phase, obtained from Charles River Laboratories (France), weighing 15-25 grams, were grafted with 20 $mm^3$ tumour (T226) fragment in the subcutaneous tissue. Healthy mice weighing at least 17 g were included in the grafting procedure. Mice were allocated to different groups according to their tumour volume to give homogenous mean and median tumour volume in each treatment arms. Groups of 5 mice with established growing tumours and tumour volume ranging 60 to 200 $mm^3$ were injected i.v. with either vehicle, Kadcyla (1.3 mg/kg (mpk)), ADCs 81, 82, 83 and 84 (at 9 mg/kg). Tumours were measured twice weekly for a period of 60 days. The results on tumour volume are depicted in FIG. 8A (median data depicted).

Example 33b: HER2 Efficacy Studies [HBCx-13b PDX-Model]

Figure 8B:
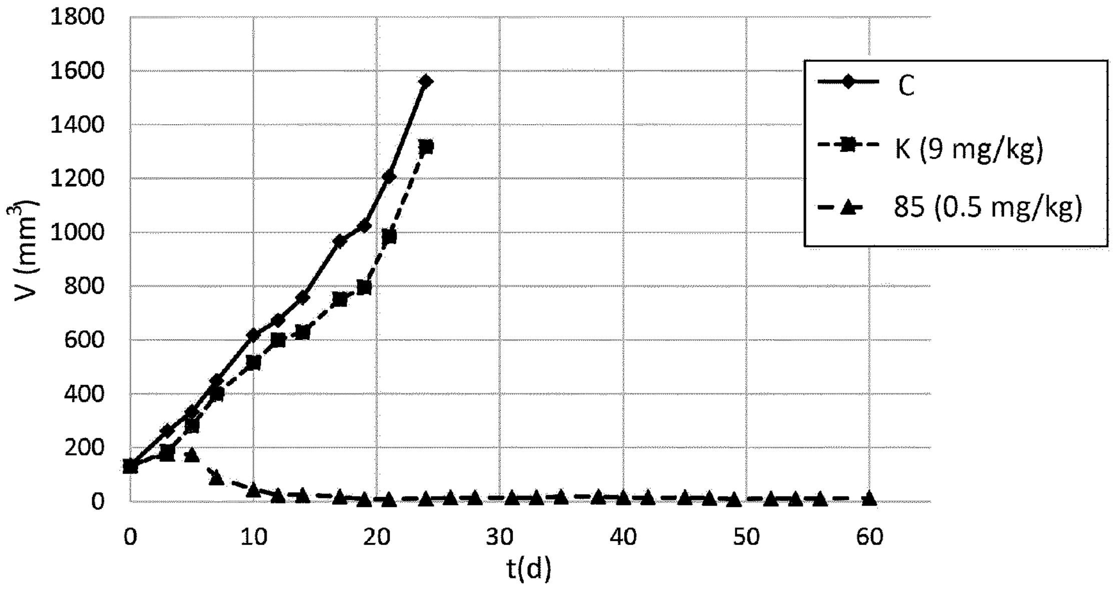
FIG. 8D depicts the results of the efficacy studies of Example 33d for control antibody-conjugate Kadcyla (K) and antibody-conjugates according to the invention 84.
Figure 8C:
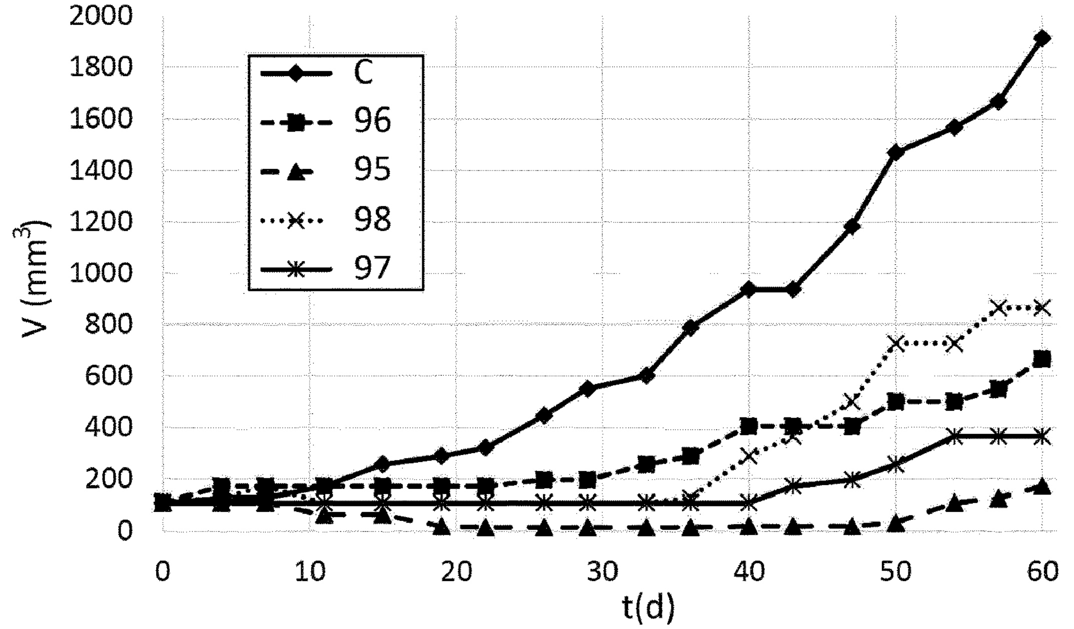

Female SHO mice (Crl:SHO-Prkdcscid Hrhr), 6- to 9-week-old at the beginning of the experimental phase, obtained from Charles River Laboratories (France), weighing 15-25 grams, were grafted with 20 $mm^3$ tumour (HBCx-13b) fragment in the subcutaneous tissue. When the tumour volume was in the range of 62 and 256 $mm^3$, mice were allocated according to their tumour volume to give homogenous mean and median tumour volume in each treatment arm. Groups of five mice were injected twice (at day 0 and day 8) i.v. with a dose of either vehicle, ADC 95, 96, 97 or 98 (at 6 mg/kg). Tumours were measured twice weekly for a period of 60 days. The results on tumour volume are depicted in FIG. 8C (median data depicted).

Example 33c: HER2 Efficacy Studies [HBCx-15 PDX-Model]

Female SHO mice (Crl:SHO-Prkdcscid Hrhr), 6- to 9-week-old at the beginning of the experimental phase, obtained from Charles River Laboratories (France), weighing 15-25 grams were grafted with 20 $mm^3$ tumour (HBCx-15) fragment in the subcutaneous tissue. When the tumour volume was in the range of 62 and 256 $mm^3$, mice were allocated according to their tumour volume to give homogenous mean and median tumour volume in each treatment arm. Groups of five mice were injected i.v. with a single dose of either vehicle, Kadcyla (9 mg/kg) or 85 (at 0.5 mg/kg). Tumours were measured twice weekly for a period of 60 days. The results on tumour volume are depicted in FIG. 8B (mean data depicted).

Example 33d: HER2 Efficacy Studies [T226 PDX-Model]

Figure 8D:
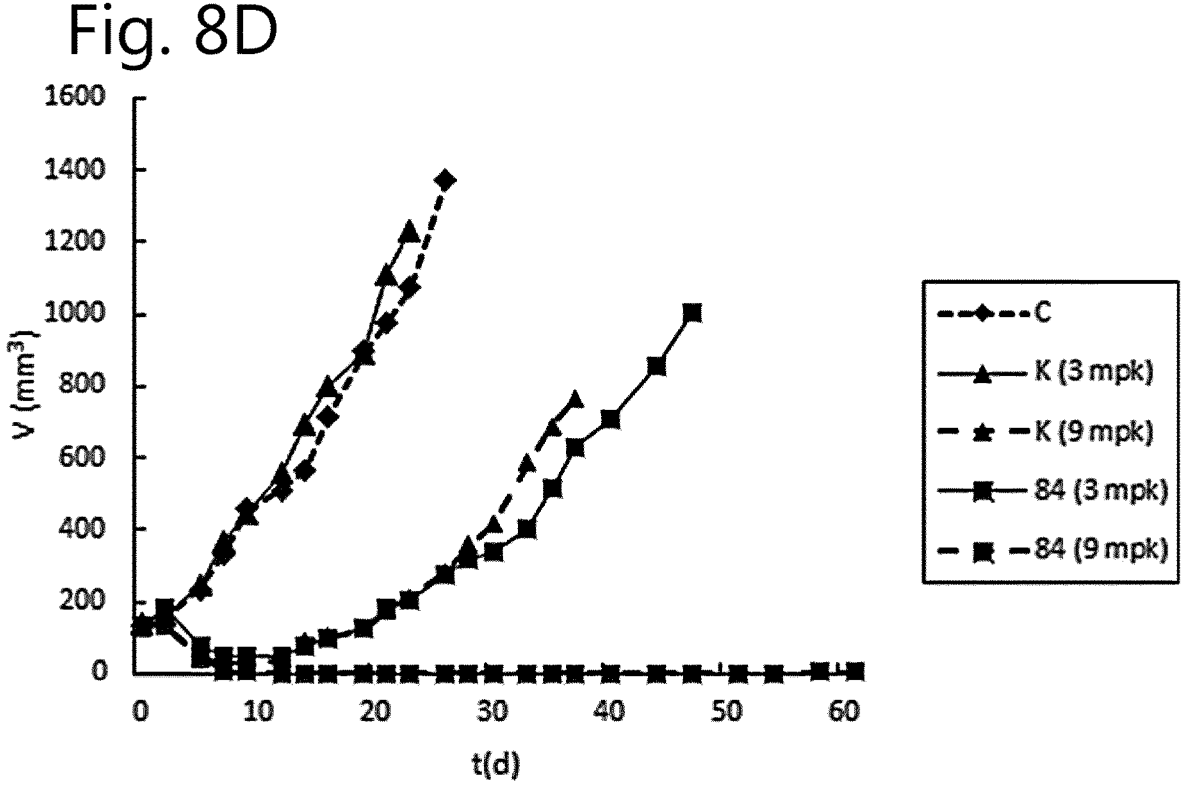

Female SHO mice (Crl:SHO-Prkdcscid Hrhr), 6- to 9-week-old at the beginning of the experimental phase, obtained from Charles River Laboratories (France), weighing 15-25 grams, were grafted with 20 $mm^3$ tumour (T226) fragment in the subcutaneous tissue. Healthy mice weighing at least 17 g were included in the grafting procedure. Mice were allocated to different groups according to their tumour volume to give homogenous mean and median tumour volume in each treatment arms. Groups of 5 mice with established growing tumours and tumour volume ranging 60 to 200 $mm^3$ were injected i.v. with either vehicle, Kadcyla (at 3 and 9 mg/kg (mpk)) or 84 (at 3 and 9 mg/kg). Tumours were measured twice weekly for a period of 60 days. The results on tumour volume are depicted in FIG. 8D (mean data depicted).

Example 34a: HER2 Tolerability Studies

Sprague Dawley rats (3 males and 3 females per group): OFA:SD, 6-week-old at the beginning of the experimental phase, obtained from Charles River Laboratories, Saint-Germain-Nuelles, France, were treated with 97 ((1) at 20 mg/kg and (2) 40 mg/kg), or 98 ((1) at 20 mg/kg and (2) 40 mg/kg) intravenous (bolus) injection using a microflex infusion set introduced into a tail vein (2 mL/kg at 1 mL/min). One group of animals (control) was treated with vehicle. After dosing, all animals were maintained for a 5-day observation period. Surviving animals were killed on day 5. Each animal were weighed at the time of randomization/selection, prior to dosing (day 0) and on days 2 and 4. All animals (including any found dead or killed moribund) were submitted to full necropsy procedures. Histopathological examinations of the liver, spleen and sciatic nerve was performed for all animals. Blood samples (including for animals killed moribund) were collected and subjected to determination of both hematological as well as serum clinical chemistry parameters. The results demonstrate that the animals were able to tolerate the conjugate according to the invention (97) and the conjugate with a prior art linker (98) equally well. No significant differences in platelet count and body weight were observed, while both parameters decreased rapidly for the Kadcyla-treated rats.

Example 34b: HER2 Tolerability Studies

Sprague Dawley rats (2 females per group), 6-week-old at the beginning of the experimental phase, obtained from Charles River Laboratories, USA, were treated with ADC 84 (at 20 mg/kg (mpk), 35 mpk, 50 mpk and 60 mpk), or ADCs 81, 82 and 83 (at 40 mg/kg (mpk), 70 mpk, 100 mpk and 120 mpk) intravenous (bolus) injection using a microflex infusion set introduced into a tail vein (2 mL/kg at 1 mL/min). One group of animals (control) was treated with vehicle and another group was treated with Kadcyla (at 20 mg/kg (mpk), 35 mpk, 50 mpk and 60 mpk). After dosing, all animals were maintained for a 12-day observation period. Surviving animals were killed on day 12. Each animal was weighed at the time of randomization/selection, prior to dosing (day 0) and on all consecutive days of treatment. All animals (including any found dead or killed moribund) were submitted to full necropsy procedures. Gross histopathological examinations of the liver, spleen and sciatic nerve was performed for all animals. Blood samples (including for animals killed moribund) were collected and subjected to determination of both hematological parameters. The results for the percentage bodyweight loss of the rats for the different dose regimes per ADC are depicted in FIG. 7. It was clear form these results that the bodyweight-based MTD for Kadcyla is between 50 mpk and 60 mpk whereas for the bodyweight-based MTD for ADC 84 (DAR4) was found to be between >60 mpk. For the ADCs 81, 82 and 83 (all DAR2) the bodyweight-based MTDs were found to be >120 mpk with no significant bodyweight loss observed for any of these ADCs at the highest dose-level.

Example 35-37: Preparation of Linker-Conjugate 44

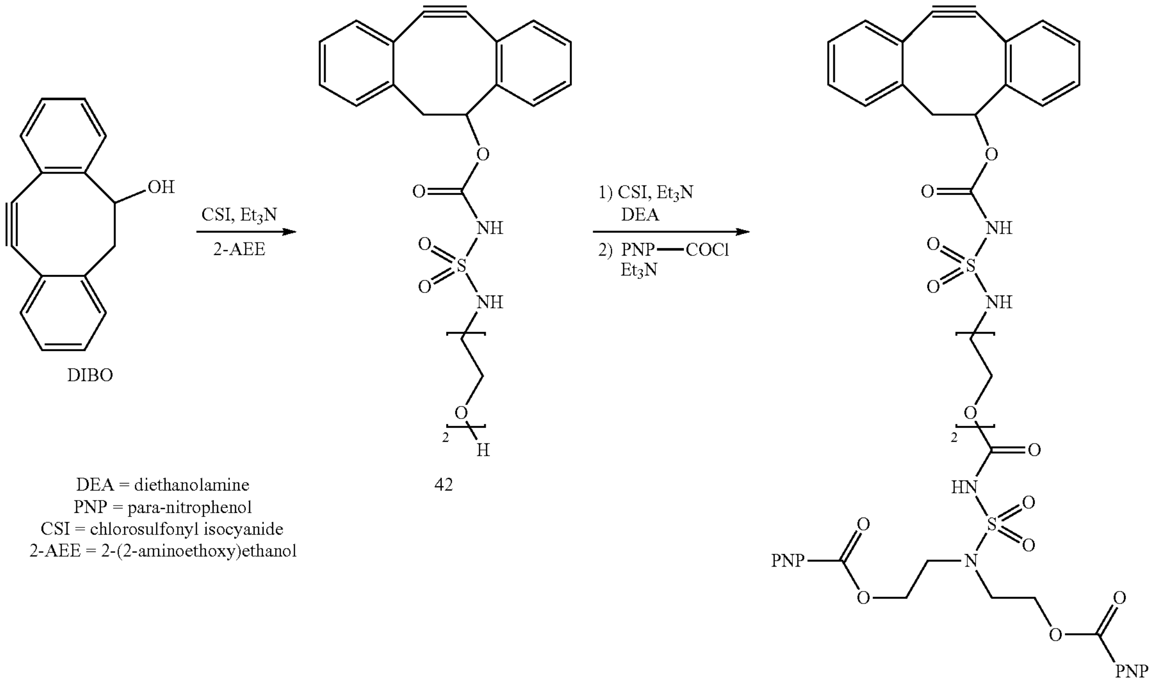

DIBO

42

43

DEA = diethanolamine
PNP = para-nitrophenol
CSI = chlorosulfonyl isocyanide
2-AEE = 2-(2-aminoethoxy)ethanol -continued

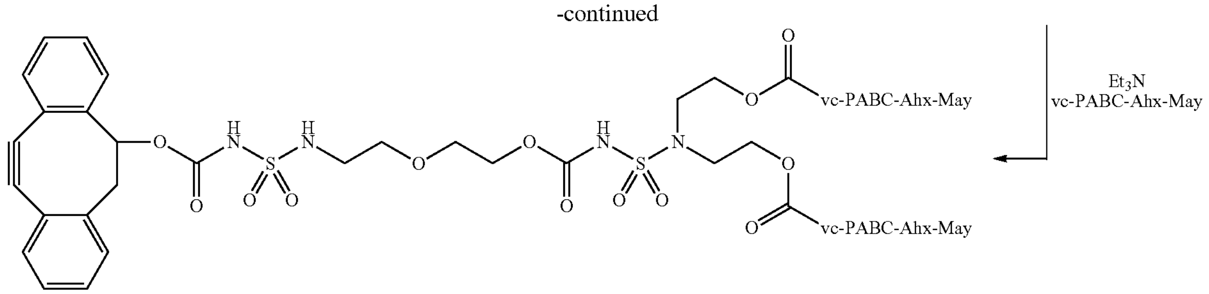

44

Example 35: Synthesis of Compound 42

To a solution of DIBO (0.220 g, 1.00 mmol, 1.00 equiv) in DCM (15.0 mL) under nitrogen was added dropwise chlorosulfonyl isocyanide (CSI, 88.1 μL, 1.00 mmol, 1.00 equiv). The resulting reaction mixture was stirred at room temperature for 20 minutes, followed by the dropwise addition of $Et_3N$ (282 μL, 2.00 mmol, 2.00 equiv). The reaction mixture was stirred for 5 minutes, followed by the addition of 2-(2-aminoethoxy)ethanol (2-AEE, 112 μL 1.10 mmol, 1.10 equiv). The reaction was quenched after stirring for 20 minutes at room temperature through the addition of sat. aq. $NH_4Cl$ (pH 4.0, 30.0 mL). The resulting mixture was extracted with DCM (25 mL, 2×) and EtOAc (20 mL, 2×) and the combined organic layers were dried ($Na_2SO_4$) and then concentrated in vacuo. The residue was purified by flash column chromatography (0-7% MeOH in DCM), affording compound 42 (422 mg, 98%) as a light yellow oil. $^1H$ NMR ($CDCl_3$): 7.60-7.57 (m, 1H), 7.47-7.40 (m, 2H), 7.40-7.27 (m, 5H), 5.55-5.51 (m, 1H), 3.60-3.53 (m, 4H), 3.48-3.42 (m, 2H), 3.35-3.28 (m, 6H), 3.28-3.22 (m, 2H), 2.93-2.82 (m, 1H). LCMS ($ESI^+$) calculated for $C_{21}H_{22}N_2NaO_6S^+$ ($M+Na^+$) 453.11 found 452.98.

Example 36: Synthesis of Compound 43

To a solution of compound 42 (0.192 g, 0.446 mmol, 1.00 equiv) in DCM (30.0 mL) under nitrogen was added dropwise chlorosulfonyl isocyanide (CSI, 38.8 μL, 0.446 mmol, 1.00 equiv). The resulting reaction mixture was stirred at room temperature for 20 minutes, followed by the dropwise addition of $Et_3N$ (311 μL, 2.23 mmol, 5.00 equiv). The resulting reaction mixture was stirred for 5 minutes at room temperature, followed by the addition of a solution of diethanolamine (DEA, 51.3 μL, 0.535 mmol, 1.20 equiv) in DMF (1.5 mL). The reaction mixture was stirred for 60 minutes at room temperature, followed by the addition of 4-nitrophenyl chloroformate (0.180 g, 0.893 mmol, 2.00 equiv) and additional $Et_3N$ (187 μL, 1.34 mmol, 3.01 equiv). The resulting reaction mixture was stirred for 18 hours and then concentrated in vacuo. The residue was purified by flash column chromatography (0-6% MeOH in DCM), affording compound 43 (187 mg) as a white solid. $^1H$ NMR ($CDCl_3$): 8.29-8.18 (m, 5H), 7.41-7.28 (m, 11H), 5.85-5.72 (m, 1H), 5.61-5.55 (s, 1H), 4.59-4.49 (t, J=5.26 Hz, 1H), 4.47-4.36 (t, J=5.35 Hz, 4H), 4.18-4.08 (m, 2H), 3.78-3.67 (t, J=5.33 Hz, 4H), 3.65-3.49 (m, 4H), 3.35-3.25 (m, 2H), 3.26-3.15 (m, 1H), 3.01-2.93 (m, 1H). LCMS ($ESI^+$) calculated for $C_{40}H_{38}N_6NaO_{19}S_2^+$ ($M+Na^+$) 993.15 found 992.97.

Example 37: Preparation of Linker-Conjugate 44

To a solution of compound 43 (11.4 mg, 11.7 μmol, 1.00 equiv) in DCM (0.400 mL) was added $Et_3N$ (6.00 μL, 58.7 μmol, 5.00 equiv), followed by the addition of a solution of Val-Cit-PAB-Maytansin.TFA (vc-PABC-May.TFA, 30.0 mg, 23.4 μmol, 2.00 equiv) in DMF (450 μL). The resulting reaction mixture was left at room temperature for 96 hours. The reaction was quenched with 2,2-(ethylenedioxy)bis (ethylamine) (15.0 μL, 99.7 μmol, 8.52 equiv) and left at room temperature for 2 hours. The mixture was then purified by HPLC. Concentration of the collected fraction in vacuo yielded compound 44 (10.9 mg) as a light pink solid. LCMS ($ESI^+$) calculated for $C_{140}H_{190}Cl_2N_{22}O_{37}S_2^{2+}$ ($M-2H_2O-2CO_2+2H^+$) 1453.13 found 1453.23.

Example 38-41: Preparation of Linker-Conjugate 48

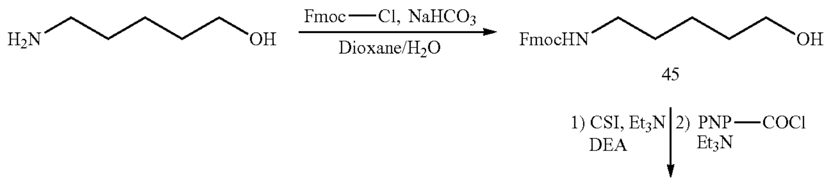

45

-continued

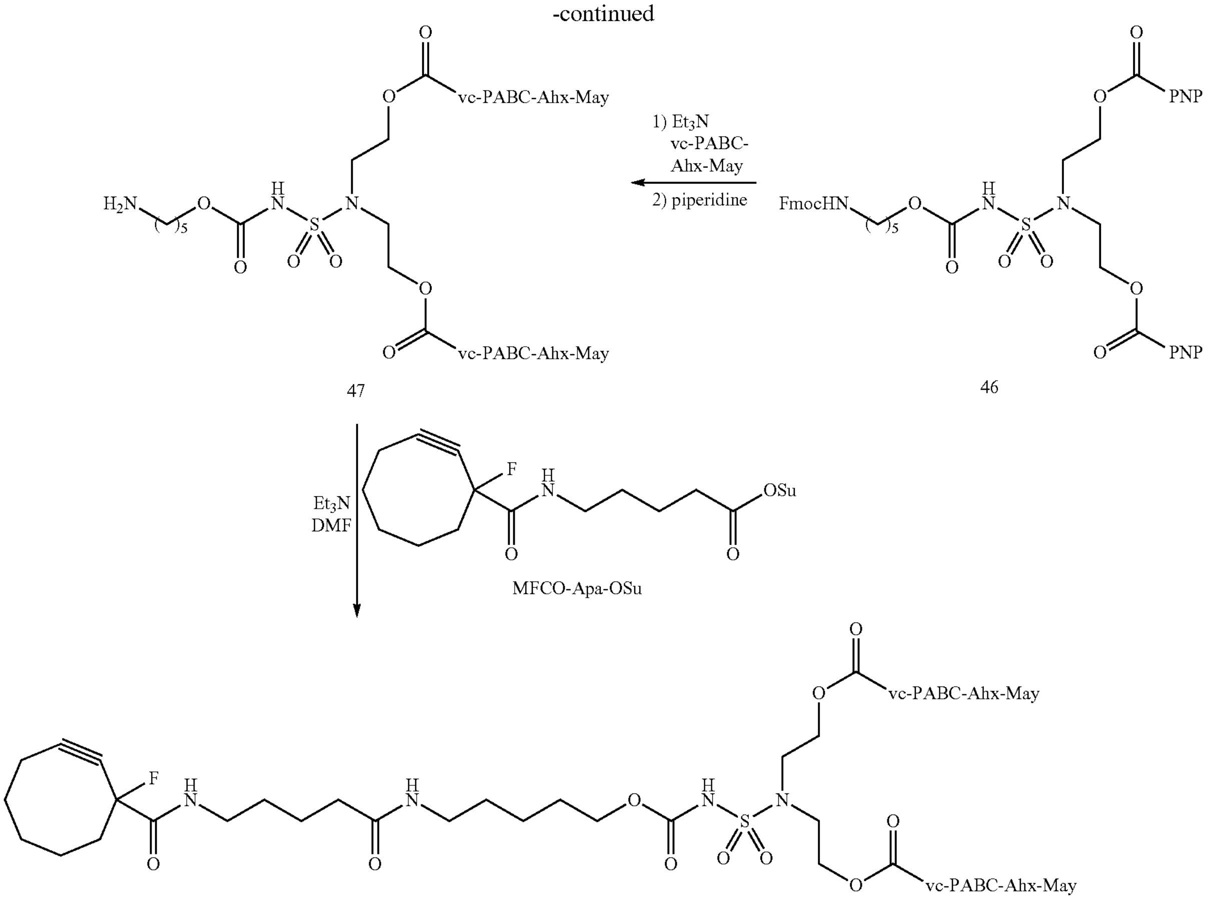

47

46

MFCO-Apa-OSu

48

Example 38: Synthesis of Compound 45

Dioxane (30 mL) and sat. aq. $NaHCO_3$ (60 mL) were mixed and the resulting suspension was filtered over a glassfilter. To the this solution was added 5-amino-1-pentanol (2.03 g, 19.7 mmol, 1.00 equiv), followed by a solution of Fmoc-Cl (5.16 g, 19.9 mmol, 1.01 equiv) in dioxane (30 mL). The reaction was stirred at room temperature for 2.5 hours and then quenched with 1M aq. HCl (300 mL). The mixture was extracted with EtOAc (600 mL) and the organic layer was washed with 1M aq. HCl (250 mL), sat. aq. $NaHCO_3$ (150 mL), brine (150 mL), dried ($Na_2SO_4$) and concentrated in vacuo. The residue was purified by flash column chromatography (0-2% MeOH in $CHCl_3$), providing compound 45 (5.39 g, 84%) as a white solid. $^1H$ NMR ($CDCl_3$): 7.77 (d, J=7.47 Hz, 2H), 7.59 (d, J=7.53 Hz, 2H), 7.46-7.37 (m, 2H), 7.37-7.28 (m, 2H), 4.86-4.74 (bs, 1H), 4.51-4.36 (m, 2H), 4.21 (t, J=6.91 Hz, 1H), 3.65 (q, J=5.29 Hz, 2H), 3.26-3.03 (m, 2H), 1.61-1.48 (m, 4H), 1.48-1.26 (m, 3H).

Example 39: Synthesis of Compound 46

To a solution of compound 45 (0.397 g, 1.22 mmol, 1.00 equiv) in DCM (55.0 mL) under nitrogen was added dropwise chlorosulfonyl isocyanide (CSI, 106 μL, 1.22 mmol, 1.00 equiv) and the resulting reaction mixture was stirred at room temperature for 20 minutes. $Et_3N$ (0.850 mL, 6.10 mmol, 5.00 equiv) was added dropwise and the mixture was stirred for 10 minutes at room temperature, followed by the addition of a solution of diethanolamine (DEA, 0.144 g, 1.37 mmol, 1.12 equiv) in DMF (1.7 mL). The reaction mixture was stirred for 2 hours at room temperature, followed by the addition of 4-nitrophenyl chloroformate (0.492 g, 2.44 mmol, 2.00 equiv) and additional $Et_3N$ (0.340 mL, 2.44 mmol, 2.00 equiv). The resulting reaction mixture was stirred for 18 hours and then concentrated in vacuo. The residue was diluted with DCM (100 mL) and sat. aq. $NH_4Cl$ (pH=3.3, 50 mL) was added. The resulting biphasic system was separated and the water layer was extracted with DCM (50 mL). The combined organic layers were dried ($Na_2SO_4$) and then concentrated in vacuo. The residue was purified by flash column chromatography (0-5% MeOH in DCM), followed by a second purification by flash column chromatography (65% EtOAc in heptane), affording compound 46 (342 mg) as a white powder. $^1H$ NMR ($CDCl_3$): 8.54-8.32 (bs, 1H), 8.27-8.21 (m, 4H), 7.76 (d, J=7.38 Hz, 2H), 7.59 (d, J=7.53 Hz, 2H), 7.42-7.33 (m, 6H), 7.33-7.27 (m, 2H), 4.86 (t, J=5.72 Hz, 1H), 4.51 (t, J=5.45 Hz, 4H), 4.43 (d, J=6.81, 2H), 4.21 (t, J=6.58, 1H), 4.17-4.09 (m, 2H), 3.84 (t, J=5.46 Hz, 4H), 3.19 (q, J=7.50 Hz, 2H), 1.72-1.63 (m, 2H), 1.63-1.48 (m, 2H), 1.48-1.36 (m, 2H).

Example 40: Synthesis of Compound 47

To a vial containing compound 46 (10.0 mg, 11.5 μmol, 1.00 equiv) was added a solution of $Et_3N$ (8.00 μL, 57.7 μmol, 5.00 equiv) and Val-Cit-PABC-Maytansin.TFA (vc- PABC-May.TFA, 30.0 mg, 23.4 μmol, 2.02 equiv) in DMF (450 μL). The resulting reaction mixture was left at room temperature for 72 hours. The reaction was quenched with 2,2-(ethylenedioxy)-bis(ethylamine) (15.0 μL, 99.7 μmol, 8.67 equiv) and left for 1.5 hours. Next, piperidine (10.0 μL, 101 μmol, 8.76 equiv) was added the mixture was left at room temperature for 1 hour and then purified by HPLC. Concentration of the collected fraction in vacuo yielded compound 47 (10.0 mg) as a light yellow oil. LCMS ($ESI^+$) calculated for $C_{129}H_{186}Cl_2N_{22}O_{37}S_2^{2+}$ ($M-2H_2O-2CO_2+2H^+$) 1289.62 found 1290.15.

Example 41: Preparation of Linker-Conjugate 48

To a solution of compound 47 (1.00 mg, 0.370 μmol, 1.00 equiv) in DMF (50.0 μL) was added a 10% v/v solution of $Et_3N$ in DMF (3.6 μL, 2.58 μmol, 6.98 equiv), followed by a solution of OSu-activated monofluoro-substituted cyclooctyn (MFCO-Apa-OSu (obtained from Berry & Associates, Dexter, USA), 0.140 mg, 0.368 μmol, 0.99 equiv) in DMF (5 μL). The resulting mixture was left at room temperature for 6 hours and then purified by HPLC. Concentration of the collected fraction in vacuo yielded compound 48 (0.95 mg) as a white solid. UPLC-MS ($ESI^+$) calculated for $C_{141}H_{205}Cl_2FN_{22}O_{40}S^{2+}$ ($M+2H^+$) 1484.19 found 1484.3.

Example 42-44: Preparation of Linker-Conjugate 51

Example 42: Synthesis of Compound 49

To a solution of 4-pentyn-1-ol (0.931 mL, 10.0 mmol, 1.00 equiv) in DCM (150 mL) was added dropwise chlorosulfonyl isocyanide (CSI, 0.870 mL, 10.0 mmol, 1.00 equiv). The resulting reaction mixture was stirred at room temperature for 15 minutes, followed by the slow addition of $Et_3N$ (2.80 mL, 20.0 mmol, 2.00 equiv). The reaction mixture was stirred for 6 minutes, followed by the addition of 2-(2-aminoethoxy)ethanol (2-AEE, 1.11 mL, 11.0 mmol, 1.10 equiv). The reaction was quenched after stirring for 13 minutes at room temperature through the addition of sat. aq. $NH_4Cl$ (pH 3.75, 150 mL). The resulting mixture was extracted with DCM (150 mL, 2×) and the combined organic layers were dried ($Na_2SO_4$) and then concentrated in vacuo. The residue was purified by flash column chromatography (1-10% MeOH in DCM), affording compound 49 (392 mg) as a yellow oil. $^1H$ NMR ($CDCl_3$): 6.10-5.90 (bs, 1H), 4.37-4.25 (t, J=6.21 Hz, 2H), 3.81-3.73 (m, 2H), 3.63 (t, J=4.52 Hz, 2H), 3.61-3.56 (m, 2H), 3.43-3.27 (m, 2H), 2.38-2.25 (m, 2H), 2.00 (t, J=2.70, Hz, 1H), 1.90 (p, J=6.45 Hz, 2H).

Example 43: Synthesis of Compound 50

To a solution of compound 49 (0.258 g, 0.877 mmol, 1.00 equiv) in DCM (60.0 mL) under nitrogen was added dropwise chlorosulfonyl isocyanide (CSI, 76.0 μL, 0.877 mmol, 1.00 equiv) and the resulting reaction mixture was stirred at room temperature for 15 minutes. $Et_3N$ (0.611 mL, 4.39

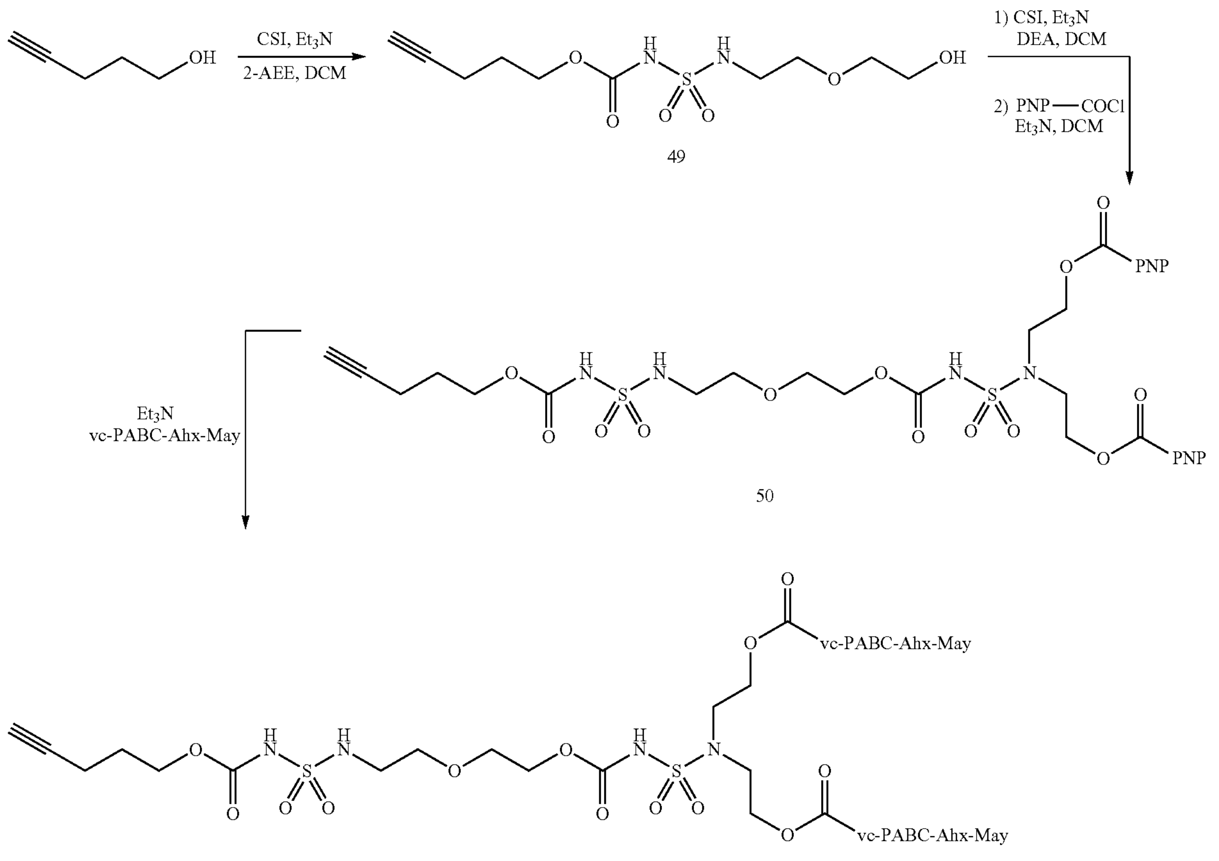

49

50

51 mmol, 5.00 equiv) was added dropwise and the mixture was stirred for 5 minutes at room temperature, followed by the addition of a solution of diethanolamine (DEA, 100 μL, 1.04 mmol, 1.19 equiv) in DMF (5 mL). The reaction mixture was stirred for 35 minutes at room temperature, followed by the addition of 4-nitrophenyl chloroformate (0.356 g, 1.77 mmol, 2.00 equiv) and additional $Et_3N$ (0.367 mL, 2.63 mmol, 3.00 equiv). The resulting reaction mixture was stirred for 18 hours and then concentrated in vacuo. The residue was diluted with DCM (50 mL) and sat. aq. $NH_4Cl$ (20 mL) was added. The resulting biphasic system was separated and the water layer was extracted with DCM (50 mL, 2×) and EtOAc (50 mL, 2×). The combined organic layers were dried ($Na_2SO_4$) and then concentrated in vacuo. The residue was purified by flash column chromatography (0-6% MeOH in DCM), affording compound 50 (265 mg, ~67% pure) as a yellow oil, containing circa 30% DMF, which was used without further purification. $^1H$ NMR ($CDCl_3$): 8.30-8.21 (m, 4H), 7.42-7.34 (m, 4H), 5.92-5.80 (m, 1H), 4.57-4.45 (m, 4H), 4.31-4.27 (m, 2H), 4.27-4.23 (m, 2H), 3.85 (m, J=5.42 Hz, 4H), 3.76-3.70 (m, 1H), 3.70-3.64 (m, 2H), 3.64-3.58 (m, 3H), 3.35-3.21 (m, 2H), 2.33-2.23 (m, 2H), 2.02-1.96 (m, 1H), 1.92-1.83 (m, 2H).

Example 44: Preparation of Linker-Conjugate 51

To a solution of compound 50 (15.1 mg, 11.6 μmol, 1.00 equiv) in DCM (0.400 mL) was added $Et_3N$ (8.15 μL, 58.4 μmol, 5.04 equiv), followed by the addition of a solution of Val-Cit-PABC-Maytansine-TFA (vc-PABC-May.TFA, 30.0 mg, 23.4 μmol, 2.02 equiv) in DMF (450 μL). The resulting reaction mixture was left at room temperature for 48 hours. The reaction was quenched with 2,2-(ethylenedioxy)bis (ethylamine) (15.0 μL, 99.7 μmol, 8.60 equiv) and left for 2 hours at room temperature and then concentrated in vacuo. The residue was taken up in a total of 900 μL of DMF and then purified by HPLC. Concentration of the collected fraction in vacuo yielded compound 51 (13.1 mg) as a pink/red solid. LCMS ($ESI^+$) calculated for $C_{129}H_{186}Cl_2N_{22}O_{37}S_2^{2+}$ ($M-2H_2O-2CO_2+2H^-$) 1385.11 found 1385.33.

Examples 45-49: Preparation of Linker-Conjugate 59

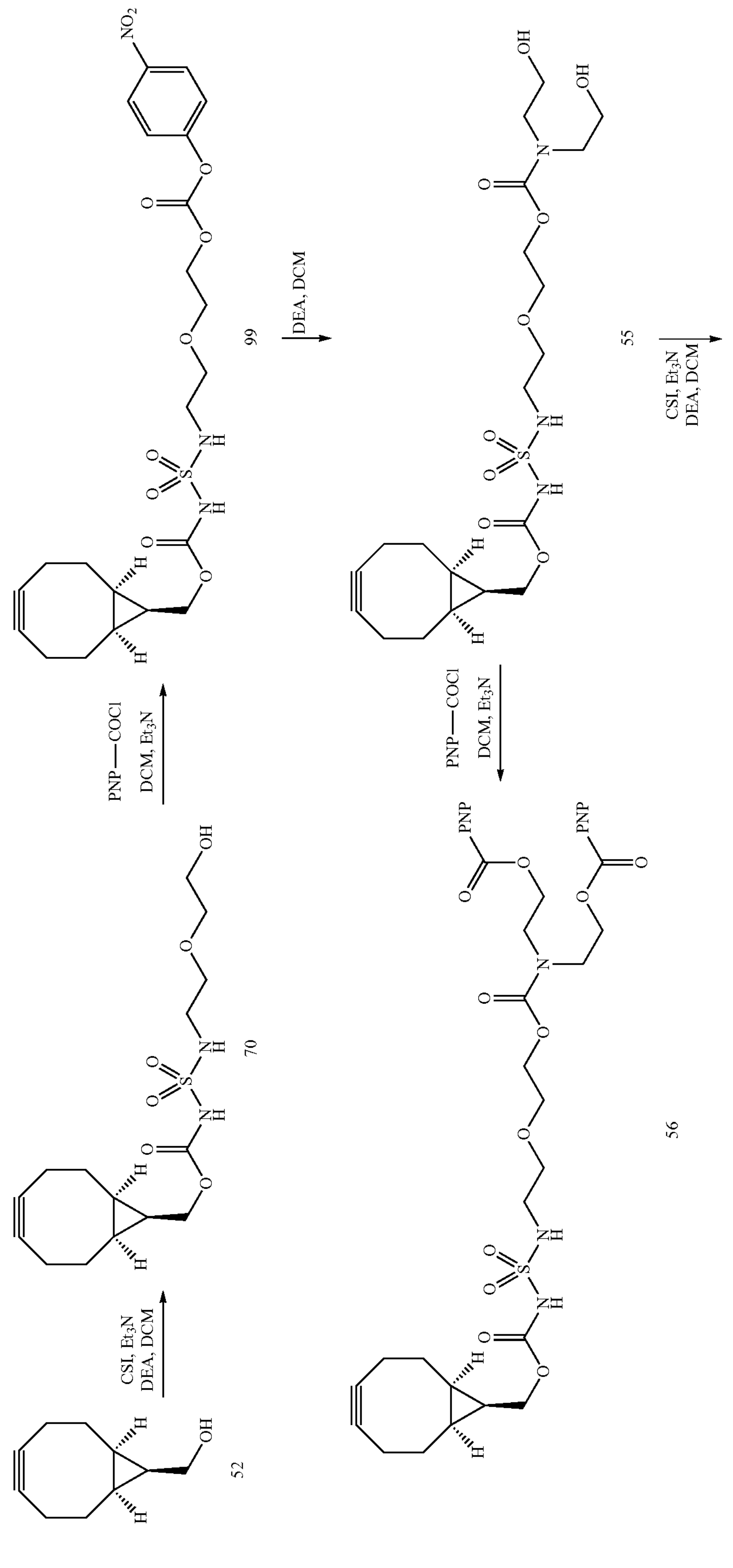
52
70
99
55
56

-continued
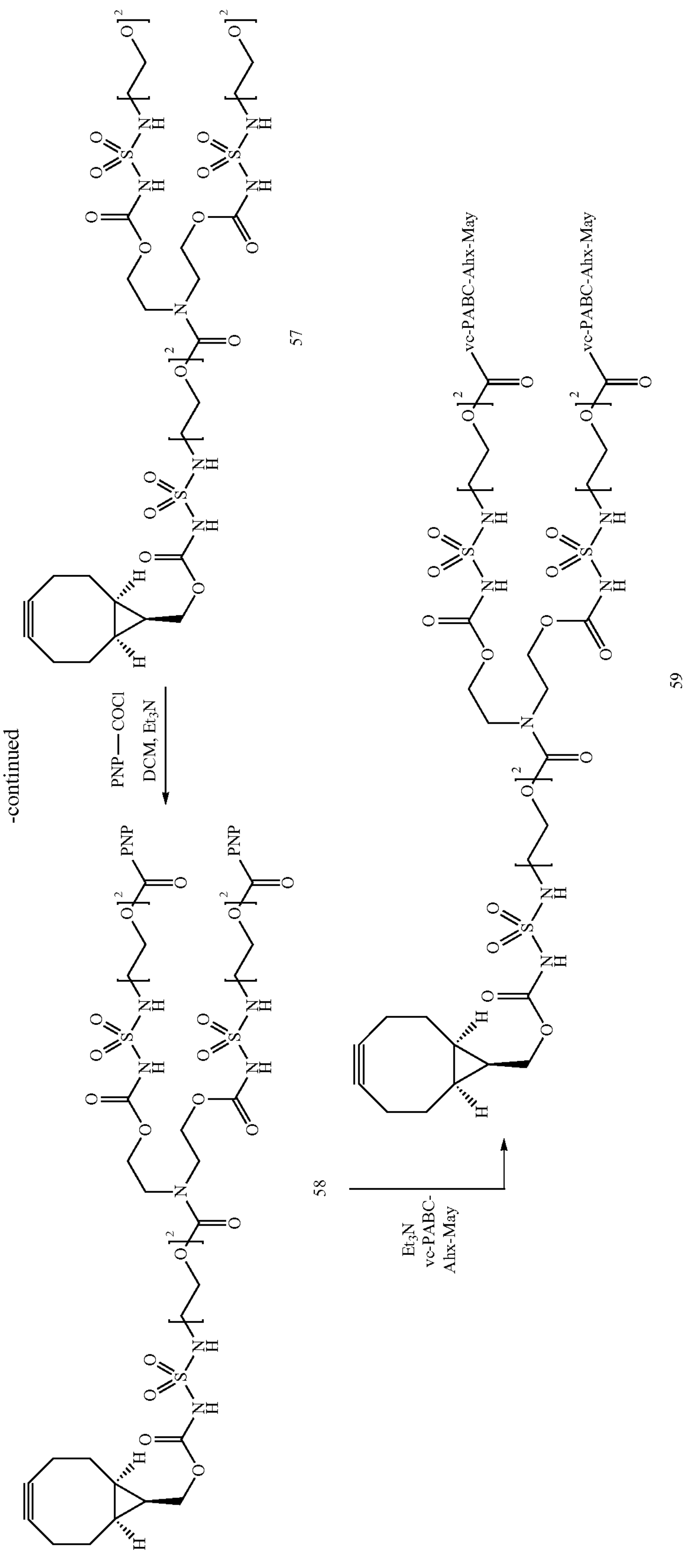
57
58
59

Example 45: Synthesis of 55

To a solution of 99 (1.44 g, 2.74 mmol) in DCM (120 mL) were added a solution of diaminoethanol (0.35g, 3.29 mmol) in DMF (8 mL) and $Et_3N$ (0.83 g, 1.15 mL, 8.22 mmol). The resulting mixture was stirred for 18 h and saturated aqueous $NH_4Cl$ was added. After separation, the aqueous phase was extracted with dichloromethane (3×120 mL). The combined organic layers were dried ($Na_2SO_4$) and concentrated. The residue was purified by silica chromatography (0→15% MeOH in DCM). The fractions containing the desired product were pooled and concentrated. The residue was dissolved in EtOAc (100 mL) and concentrated. The desired product was obtained as a colorless film (0.856 g, 1.74 mmol, 64%). $^1H$ NMR (400 MHz, $CDCl_3$) δ ppm 6.28 (bs, 1H), 4.33-4.30 (m, 2H, 4.28 (d, 2H, J=8.2 Hz), 3.89-3.81 (m, 4H), 3.70-3.64 (m, 2H), 3.63-3.58 (m, 2H), 3.52 (t, 4H, J=5.0 Hz), 3.32 (t, 2H, J=4.8 Hz), 2.36-2.18 (m, 6H), 1.64-1.50 (m, 2H), 1.39 (quintet, 1H, J=8.6 Hz), 1.05-0.94 (m, 2H).

Example 46: Synthesis of 56

To a solution of 55 (635 mg, 1.29 mmol) in DCM (40 mL) were added 4-nitrophenyl chloroformate (520 mg, 2.58 mmol) and $Et_3N$ (0.65 g, 0.90 mL). The resulting mixture was stirred for 20 h and concentrated. The residue was purified by silica chromatography ($1^{st}$ column: 50%→100% EtOAc in heptane; $2^{nd}$ column: 50%→100% EtOAc (1% AcOH)). The fractions containing the desired product were pooled and concentrated. The residue was dissolved in DCM (2 mL), heptane (8 mL) was added and the mixture was concentrated. The desired product was obtained as a white solid (306 mg, 0.37 mmol, 29%). $^1H$ NMR (400 MHz, $CDCl_3$) δ ppm 8.31-8.25 (m, 4H), 7.44-7.37 (m, 4H), 5.74-5.68 (m, 1H), 4.53-4.45 (m, 4H), 4.36-4.31 (m, 2H), 4.26 (m, 2H, J=8.2 Hz), 3.80-3.71 (m, 4H), 3.70-3.65 (m, 2H), 3.62-3.57 (m, 2H), 3.28 (q, 2H, J=4.8 Hz), 2.35-2.15 (m, 6H), 1.60-1.50 (m, 2H), 1.36 (quintet, 1H, J=8.7 Hz), 1.04-0.94 (m, 2H).

Example 47: Synthesis of 57

To a solution of 55 (80 mg, 0.163 mmol) in DCM (10 mL) were added chlorosulfonyl isocyanate (CSI, 46 mg, 18 μL, 0.33 mmol), $Et_3N$ (82.8 mg, 114 μL, 0.815 mmol) and 2-(2-aminoethoxy)ethanol (43 mg, 41 μL, 0.41 mmol). After 2 hours of stirring, water (10 mL) was added and the layers were separated. After addition of EtOAc to the aqueous phase, the pH of the aqueous phase was adjusted to 4.0 through careful addition of aqueous HCl (1N). The layers were separated and the aqueous phase was extracted with EtOAc (20 mL). The pH of the aqueous layer was 4 during extraction. The combined organic layers were dried ($Na_2SO_4$) and concentrated. The product was purified by silica gel chromatography (0→20% MeOH in DCM). The fractions containing the desired product were pooled and concentrated. The residue was dissolved in EtOAc (6 mL), and the mixture was concentrated (2×). The desired product was obtained as a colorless thick oil (53 mg, 0.058 mmol, 36%). $^1H$ NMR (400 MHz, CD3OD) δ ppm 4.36-4.22 (m, 8H), 3.75-3.50 (m, 20H), 3.25-3.20 (m, 6H), 2.34-2.14 (m, 6H), 1.70-1.55 (m, 2H), 1.44 (quintet, 1H, J=8.7 Hz), 1.04-0.94 (m, 2H).

Example 48: Synthesis of 58

To a solution of 57 (49 mg, 54 μmol) in DMF (0.5 mL) were added DCM (5 mL), 4-nitrophenyl chloroformate (22 mg, 107 μmol) and $Et_3N$ (27 mg, 38 μL, 270 μmol). The mixture was stirred for 2 days, concentrated and the residue was purified by silica gel chromatography (0→10% MeOH in DCM 2×). The desired product was obtained as a colorless film (4.5 mg, 3.6 μmol, 14%). Additionally, from the first silica gel column purification, fractions containing the intermediate mono-4-nitrophenylcarbonate functionalized product were pooled and concentrated. The resulting mono-functionalized product (27 mg, 25 μmol) was redissolved in DCM (2 mL) and 4-nitrophenyl chloroformate (5.1 mg, 25 μmol) and $Et_3N$ (7.6 mg, 10 μL, 75 μmol) were added. The resulting mixture was stirred for 19 h. and more 4-nitrophenyl chloroformate (6.5 mg, 32 μmol) was added. The mixture was stirred for an additional 4.5 h and concentrated. The residue was purified by silica column chromatography and afforded additional desired product as a colourless film. (11 mg, 8.9 μmol, 35%). 1H NMR (400 MHz, $CDCl_3$) δ ppm 8.31-8.25 (m, 4H), 7.44-7.39 (m, 4H), 6.18 (bs, 1H), 6.05-5.96 (m, 1H), 5.94-5.84 (m, 1H), 4.47-4.43 (m, 4H), 4.37-4.24 (m, 8H), 3.80-3.76 (m, 4H), 3.72-3.52 (m, 12H), 3.37-3.29 (m, 6H), 2.36-2.16 (m, 6H), 1.65-1.45 (m, 2H), 1.38 (quintet, 1H, J=8.6 Hz), 1.03-0.93 (m, 2H).

Example 49: Preparation of Linker-Conjugate 59

To a solution of 58 (15.5 mg, 12.5 μmol) in DMF (400 μL) were added $Et_3N$ (6.3 mg, 8.7 μL) and a solution of vc-PABC-May.TFA (32 mg, 25 μmol) in DMF (480 μL). The resulting mixture was left standing for 2 days after which 2,2'-(ethylenedioxy)bis(ethylamine) (14.6 μL, 15 mg, 100 μmol) was added to quench the reaction. After 2 hour the reaction mixture was purified via reversed phase (C18) HPLC chromatography (30→90% MeCN (1% AcOH) in $H_2O$ (1% AcOH). The desired product was obtained as white solid (18.1 mg, 5.5 μmol, 44%). LCMS ($ESI^+$) calculated for $C_{144}H_{212}Cl_2N_{25}O_{45}S_3^{3+}$ $((M-2CO_2-2H_2O)+3H^+)/3$ 1059.12 found 1059.71.

Examples 50-51: Preparation of Linker-Conjugate 54

110

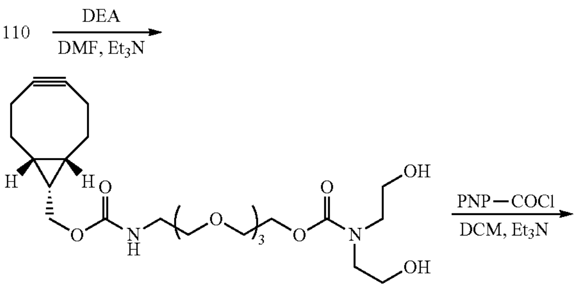

53a

-continued

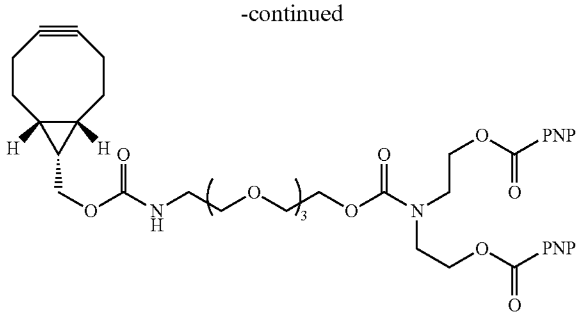

53b

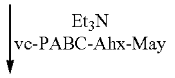

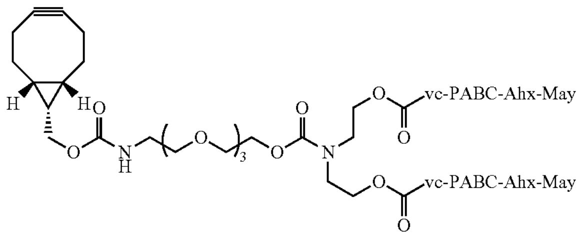

54

(m, 2H), 3.52-3.44 (m, 4H), 3.40-3.32 (m, 2H), 2.35-2.15 (m, 6H), 1.65-1.50 (m, 2H), 1.42-1.30 (m, 1H), 0.99-0.88 (m, 2H).

Example 50-2: Synthesis of 53b

To a solution of 53a (93 mg, 0.19 mmol) in DCM (20 mL) were added 4-nitrophenyl chloroformate (94 mg, 0.47 mmol) and triethylamine (132 μL; 96 mg; 0.95 mmol). The resulting reaction mixture was stirred for 17 h, washed with water (10 mL), dried ($Na_2SO_4$) and concentrated. The residue was purified by flash column chromatography (DCM→MeOH/DCM 1/9). The desired product was obtained as a slightly coloured oil (45 mg; 0.054 mmol; 28%) 1H NMR (400 MHz, $CDCl_3$) δ (ppm) 8.30-8.23 (m, 4H), 7.42-7.33 (m, 4H), 5.32-5.23 (m, 1H), 4.44 (t, 4H, J=5.4 Hz), 4.32-4.26 (m, 2H), 4.14 (d, 2H, J=8.0 Hz), 3.78-3.67 (m, 6H), 3.67-3.57 (m, 8H), 3.54 (t, 2H, J=5.1 Hz), 3.40-3.30 (m, 2H), 2.33-2.13 (m, 6H), 1.64-1.46 (m, 2H), 1.41-1.27 (m, 1H), 0.99-0.86 (m, 2H).

Example 51: Preparation of Linker Conjugate 54

To a solution of vc-PABC-Ahx-May (5.3 mg, 4.1 μmol) in DMF (499 μL) were added $Et_3N$ (1.4 μL, 1.0 mg, 10.3 μmol) and a solution of 53b (1.7 mg, 2.0 μmol) in DMF (128 μL). The resulting mixture was heated to 35° C., left for 20 min., heated to 45° C. and left for 21h. 2,2'-(Ethylenedioxy)bis (ethylamine) (6.0 μL, 6.1 mg, 41 μmol) was added and after 1 hour the mixture was purified via reversed phase (C18) HPLC chromatography (30→90% MeCN (1% AcOH) in $H_2O$ (1% AcOH). The desired product was obtained as white solid (3.0 mg, 1.04 μmol, 52%). LCMS (ESI+) calculated for $C_{140}H_{202}Cl_2N_{20}O_{41}{}^{2+}$ ($M+2H^+$)/2 1444.69 found 1446.78.

Example 52: Preparation of Linker-Conjugate 60

56

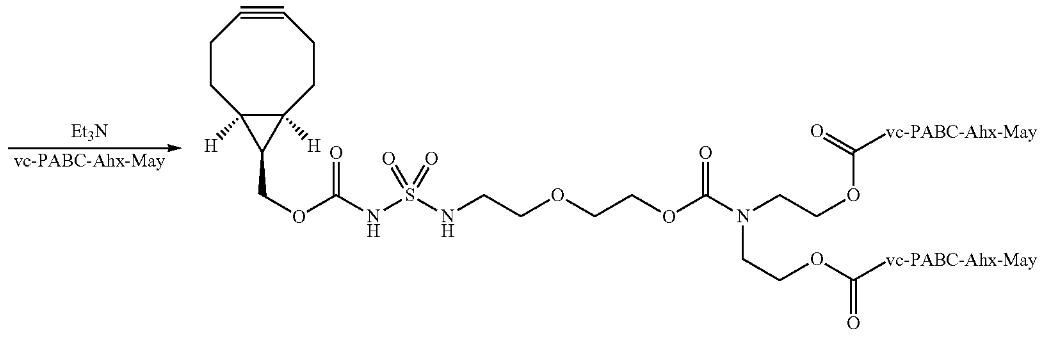

60

Example 50-1: Synthesis of 53a

To a solution of 110 (0.15 g; 0.28 mmol) in DCM (20 mL) were added a solution of diethanolamine (47 mg; 0.45 mmol) in DMF (1 mL) and $Et_3N$ (117 μL; 85 mg; 0.84 mmol). The resulting mixture was stirred at rt for 16 h, washed with a saturated aqueous solution of $NH_4Cl$, dried ($Na_2SO_4$) and concentrated. The residue was purified by flash column chromatography (DCM→MeOH/DCM 1/9). The product was obtained as a colourless oil (95 mg; 0.19 mmol; 68%). 1H NMR (400 MHz, $CDCl_3$) δ (ppm) 5.63 (bs, 1H), 4.32-4.27 (m, 2H), 4.14 (d, 2H, J=8.0 Hz), 3.89-3.77 (m, 4H), 3.73-3.68 (m, 2H), 3.67-3.60 (m, 8H), 3.58-3.53

A solution of 56 (17 μL, 53 mg/mL in DMF, 1.11 μmol), a solution of vc-PABC-Ahx-May.TFA (286 μL, 10 mg/mL in DMF, 2.22 μmol, 2 equiv.) and a solution of $Et_3N$ (7.7 μL, 10% in DMF, 5.5 μmol, 5 equiv.) were added together, mixed and left to stand at RT without stirring for 23 h. The reaction mixture was quenched with 2,2'-(ethylenedioxy)bis (ethylamine) (1.3 μL, 8.9 μmol, 8 equiv.) and left standing for 1 h. The crude product was purified by preparative HPLC (30 to 90% MeCN in $H_2O$, 1% AcOH, 50 fractions, product found in fractions 34 and 35). Yield: 1.8 mg (57%). Exact Mass=2878.28. LC-MS (C18 Waters, 25 min): Rt=14.07 min.; found m/z=935, 920, 701, 485.

Examples 53-54: Preparation of Linker-Conjugate 62

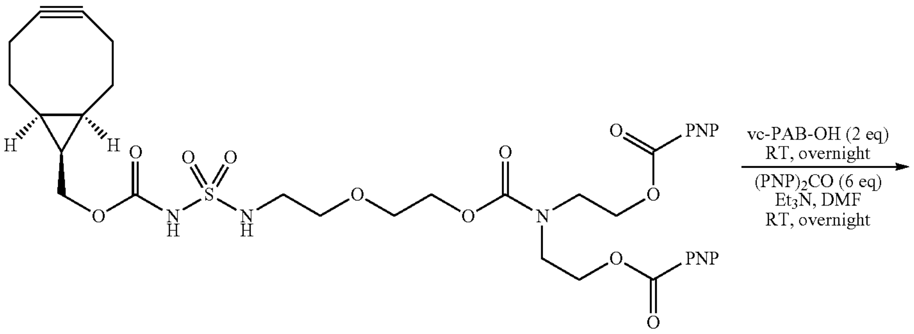

56

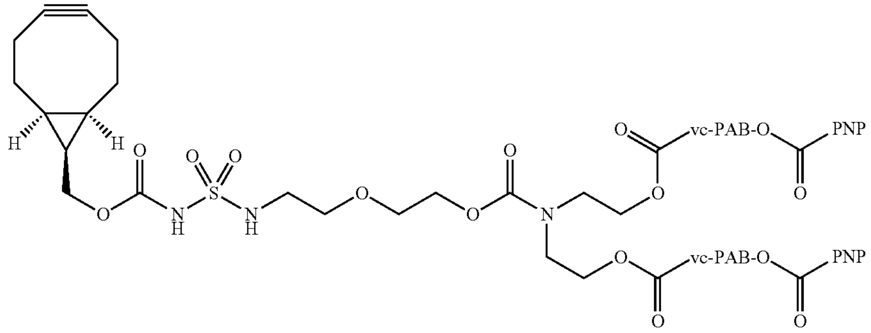

61

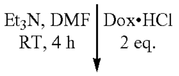

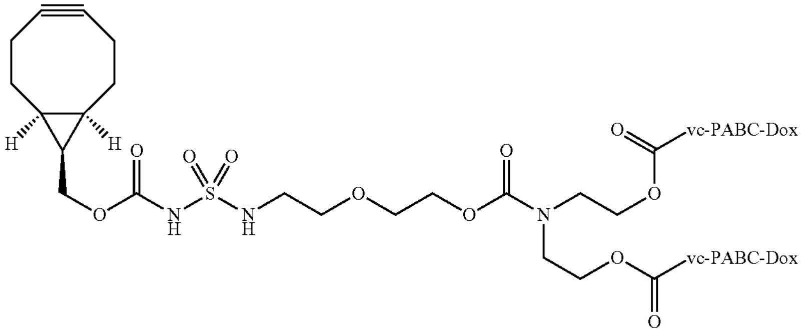

62 vc-PAB-OH =

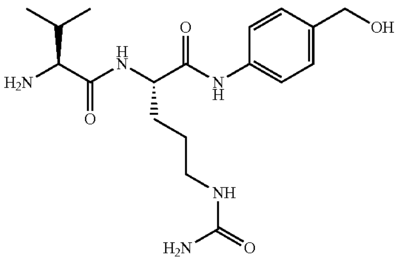

Example 53: Synthesis of Compound 61

A solution of 56 (1250 μL, 80 mM in DMF, 100 μmol), a solution of vc-PAB-OH (80 mg, 210 μmol, 2.1 equiv., in 2 mL DMF) and $Et_3N$ (84 μL, 600 μmol, 6 equiv.) were added together and stirred at RT for 40 h. Bis-(p-nitrophenyl) carbonate ($(PNP)_2CO$, 183 mg, 600 μmol, 6 equiv.) and $Et_3N$ (84 μL, 600 μmol, 6 equiv.) were added and the mixture was stirred at RT for 16 h. The mixture was then purified by silica column chromatography (12 g silica, 45 fractions, 20 mL/fraction, 20 mL/min, 0 to 15% MeOH in DCM, product found in fractions 26-32, Rf (DCM/MeOH, 9/1)=0.14). Yield: 96.6 mg (colourless oil, 59%). Exact Mass=1631.61. LC-MS (C18 Waters, 25 min): Rt=14.72 min.; found m/z=985, 906, 756, 633, 611, 559, 579.

Example 54: Preparation of Linker-Conjugate 62

A solution of 61 (116 μL, 20 mM in DMF, 2.3 μmol) was added to a solution containing doxorubicine.HCl (5.4 mg, 9.3 μmol, 4 equiv.), $Et_3N$ (51 μL, 10% in DMF, 37 μmol, 16 equiv.) and DMF (400 μL). The resulting solution was mixed and left to stand at RT without stirring for 4 h. The crude reaction mixture was purified by preparative HPLC (30 to 90% MeCN in $H_2O$, 1% AcOH, 50 fractions, product found in fractions 26-27). Yield: 2.9 mg (red solid, 52%). Mol. Wt=2441.50; Exact Mass=2439.90. LC-MS (C18 Waters, 25 min): Rt=11.98 min.; m/z=1243.

Examples 56-58: Preparation of Linker-Conjugates 63-66

Example 55: Preparation of Linker-Conjugate 63

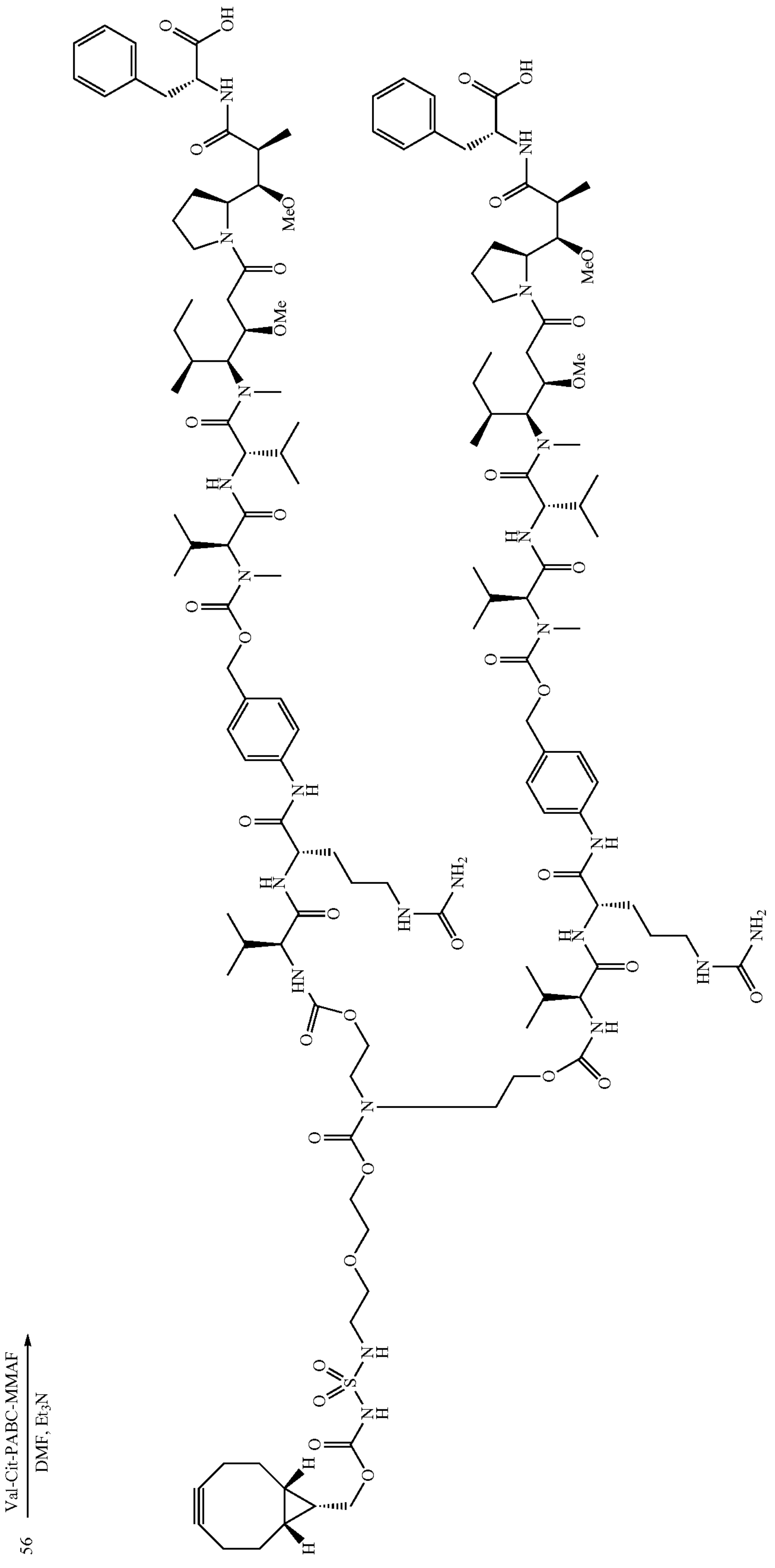
56

To a solution of vc-PABC-MMAF.TFA (5.5 mg, 4.4 μmol) in DMF (529 μL) were added $Et_3N$ (1.1 mg, 1.5 μL, 11 μmol) and a solution of 56 (1.8 mg, 2.2 μmol) in DMF (34 μL). The resulting mixture was left standing for 19h. Additional $Et_3N$ (1.1 mg, 1.5 μL) was added and the mixture was left standing for another 23h after which 2,2'-(ethylenedioxy)bis(ethylamine) (2.6 μL, 2.6 mg, 18 μmol) was added to quench the reaction. After 4 hours the mixture was purified via reversed phase (C18) HPLC chromatography (30→90% MeCN (1% AcOH) in $H_2O$ (1% AcOH). The desired product was obtained as a colorless film (3.6 mg, 1.3 μmol, 58%). LCMS ($ESI^+$) calculated for $(C_{138}H_{226}N_{23}O_{37}S^{3+})/3$ ((M+ $3H^+$)/3) 939.85 found 940.47.

Example 56: Preparation of Linker-Conjugate 64

To a solution of vc-PABC-MMAE.TFA (32.3 mg, 26 μmol) in DMF (1.0 mL) were added $Et_3N$ (7.4 mg, 10 μL, 72.6 μmol) and a solution of 56 (20 mg, 24.2 μmol) in DMF (500 μL). The resulting mixture was diluted with DMF (200 μL) and left standing for 19h. After addition of DCM (1 mL), the resulting mixture was purified by silica column chromatography (DCM→20% MeOH in DCM (2×)) yielding two products. The monofunctionalized product (1 arm with vc-PABC-MMAE and 1 arm with PNP, 64a) was obtained as a white colourless film (15.9 mg, 8.8 μmol, 36%). LCMS ($ESI^+$) calculated for $(C_{86}H_{130}N_{14}O_{26}S^{2+})/2$ ((M+$2H^+$)/2 903.45 found 904.15. The bisfunctionalized product (64) was obtained as a white colourless film (8.4 mg, 3.0 μmol,

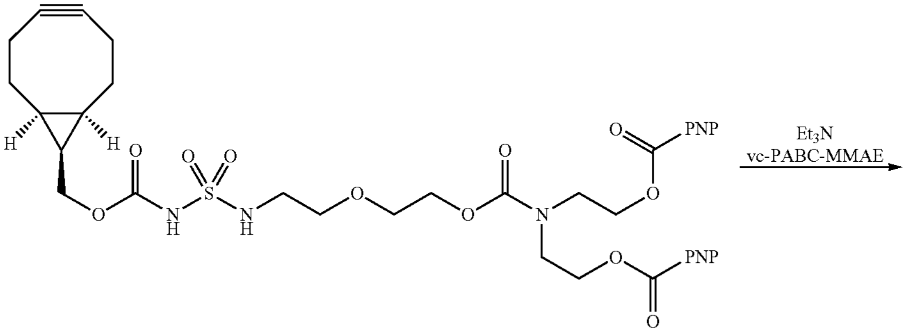

56

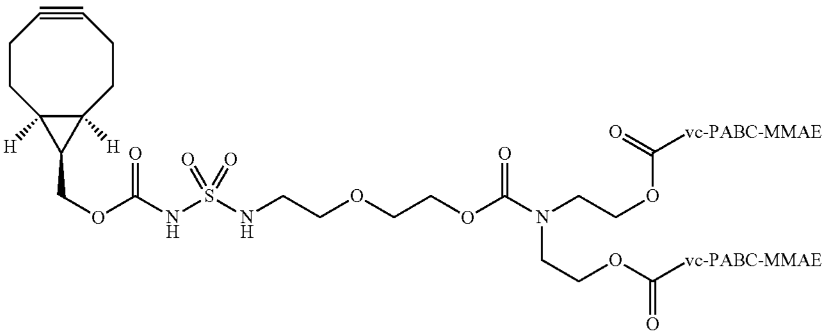

64

+

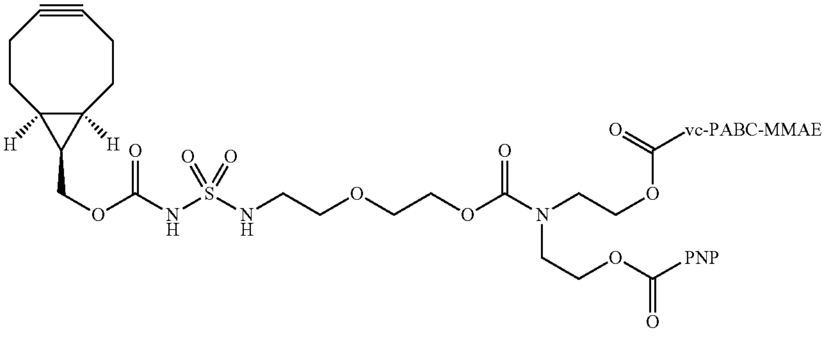

64a

12%). LCMS ($ESI^+$) calculated for $(C_{138}H_{220}N_{23}O_{35}S^{3+})/3$ $((M+3H^+)/3)$ 930.53 found 931.18a.

Example 57: Preparation of Linker-Conjugate 65

72
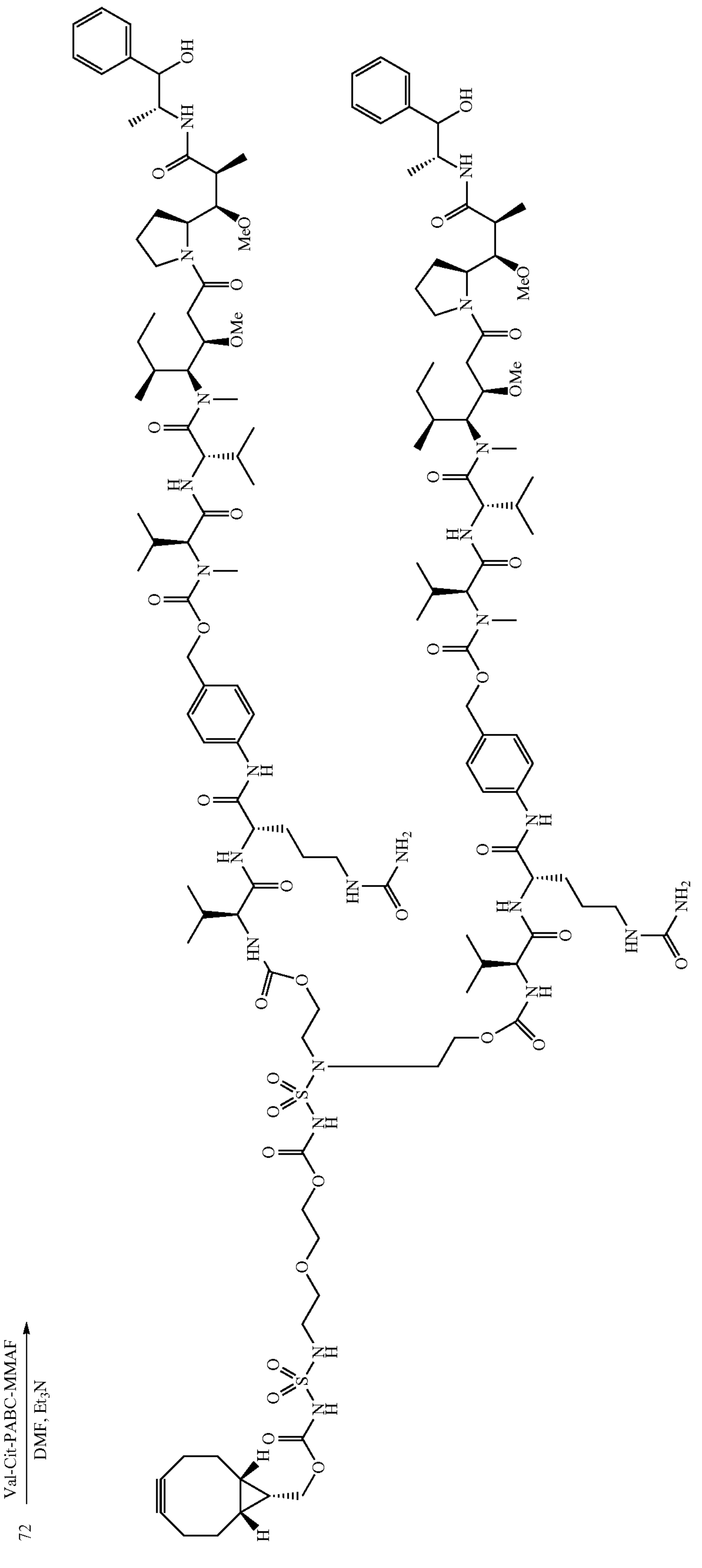

A solution of vc-PABC-MMAE.TFA (10 mg, 8.9 μmol) in DMF (0.5 mL) and $Et_3N$ (2.8 mg, 3.1 μL, 28 μmol) was added to 72 (4.0 mg, 4.5 μmol). The resulting mixture was left standing for 20.5 hours after which 2,2'-(ethylenedioxy) bis(ethylamine) (13 μL, 14 mg, 92 μmol) was added to quench the reaction. After 3.5 hours the mixture was purified via reversed phase (C18) HPLC chromatography (30→90% MeCN (1% AcOH) in $H_2O$ (1% AcOH). The desired product was obtained as a white solid (8.8 mg, 3.1 μmol, 68%). LCMS ($ESI^+$) calculated for $(C_{138}H_{221}N_{24}O_{37}S_2^{3+})/3$ ((M+ $3H^+$)/3) 956.85 found 957.71.

Example 58: Preparation of Linker-Conjugate 66

To a solution of vc-PABC-MMAF.TFA (1.4 mg, 1.11 μmol) were added 10% $Et_3N$ in DMF (4.6 μL, 0.34 mg, 3.33 μmol) and a solution of 64a (2.0 mg, 1.11 μmol) in DMF (111 μL). The resulting mixture was left standing for 22 h. A 10 vol % solution of 2,2'-(ethylenedioxy)-bis(ethylamine) in DMF was added (6.5 μL, 0.66 mg, 4.5 μmol) after 2.5 hours to quench the reaction. The crude mixture was purified via reversed phase ($C_{18}$) HPLC chromatography (30-90% MeCN (1% AcOH) in $H_2O$ (1% AcOH). The desired product was obtained as a white solid (1.8 mg, 0.64 μmol, 58%). LCMS ($ESI^+$) calculated for $(C_{138}H_{217}N_{23}O_{36}S^{2+})/2$ ((M+ $2H^+$)/2) 1402.28 found 1403.47.

Example 59-60: Preparation of Linker-Conjugate 68

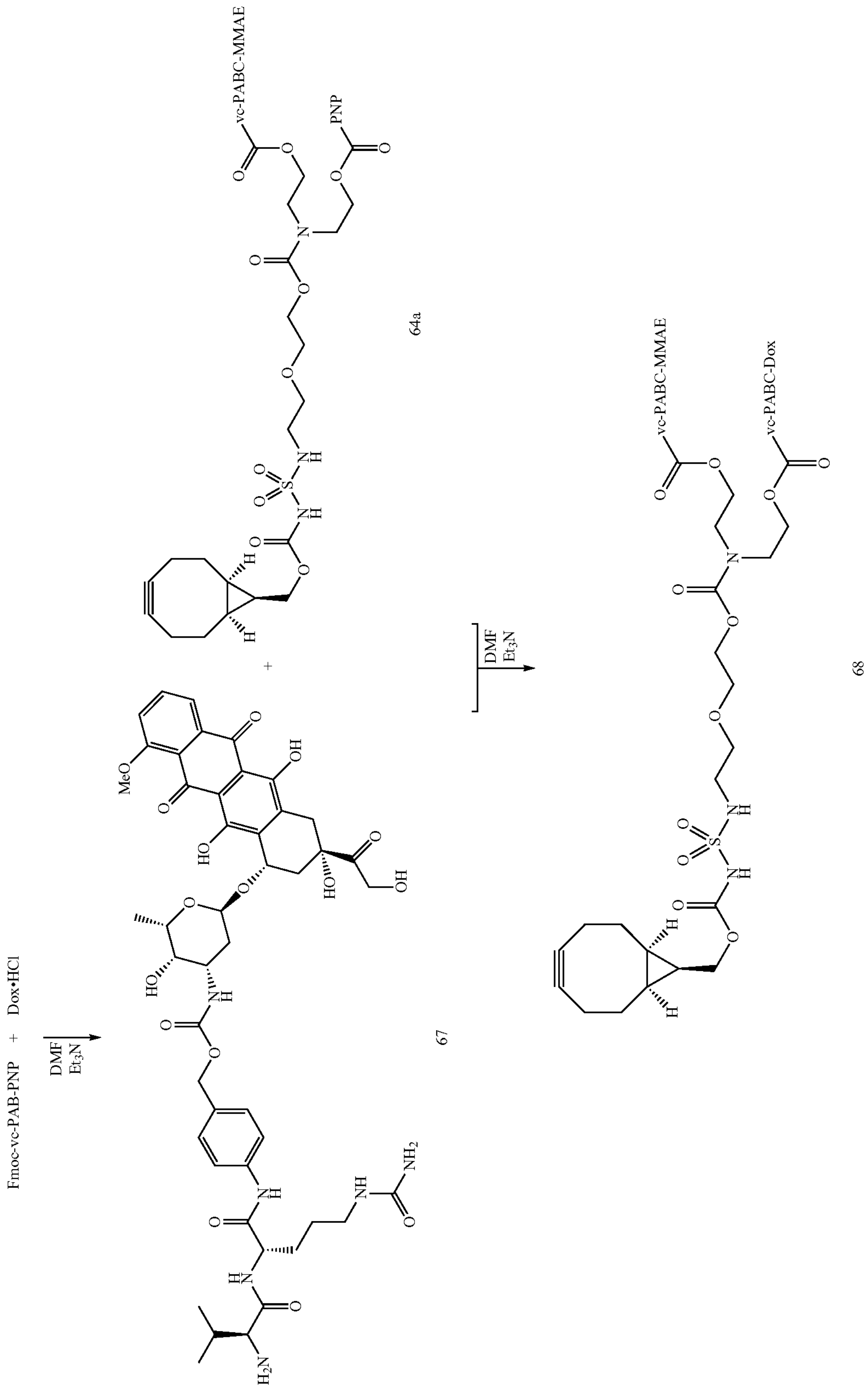
67
64a
68

Example 59: Synthesis of Compound 67

A solution of doxorubicine.HCl (66 mg, 86 μmol) and $Et_3N$ (36 μL, 258 μmol, 3 equiv.) in DMF (2 mL) and a solution of Fmoc-Val-Cit-PAB-PNP (obtained from Iris Biotech, Marktredwitz, Germany, 50 mg, 86 μmol, 1 equiv.) in DMF (2 mL) were added together and stirred at RT for 88 h. Besides coupling of doxorubicine to vc-PAB-PNP, Fmoc deprotection also occurred when leaving the reaction for a prolonged period of time. The mixture was concentrated in vacuo to a volume of 400 μL and purified by silica column chromatography (12 g silica, 45 fractions, 20 mL/fraction, 10 mL/min, 0 to 50% MeOH in DCM, product found in fractions 20-23, Rf (DCM/MeOH, 4/1)=0.04). The combined fractions 20-23 were concentrated in vacuo (27 mg) and further purified by preparative HPLC (5 to 95% MeCN in $H_2O$, 1% AcOH, 50 fractions, product found in fractions 21-28). Yield: 18.8 mg (red solid, 23%). Mol. Wt=948.98; Exact Mass=948.38. LC-MS (C18 Waters, 25 min): Rt=9.13 min.; m/z=949.

Example 60: Preparation of Linker-Conjugate 68

To a solution of vc-PABC-Dox (1.7 mg, 1.8 μmol) in DMF (44 μL) were added 10% $Et_3N$ in DMF (4.6 μL, 0.34 mg, 3.33 μmol) and a solution of 64a (2.0 mg, 1.11 μmol) in DMF (111 μL). The resulting mixture was left standing for 23 h. A 10 vol % solution of 2,2'-(ethylenedioxy)-bis(ethylamine) in DMF was added (6.5 μL, 0.66 mg, 4.5 μmol) to quench the reaction. After 2 hours the mixture was purified via reversed phase ($C_{18}$) HPLC chromatography (30-90% MeCN (1% AcOH) in $H_2O$ (1% AcOH). The fractions containing the product were pooled and concentrated and then purified by silica chromatography (0→20% MeOH in DCM), which yielded 2.6 mg (0.99 μmol) of the desired product. LCMS ($ESI^+$) calculated for $C_{126}H_{179}N_{19}Na_2O_{39}S^{2+}$ $(M+2Na^+)/2$ 1330.61 found 1331.07.

Examples 61-63: Preparation of Linker-Conjugates 69, 111 and 112

Example 61: Preparation of Linker-Conjugate 69

To a solution of vc-PABC-Ahx-May.TFA (1.4 mg, 1.11 μmol) in DMF (70 μL) were added 10% $Et_3N$ in DMF (4.6 μL, 0.34 mg, 3.33 μmol) and a solution of 64a (2.0 mg, 1.11 μmol) in DMF (111 μL). The resulting mixture was left standing for 2 days. A 10 vol % solution of 2,2'-(ethylenedioxy)bis(ethylamine) in DMF was added (6.5 μL, 0.66 mg, 4.5 μmol) to quench the reaction. After 2.5 hours the mixture was purified via reversed phase (C18) HPLC chromatography (30→90% MeCN (1% AcOH) in $H_2O$ (1% AcOH). The resulting product was obtained as a white solid (2.6 mg, 0.92 μmol, 83%). LCMS ($ESI^+$) calculated for $C_{136}H_{203}ClN_{22}Na_2O_{35}S^{2+}$ $((M-CO_2—H_2O)+2Na^{=})/2$ 1408.70 found 1409.65.

Example 62: Preparation of Linker-Conjugate 111

A solution of 54 (4.7 mg, 8.9 μmol) in DMF (200 μL) and $Et_3N$ (2.7 mg, 3.7 μL) were added to vc-PABC-MMAE.TFA (10 mg, 8.9 μmol). The resulting mixture was left standing for 23 h. after which 2,2'-(Ethylenedioxy)bis(ethylamine) (13 μL, 14 mg, 92 μmol) was added to quench the reaction. After 4 hours the mixture was purified via reversed phase ($C_{18}$) HPLC chromatography (30-90% MeCN (1% AcOH) in $H_2O$ (1% AcOH). The desired product was obtained as a colourless film (10.7 mg, 7.1 μmol, 80%). LCMS ($ESI^+$) calculated for $C_{74}H_{117}N_{12}O_{19}S^+$ $(M+H^+)$ 1509.83 found 1510.29.

Example 63: Preparation of Linker-Conjugate 112

To a solution of vc-PABC-MMAE.TFA (13.9 mg, 11.2 μmol) in DMF (400 μL) were added $Et_3N$ (3.4 μL, 2.5 mg, 24.3 μmol) and a solution of 110 (3.0 mg, 5.6 μmol) in DMF (200 μL). The reaction mixture was diluted with DMF (50 μL). After 25 min., additional $Et_3N$ (0.80 mg, 1.1 μL) and 110 (2.2 mg, 4.2 μmol) in DMF (33 μL) were added. The resulting mixture was left standing for 17 h. after which the mixture was purified via reversed phase (C18) HPLC chromatography (30-90% MeCN (1% AcOH) in $H_2O$ (1% AcOH). The desired product was obtained as a colourless film (10.9 mg, 7.2 μmol, 73%). LCMS ($ESI^+$) calculated for $C_{78}H_{124}N_{11}O_{19}+$ $(M+H^+)$ 1518.91 found 1519.09.

Examples 64-78: Preparation of Antibody-Drug-Conjugates

Example 64: Conjugation of 13d with 44 to Obtain Conjugate XI

A bioconjugate according to the invention was prepared by conjugation of compound 44 as linker-conjugate to azide-modified trastuzumab as biomolecule. To a solution of trastuzumab-(6-$N_3$-GalNAc)$_2$ (13d) (4.239 mL, 120 mg, 28.31 mg/ml in PBS pH 7.4) was added PBS pH 7.4 (1.761 mL), DMF (1.680 mL) and compound 44 (0.320 mL, 10 mM solution in DMF). The reaction was incubated at rt overnight followed by purification on a HiLoad 26/600 Superdex200 PG (GE Healthcare) on an AKTA Purifier-10 (GE Healthcare). Mass spectral analysis of the fabricator-digested sample showed one major product (observed mass 27398 Da, approximately 90% of total Fc/2 fragment), corresponding to the conjugated Fc/2 fragment. RP-HPLC analysis of the reduced sample indicated an average DAR of 3.77.

Example 65: Conjugation of 13d with 48 to Obtain Conjugate XII

A bioconjugate according to the invention was prepared by conjugation of compound 48 as linker-conjugate to azide-modified trastuzumab as biomolecule. To a solution of trastuzumab-(6-$N_3$-GalNAc)$_2$ (13d) (10 μL, 330 μg, 33.0 mg/ml in PBS pH 7.4) was added propylene glycol (2.5 μL), and compound 48 (2.5 μL, 10 mM solution in DMF). The reaction was incubated at rt overnight. Mass spectral analysis of the fabricator-digested sample showed one major product (observed mass 27336 Da, approximately 90% of total Fc/2 fragment), corresponding to the conjugated Fc/2 fragment. RP-HPLC analysis of the reduced sample indicated an average DAR of 1.40.

Example 66: Conjugation of 13d with 51 to Obtain Conjugate XIII

A bioconjugate according to the invention was prepared by conjugation of compound 51 as linker-conjugate to azide-modified trastuzumab as biomolecule. To a solution of trastuzumab-(6-$N_3$-GalNAc)$_2$ (13d) (12.25 μL, 286 μg, 23.34 mg/ml in PBS pH 7.4) was added PBS pH 7.4 (11.85 μL) and compound 51 (7.60 μL, 2 mM solution in DMF). In a separate tube, to a solution of $CuSO_4$ (35.5 μL, 15 mM solution in PBS pH 7.4) was added tris[(1-hydroxypropyl-1H-1,2,3-triazol-4-yl)methyl]amine (THPTA) (6.7 μL, 160 mM solution in DMF), amino guanidine.HCl (26.6 μL, 100 mM solution in PBS pH 7.4) and sodium ascorbate (20 μL, 400 mM solution in PBS pH 7.4). The THPTA-$CuSO_4$ complex was mixed and incubated at rt for 10 minutes. An aliquot of the THPTA-$CuSO_4$ complex (6.3 μL) was added to the solution containing trastuzumab-(6-$N_3$-GalNAc)$_2$ (13d) and compound 51. The reaction was mixed and incubated at rt. After 2 hrs the buffer was exchanged to PBS pH 7.4 by spinfiltration (Amicon Ultra-0.5, Ultracel-10 Membrane, Millipore) to remove the THPTA-$CuSO_4$ complex and excess alkyne. Mass spectral analysis of the fabricator-digested sample showed one major product (observed mass 27261 Da, approximately 90% of total Fc/2 fragment), corresponding to the conjugated Fc/2 fragment. RP-HPLC analysis of the reduced sample indicated an average DAR of 3.69.

Example 67: Conjugation of 13d with 59 to Obtain Conjugate XIV

A bioconjugate according to the invention was prepared by conjugation of compound 59 as linker-conjugate to azide-modified trastuzumab as biomolecule. To a solution of trastuzumab-(6-$N_3$-GalNAc)$_2$ (13d) (4.769 mL, 135 mg, 28.31 mg/ml in PBS pH 7.4) was added PBS pH 7.4 (1.981 mL), DMF (1.890 mL) and compound 59 (360 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 27668 Da, approximately 90% of total Fc/2 fragment), corresponding to the conjugated Fc/2 fragment. RP-HPLC analysis of the reduced sample indicated an average DAR of 3.68.

Example 68: Conjugation of 13d with 60 to Obtain Conjugate XV

A bioconjugate according to the invention was prepared by conjugation of compound 60 as linker-conjugate to azide-modified trastuzumab as biomolecule. To a solution of trastuzumab-(6-$N_3$-GalNAc)$_2$ (13d) (4.769 mL, 135 mg, 28.31 mg/ml in PBS pH 7.4) was added propylene glycol (4.95 mL), and compound 60 (270 μL, 20 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 27248 Da, approximately 90% of total Fc/2 fragment), corresponding to the conjugated Fc/2 fragment. RP-HPLC analysis of the reduced sample indicated an average DAR of 3.54.

Example 69: Conjugation of 13d with 63 to Obtain Conjugate XVII

A bioconjugate according to the invention was prepared by conjugation of compound 63 as linker-conjugate to azide-modified trastuzumab as biomolecule. To a solution of trastuzumab-(6-$N_3$-GalNAc)$_2$ (13d) (8.18 mL, 270 mg, 33.0 mg/ml in PBS pH 7.4) was added PBS pH 7.4 (7.12 mL), DMF (2.48 mL) and compound 63 (225 μL, 40 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25921 Da, approximately 90% of total Fc/2 fragment), corresponding to the conjugated Fc/2 fragment. RP-HPLC analysis of the reduced sample indicated an average DAR of 1.90.

Example 67: Conjugation of 13d with 68 to Obtain Conjugate XXI

A bioconjugate according to the invention was prepared by conjugation of compound 68 as linker-conjugate to azide-modified trastuzumab as biomolecule. To a solution of trastuzumab-(6-$N_3$-GalNAc)$_2$ (13d) (129 μL, 2.57 mg, 19.85 mg/ml in PBS pH 7.4) was added compound 68 (60 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 26980 Da, approximately 80% of total Fc/2 fragment), corresponding to the conjugated Fc/2 fragment. RP-HPLC analysis of the reduced sample indicated an average DAR of 3.55.

Example 71: Conjugation of 13d with 62 to Obtain Conjugate XVI

A bioconjugate according to the invention was prepared by conjugation of compound 62 as linker-conjugate to azide-modified trastuzumab as biomolecule. To a solution of trastuzumab-(6-$N_3$-GalNAc)$_2$ (13d) (202 μL, 4.0 mg, 19.9 mg/ml in PBS pH 7.4) was added propylene glycol (170 μL) and compound 62 (32 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 26806 Da, approximately 90% of total Fc/2 fragment), corresponding to the conjugated Fc/2 fragment. RP-HPLC analysis of the reduced sample indicated an average DAR of 3.70.

Example 72: Conjugation of 13d with 64 to Obtain Conjugate XVIII

A bioconjugate according to the invention was prepared by conjugation of compound 64 as linker-conjugate to azide-modified trastuzumab as biomolecule. To a solution of trastuzumab-(6-$N_3$-GalNAc)$_2$ (13d) (360 μL, 7.0 mg, 19.5 mg/ml in PBS pH 7.4) was added PBS pH 7.4 (13.5 μL), DMF (81.6 μL) and compound 64 (11.7 μL, 20 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 27155 Da, approximately 90% of total Fc/2 fragment), corresponding to the conjugated Fc/2 fragment. RP-HPLC analysis of the reduced sample indicated an average DAR of 3.58.

Example 73: Conjugation of 13d with 65 to Obtain Conjugate XIX

A bioconjugate according to the invention was prepared by conjugation of compound 65 as linker-conjugate to azide-modified trastuzumab as biomolecule. To a solution of trastuzumab-(6-$N_3$-GalNAc)$_2$ (13d) (334 μL, 6.67 mg, 20.0 mg/ml in PBS pH 7.4) was added DMF (100 μL) and compound 65 (11.13 μL, 20 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 27238 Da, approximately 90% of total Fc/2 fragment), corresponding to the conjugated Fc/2 fragment. RP-HPLC analysis of the reduced sample indicated an average DAR of 3.58.

Example 74: Conjugation of 13d with 66 to Obtain Conjugate XX

A bioconjugate according to the invention was prepared by conjugation of compound 66 as linker-conjugate to azide-modified trastuzumab as biomolecule. To a solution of trastuzumab-(6-$N_3$-GalNAc)$_2$ (13d) (353 μL, 7.0 mg, 19.9 mg/ml in PBS pH 7.4) was added PBS pH 7.4 (210 μL), DMF (44.7 μL) and compound 66 (48.6 μL, 9.6 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 27169 Da, approximately 90% of total Fc/2 fragment), corresponding to the conjugated Fc/2 fragment.

Example 75: Conjugation of 13d with 69 to Obtain Conjugate XXII

A bioconjugate according to the invention was prepared by conjugation of compound 69 as linker-conjugate to azide-modified trastuzumab as biomolecule. To a solution of trastuzumab-(6-$N_3$-GalNAc)$_2$ (13d) (360 μL, 7.0 mg, 19.5 mg/ml in PBS pH 7.4) was added DMF (23.4 μL) and compound 69 (93.3 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 27200 Da, approximately 90% of total Fc/2 fragment), corresponding to the conjugated Fc/2 fragment.

Example 76: Conjugation of 13d with 111 to Obtain Conjugate XXIII

A bioconjugate according to the invention was prepared by conjugation of compound 111 as linker-conjugate to azide-modified trastuzumab as biomolecule. To a solution of trastuzumab-(6-$N_3$-GalNAc)$_2$ (13d) (360 μL, 7.0 mg, 19.5 mg/ml in PBS pH 7.4) was added PBS pH 7.4 (60.1 μL), DMF (42.0 μL) and compound 111 (4.67 μL, 40 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25874.2 Da, approximately 90% of total Fc/2 fragment), corresponding to the conjugated Fc/2 fragment. RP-HPLC analysis of the reduced sample indicated an average DAR of 3.69.

Example 77: Conjugation of 13d with 112 to Obtain Conjugate XXIV

A bioconjugate according to the invention was prepared by conjugation of compound 21 as linker-conjugate to azide-modified trastuzumab as biomolecule. To a solution of trastuzumab-(6-$N_3$-GalNAc)$_2$ (13d) (235 μL, 6.7 mg, 28.5 mg/ml in PBS pH 7.4) was added PBS pH 7.4 (99 μL), DMF (100.3 μL) and compound 112 (11.2 μL, 40 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25884 Da, approximately 90% of total Fc/2 fragment), corresponding to the conjugated Fc/2 fragment. RP-HPLC analysis of the reduced sample indicated an average DAR of 3.72.

Example 78: Conjugation of 13d with 54 to Obtain Conjugate IV

A bioconjugate according to the invention was prepared by conjugation of compound as linker-conjugate to azide-modified trastuzumab as biomolecule. To a solution of trastuzumab-(6-N3-GalNAc)$_2$ (235 μL, 6.7 mg, 28.5 mg/ml in PBS pH 7.4) was added propylene glycol (190 μL) and compound 54 (45 μL, 10 mM solution in DMF). The reaction was incubated at rt for 36 hours followed by purification on a HiLoad 26/600 Superdex200 PG (GE Healthcare) on an AKTA Purifier-10 (GE Healthcare). Mass spectral analysis of the fabricator-digested sample showed one major product (observed mass 27254 Da, approximately 90% of total Fc/2 fragment), corresponding to the conjugated Fc/2 fragment. RP-HPLC analysis of the reduced sample indicated an average DAR of 3.46.

The invention claimed is:

1. A method for targeting HER2-expressing cells, comprising administering to a subject in need thereof an antibody-conjugate, comprising an antibody AB connected to a target molecule D via a linker L, wherein the antibody-conjugate is obtainable by:

(i) contacting a glycoprotein comprising 1 or 2 core N-acetylglucosamine moieties with a compound of the formula $S(F^1)_x$-P in the presence of a catalyst, wherein $S(F^1)_x$ is a sugar derivative comprising x functional groups $F^1$ capable of reacting with a functional group $Q^1$, x is 1 or 2 and P is a nucleoside mono- or diphosphate, and wherein the catalyst is capable of transferring the $S(F^1)_x$ moiety to the core-GlcNAc moiety, to obtain a modified antibody according to Formula (24):

(24)

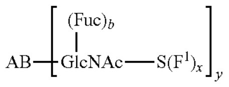

wherein $S(F^1)_x$ and x are as defined above; AB represents an antibody; GlcNAc is N-acetylglucosamine; Fuc is fucose; b is 0 or 1; and y is 1 or 2; and (ii) reacting the modified antibody with a linker-conjugate comprising a functional group $Q^1$ capable of reacting with functional group $F^1$ and a target molecule D connected to $Q^1$ via a linker $L^2$ to obtain the antibody-conjugate wherein linker L comprises S—$Z^3$-$L^2$ and wherein $Z^3$ is a connecting group resulting from the reaction between $Q^1$ and $F^1$, wherein the antibody AB is trastuzumab, $S(F^1)_x$ is connected to the core-GlcNAc linked to amino acid N300, $S(F^1)_x$ is 6-azido-6-deoxy-N-acetylgalactosamine, $Q^1$ is according to formula (9q), $L^2$ is —$CH_2$—O—C(O)—NH—$S(O)_2$—NH—($CH_2$—$CH_2$—O)$_2$—C(O)-Val-Cit-PABC- and target molecule D is Ahx-May, wherein Ahx-May is:

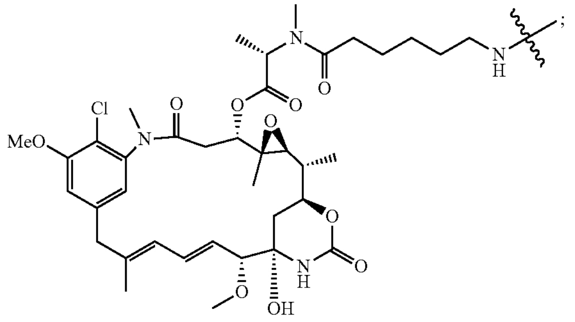 [SMILES: *NCCCCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

and wherein formula (9q) is

9q

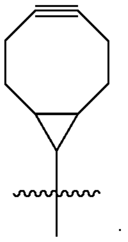

2. The method according to claim 1, wherein the targeting HER2-expressing cells includes one or more of treating, imaging, diagnosing, preventing the proliferation of, containing and reducing HER2-expressing cells, in particular HER2-expressing tumours.

3. The method according to claim 1, wherein the subject suffers from a disorder selected from breast cancer, bladder cancer, pancreatic cancer, gastric cancer.

4. The method according to claim 1, wherein the antibody-conjugate exhibits increased therapeutic index.

5. The method according to claim 4, wherein the increased therapeutic index is selected from:

(a) increasing the therapeutic efficacy of the antibody-conjugate; and/or (b) increasing the tolerability of the antibody-conjugate.

6. A method for targeting HER2-expressing cells, comprising administering to a subject in need thereof an antibody-conjugate, comprising an antibody AB connected to a target molecule D via a linker L, wherein the antibody-conjugate is represented by Formula (41):

(41)

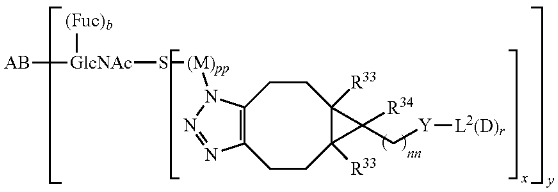

wherein:

$R^{33}$ and $R^{34}$ are hydrogen;

nn=1

Y=O $L^2(D)_r$=—O—C(O)—NH—$S(O)_2$—NH—($CH_2$—$CH_2$—O)$_2$—C(O)-Val-Cit-PABC-Ahx-May, wherein Ahx-May is:

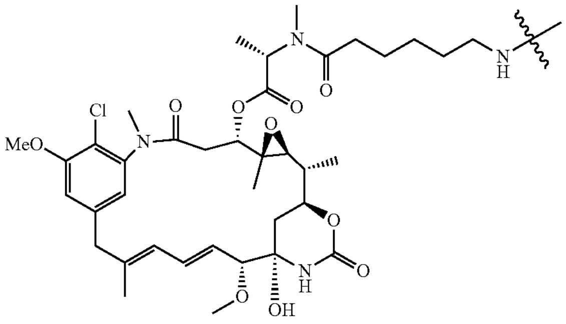

;

pp is 0 y is 1 or 2;

Fuc is fucose;

GlcNAc is N-acetylglucosamine, which is linked to amino acid N300;

S is 6-deoxy-N-acetylgalactosaminyl; and antibody AB is trastuzumab.

7. The method according to claim 6, wherein the targeting HER2-expressing cells includes one or more of treating, imaging, diagnosing, preventing the proliferation of, containing and reducing HER2-expressing cells, in particular HER2-expressing tumours.

8. The method according to claim 6, wherein the subject suffers from a disorder selected from breast cancer, bladder cancer, pancreatic cancer, gastric cancer.

9. The method according to claim 6, wherein the antibody-conjugate exhibits increased therapeutic index.

10. The method according to claim 9, wherein the increased therapeutic index is selected from:

(a) increasing the therapeutic efficacy of the antibody-conjugate; and/or (b) increasing the tolerability of the antibody-conjugate.

* * * * *